US010167519B2

(12) United States Patent
Luo et al.

(10) Patent No.: US 10,167,519 B2
(45) Date of Patent: Jan. 1, 2019

(54) FUSION GENES ASSOCIATED WITH PROGRESSIVE PROSTATE CANCER

(71) Applicant: UNIVERSITY OF PITTSBURGH—OF THE COMMONWEALTH SYSTEM OF HIGHER EDUCATION, Pittsburgh, PA (US)

(72) Inventors: Jianhua Luo, Wexford, PA (US); Yangping Yu, Wexford, PA (US); Joel B. Nelson, Pittsburgh, PA (US); George Konstantine Michalopoulos, Pittsburgh, PA (US); Chien-Cheng Tseng, Pittsburgh, PA (US); Ying Ding, San Diego, CA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 15/896,818

(22) Filed: Feb. 14, 2018

(65) Prior Publication Data
US 2018/0187268 A1 Jul. 5, 2018

Related U.S. Application Data

(63) Continuation of application No. 15/199,056, filed on Jun. 30, 2016, now Pat. No. 9,932,641, which is a continuation of application No. PCT/US2014/072268, filed on Dec. 23, 2014.

(60) Provisional application No. 61/921,836, filed on Dec. 30, 2013, provisional application No. 62/014,487, filed on Jun. 19, 2014, provisional application No. 62/025,923, filed on Jul. 17, 2014.

(51) Int. Cl.
C07H 21/02 (2006.01)
C07H 21/04 (2006.01)
A61K 48/00 (2006.01)
C12Q 1/6886 (2018.01)

(52) U.S. Cl.
CPC ...... C12Q 1/6886 (2013.01); C12Q 2600/118 (2013.01); C12Q 2600/156 (2013.01); C12Q 2600/158 (2013.01); C12Q 2600/16 (2013.01)

(58) Field of Classification Search
CPC .. C12N 2310/14; C12N 15/113; C12N 15/111
See application file for complete search history.

(56) References Cited

U.S. PATENT DOCUMENTS

2008/0274909 A1   11/2008   Brothman
2012/0220672 A1   8/2012    Pestano et al.
2013/0079241 A1   3/2013    Luo et al.
2013/0225420 A1   8/2013    Albertson et al.

FOREIGN PATENT DOCUMENTS

| WO | WO 2008/016374 A2 | 2/2008 |
| WO | WO 2008/023087 A2 | 2/2008 |
| WO | WO 2010/056337 A2 | 5/2010 |
| WO | WO 2010/138460 A1 | 12/2010 |
| WO | WO 2012/139134 A2 | 10/2012 |
| WO | WO 2013/037118 A1 | 3/2013 |
| WO | WO 2014/018673 A2 | 1/2014 |
| WO | WO 2014/039556 A1 | 3/2014 |
| WO | WO 2015/106341 A1 | 7/2015 |

OTHER PUBLICATIONS

U.S. Appl. No. 13/619,556 (US 2013/0079241), filed Sep. 14, 2012 (Mar. 28, 2013) (Abandoned).
U.S. Appl. No. 14/336,965 (US 2015/0050647), filed Jul. 21, 2014 (Feb. 19, 2015).
U.S. Appl. No. 15/199,056 (U.S. Pat. No. 9,932,641), filed Jun. 30, 2016 (Apr. 3, 2018).
U.S. Appl. No. 15/406,472 (US 2017/0240924), filed Jan. 13, 2017 (Aug. 24, 2017).
U.S. Appl. No. 15/896,931, filed Feb. 14, 2018.
U.S. Appl. No. 13/619,556, Sep. 30, 2014 Notice of Abandonment.
U.S. Appl. No. 13/619,556, Jul. 3, 2014 Advisory Action.
U.S. Appl. No. 13/619,556, Jun. 19, 2014 Response to Final Office Action.
U.S. Appl. No. 13/619,556, Feb. 21, 2014 Final Office Action.
U.S. Appl. No. 13/619,556, Nov. 14, 2013 Response to Non-Final Office Action.
U.S. Appl. No. 13/619,556, Jul. 16, 2013 Non-Final Office Action.
U.S. Appl. No. 13/619,556, May 13, 2013 Response to Restriction Requirement.
U.S. Appl. No. 13/619,556, Mar. 12, 2013 Restriction Requirement.
U.S. Appl. No. 14/336,965, Mar. 20, 2018 Non-Final Office Action.
U.S. Appl. No. 14/336,965, Jun. 7, 2017 Amendment and Request for Continued Examination (RCE).
U.S. Appl. No. 14/336,965, Feb. 7, 2017 Final Office Action.

(Continued)

Primary Examiner — Amy H Bowman
(74) Attorney, Agent, or Firm — Baker Botts L.L.P.

(57) ABSTRACT

The present invention relates to methods and compositions for determining whether a subject having prostate cancer is at greater risk of developing progressive disease, and methods of treating the subjects. It is based, at least in part, on the discovery that approximately 90% of men carrying at least one of the following fusion genes: TRMT11-GRIK2, SLC45A2-AMACR, MTOR-TP53BP1, LRRC59-FLJ60017, TMEM135-CCDC67 and CCNH-05orf30 experienced prostate cancer recurrence, metastases and/or prostate cancer-specific death after radical prostatectomy (each examples of "progressive prostate cancer"), while these outcomes occurred in only 36% of men not carrying any of these fusion genes. It is also based, at least in part, on the discovery that no patient studied survived five years without recurrence if their primary prostate cancer contained a TRMT11-GRIK2 or MTOR-TP53BP1 fusion gene. It is also based, at least in part, on the discovery that the protein encoded by the MAN2A1-FER fusion gene exhibits kinase activity.

19 Claims, 60 Drawing Sheets

Figure 1:
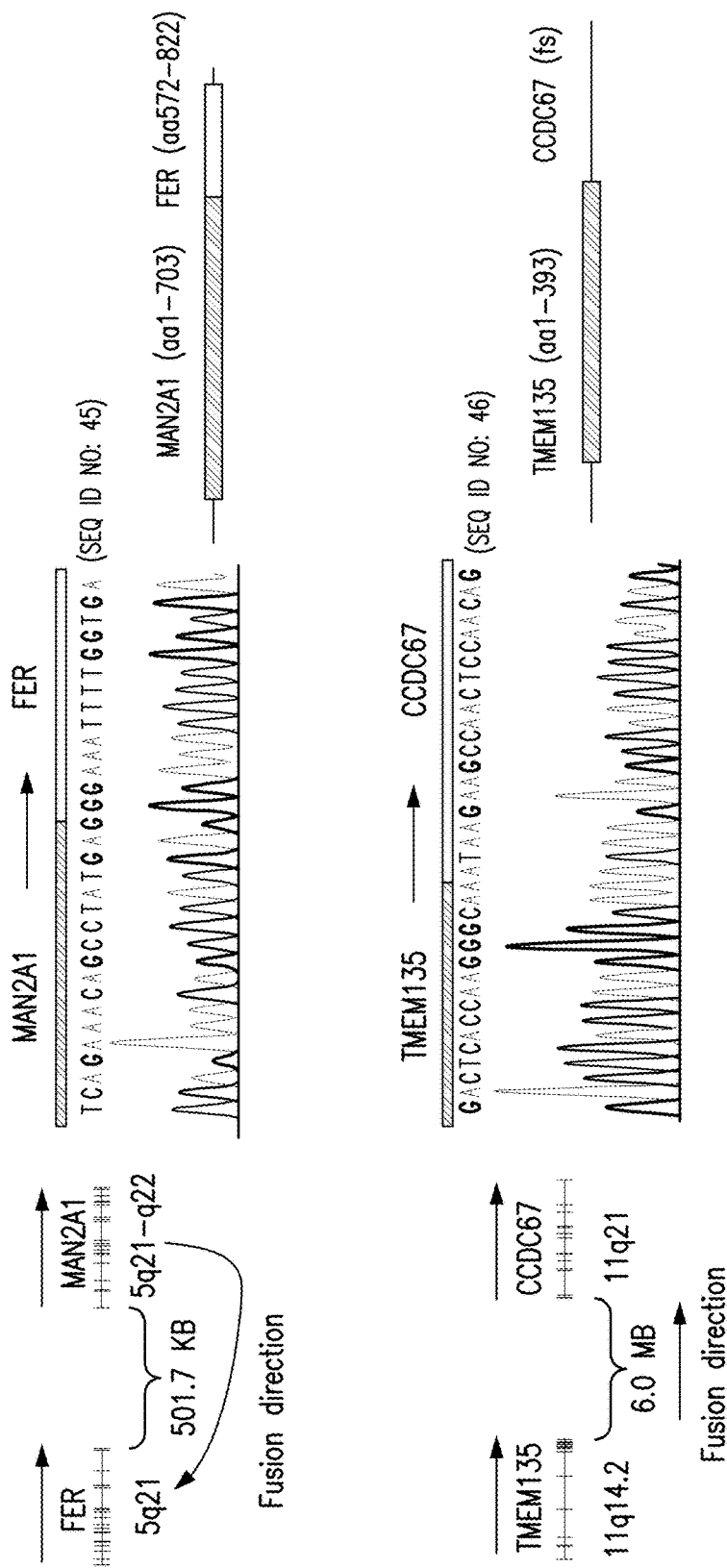
Figure 1:
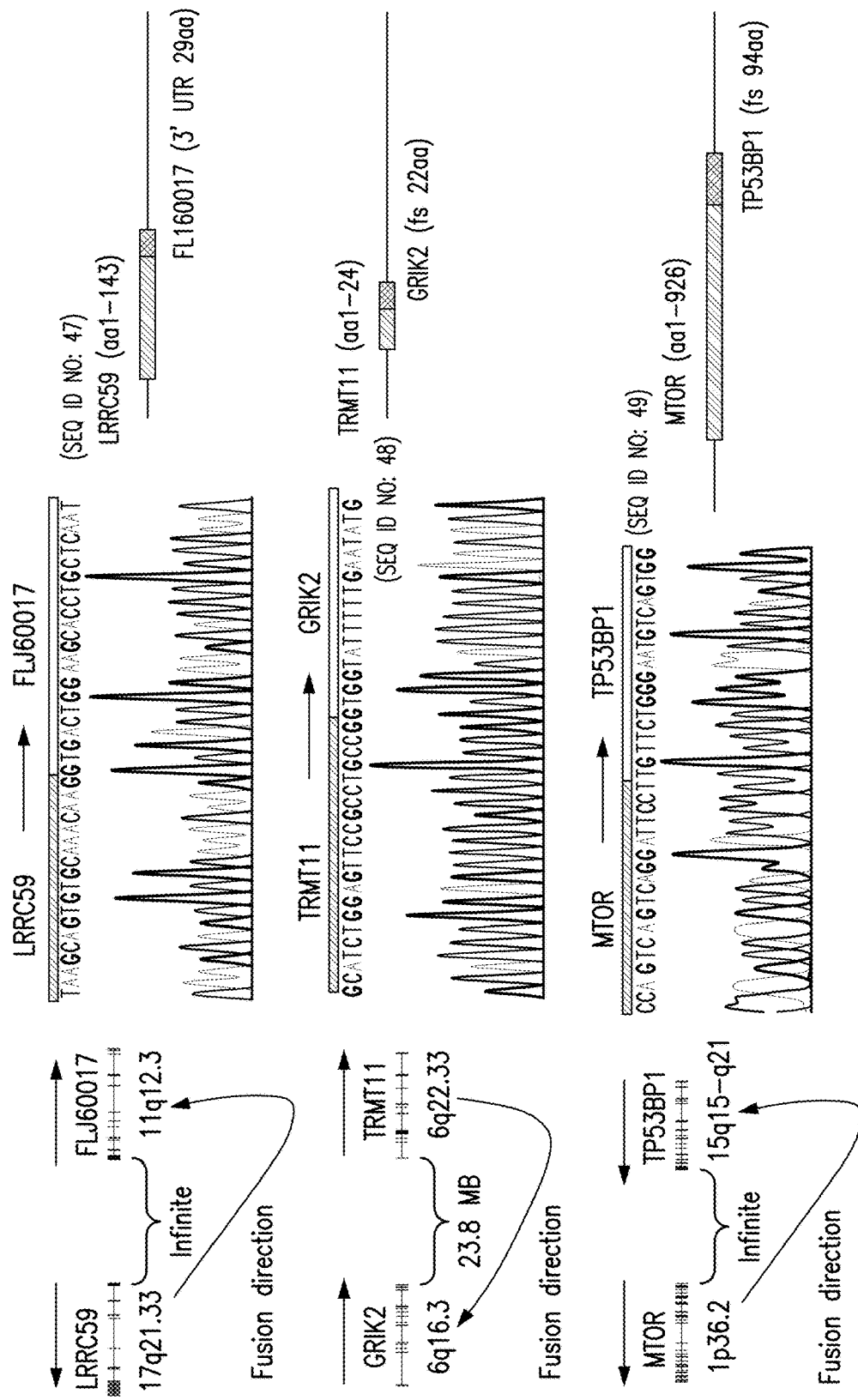
Figure 1:
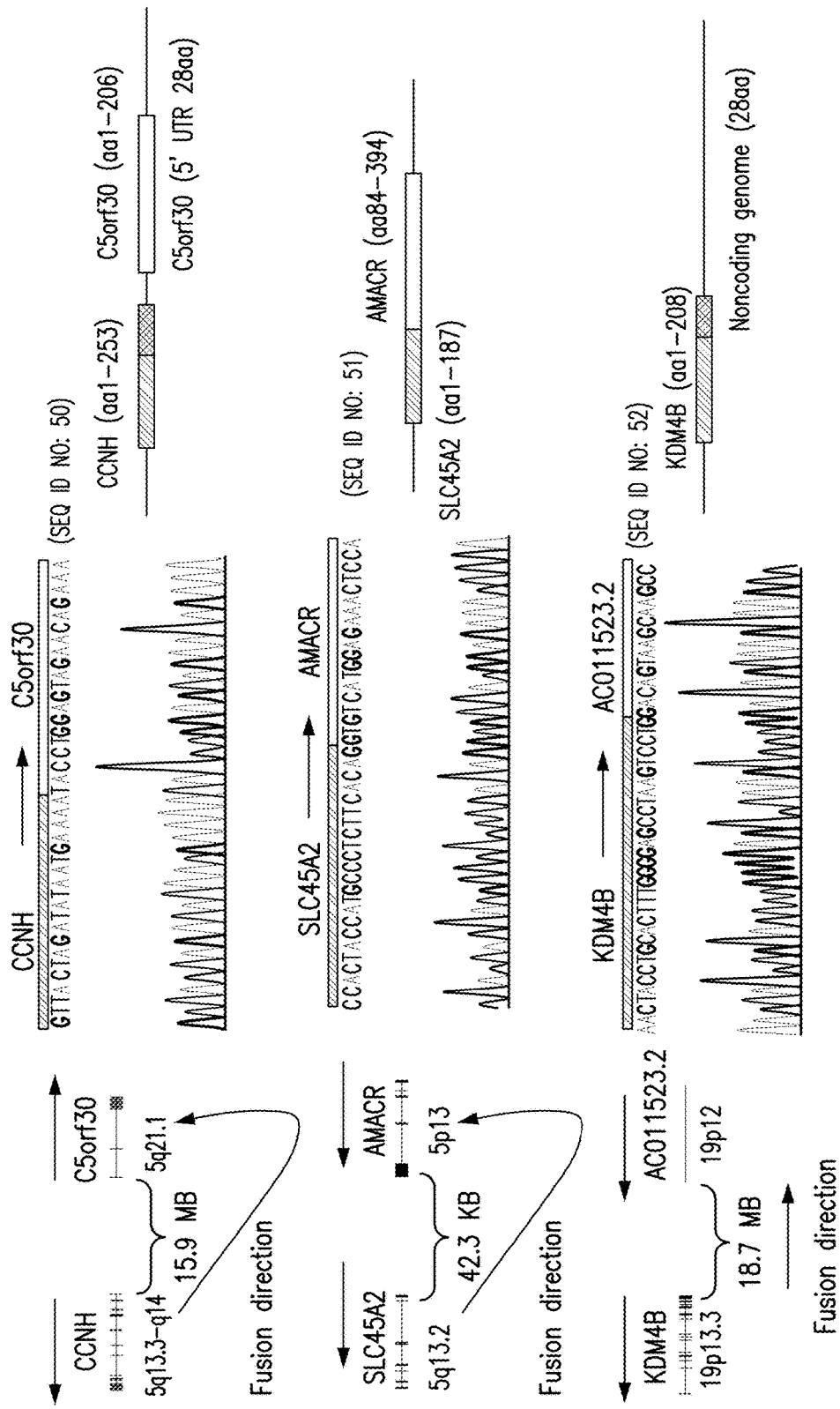

Specification includes a Sequence Listing.

(56) References Cited

OTHER PUBLICATIONS

U.S. Appl. No. 14/336,965, Nov. 2, 2016 Response to Non-Final Office Action.
U.S. Appl. No. 14/336,965, May 2, 2016 Non-Final Office Action.
U.S. Appl. No. 14/336,965, Feb. 3, 2016 Response to Restriction Requirement.
U.S. Appl. No. 14/336,965, Aug. 3, 2015 Restriction Requirement.
U.S. Appl. No. 15/199,056, Mar. 8, 2018 Notice of Allowance.
U.S. Appl. No. 15/199,056, Jan. 16, 2018 Issue Fee Payment.
U.S. Appl. No. 15/199,056, Oct. 16, 2017 Notice of Allowance.
U.S. Appl. No. 15/199,056, Aug. 25, 2017 Request for Continued Examination (RCE).
U.S. Appl. No. 15/199,056, Aug. 23, 2017 Notice of Allowance.
Agarwal et al., (2003) Zinc metalloproteinase, ZMPSTE24, is mutated in mandibuloacral dysplasia, Human Molecular Genetics 12(16):1995-2001 (2003).
Ahn al., "Fer Protein-Tyrosine Kinase Promotes Lung Adenocarcinoma Cell Invasion and Tumor Metastasis," Mol Cancer Res 11(8):952-963 (2013).
Anderson et al., "A simple method for the rapid generation of recombinant adenovirus vectors," Gene Therapy 7:1034-1038 (2000).
Antonarakis et al., "Changes in PSA Kinetics Predict Metastasis-Free Survival in Men with PSA-Recurrent Prostate Cancer Treated with Nonhormonal Agents: Combined Analysis of 4 Phase II Trials," Cancer 118:1533-1542 (2012).
Baca et al., "Punctuated Evolution of Prostate Cancer Genomes," Cell 153:666-677 (2013).
Bae, et al., "Low Frequency Mutation of the Ephrin Receptor A3 Gene in Hepatocellular Carcinoma", Neoplasma, 56(4):331-334 (2009).
Bar-Peled et al., "A Tumor Suppressor Complex with GAP Activity for the Rag GTPases That Signal Amino Acid Sufficiency to mTORC1," Science 340:1100-1106 (2013).
Berger et al., "The genomic complexity of primary human prostate cancer," Nature 4 70:214-220 (2011).
Bettendorf, et al., "Cytogenetic Changes and Loss of Heterozygosity in Atypical Adenomatous Hyperplasia, in Carcinoma of the Prostate and in Non-Neoplastic Prostate Tissue Using Comparative Genomic Hybridization and Multiplex-PCR", International Journal of Oncology, 26(1):267-274 (2005).
Blackford, et al., "Genetic Mutations Associated with Cigarette Smoking in Pancreatic Cancer", Cancer Research, 69(8):3681-3688 (2009).
Budd, et al., "Circulating Tumor Cells Versus Imaging-Predicting overall survival in Metastatic Breast Cancer", Clinical Cancer Research, 12(21):6403-6409 (2006).
Carver et al., "ETS rearrangements and prostate cancer initiation," Nature 457:E1; discussion E2-3 (2009).
Chen et al., "Targeting genomic rearrangements in tumor cells through Cas9-mediated insertion of a suicide gene," Nature Biotechnology, 35(6):543-550 (2017).
Chi et al., "ETV1 is a lineage survival factor that cooperates with KIT in gastrointestinal stromal tumours," Nature 467:849-853 (2010).
Clark et al., "ETS gene fusions in prostate cancer," Nat Rev Urol. 6:429-439 (2009).
Clifford, et al., "The EphA3 Receptor is Expressed in a Subset of Rhabdomyosarcoma Cell Lines and Suppresses Cell Adhesion and Migration", Journal of Cellular Biochemistry, 105:1250-1259 (2008).
Corban-Wilhelm et al., "Cytosine deaminase versus thymidine kinase: a comparison of the antitumor activity," Clinical and Experimental Medicine, 3(3):150-156 (2003).
Demichelis et al., "TMPRSS2:ERG gene fusion associated with lethal prostate cancer in a watchful waiting cohort," Oncogene 26:4596-4599 (2007).
Derwent Abstract Accession No. 2013-E07845 (accessed on Sep. 21, 2016).
Edgren et al., "Identification of fusion genes in breast cancer by paired-end RNA-sequencing," Genome Biol. 12:R6 (2011).

El Gammal et al., "Chromosome 8p Deletions and 8q Gains are Associated with Tumor Progression and Poor Prognosis in Prostate Cancer," Clin Cancer Res 16:56-64 (2010).
Enard et al., "Intra- and Interspecific Variation in Primate Gene Expression Patterns," Science 296:340-343 (2002).
Enninga et al., "Sec13 Shuttles between the Nucleus and the Cytoplasm and Stably Interacts with Nup96 at the Nuclear Pore Complex," Molecular and Cellular Biology 23(20):7271-7284 (2003).
Esvelt et al., "Concerning RNA-guided gene drives for the alteration of wild populations," eLife 3:e03401 (2014).
Fisher et al., "A Novel Cyclin Associates with M015/CDK7 to Form the CDK-Activating Kinase," Cell 78:713-724 (1994).
Fitzgerald et al., "Association of TMPRSS2-ERG gene fusion with clinical characteristics and outcomes: results from a population-based study of prostate cancer," BMC Cancer 8:230 (2008).
Freedland et al., "Death in Patients with Recurrent Prostate Cancer After Radical Prostatectomy: Prostate-Specific Antigen Doubling Time Subgroups and Their Associated Contributions to All-Cause Mortality," J Clin Oncol. 25(13):1765-1771 (2007).
Golub, et al., "Molecular Classification of Cancer: Class Discovery and Class Prediction by Gene Expression Monitoring", Science, 286:531-537 (1999).
Green, et al., "Integrative analysis Reveals Selective 9p24.1 Amplification, Increased PD-1 Ligand Expression, and Further Induction Via JAK2 in Nodular Sclerosing Hodgkin Lymphoma and Primary Mediastinal Large B-Cell Lymphoma", Blood, 116(17):3268-3277 (2010).
Guo et al., "FER tyrosine kinase (FER) overexpression mediates resistance to quinacrine through EGF-dependent activation of NF-γB," PNAS USA 108(19):7968-7973 (2011).
Ha et al., "Identification of gene fusion transcripts by transcriptome sequencing in BRCA1-mutated breast cancers and cell lines," BMC Medical Genomics 4:75 (2011).
Hakkarainen et al., "A conditionally replicative adenovirus that codes for a TKGFP fusion protein (Ad5Delta24TK-GFP) for evaluation of the potency of oncolytic virotherapy combined with molecular chemotherapy," International Journal of Molecular Medicine, 18(4):751-759 (2006).
Han et al., "Interaction of integrin-linked kinase (ILK) and MCM7 mediating integrin α7 induced cell growth suppression," Cancer Research 70(11):4375-4384 (2010).
Han et al., "Metallothionein 1 h tumour suppressor activity in prostate cancer is mediated by euchromatin methyltransferase 1," The Journal of Pathology 230(2):184-193 (2013).
Hanczar, et al., "Small-Sample Precision of ROC-Related Estimates", Bioinformatics, 26(6):822-830 (2010).
Hanks, et al., "Pretreatment Prostate-Specific Antigen Doubling times: Clinical Utility of this Predictor of Prostate Cancer Behavior", Int. J. Radiation Oncology Biol. Phys., 34(3):549-553 (1996).
Hao et al., "Isolation and Sequence Analysis of a Novel Human Tyrosine Kinase Gene," Mol Cell Biol. 9(4):1587-1593 (1989).
Heitzer et al., "Tumor-associated copy number changes in the circulation of patients with prostate cancer identified through whole-genome sequencing," Genome Medicine 5:30 (2013).
Hieronymus et al., "Copy number alteration burden predicts prostate cancer relapse," PNAS 111(30):11139-11144 (2014).
International Search Report and Written Opinion dated Apr. 1, 2015 in International Application No. PCT/US2014/072268.
International Search Report dated Oct. 17, 2016 in International Application No. PCT/US2016/046051.
International Search Report dated Oct. 7, 2015 in International Application No. PCT/US2015/041029.
Isaacs, "Molecular Markers for Prostate Cancer Metastasis", American Journal of Pathology, 150(5):1511-1521 (1997).
Ivanova et al., "FER kinase promotes breast cancer metastasis by regulating α6- and β1-integrin-dependent cell adhesion and anoikis resistance," Oncogene 32:5582-5592 (2013).
Jane-Valbuena et al., "An Oncogenic Role for ETV1 in Melanoma," Cancer Research 70(5):2075-2084 (2010).
Jemal et al., "Global Cancer Statistics," CA Cancer J Clin. 61(2):69-90 (2011).
Jemal, et al., "Global Cancer Statistic", CA Cancer J. Clin., 59:225-249 (2009).

(56) References Cited

OTHER PUBLICATIONS

Jemal, et al., "Global Cancer Statistic", CA Cancer J. Clin., 60:277-300 (2010).
Jeon et al., "A variant Ewing's sarcoma translocation (7;22) fuses the EWS gene to the ETS gene ETV1," Oncogene 10:1229-1234 (1995).
Jinek et al., "A Programmable Dual-RNA-Guided DNA Endonuclease in Adaptive Bacterial Immunity," Science 337:816-821 (2012).
Jing et al., "Expression of Myopodin Induces Suppression of Tumor Growth and Metastasis," The American Journal of Pathology 164(5):1799-1806 (2004).
Jung et al., "Discovery of ALK-PTPN3 Gene Fusion from Human Non-Small Cell Lung Carcinoma Cell Line Using Next Generation RNA Sequencing," Genes, Chromosomes & Cancer 51:590-597 (2012).
Kawakami et al., "FER overexpression is associated with poor postoperative prognosis and cancer-cell survival in non-small cell lung cancer," Int J Clin Exp Pathol 6(4):598-612 (2013).
Kim, et al., "Integrative analysis of Genomic Aberrations Associated with Prostate Cancer Progression", Cancer Research, 67(17):8229-8239 (2007).
Koutras, et al., "The Upgrade Role of HER3 and HER4 Receptors in Breast cancer", Critical Reviews in Oncology/Hematology, 74:73-78 (2010).
Krastev et al., "A systematic RNAi synthetic interaction screen reveals a link between p53 and snoRNP assembly," Nature Cell Biology 13(7):809-818 (2011).
Kraus, et al., "High-Resolution genomic Profiling of Occult Micrometastatic Tumor Cells", Genes, Chromosomes & cancer, 36:159-166 (2003).
Krolewski et al., "Identification and chromosomal mapping of new human tyrosine kinase genes," Oncogene 5:277-282 (1990).
Kwok et al., "FES Kinase Promotes Mast Cell Recruitment to Mammary Tumors via the Stem Cell Factor/KIT Receptor Signaling Axis," Mol. Cancer Res 10(7):881-891 (2012).
LaGrange et al., "Renal Cell Carcinoma Associated with TFE3 Gene Fusion in an Elderly Woman," Urology 70:590.e11-590.e12 (2007).
Lee, et al., "Somatic Mutation in Epidermal Growth Factor Receptor Signaling Pathway Genes in Non-Small Cell Lung Cancers", Journal of Thoracic Oncology, 5(11):1734-1740 (2010).
Li et al., "Fast and accurate long-read alignment with Burrows-Wheeler transform," Bioinformatics 26(5):589-595 (2010).
Li et al., "Identification of tyrosine-phosphorylated proteins associated with metastasis and functional analysis of FER in human hepatocellular carcinoma cells," BMC Cancer 9:366 (2009).
Liu et al., "Comprehensive Assessment of DNA Copy Number Alterations in Human Prostate Cancers Using Affymetrix 100K SNP Mapping Array," Genes, Chromosomes & Cancer 45:1018-1032 (2006).
Liu, et al., "Copy Number Analysis Indicates Monoclonal Origin of Lethal Metastatic Prostate Cancer", Nature Medicine, 15(5):559-565.
Loimas et al., "Human prostate carcinoma cells as targets for herpes simplex virus thymidine kinase-mediated suicide gene therapy," Cancer Gene Therapy, 8(2):137-144 (2001).
Luo et al., "(−)-Epigallocatechin-3-gallate induces Du145 prostate cancer cell death via downregulation of inhibitor of DNA binding 2, a dominant negative helix-loop-helix protein," Cancer Science 101(3):707-712 (2010).
Luo et al., "Discovery and Classification of Fusion Transcripts in Prostate Cancer and Normal Prostate Tissue," Am J Pathol 185:1834-1845 (2015).
Luo et al., "Gene Expression Analysis of Prostate Cancers," Molecular Carcinog. 33:25-35 (2002).
Macoska, et al., "Evolution of 8p Loss in Transformed Human Prostate Epithelial cells", Cancer Genetics and Cytogenetics, 154:36-43 (2004).
Matsui, et al., "Molecular Characterization of a Consistent 4.5-Megabase Deletion at 4q28 in Prostate Cancer Cells", Cancer Genetics and Cytogenetics, 159:18-26 (2005).
McGarty, "CRISPRs and Cancer," White Paper No. 111, pp. 1-21 (Apr. 2014).
Misago et al., "Molecular cloning and expression of cDNAs encoding human α-mannosidase II and a previously unrecognized α-mannosidase IIx isozyme," Proc Natl Acad Sci USA 92:11766-11770 (1995).
Miyata et al., "Feline sarcoma-related protein expression correlates with malignant aggressiveness and poor prognosis in renal cell carcinoma," Cancer Sci 104(6):681-686 (2013).
Mojica et al., "Intervening Sequences of Regularly Spaced Prokaryotic Repeats Derive from Foreign Genetic Elements," J Mol Evol 60:174-182 (2005).
Monaco, "Fatty Acid Metabolism in Breast Cancer Subtypes," Oncotarget 8(17):29487-29500 (2017).
Moremen et al., "Isolation, Characterization, and Expression of cDNAs Encoding Murine α-Mannosidase II, a Golgi Enzyme That Controls Conversion of High Mannose to Complex N-Glycans," J Cell Biol 115(6):1521-1534 (1991).
Moreno, et al., "Detection of Hematogenous Micrometastasis in Patients with Prostate Cancer", Cancer Research, 52:6110-6112 (1992).
Nam et al., "Expression of TMPRSS2 ERG Gene Fusion in Prostate Cancer Cells is an Important Prognostic Factor for Cancer Progression," Cancer Biology & Therapy 6(1):40-45 (2007).
Nellist et al., "Phosphorylation and binding partner analysis of the TSC1-TSC2 complex," Biochemical and Biophysical Research Communications 333:818-826 (2005).
Nunez, et al., "WWOX Protein Expression Varies Among Ovarian Carcinoma Histotypes and Correlates with Less Favorable Outcome", BMC Cancer, 5:64 (2005).
Pang, et al., "Cytogenetic and Expression Profiles Associated with Transformation to Androgen-Resistant Prostate Cancer", The Prostate, 66:157-172 (2006).
Parkin, et al., "Acquired Genomic Copy Number Aberrations and Survival in Adult Acute Myelogenous Leukemia", Blood, 116(23):4958-4967 (2010).
Parr-Sturgess et al., "Copper Modulates Zinc Metalloproteinase-Dependent Ectodomain Shedding of Key Signaling and Adhesion Proteins and Promotes the Invasion of Prostate Cancer Epithelial Cells," Mol Cancer Res 10(10):1282-1293 (2012).
Partial Supplemental European Search Report dated Jul. 12, 2017 in EP Application No. 14875963.2.
Perner et al., "784-TMPRSS2-ERG Gene Fusion Defines a Metastatic Phenotype of Prostate Cancer," Eur Urol Suppl 8(4):316 (2009).
Prakash et al., "Expression of Conjoined Genes: Another Mechanism for Gene Regulation in Eukaryotes," PLoS One 5(10):e13284 (2010).
Ran et al., "Double Nicking by RNA-Guided CRISPR Cas9 for Enhanced Genome Editing Specificity," Cell, 154:1380-1389 (2013).
Ren et al., "Analysis of Integrin α7 Mutations in Prostate Cancer, Liver Cancer, Glioblastoma Multiforme, and Leiomyosarcoma," J Natl Cancer Inst 99:868-880 (2007).
Ren et al., "MCM7 amplification and overexpression are associated with prostate cancer progression," Oncogene 25:1090-1098 (2006).
Rickman et al., "SLC45A3-ELK4 is a Novel and Frequent Erythroblast Transformation-Specific Fusion Transcript in Prostate Cancer," Cancer Research 69(7):2734-2738 (2009).
Robin et al., "pROC: an open-source package for R and S+ to analyze and compare ROC curves," BMC Bioinformatics 12:77 (2011).
Rocha et al., "The Fer tyrosine kinase acts as a downstream interleukin-6 effector of androgen receptor activation in prostate cancer," Mol Cell Endocrinol 381:140-149 (2013).
Sander et al., "CRIRISPR-Cas systems for editing, regulating and targeting genomes," Nature Biotechnology, 32(4):347-355 (2014).
Savolainen et al., "A mouse model for α-methylacyl-CoA racemase deficiency: adjustment of bile acid synthesis and intolerance to dietary methyl-branched lipids," Hum Mol Genet 13(9):955-965 (2004).

(56) References Cited

OTHER PUBLICATIONS

Shchors et al., "Cell Death Inhibiting RNA (CDIR) Derived from a 3'-Untranslated Region Binds AUF1 and Heat Shock Protein 27*," The Journal of Biological Chemistry 277(49):47061-47072 (2002).
Shi et al., "Inhibition of prostate cancer growth and metastasis using small interference RNA specific for minichromosome complex maintenance component 7," Cancer Gene Therapy 17(10):694-699 (2010).
Siegel et al., "Cancer Statistics, 2012," CA Cancer J Clin. 62:10-29 (2012).
Siegel et al., "Cancer Statistics, 2015," CA Cancer J Clin 65:5-29 (2015).
Sinclair et al., "A Fluorescence in situ Hybridization Map of 6q Deletions in Acute Lymphocytic Leukemia: Identification and Analysis of a Candidate Tumor Suppressor Gene," Cancer Res. 64:4089-4098 (2004).
Smith et al., "A New Nucleoside Analog, 9-[[2-Hydroxy-1-(Hydroxymethyl)Ethoxy]Methyl] Guanine, Highly Active In Vitro Against Herpes Simplex Virus Types 1 and 2," Antimicrobial Agents and Chemotherapy 22:55-61 (1982).
Stephenson, et al., "Salvage Radiotherapy for Recurrent Prostate Cancer After Radical Prostatectomy", JAMA, 291(11):1325-1332 (2004).
Strassburger, et al., "Compatible Simultaneous Lower Confidence Bounds for the Holm Procedure and other Bonferroni-Based Closed Tests", Statistics in Medicine, 27:4914-4927 (2008).
Strausberg, et al., "Generation and Initial Analysis of More Than 15,000 Full-Length Human and Mouse cDNA Sequences", PNAS, 99(26):16899-16903 (2002).
Supplementary Partial European Search Report dated Apr. 10, 2018 in Application No. EP 15821594.
Swanson et al., "TMPRSS2/ERG Fusion Gene Expression Alters Chemo- and Radio-Responsiveness in Cell Culture Models of Androgen Independent Prostate Cancer," The Prostate 71:1548-1558 (2011).
Taylor et al., "Integrative Genomic Profiling of Human Prostate Cancer", Cancer Cell, 18:11-22, including supplementary material (2010).
Teixeira, et al., "Genomic analysis of Prostate Carcinoma Specimens Obtained via Ultrasound-guided Needle Biopsy May Be of Use in Preoperative Decision-Making", American Cancer Society, 101:1786-1793 (2004).
Tomlins et al., "Recurrent Fusion of TMPRSS2 and ETS Transcription Factor Genes in Prostate Cancer," Science 310:644-648 (2005).
Towns et al., "Transfer RNA Methytransferases and their Corresponding Modifications in Budding Yeast and Humans: Activities, Predications, and Potential Roles in Human Health," DNA and Cell Biology 31(4):434-454 (2012).
Trapnell et al., "Differential gene and transcript expression analysis of RNA-seq experiments with TopHat and Cufflinks," Nat Protoc. 7(3):562-578 (2012).
Trapnell et al., "TopHat: discovering splice junctions with RNA-Seq.," Bioinformatics 25(9):1105-1111 (2009).
Trapnell et al., "Transcript assembly and quantification by RNA-Seq reveals unannotated transcripts and isoform switching during cell differentiation," Nat. Biotechnol. 28(5):511-515 (2010).
Tsang, et al., "SCAPER, a Novel Cyclin A-Interacting Protein that Regulates Cell Cycle Progression", Journal of Cell Biology, 178(4):621-633 (2007).
Vitari et al., "COP1 is a tumour suppressor that causes degradation of ETS transcription factors," Nature 474:402-408 (2011).
Voisset et al., "The tyrosine kinase FES is an essential effector of KITD816V proliferation signal," Blood 110(7):2593-2599 (2007).

Wang et al., "Expression of Variant TMPRSS2/ERG Fusion Messenger RNAs is Associated with Aggressive Prostate Cancer," Cancer Research 66(17):8347-8351 (2006).
Wang et al., "p53-induced Gene 3 Mediates Cell Death Induced by Glutathione Peroxidase 3," J Biol Chem 287(20):16890-16902 (2012).
Watabe-Uchida et al., "The Rac Activator DOCK7 Regulates Neuronal Polarity through Local Phosphorylation of Stathmin/Op18," Neuron 51:727-739 (2006).
Wei et al., "High expression of FER tyrosine kinase predicts poor prognosis in clear cell renal cell carcinoma," Oncol Lett 5:473-478 (2013).
Weinberg et al., "A New World Order: Tailored Gene Targeting and Regulation Using CRISPR," Molecular Therapy 22(5):893 (2014).
Willardsen et al., "The ETS transcription factor Etv1 mediates FGF signaling to initiate proneural gene expression during Xenopus laevis retinal development," Mechanisms of Development 131:57-67 (2014).
Yakicier, et al., "Identification of Homozygous Deletions at Chromosome 16q23 in Aflatoxin B1 Exposed Hepatocellular Carcinoma", Oncogene, 20:5232-5238 (2001).
Yang et al., "mTOR kinase structure, mechanism and regulation," Nature 497:217-223 (2013).
Yang et al., "The Histone Demethylase JMJD2B is Regulated by Estrogen Receptor α and Hypoxia, and Is a Key Mediator of Estrogen Induced Growth," Cancer Res 70(16):6456-6466 (2010).
Yang, et al., "Deletion of the WWOX gene and Frequent Loss of its Protein Expression in Human Osteosarcoma", Cancer Letter, 291:31-38 (2010).
Youden, "Index for Rating Diagnostic Tests," Cancer 3:32-35 (1950).
Yu et al., "CSR1 Suppresses Tumor Growth and Metastasis of Prostate Cancer," American Journal of Pathology 168(2):597-607 (2006).
Yu et al., "Gene Expression Alterations in Prostate Cancer Predicting Tumor Aggression and Preceding Development of Malignancy," J Clin Oncol. 22(14):2790-2799 (2004).
Yu et al., "Genomic Copy Number Variations in the Genomes of Leukocytes Predict Prostate Cancer Clinical Outcomes," PloS ONE 10(8):E0135982 (2015).
Yu et al., "Glutathione Peroxidase 3, Deleted or Methylated in Prostate Cancer, Suppresses Prostate Cancer Growth and Metastasis," Cancer Res. 67(17):8043-8050 (2007).
Yu et al., "Novel Fusion Transcripts Associate with Progressive Prostate Cancer," The American Journal of Pathology 184(10):2840-2849 (2014).
Yu, et al., "Genome Abnormalities Precede Prostate Cancer and Predict Clinical Relapse", The American Journal of Pathology, 180(6):2240-2248 (2012).
Zeng et al., "Visualizing Interchange Patterns in Massive Movement Data," Computer Graphics Forum 32(3):271-280 (2013).
Zha et al., "α-Methylacyl-CoA Racemase as an Androgen-Independent Growth Modifier in Prostate Cancer," Cancer research 63:7365-7376 (2003).
Zhao, et al., "Genome-Wide Characterization of Gene Expression Variations and DNA Copy Number Changes on Prostate Cancer Cell Lines", The Prostate, 63:187-197 (2005).
Zhen et al., "Nuclear Import of Exogenous FGF1 Requires the ER-Protein LRRC59 and the Importins Kpnα1 and Kpnβ1," Traffic 13:650-664 (2012).
Zhu et al., "CSR1 induces cell death through inactivation of CPSF3," Oncogene 28:41-51 (2009).
Zhu et al., "Integrin Alpha 7 Interacts with High Temperature Requirement A2 (HtrA2) to Induce Prostate Cancer Cell Death," The American Journal of Pathology 177(3):1176-1186 (2010).

Figure 25E:
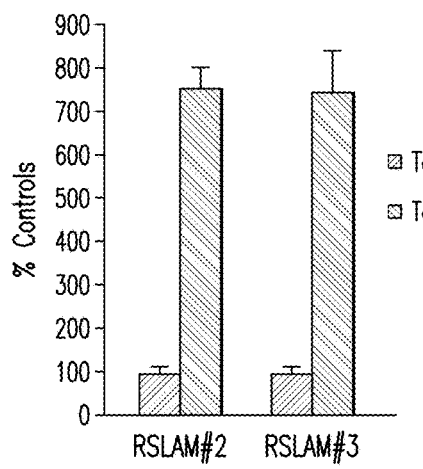
Figure 25F:
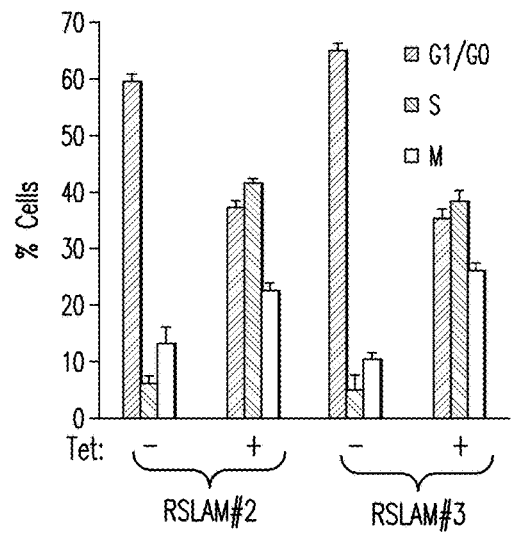

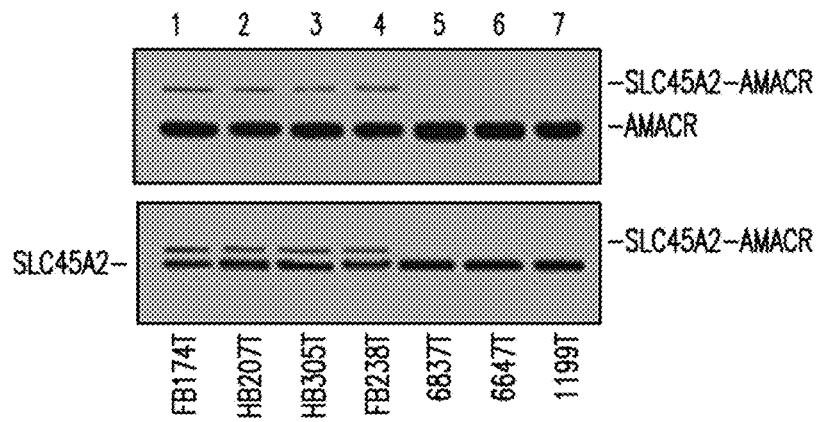
FIG. 25A
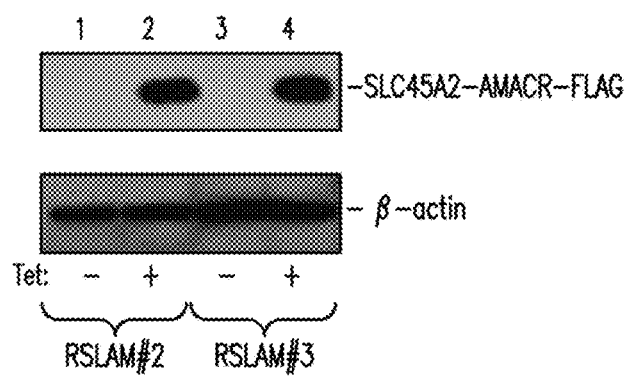
FIG. 25B
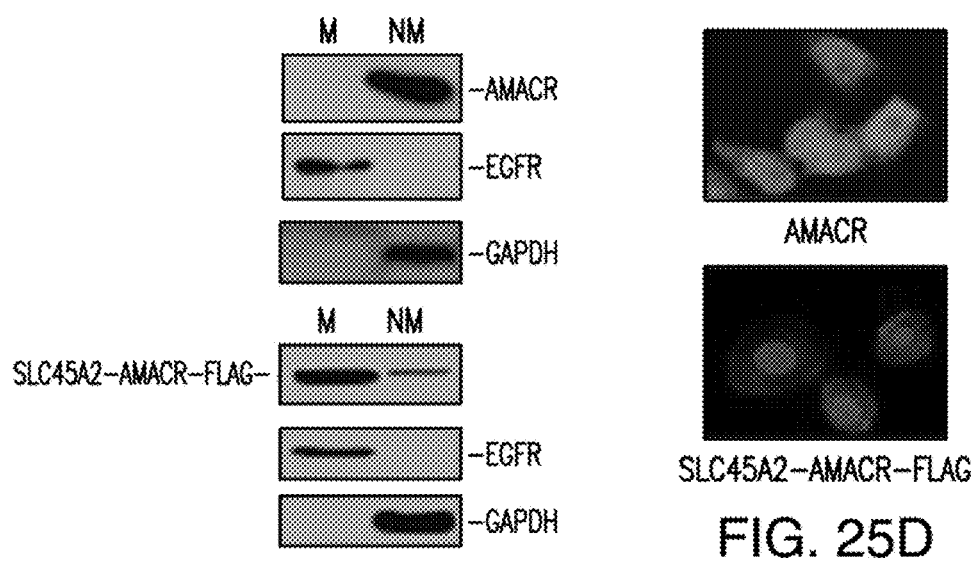
FIG. 25C
FIG. 25D

FUSION GENES ASSOCIATED WITH PROGRESSIVE PROSTATE CANCER

PRIORITY CLAIM

This application is a continuation of U.S. patent application Ser. No. 15/199,056, filed Jun. 30, 2016, which is a continuation of International Patent Application No. PCT/US2014/072268, filed Dec. 23, 2014, which claims priority to U.S. Provisional Patent Application Ser. No. 61/921,836, filed Dec. 30, 2013, U.S. Provisional Patent Application Ser. No. 62/014,487, filed Jun. 19, 2014, and U.S. Provisional Patent Application Ser. No. 62/025,923, filed Jul. 17, 2014, which are incorporated by reference herein in their entireties.

GRANT INFORMATION

This invention was made with government support under Grant Nos. RO1 CA098249 and awarded by the National Cancer Institute of the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 13, 2018, is named 072396_0705_SL.txt and is 19,395 bytes in size.

1. INTRODUCTION

The present invention relates to methods of determining which prostate cancer patients are more likely to develop progressive disease based on the presence of specific fusion genes, and methods of treating such patients.

2. BACKGROUND OF THE INVENTION

Despite a high incidence, only a fraction of men diagnosed with prostate cancer develop metastases and even fewer die from the disease. The majority of prostate cancers remain asymptomatic and clinically indolent. The precise mechanisms for the development of progressive, clinically concerning prostate cancer remain elusive. Furthermore, the inability to predict prostate cancer's potential aggressiveness has resulted in significant overtreatment of the disease. The dichotomous nature of prostate cancer—a subset of life-threatening malignancies in the larger background of histological alterations lacking the clinical features implicit with that label—is a fundamental challenge in disease management. Therefore, there is a need in the art for methods of determining whether a subject is at an increased risk of developing progressive prostate cancer.

3. SUMMARY OF THE INVENTION

The present invention relates to methods and compositions for determining whether a subject having prostate cancer is at increased risk of developing progressive disease, and methods of treating such subjects. It is based, at least in part, on the discovery that approximately 90% of men carrying at least one of the following fusion genes: TRMT11-GRIK2, SLC45A2-AMACR, MTOR-TP53BP1, LRRC59-FLJ60017, TMEM135-CCDC67 and CCNH-C5orf30 experienced prostate cancer recurrence, metastases and/or prostate cancer-specific death after radical prostatectomy (each example of "progressive prostate cancer"), while these outcomes occurred in only 36% of men not carrying any of these fusion genes. It is also based, at least in part, on the discovery that no patient studied survived five years without recurrence if their primary prostate cancer contained a TRMT11-GRIK2 or MTOR-TP53BP1 fusion gene. It is also based, at least in part, on the discovery that the protein encoded by the MAN2A1-FER fusion gene exhibits kinase activity.

In various non-limiting embodiments, the present invention provides for methods and compositions for identifying fusion genes in a subject, which are indicative that a subject is at increased or even high risk of manifesting progressive prostate cancer. Such fusion genes include TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. Further, based on the presence of specific fusion genes, the present invention provides a means for identifying subjects at increased risk for relapse and/or rapid relapse. In certain non-limiting embodiments, the present invention further provides for methods of treating a subject at increased risk of manifesting progressive prostate cancer, relapse and/or rapid relapse.

4. BRIEF DESCRIPTION OF THE FIGURES

FIG. 1. Unique fusion gene events. Left panel: Miniature diagrams of genome of the fusion genes, the transcription directions, the distances between the joining genes and directions of the fusions. Middle panel: Representative sequencing chromograms of fusion genes. The joining gene sequences were indicated (SEQ ID NOs: 45-52). Right panel: Diagrams of translation products of fusion genes. Blue-driver gene translation product; Red-passenger gene translation product; Orange-novel translation products due to frameshift or translation products from a non-gene region.

FIG. 2A-H. Fluorescence in situ hybridization suggests genome recombination in prostate cancer cells. (A) Schematic diagram of MAN2A1 and FER genome recombination and FISH probe positions. Representative FISH images were shown for normal prostate epithelial cells and cancer cells positive for MAN2A1-FER fusion. Orange denotes probe 1; Green denotes probe 2. (B) Schematic diagram of SLC45A2 and AMACR genome recombination and FISH probe positions. Representative FISH images were shown for normal prostate epithelial cells and cancer cells positive for SLC45A2-AMACR fusion. Orange denotes probe 1; Green denotes probe 2. (C) Schematic diagram of MTOR and TP53BP1 genome recombination and FISH probe positions. Representative FISH images were shown for normal prostate epithelial cells and cancer cells positive for MTOR-TP53BP1 fusion. Orange denotes probe 1; Green denotes probe 2. (D) Schematic diagram of TRMT11 and GRIK2 genome recombination and FISH probe positions. Representative FISH images were shown for normal prostate epithelial cells and cancer cells positive for TRMT11-GRIK2 fusion. Orange denotes probe 1; Green denotes probe 2. (E) Schematic diagram of LRRC59 and FLJ60017 genome recombination and FISH probe positions. Representative FISH images were shown for normal prostate epithelial cells and cancer cells positive for LRRC59-FLJ60017 fusion. Orange denotes probe 1; Green denotes probe 2. (F) Schematic diagram of TMEM135 and CCDC67 genome recombination and FISH probe positions. Representative FISH images were shown for normal prostate epithelial cells and cancer cells positive for TMEM135-CCDC67 fusion. Orange denotes probe 1; Green denotes probe 2. (G) Schematic diagram of CCNH and C5orf30 genome recombination and FISH probe positions. Representative FISH images were shown for normal prostate epithelial cells and cancer cells positive for CCNH-C5orf30 fusion. Orange denotes probe 1; Green denotes probe 2. (H) Schematic diagram of KDM4B and AC011523.2 genome recombination and FISH probe positions. Representative FISH images were shown for normal prostate epithelial cells and cancer cells positive for KDM4B-AC011523.2 fusion. Orange denotes probe 1; Green denotes probe 2.

FIG. 3A-D. Fusion genes in prostate cancer are associated with aggressive prostate cancers. (A) Distribution of 8 prostate cancer samples positive for fusion genes. Samples from patients who experienced recurrence were indicated with grey (PSADT≥15 months) or dark grey (PSADT<4 months), samples from patients who have no recurrence at least 5 years with green, and samples from patients whose clinical follow-up is ongoing but less than 5 years with white (undetermined). (B) Correlation of fusion gene events with prostate cancer recurrence. Percentage of prostate cancer relapse when fusion gene was positive in the prostate cancer samples was plotted for each fusion gene. Percentage of prostate cancer experiencing recurrence from samples positive for fusion transcripts was plotted for each fusion transcript. Left, University of Pittsburgh Medical Center cohort; Middle, Stanford University Medical Center cohort; Right, University of Wisconsin Madison Medical Center cohort. (C) ROC analyses of a panel of 8 fusion genes predicting prostate cancer recurrence (top) and short PSADT (bottom). (D) Kaplan-Meier analysis of patients who are positive for any of TRMT11-GRIK2, SLC45A2-AMACR, MTOR-TP53BP1, LRRC59-FLJ60017, TMEM135-CCDC67 and CCNH-C5orf30 versus those who are negative for these fusion events.

Figures 4A, 4B, 4C:
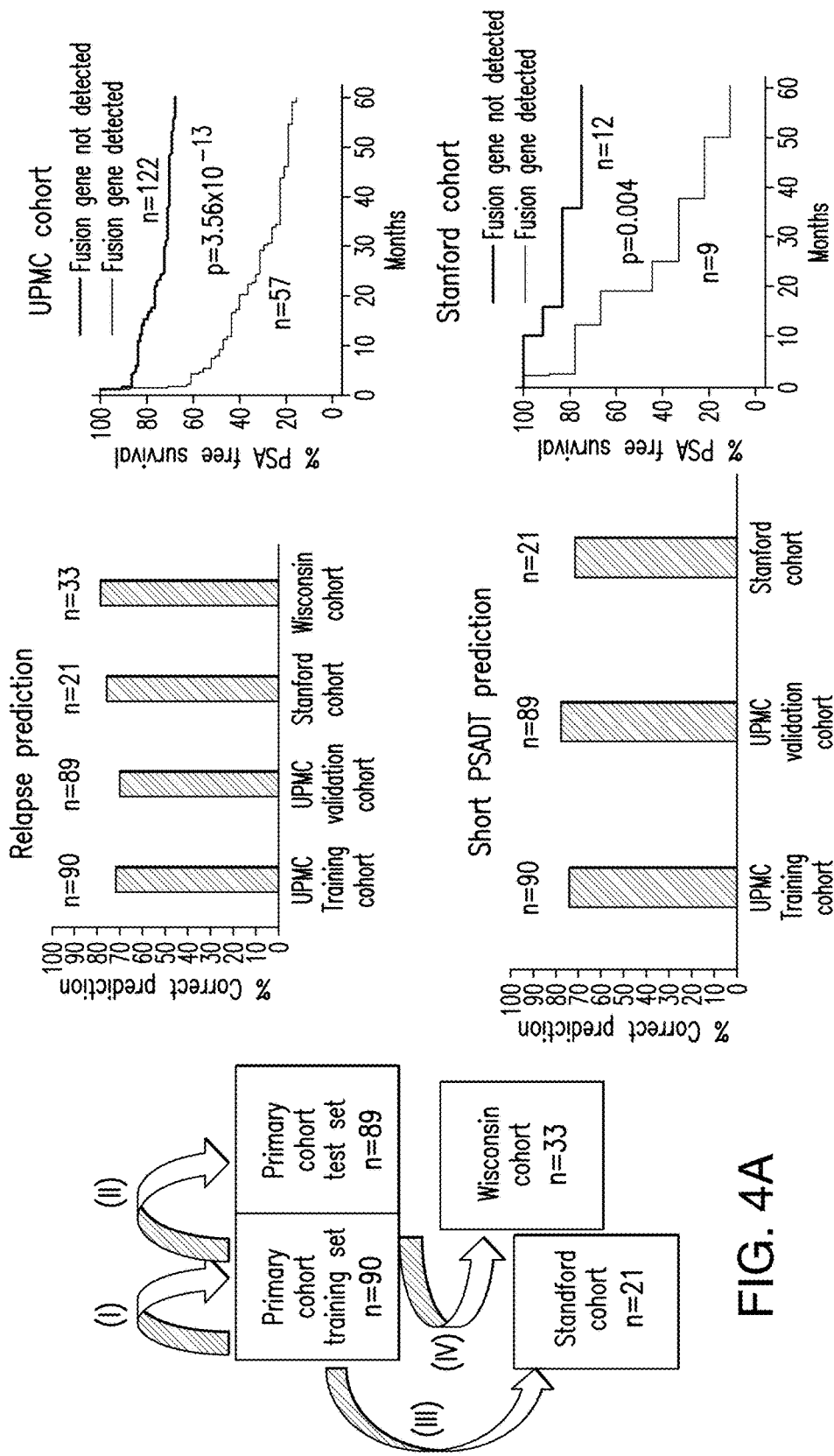

FIG. 4A-C. Fusion genes predict recurrence of prostate cancer. (A) Schema of training and validation steps in building fusion gene prediction models for prostate cancer recurrence and short PSADT. The algorithm of fusion gene prediction of prostate cancer recurrence and PSADT<4 months was obtained from 90 random-assigned prostate cancer samples from University of Pittsburgh Medical Center (I). The algorithm was then applied to 89 samples from University of Pittsburgh Medical Center (II), 21 samples from Stanford University Medical center (III) and 33 samples from University of Wisconsin Madison Medical Center (IV). (B) Prediction rate of prostate cancer recurrence (top) and PSADT<4 months using prostate cancer samples cohorts from University of Pittsburgh Medical Center, Stanford Medical Center, and University of Wisconsin Madison Medical Center, based on algorithm obtained from the 90-training sample cohort. (C) Kaplan-Meier analysis of patients who were positive for any of TRMT11-GRIK2, SLC45A2-AMACR, MTOR-TP53BP1, LRRC59-FLJ60017, TMEM135-CCDC67 and CCNH-C5orf30 versus those who were negative for these fusion events. Top, Kaplan-Meier analysis of prostate cancer sample cohort from University of Pittsburgh; P-value is indicated for the significant difference in survival between the group that is positive for at least one fusion transcript and the group that is negative. Bottom, Kaplan-Meier analysis of prostate cancer sample cohort from Stanford University Medical Center; P-value is indicated for the significant difference in survival between the group that is positive for at least one fusion transcript and the group that is negative.

Figure 5A:
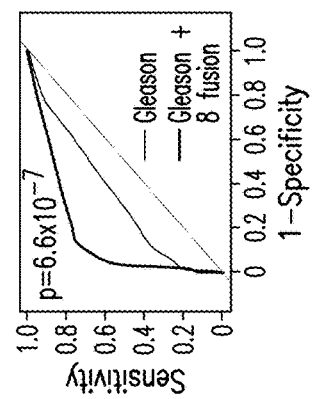
Figure 5A:
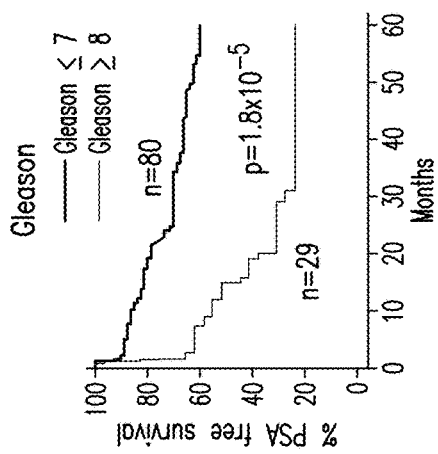
Figure 5A:
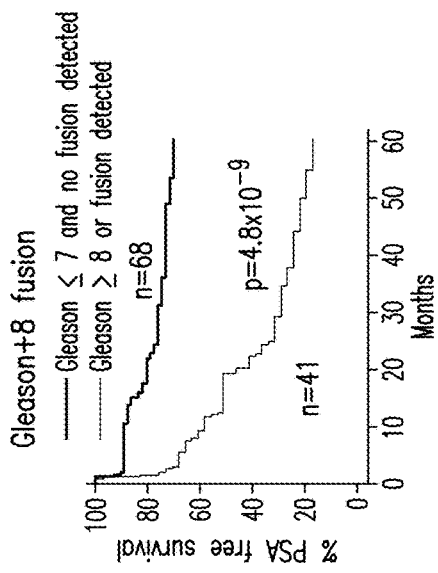
Figure 5B:
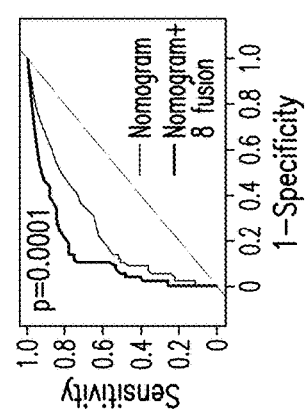
Figure 5B:
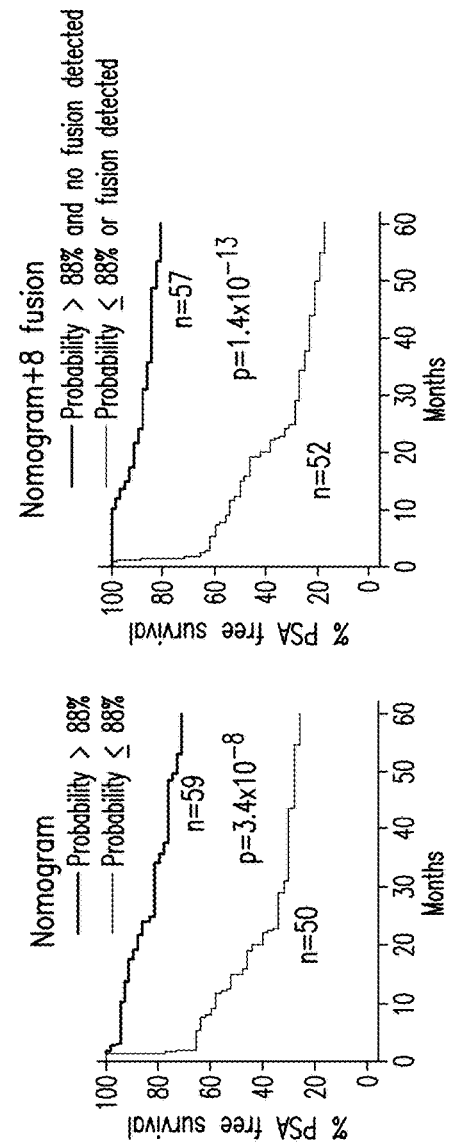

FIG. 5A-B. Combining status of fusion transcript and clinical/pathological parameter to improve prediction of prostate cancer recurrence. (A) Combining Gleason's grading and the status of 8 fusion transcripts in prostate cancer samples using LDA technique to predict the recurrence of prostate cancer. Left, ROC analysis of Gleason alone or Gleason plus the presence of fusion transcripts using LDA technique in the prediction of prostate cancer recurrence; P value (permutation test) is indicated for the significant difference between the ROC curve generated by Gleason alone and curve generated by Gleason plus the presence of fusion transcripts using LDA technique. Middle, Kaplan-Meier analysis of PSA free survival of prostate cancer patients with Gleason ≥8 versus <8 from combined UPMC testing, Wisconsin and Stanford data sets; P-value (Log-rank test) is indicated for the significant difference in survival between the group that has Gleason score at least 8 and the group that has score 7 or less. Right, Kaplan-Meier analysis of PSA free survival of prostate cancer patients with Gleason ≥8 or positive for any of the 8 fusion transcripts in the prostate cancer samples versus those <8 and negative for fusion transcripts using LDA from combined UPMC testing, Wisconsin and Stanford data sets. P-value (Log-rank test) is indicated for the significant difference in survival between the group that is positive for at least one fusion transcript or has Gleason ≥8 and the group that is negative for fusion transcript and has Gleason <8. (B) Combining nomogram and the status of 8 fusion transcripts in prostate cancer samples using LDA technique to predict the recurrence of prostate cancer. Left, ROC analysis of nomogram alone or nomogram plus the presence of fusion transcripts using LDA technique in the prediction of prostate cancer recurrence. P-value (permutation test) is indicated for the significant difference between the ROC curve generated by Nomogram alone and curve generated by Nomogram plus the presence of fusion transcripts using LDA technique. Middle, Kaplan-Meier analysis of PSA free survival of prostate cancer patients with probability >88 versus ≤88 from combined UPMC testing, Wisconsin and Stanford data sets; P-value (Log-rank test) is indicated for the significant difference in survival between the group that has probability >88 PSA free survival and the group that has ≤88 probability. Right, Kaplan-Meier analysis of PSA free survival of prostate cancer patients with Nomogram ≤88 or positive for any of the 8 fusion transcripts in the prostate cancer samples versus those >88 and negative for fusion transcripts using LDA from combined UPMC testing, Wisconsin and Stanford data sets. P-value (Log-rank test) is indicated for the significant difference in survival between the group that is negative for fusion transcript and has probability >88 PSA free survival and the group that is positive for fusion transcript or has ≤88 probability.

Figure 6:
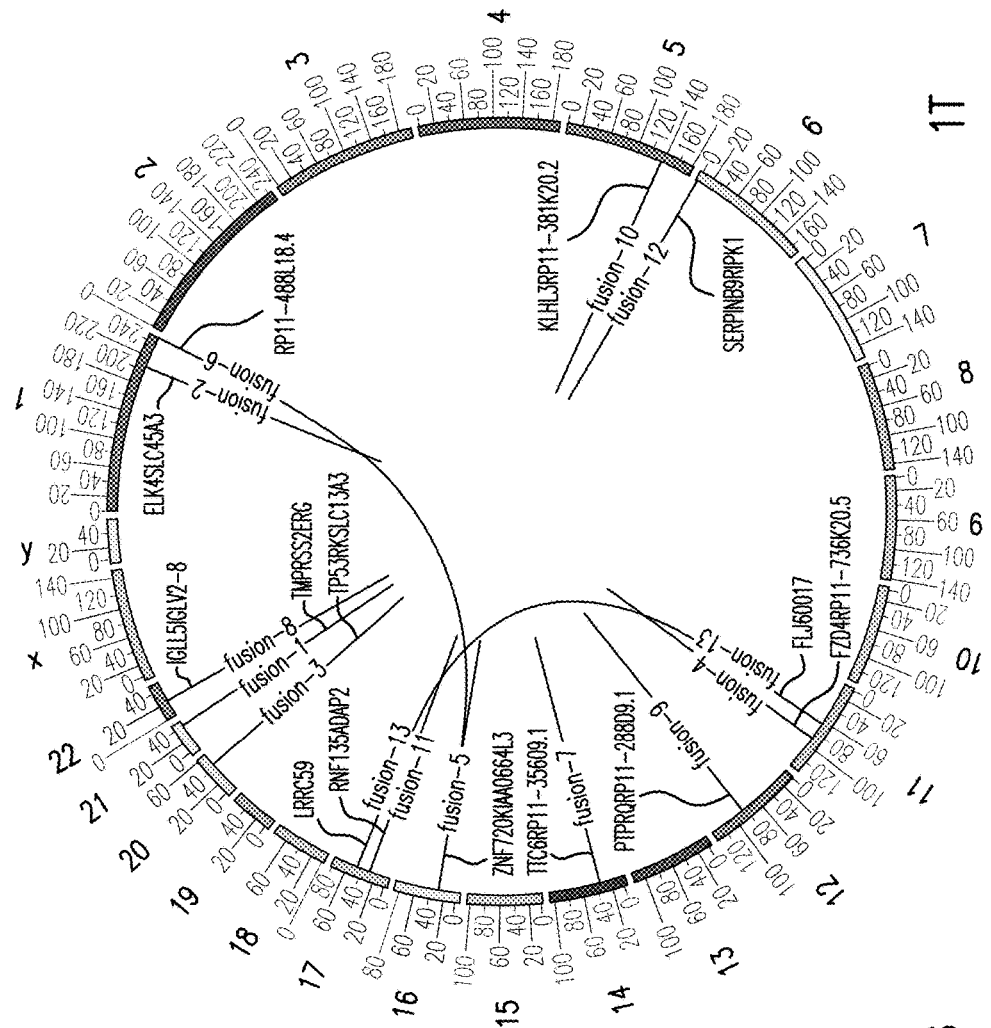
Figure 6:
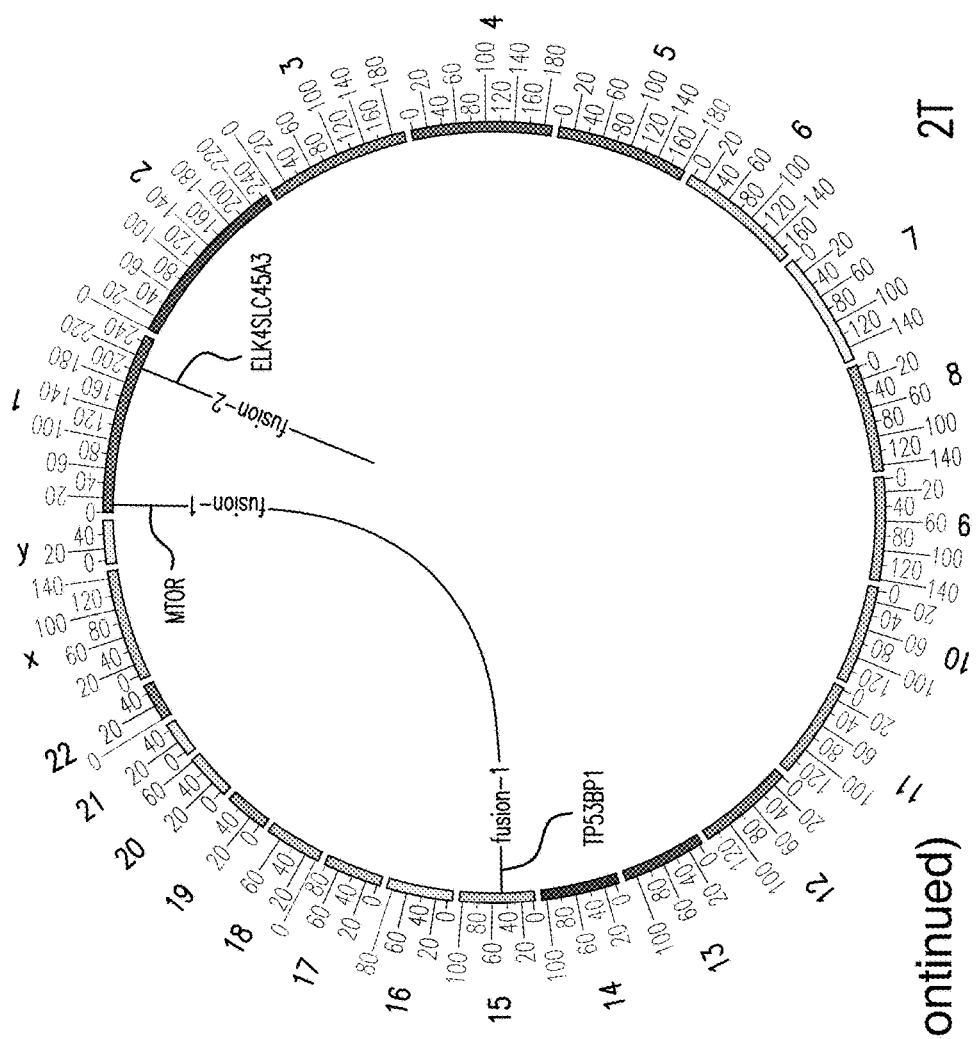
Figure 6:
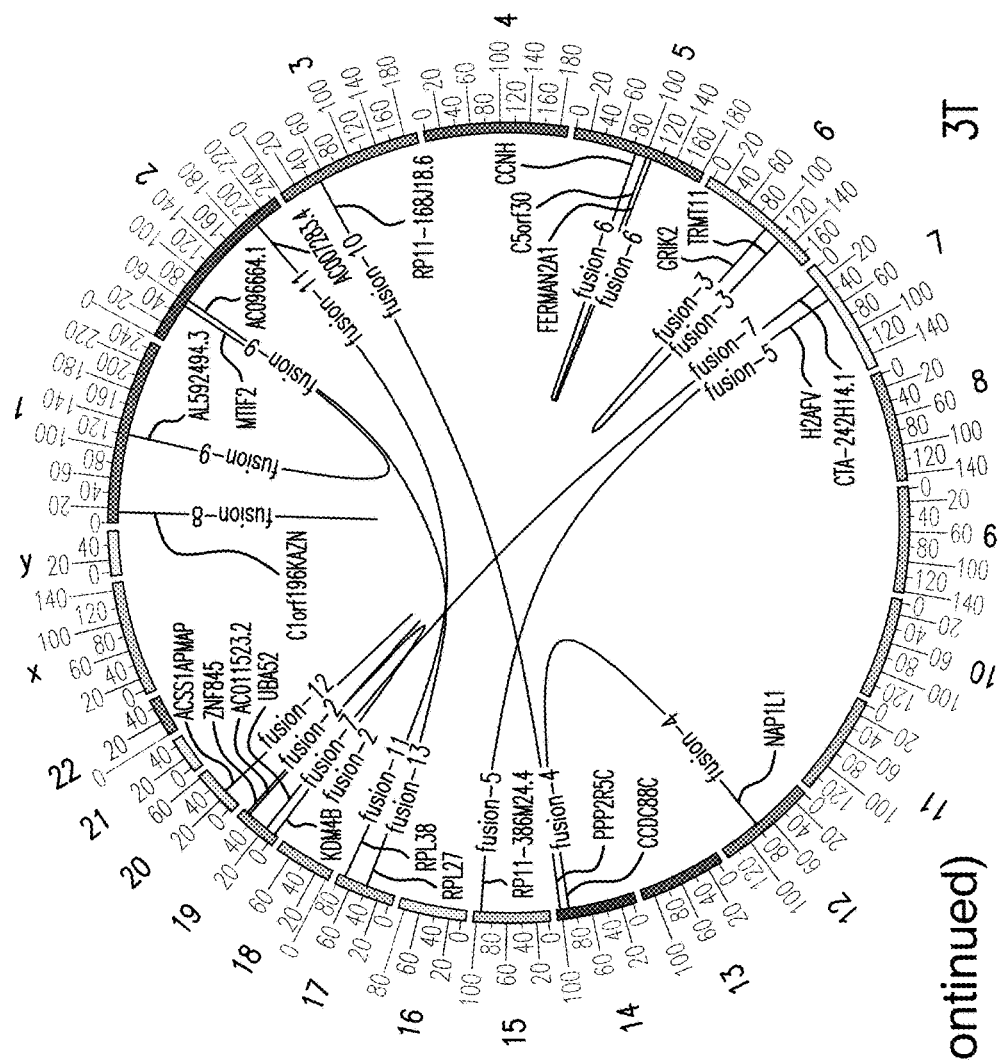
Figure 6:
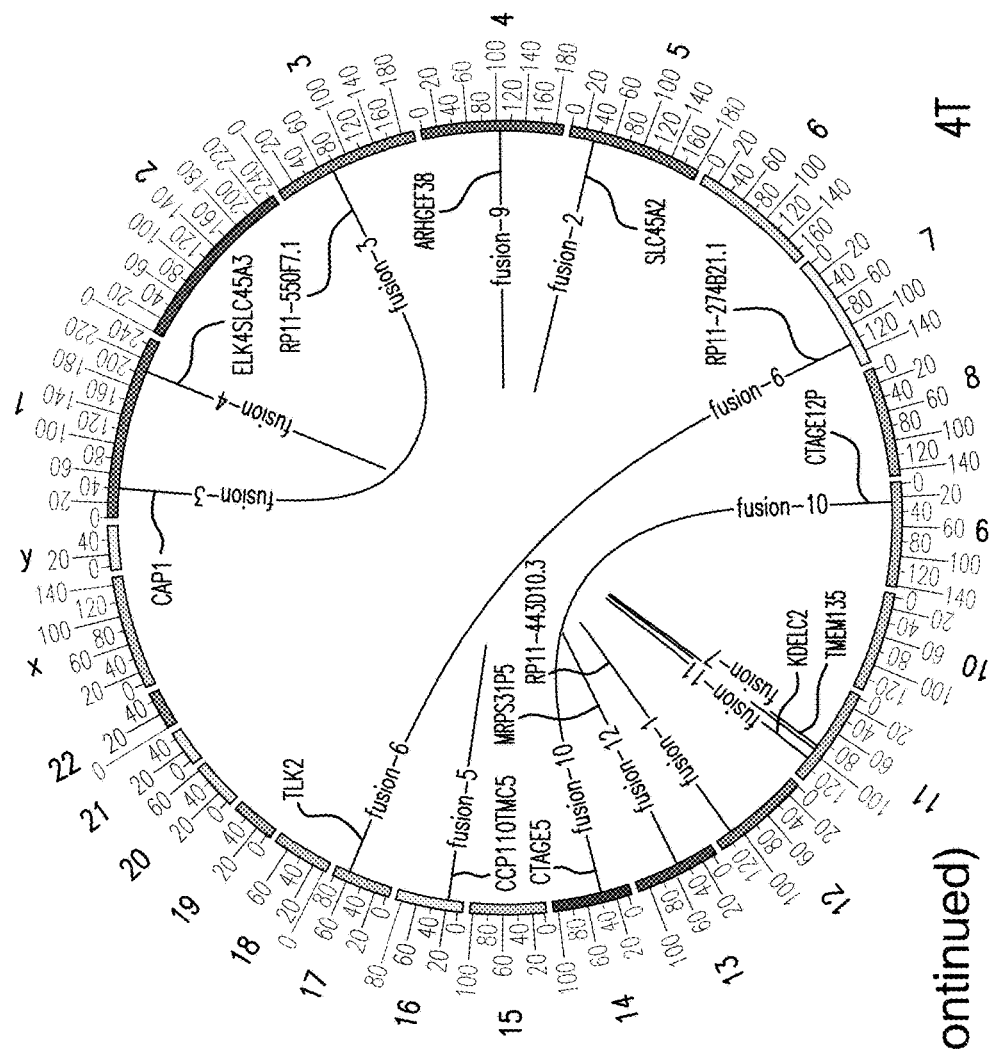
Figure 6:
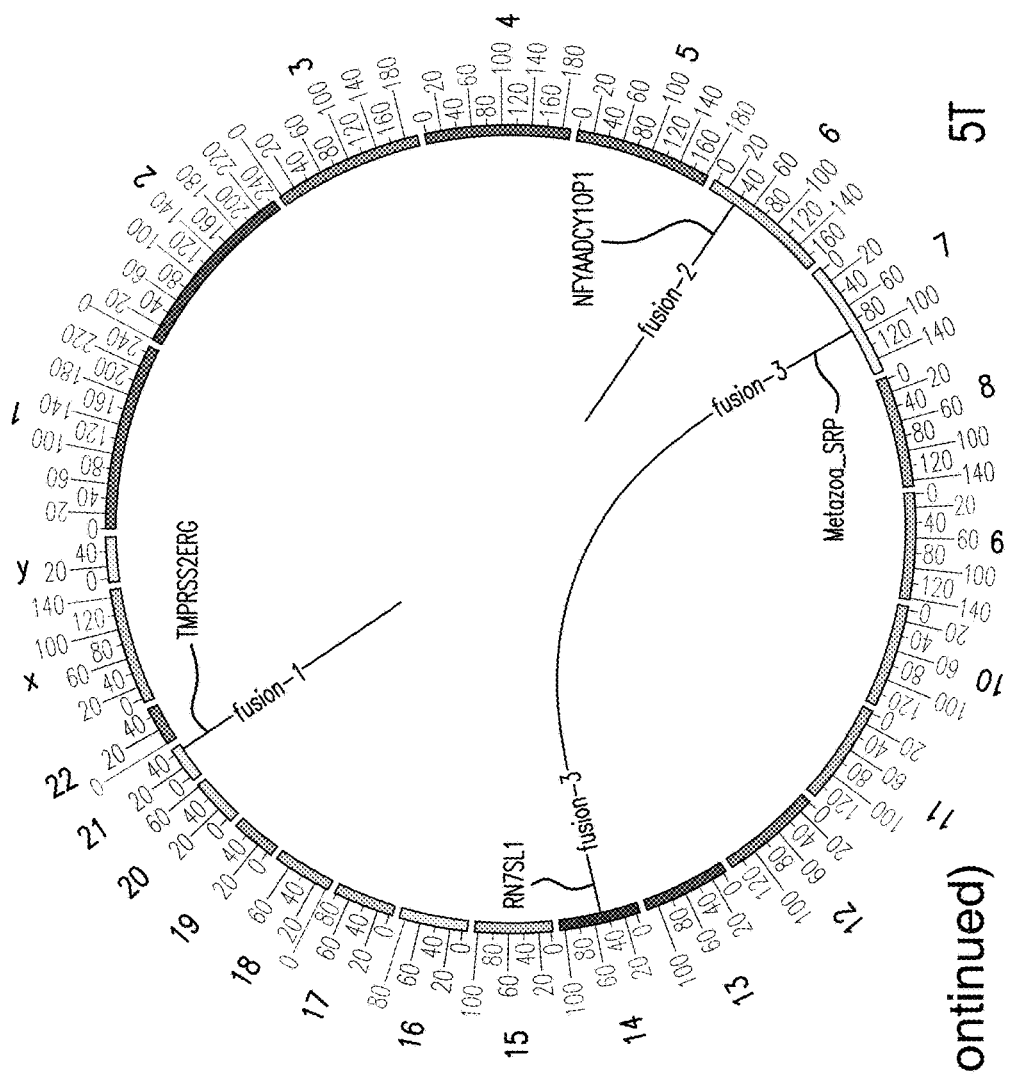

FIG. 6. CIRCOS plots of prostate cancer functional genome translocation. Five prostate cancer functional translocations were based on RNA sequencing. Fourteen of these functional translocations were supported by whole genome sequencing analysis. Functional translocation is defined as at least one transcript identified in the translocation process. Translocations in non-gene area were excluded.

Figure 7A:
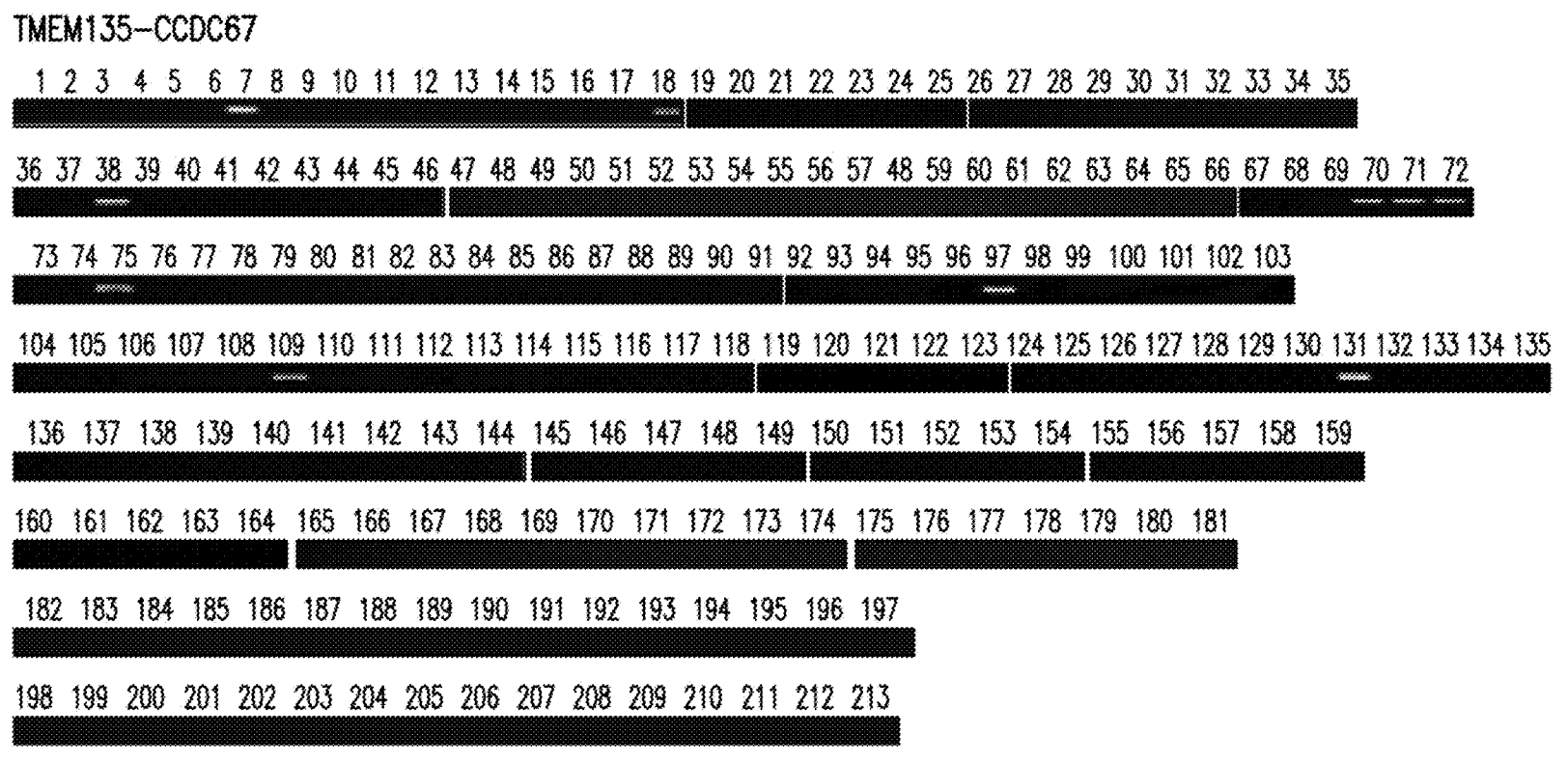
Figure 7A:
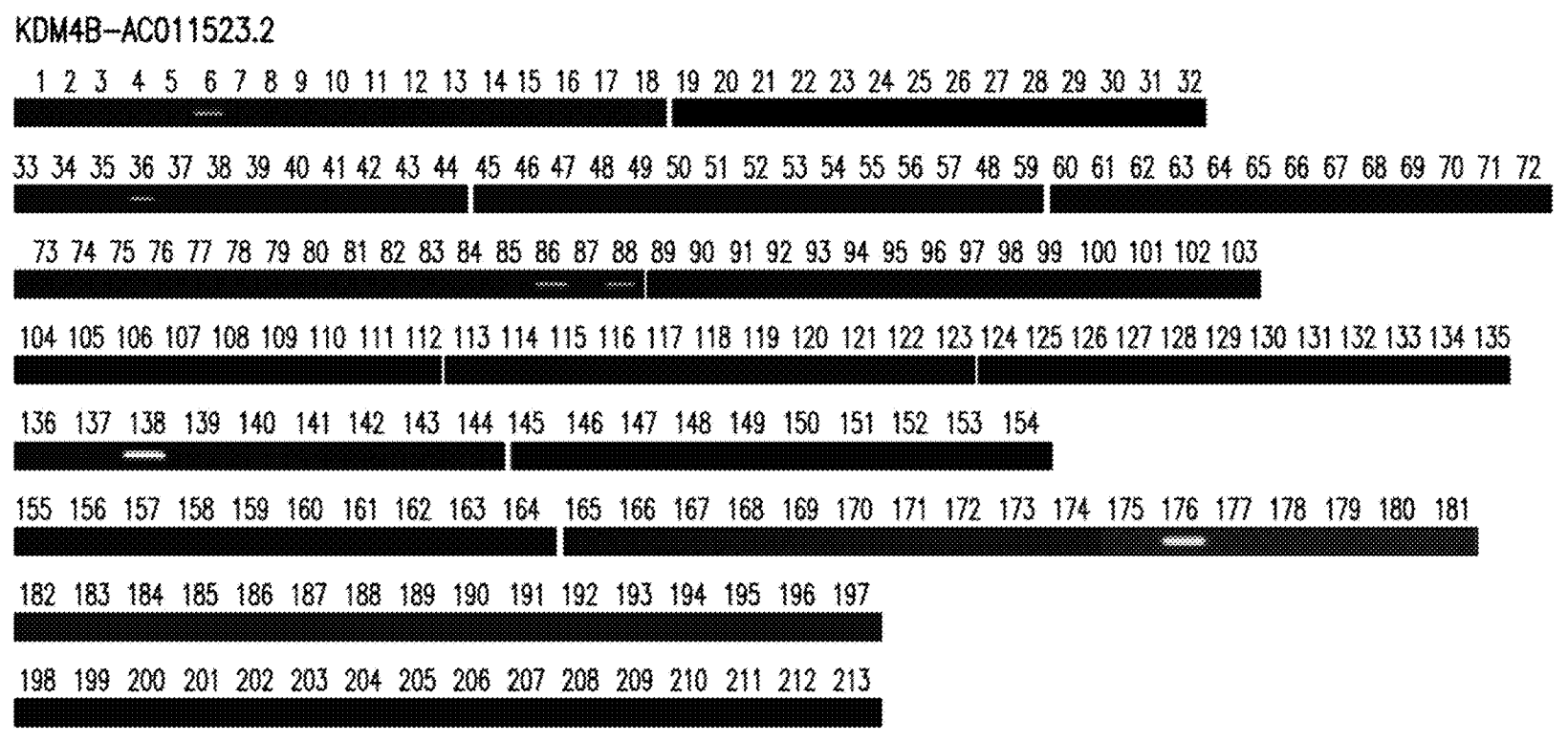
Figure 7A:
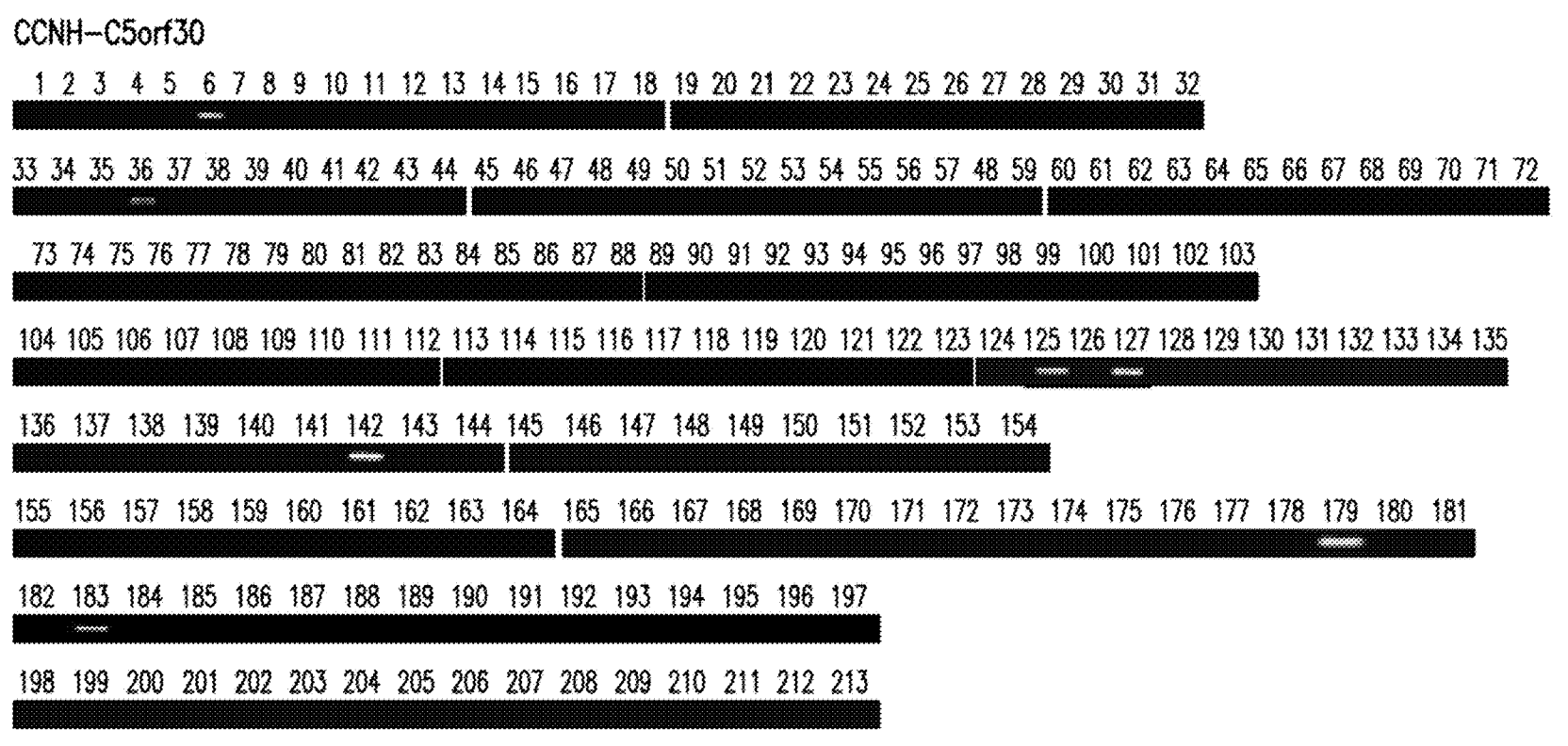
Figure 7A:
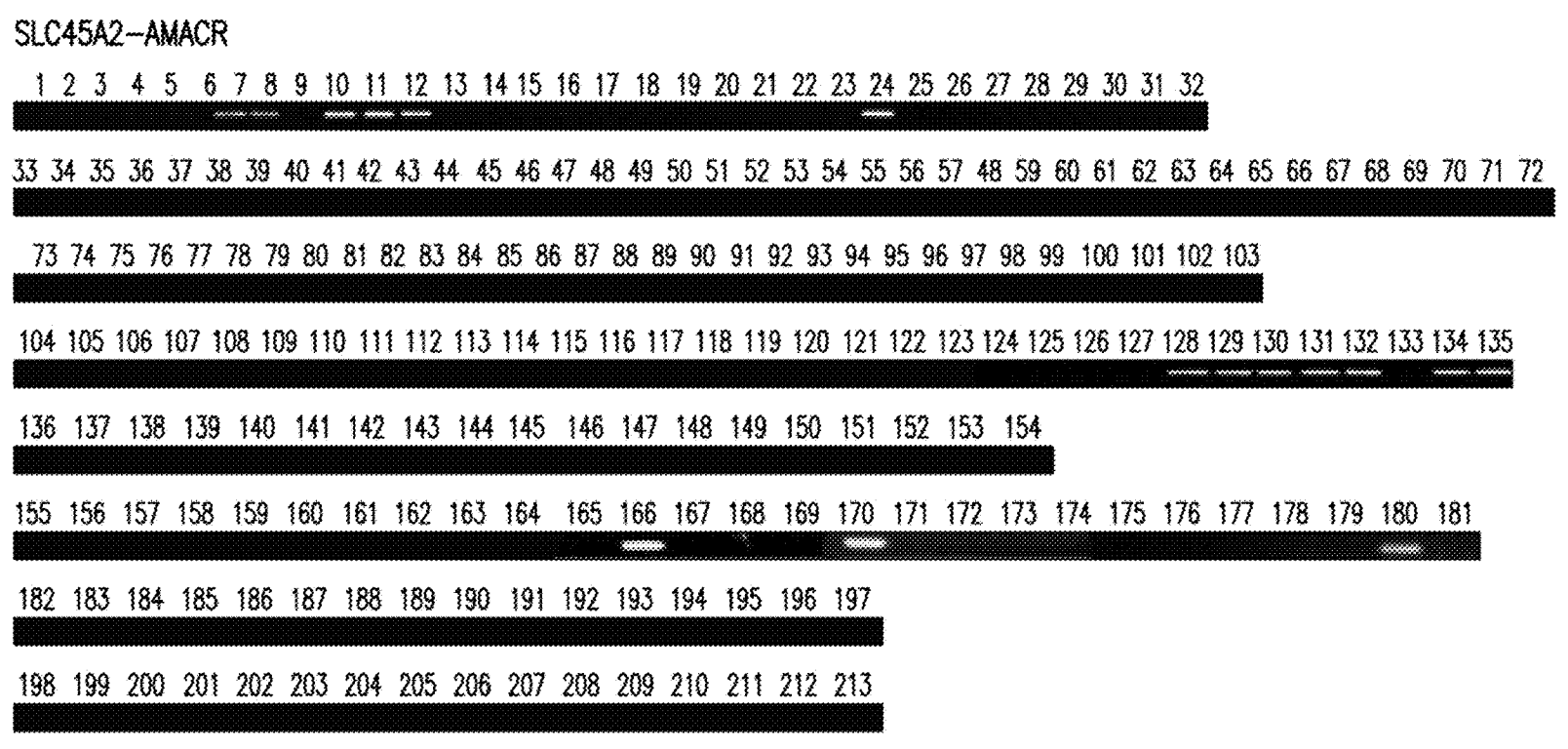
Figure 7A:
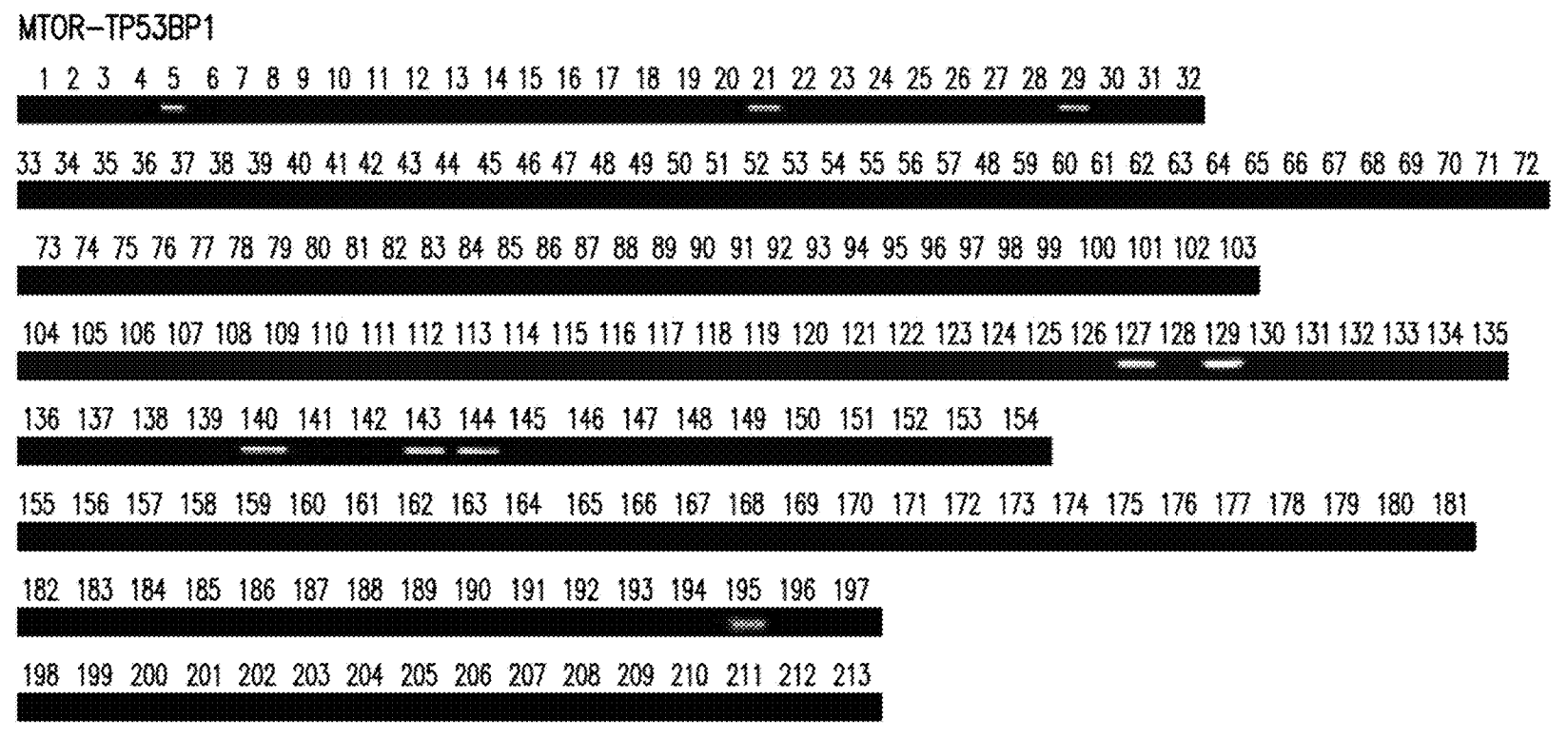
Figure 7A:
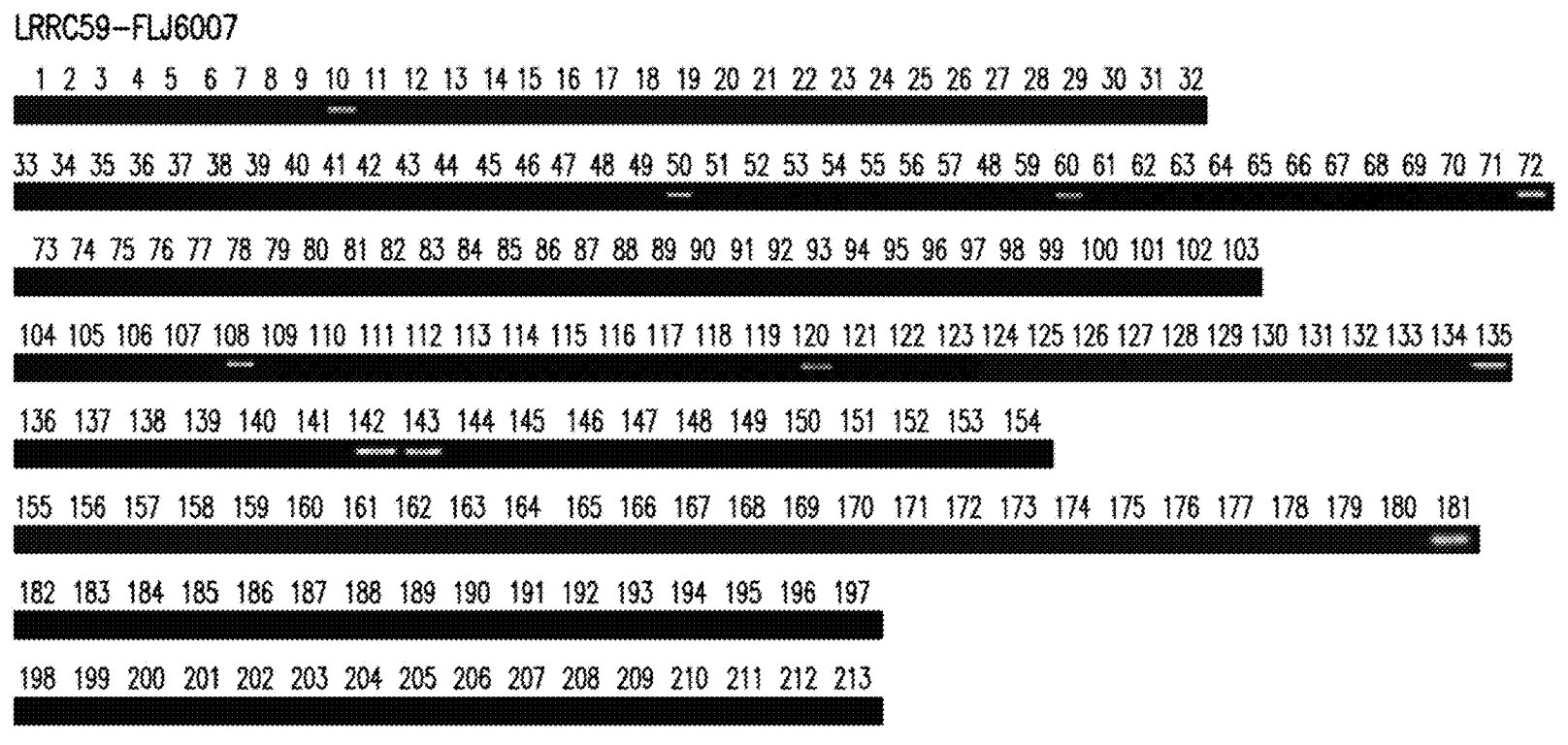
Figure 7A:
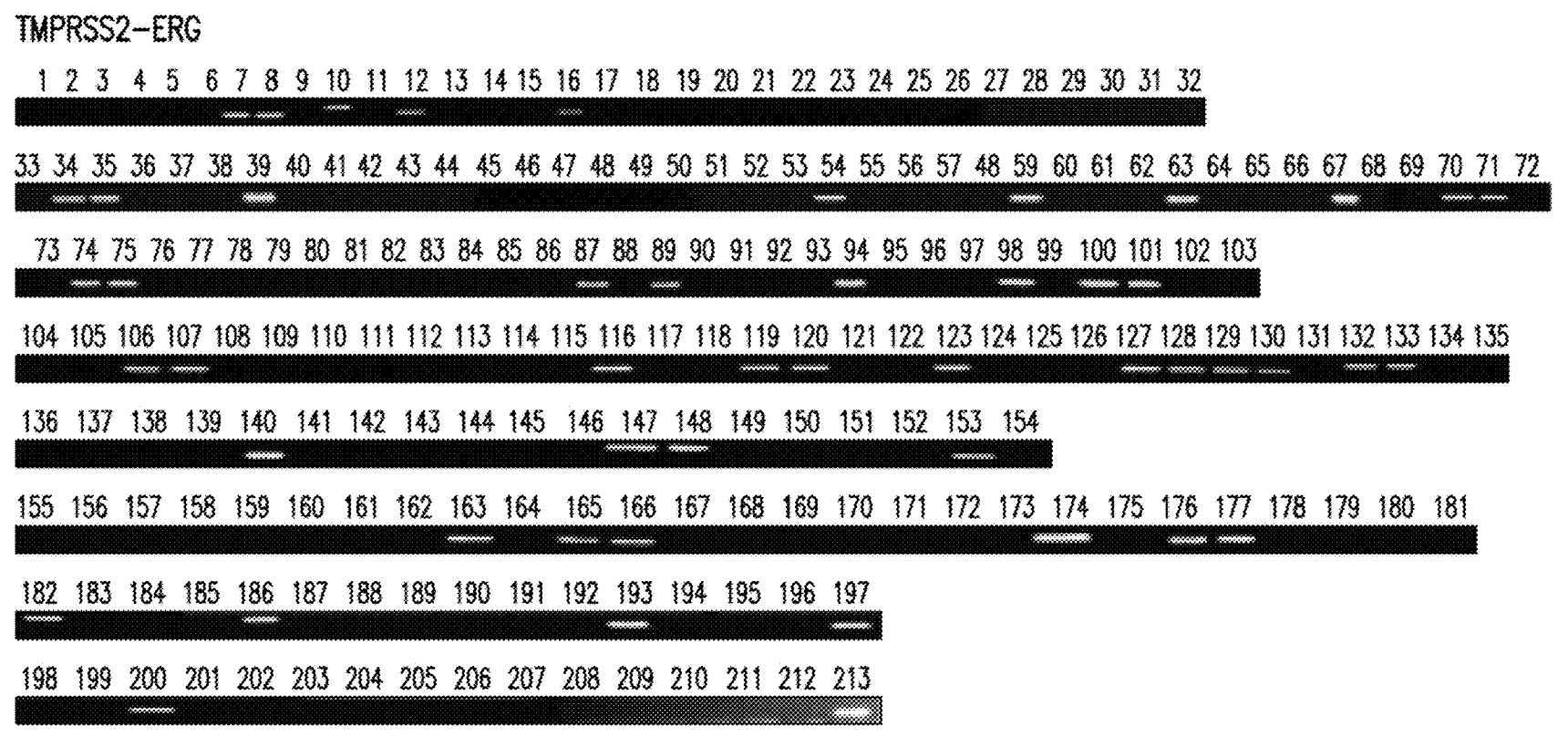
Figure 7A:
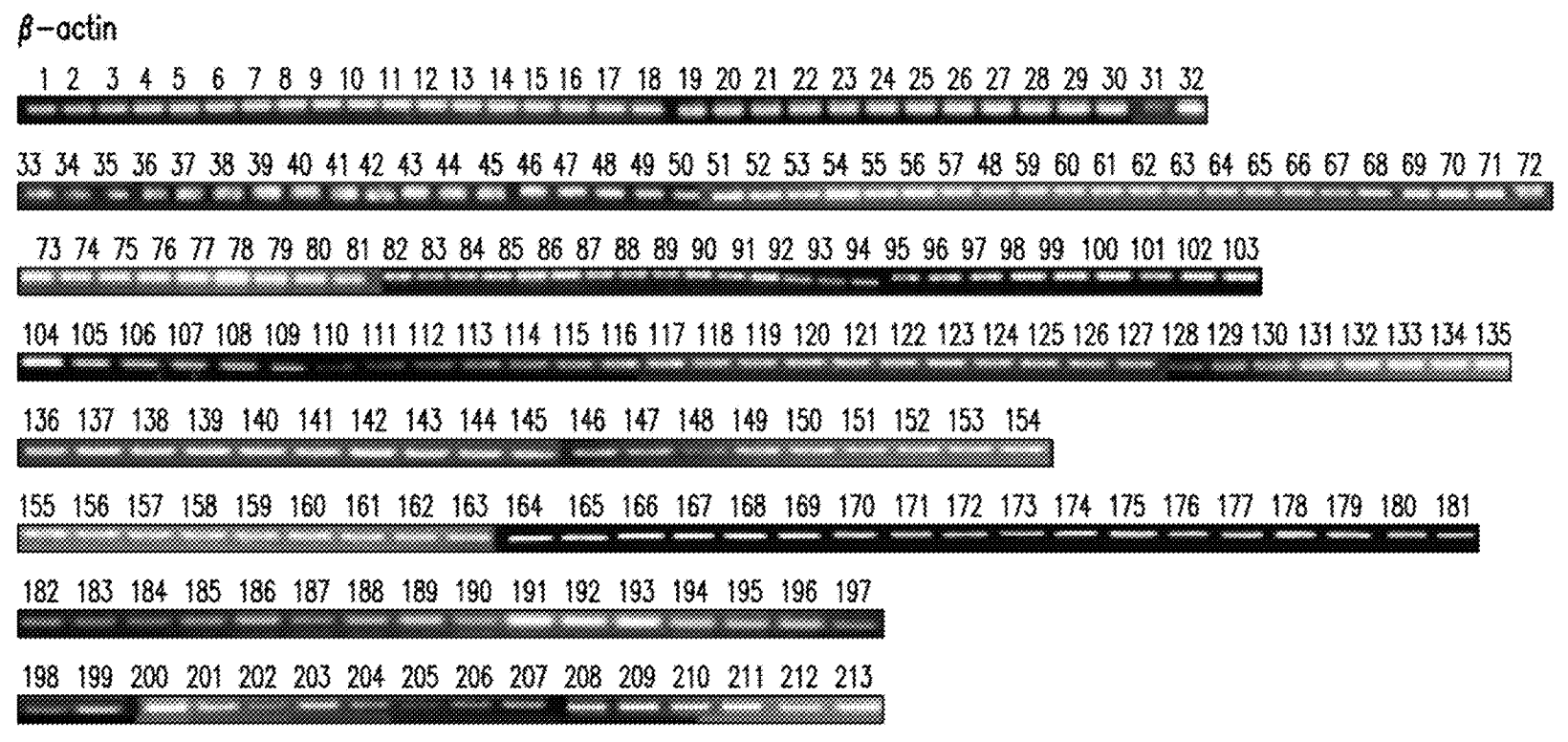
Figure 7B:
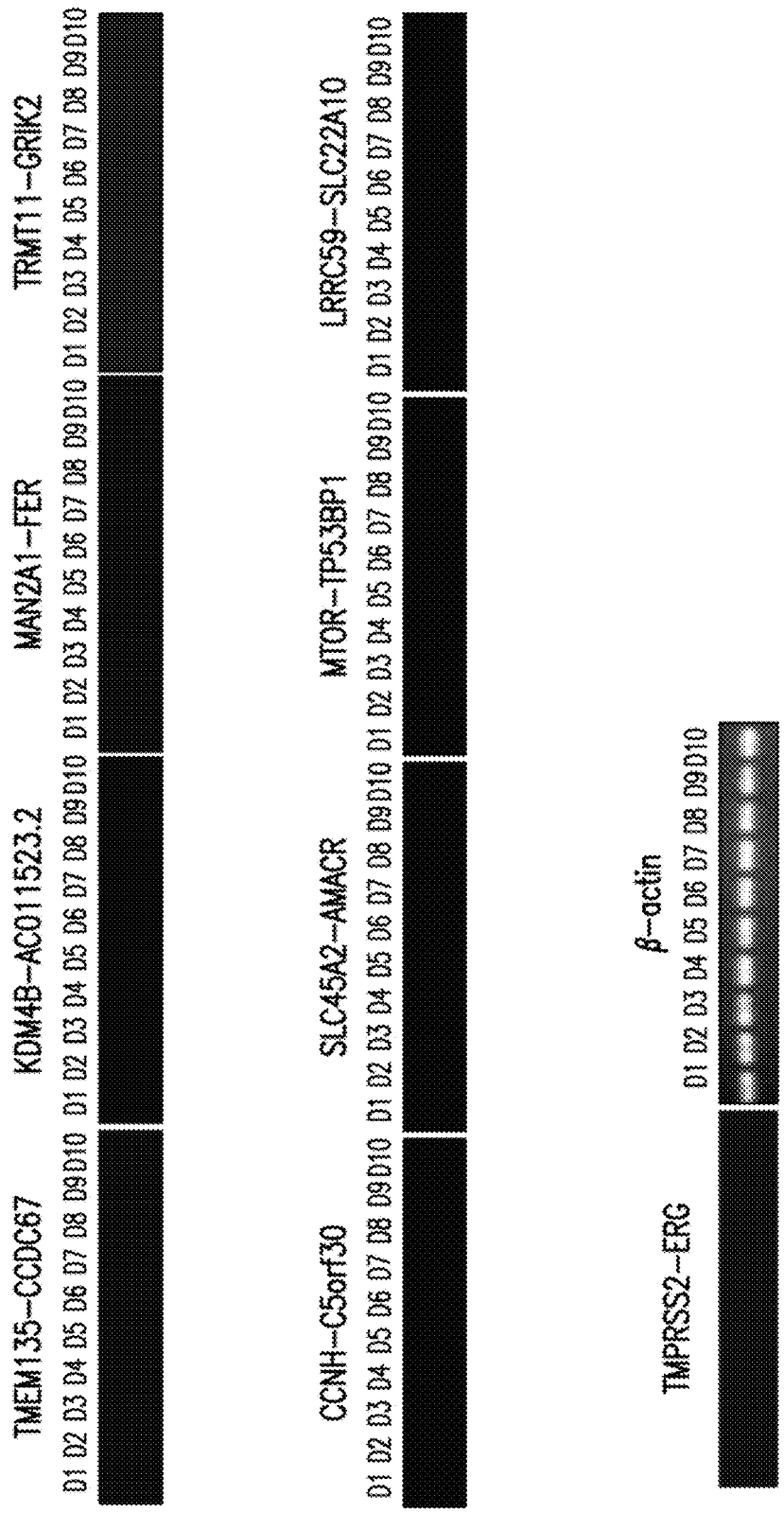

FIG. 7A-B. Identification of fusion genes in 174 prostate samples. (A) RT-PCR of TMEM135-CCDC57, KDM4B-AC011523.2, MAN2A1-FER, TRMT11-GRIK2, CCNH-C5orf30, SLC45A2-AMACR, MTOR-TP53BP1, LRRC59-FLJ6001, TMPRSS2-ERG were performed on 213 prostate cancer samples. RT-PCR of β-actin was used as quality control. The lane assignment is the following: 1-TP12-S0943T, 2-TP12-S0916T, 3-TP12-S0967T, 4-TP12-S1059T, 5-TP10-S093T, 6-JB770T, 7-TP08PPS0721T, 8-TP10-S0638T, 9-TP12-S1032T, 10-TP12-S0624T, 11-TP12-S0981T, 12-TP10PPS0420T, 13-TP12-S0966T, 14-TP12-S0988T, 15-TP12-S0704T, 16-PR053T, 17-IB110T, 18-TP12-S0928T, 19-TP12-S0816T, 20-TP12-S0789T, 21-TP12-S0805T, 22-TP12-S0803T, 23-TP12-S0765T, 24-TP12-S0770T, 25-TP12-S0799T, 26-TP12-S0795T, 27-TP12-S0786T, 28-PR534T, 29-TP12-S0790T, 30-TP12-S0740T, 31-TP12-S0723T, 32-PR536T, 33-FB76, 34-IB378T, 35-IB180T, 36-HB303T, 37-GB368, 38-HB327T, 39-HB346T, 40-PR227T, 41-HB322T, 42-HB658T, 43-IB289T, 44-HB492T, 45-IB111T, 46-TP12-S0466T, 47-TP12-S0456T, 48-TP12-S0246T, 49-TP12-S0608T, 50-TP12-S0340T, 51-TP12-S0337T, 52-TP12-S0048T, 53-TP12-S0191T, 54-TP12-S0194T, 55-TP12-S0049T, 56-HB340T, 57-TP12-S0102T, 58-PR530T, 59-1942T, 60-TP12-S1189T, 61-13745T, 62-5396T, 63-8432T, 64-HB261T, 65-FB183T, 66-HB591T, 67-HB568T, 68-HB526T, 69-TP08-S00542T, 70-IB298T, 71-TP09-S0420T, 72-PR303T, 73-GB400T, 74-PR018T, 75-HB603T, 76-PR310T, 77-JB197T, 78-PR300T, 79-PR236T, 80-JB154T, 81-PR434T, 82-7504T, 83-25313T, 84-8629T, 85-7270T, 86-2671T, 87-4308T, 88-28278T, 89-TP12-S1224T, 90-TP12-S0918T, 91-TP12-S1197T, 92-TP12-S0915T, 93-16464T, 94-2644T, 95-1199T, 96-15922T, 97-15733T, 98-16947T, 99-19381T, 100-6837T, 101-9122T, 102-6647T, 103-4336T, 104-29671T, 105-11462T, 106-8741T, 107-IB362T, 108-PR079T, 109-IB483T, 110-IB071T, 111-GB195T, 112-PR521T, 113-TP08-500530T, 114-7221T, 115-JB426T, 116-34T, 117-HB951T, 118-FB94T, 119-IB273T, 120-DB237T, 121-IB134T, 122-HB021T, 123-HB033T, 124-FB174 T, 125-KB170T, 126-FB120T, 127-HB504T, 128-HB305T, 129-FB421T, 130-TP09-S0721T, 131-FB238T, 132-HB46T, 133-TP11PP-50638T, 134-PR306T, 135-HB207T, 136-HB235T, 137-IB112T, 138-IB136T, 139-PR375T, 140-2HB591T, 141-23HB021T, 142-TP09-S0006T, 143-21B483T, 144-2HB568T, 145-M-11462T, 146-29825T, 147-3G989122T, 148-1AF8378T, 149-3Q-10614T, 150-4L98-27086T, 151-3D994336T, 152-3K5772T, 153-2K98-8378T, 154-14304T, 155-15463T, 156-15875T, 157-98TA-83782T, 158-562T, 159-14878T, 160-7943T, 161-995772T, 162-678T, 163-9927086T, 164-25265T, 165-HB705T, 166-33PR053T, 167-TP12-S0954T, 168-19PR530T, 169-34PR227T, 170-56FB76T, 171-TP09-S50704T, 172-78HB340T, 173-23FB120T, 174-23HB346T, 175-541B289T, 176-TP13-S0109T, 177-TP13-S0456T, 178-TP13-S0248T, 179-TP13-S0464T, 180-TP13-S0043T, 181-TP13-S0314T, 182-8433T, 183-863176T, 184-R6TT, 185-84876T, 186-994308T, 187-991199T, 188-9812033T, 189-855327T, 190-9814481T, 191-R3T, 192-R13T, 193-R19T, 194-84375T, 195-832972T, 196-9210207T, 197-R57T, 198-828142T, 199-R26T, 200-23R19T, 201-8713205T, 202-9217293T, 203-R18T, 204-8712362T, 205-9412443T, 206-R10T, 207-925R293T, 208-R16T, 209-849731T, 210-67R13T, 211-842620T, 212-R59T, 213-SR9R57T. (B) RT-PCR of TMEM135-CCDC67, KDM4B-AC011523.2, MAN2A1-FER, TRMT11-GRIK2, CCNH-C5orf30, SLC45A2-AMACR, MTOR-TP53BP1 and LRRC59-FLJ60017 on 10 organ donor prostate tissues.

Figure 8:
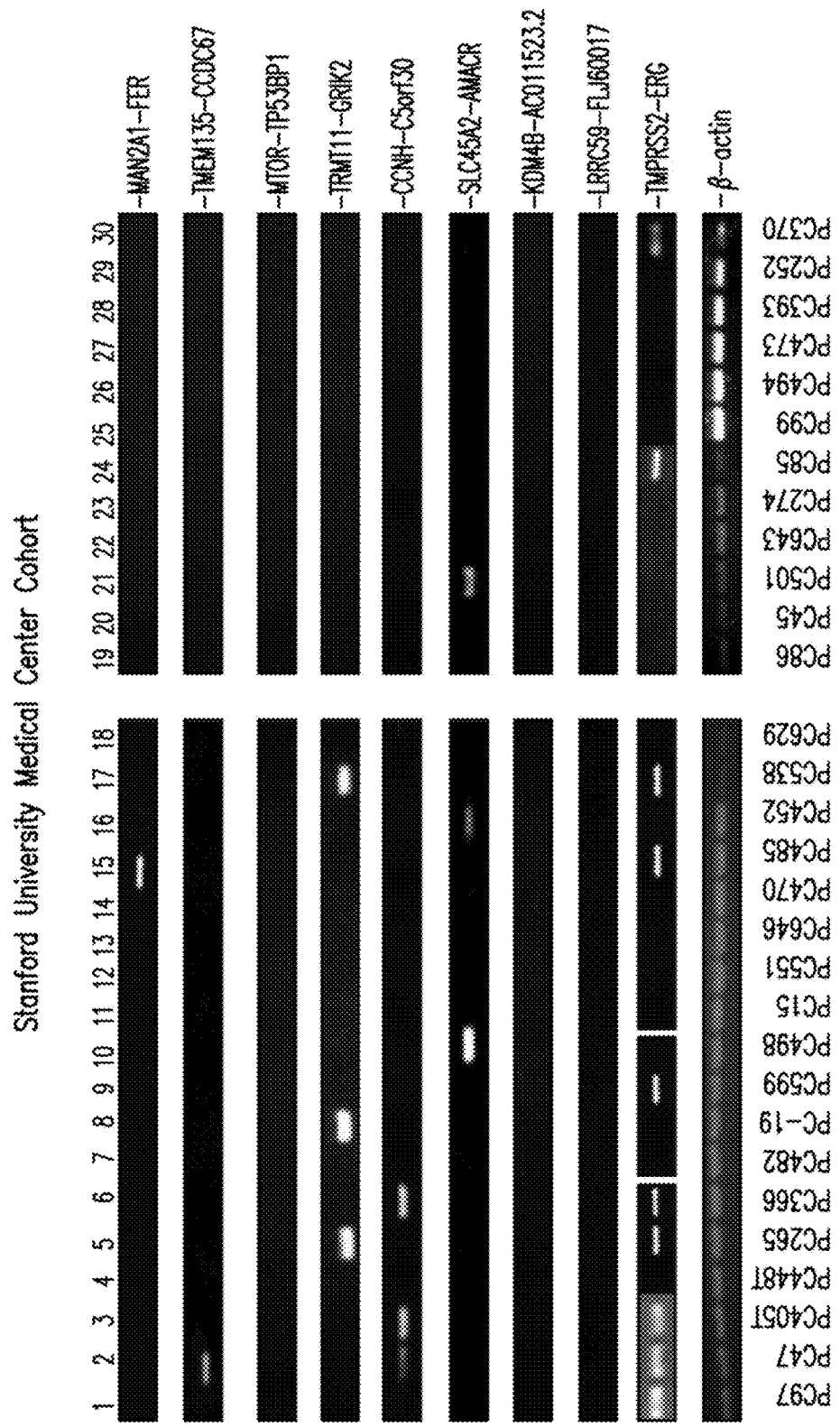

FIG. 8. Identification of fusion genes in 30 prostate samples from Stanford University Medical Center. RT-PCR of TMEM135-CCDC67, KDM4B-AC011523.2, MAN2A1-FER, TRMT11-GRIK2, CCNH-C5orf30, SLC45A2-AMACR, MTOR-TP53BP1 and LRRC59-FJL60017 were performed on 30 indicated prostate cancer samples. RT-PCR of β-actin was used as quality control.

Figure 9:
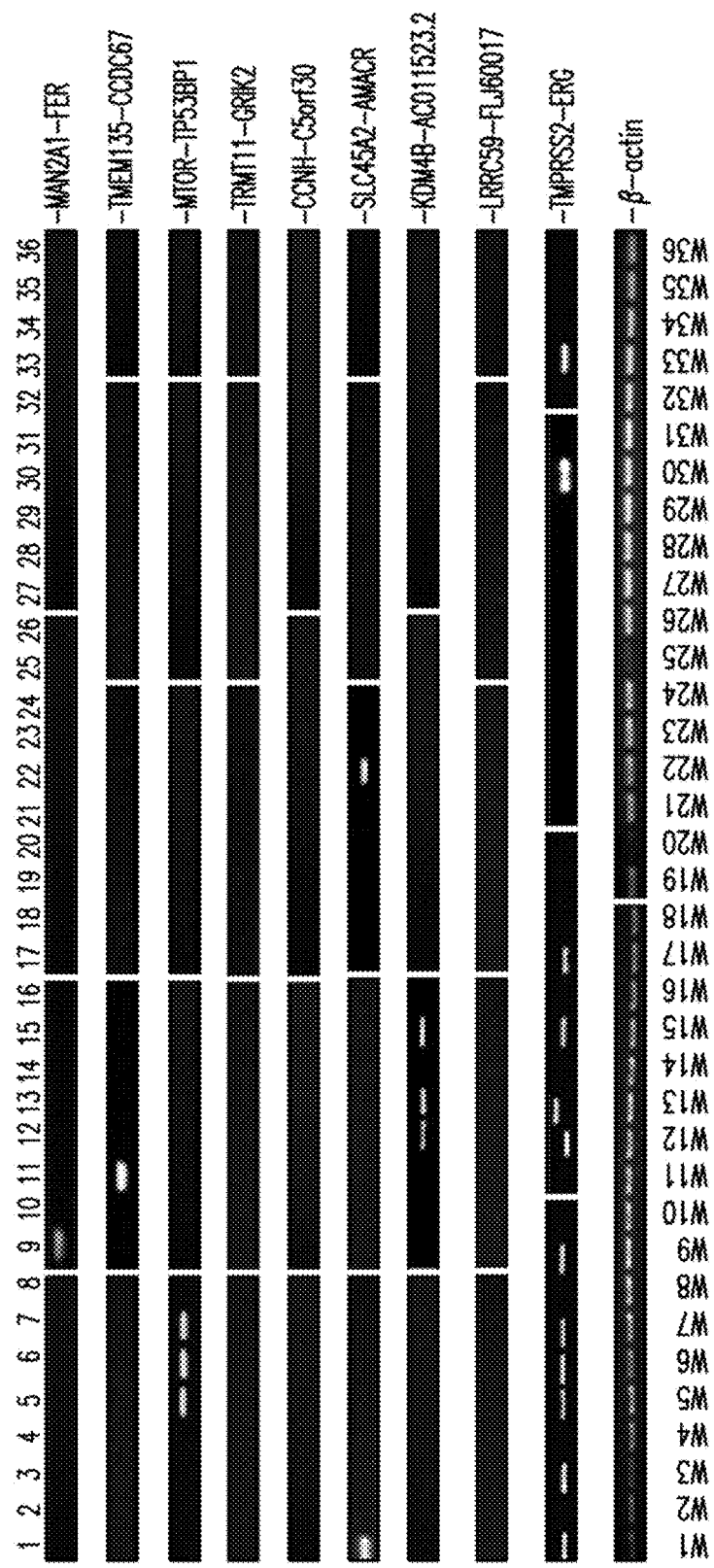

FIG. 9. Identification of fusion genes in 36 prostate samples from University of Wisconsin Madison Medical Center. RT-PCR of TMEM135-CCDC67, KDM4B-AC011523.2, MAN2A1-FER, TRMT11-GRIK2, CCNH-C5orf30, SLC45A2-AMACR, MTOR-TP53BP1 and LRRC59-FJL60017 were performed on 36 indicated prostate cancer samples. RT-PCR of β-actin was used as quality control.

Figure 10:
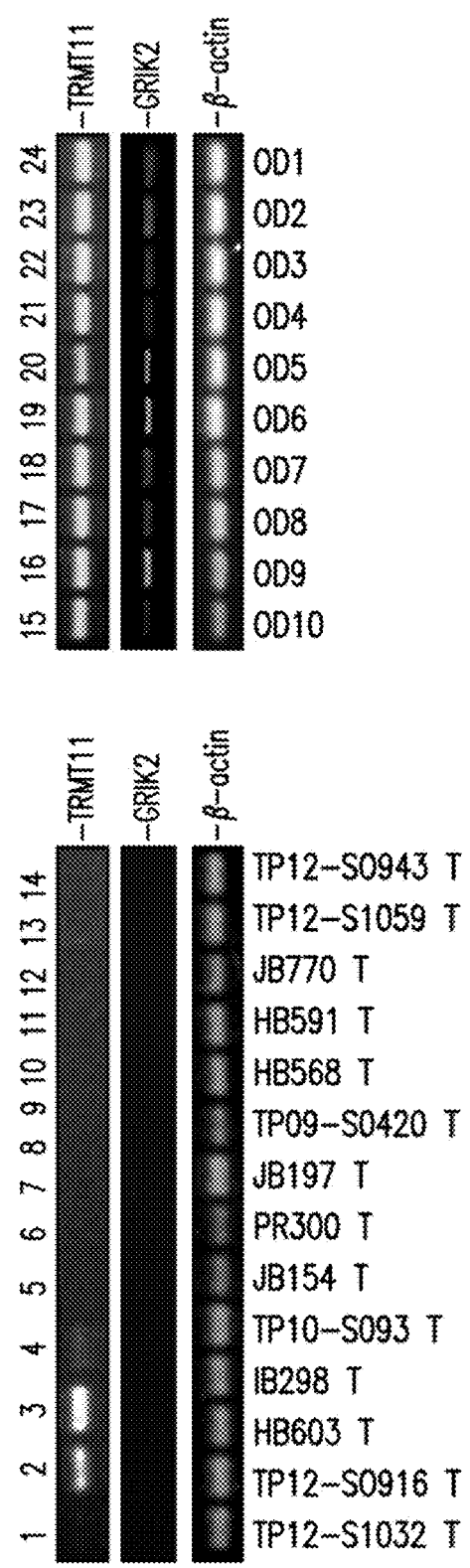

FIG. 10. Inactivation of GRIK1 and TRMT11 RNA expression in prostate cancer positive for TRMT11-GRIK2 fusion. RT-PCR was performed on RNA from TRMT11-GRIK2 fusion gene positive prostate cancer samples using primers specific for GRIK2 and TRMT11. Products of RT-PCR using primers specific for β-actin were used as template normalization control.

Figure 11:
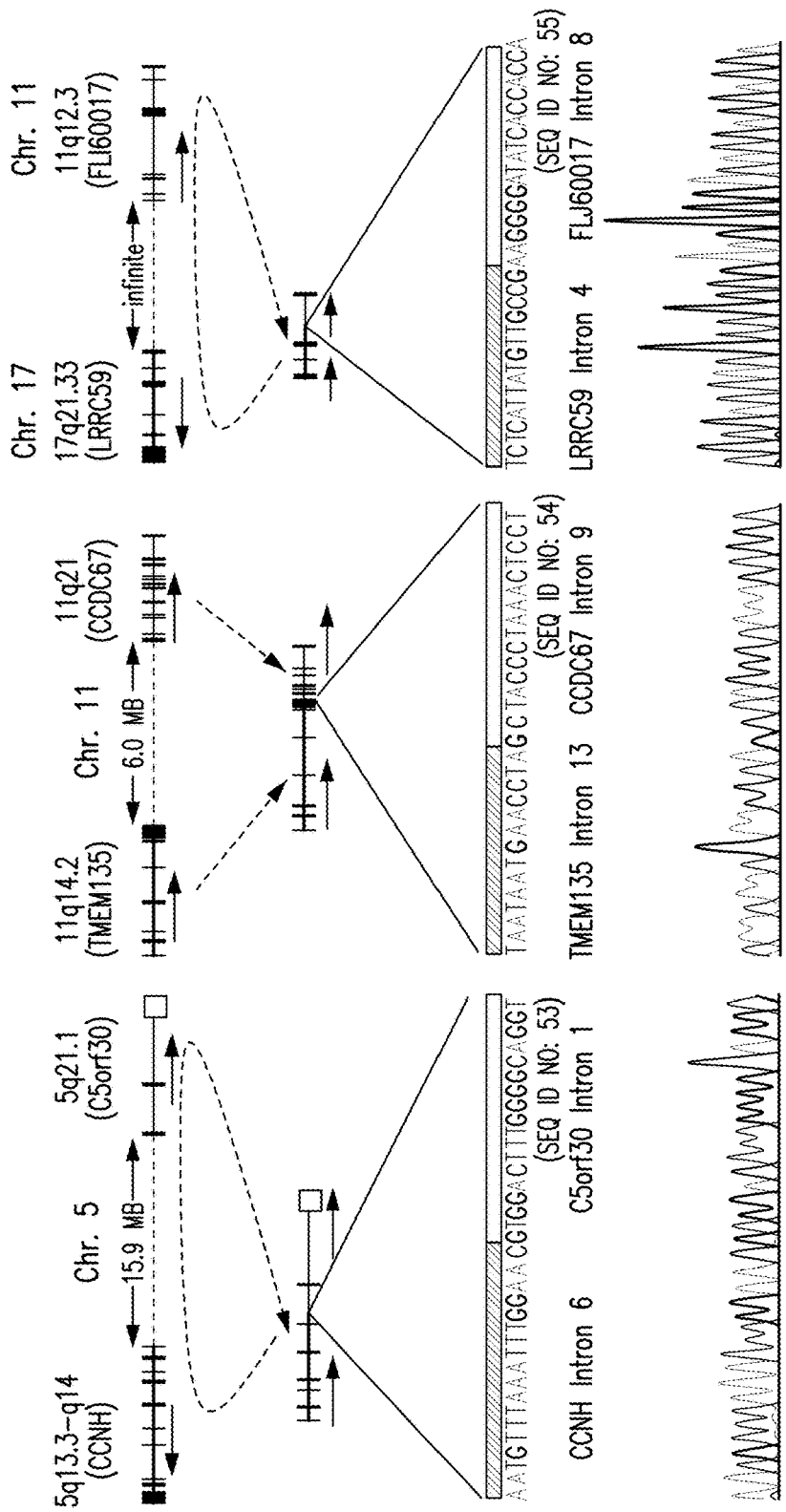

FIG. 11. Genome breakpoint analysis of fusion genes. Top panel: Miniature diagrams of genome of the fusion genes, the transcription directions, the distances between the joining genes and directions of the chromosome joining. Middle panel: Miniature of fusion genome and transcription direction. Bottom: Representative sequencing chromograms encompassing the joining breakpoint of chromosomes (SEQ ID NOs: 53-55).

Figure 12A:
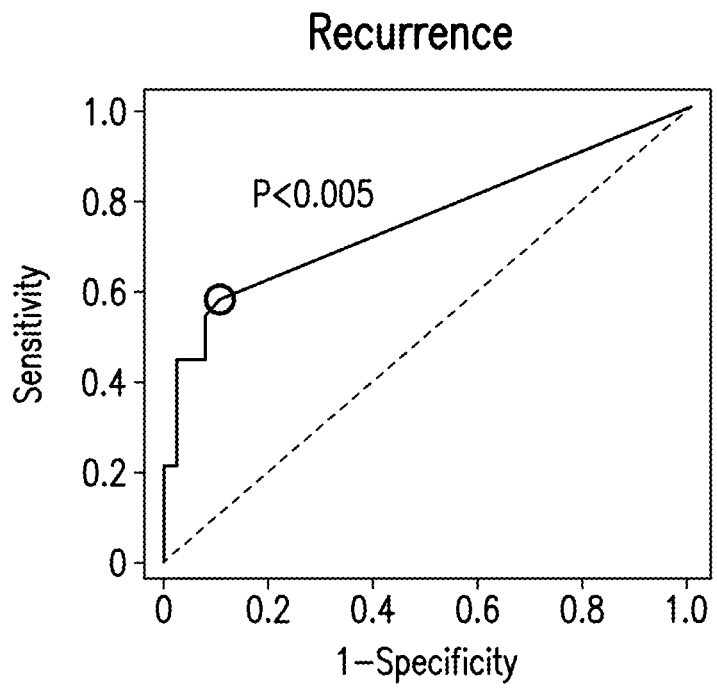
Figure 12B:
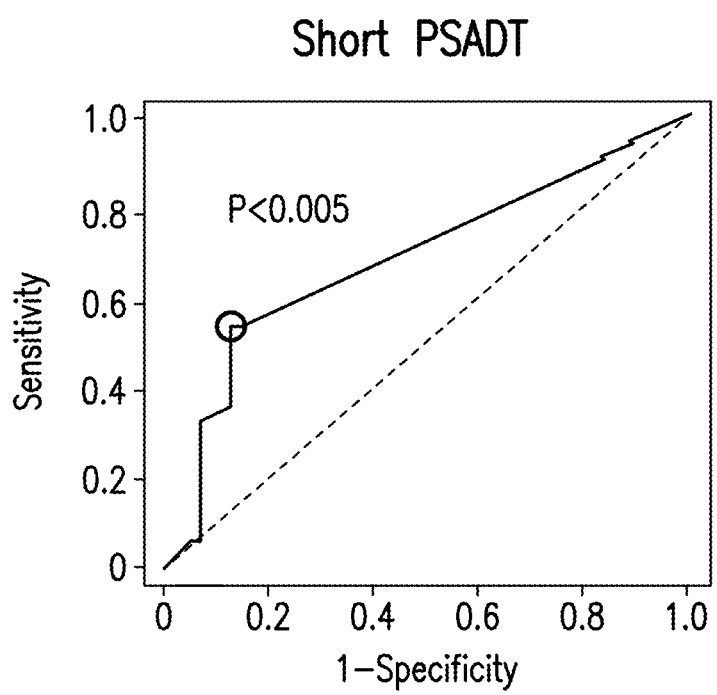

FIG. 12A-B. Prediction of prostate cancer recurrence and PSADT using a panel of 8 fusion genes. (A) ROC analyses of a panel of 8 fusion genes predicting prostate cancer recurrence using random assigned 90 prostate cancer samples from University of Pittsburgh Medical Center. Dotted line-random prediction; Black line-fusion prediction; Blue dot-optimal prediction. P-value (permutation test) is indicated for the significant difference between the ROC curve generated by fusion transcripts using LDA technique and the baseline control curve. (B) ROC analyses of a panel of 8 fusion genes predicting prostate cancer short PSADT (<4 months). Dotted line-random prediction; Black line-fusion prediction; Blue dot-optimal prediction. P-value (permutation test) is indicated for the significant difference between the ROC curve generated by fusion transcripts using LDA technique and the baseline control curve.

Figure 13A:
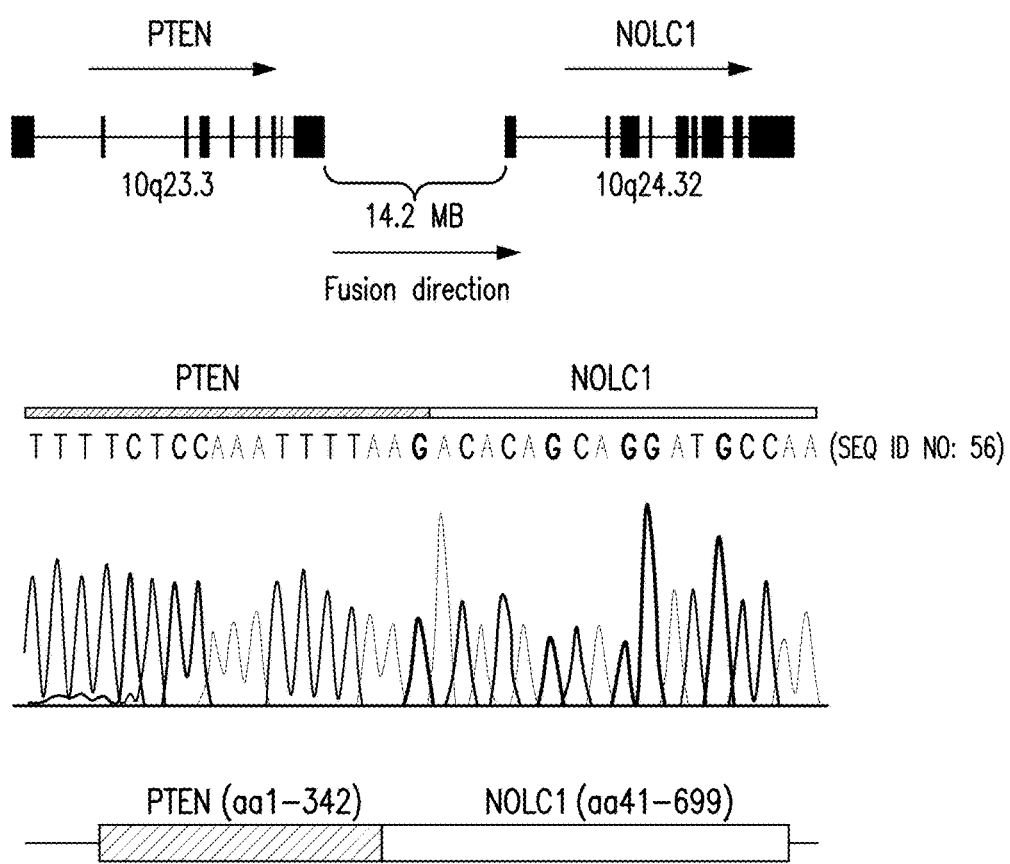
Figure 13B:
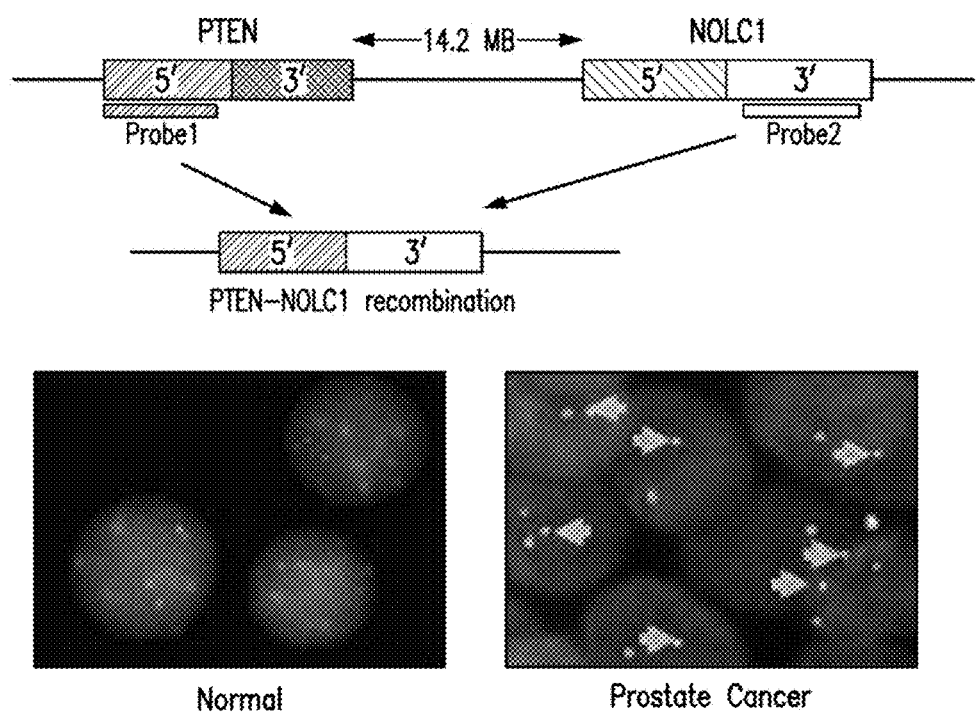
Figure 13C:
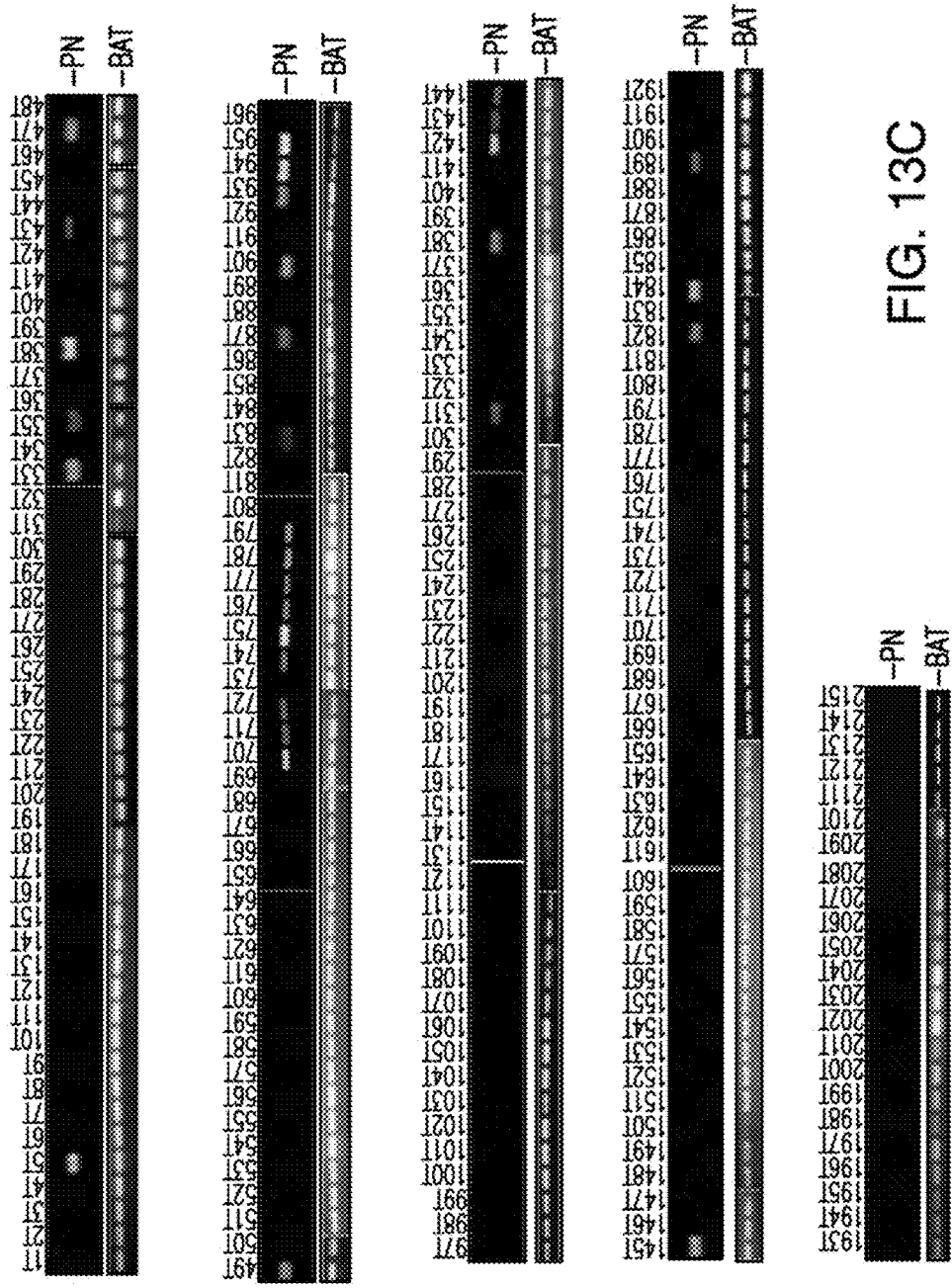

FIG. 13A-C. PTEN-NOLC1 fusion gene in prostate cancer. (A) PTEN-NOLC1 fusion transcript. Top panel: Miniature diagrams of genome of the PTEN and NOLC1 genes, the transcription direction, the distance between the joining genes and direction of the fusion. Middle panel: Representative sequencing chromogram of PTEN-NOLC1 transcript. The joining gene sequences were indicated (SEQ ID NO: 56). Lower panel: Diagram of translation product of fusion transcript. Blue-head gene translation product; Red-tail gene translation product. (B) Schematic diagram of PTEN and NOLC1 genome recombination and FISH probe positions. Representative FISH images were shown for normal prostate epithelial cells and cancer cells positive for TENNOLC1 fusion. Orange (asterisk *) denotes probe 1 (RP11-124B18); Green (plus sign+) denotes probe 2 (CTD-3082D22). Fusion joining signals are indicated by green arrows. (C) PTEN-NOLC1 expression in prostate cancer samples. RT-PCRs were performed in 215 samples of prostate cancer using primers specific for PTEN-NOLC1 (PN) fusion transcript. RT-PCRs using primers specific for β-actin (BAT) were performed as normalization controls.

Figure 14:
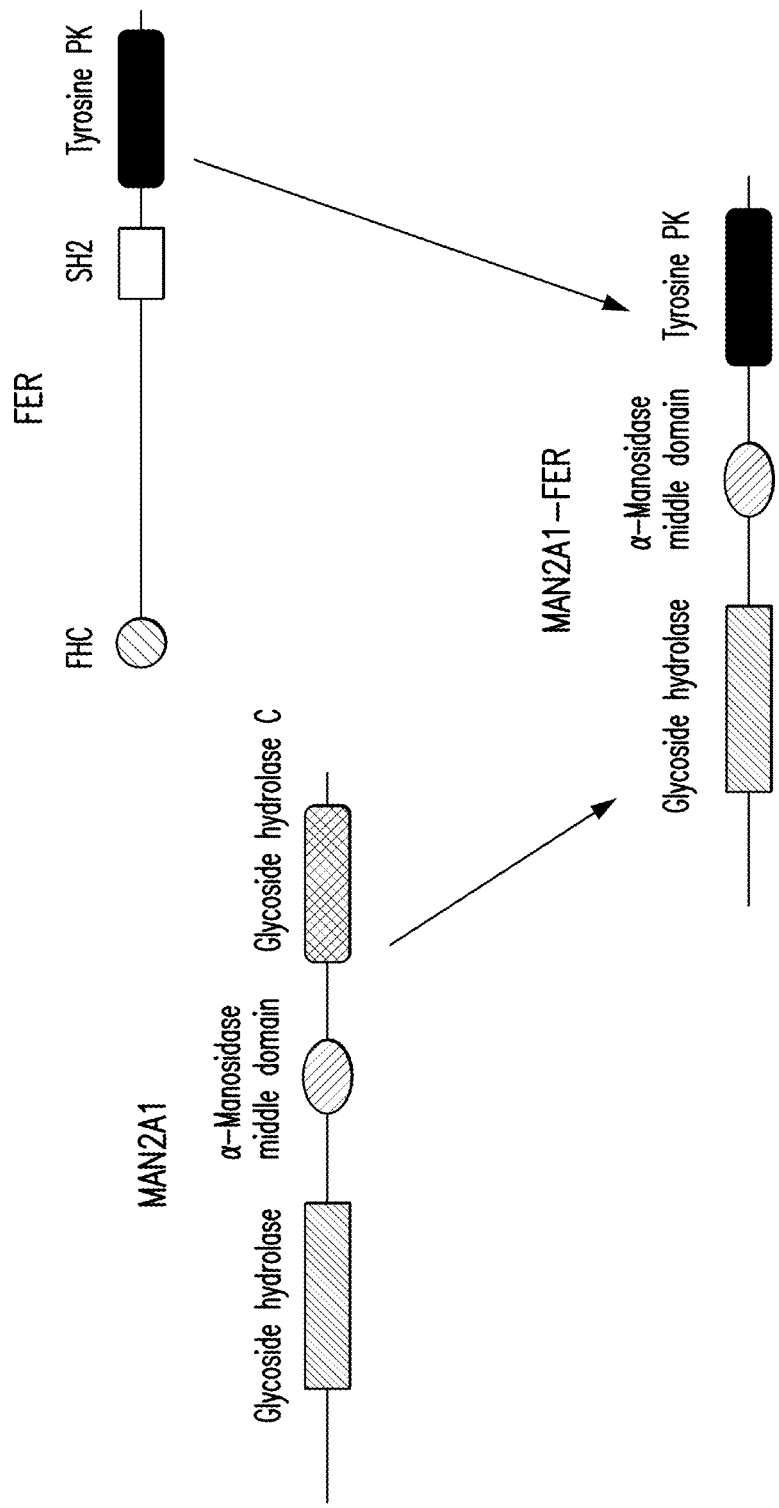

FIG. 14. Motif analysis of MAN2A1-FER. Diagram of functional domains of MAN2A1, FER and MAN2A1-FER fusion proteins.

Figure 15:
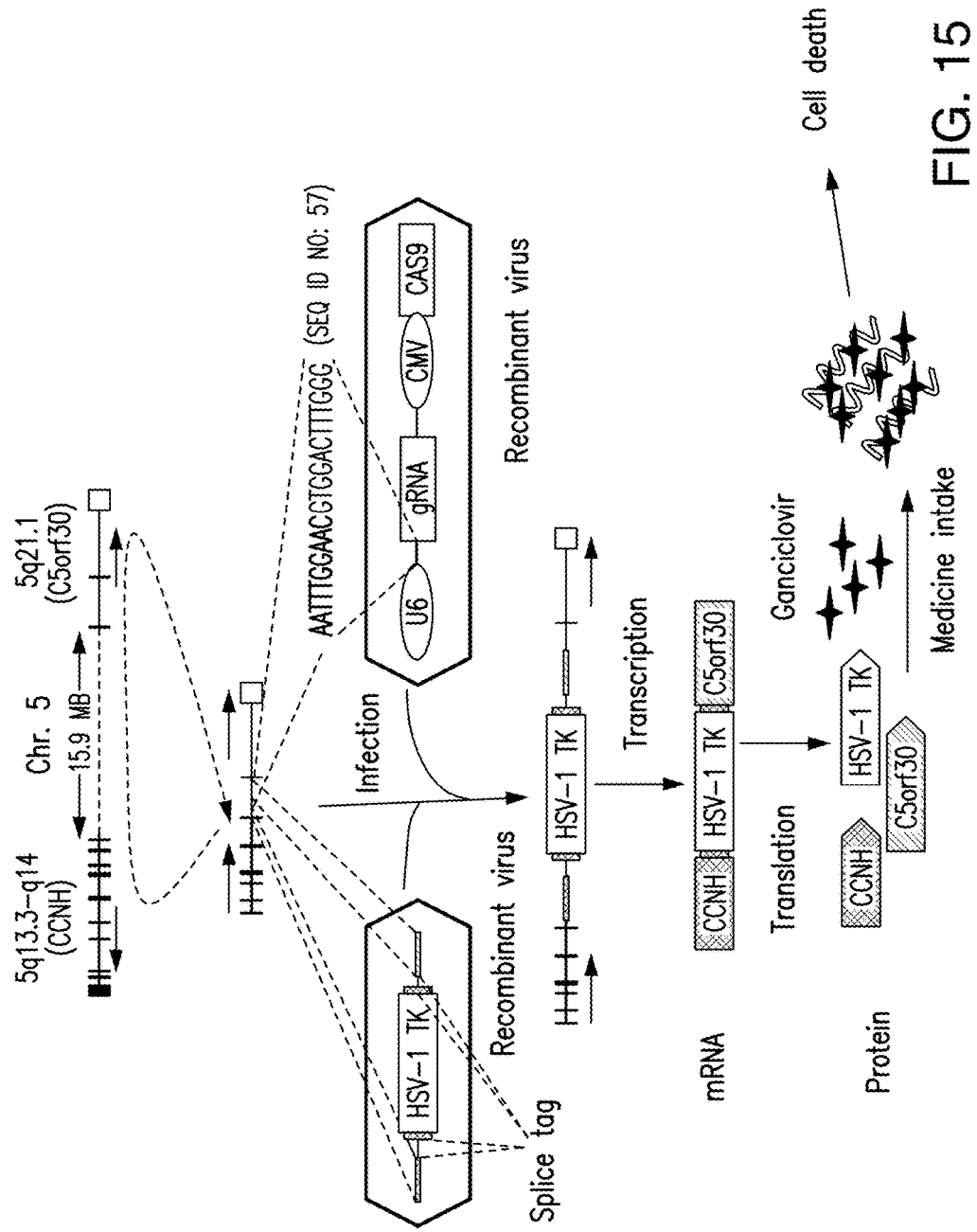

FIG. 15. Schematic diagram of Genome editing targeting at a fusion gene breakpoint in prostate cancer cells positive for CCNH-C5orf30 (SEQ ID NO: 57).

Figure 16:
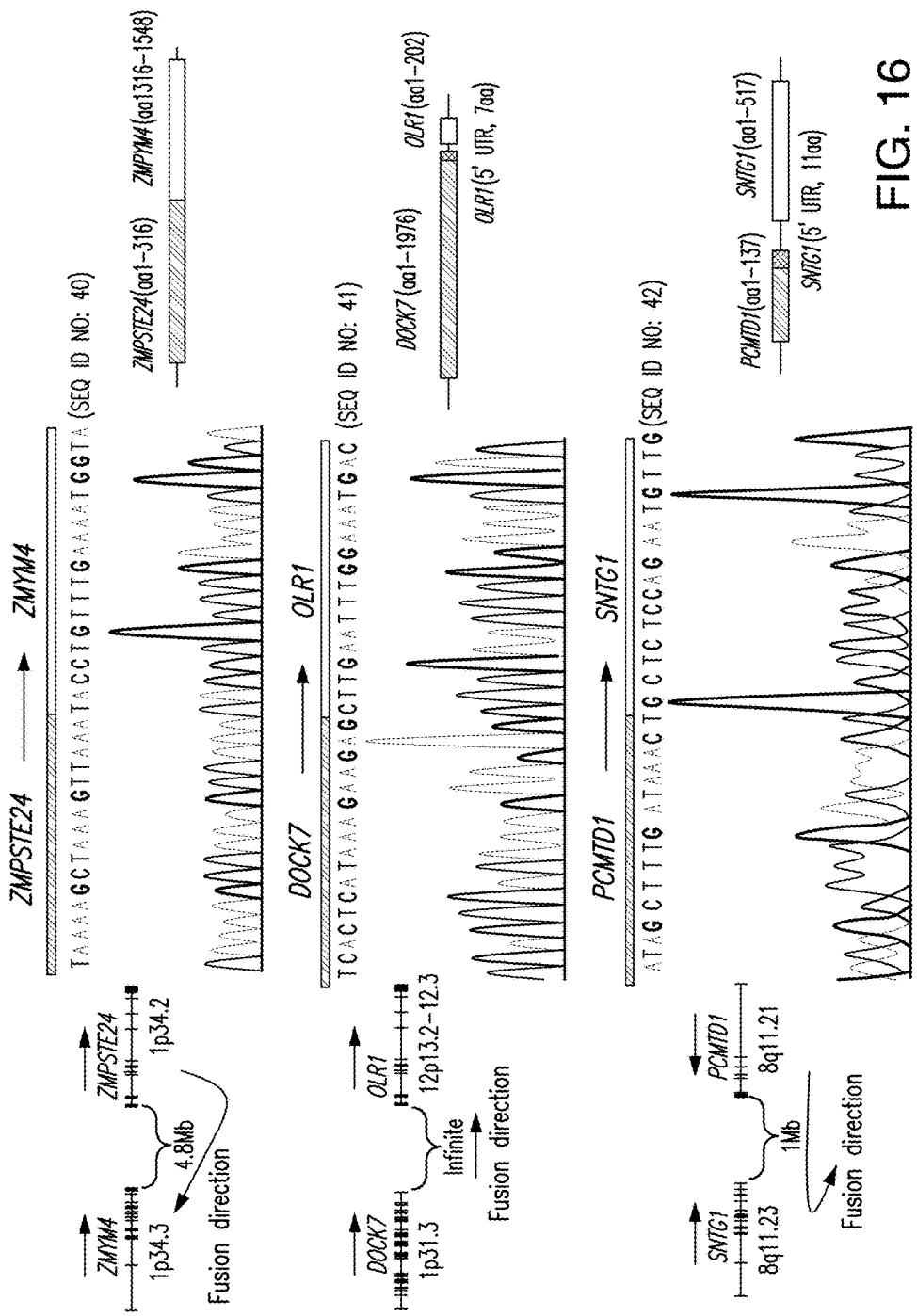
Figure 16:
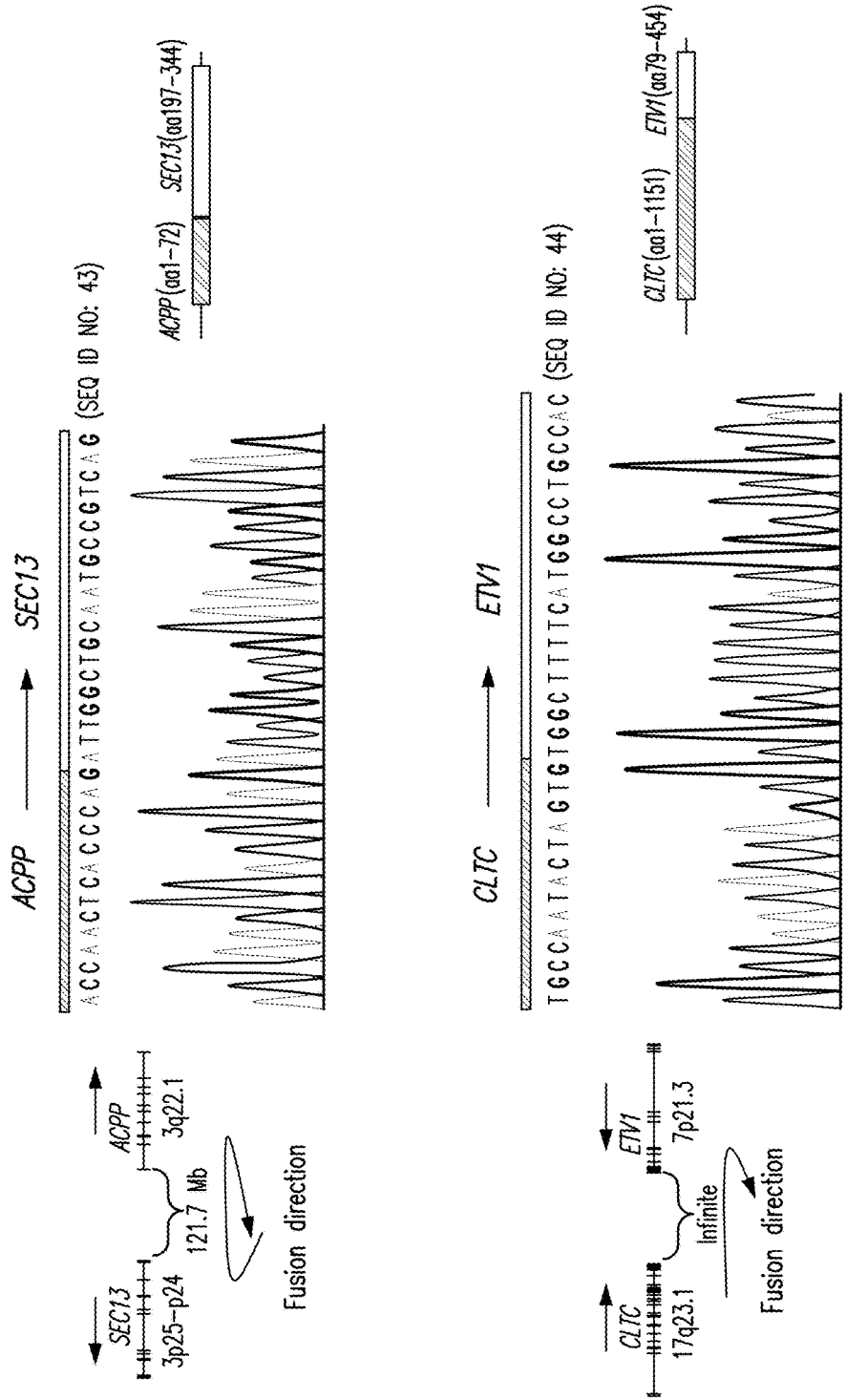

FIG. 16. Schematic diagram of fusion genes. Left panel: Schematic diagram of genome of fusion partners. Genetic locus, distance between partners, transcription direction and fusion direction are indicated. Middle panel: Histogram of Sanger sequencing surrounding the fusion point of each fusion gene (SEQ ID NOs: 40-44). Right panel: Predicted protein products of fusion genes. Blue: Head gene protein; Yellow: frameshift translation; Red: tail.

Figure 17:
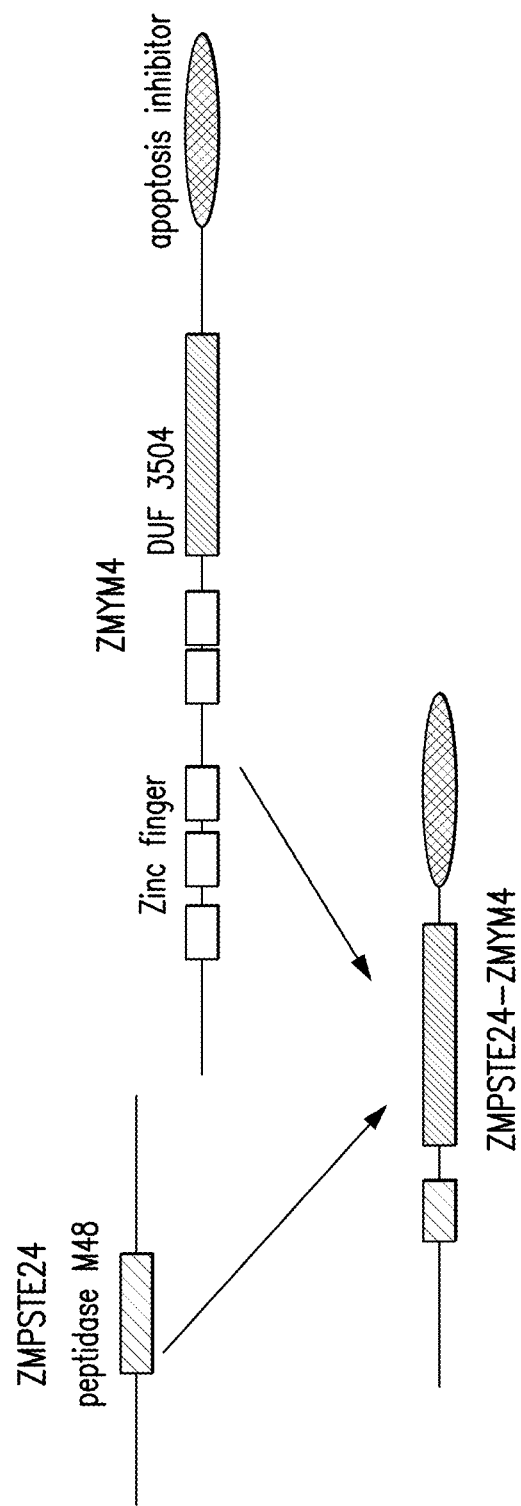

FIG. 17. Schematic diagram of ZMPSTE24-ZMYM5 fusion formation. Functional domains are indicated.

Figure 18:
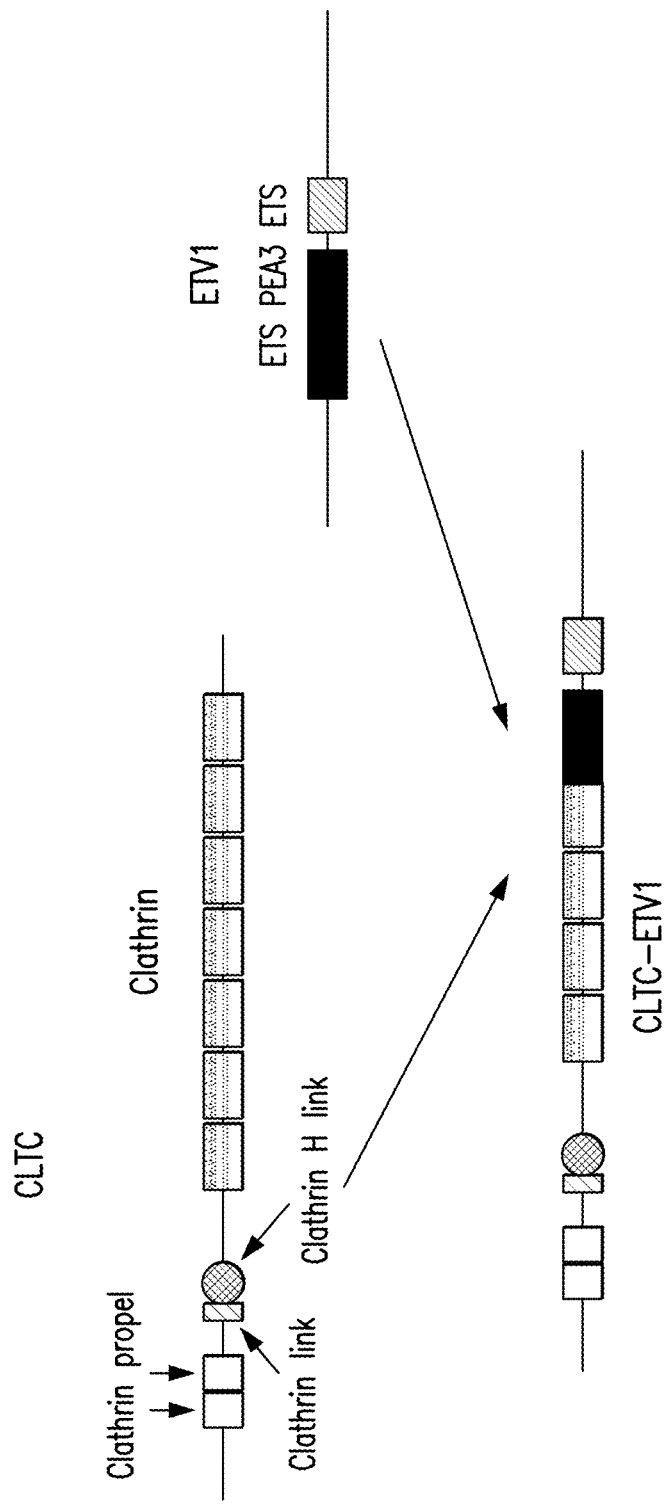

FIG. 18. Schematic diagram of CLTC-ETV1 fusion formation. Functional domains are indicated.

Figure 19:
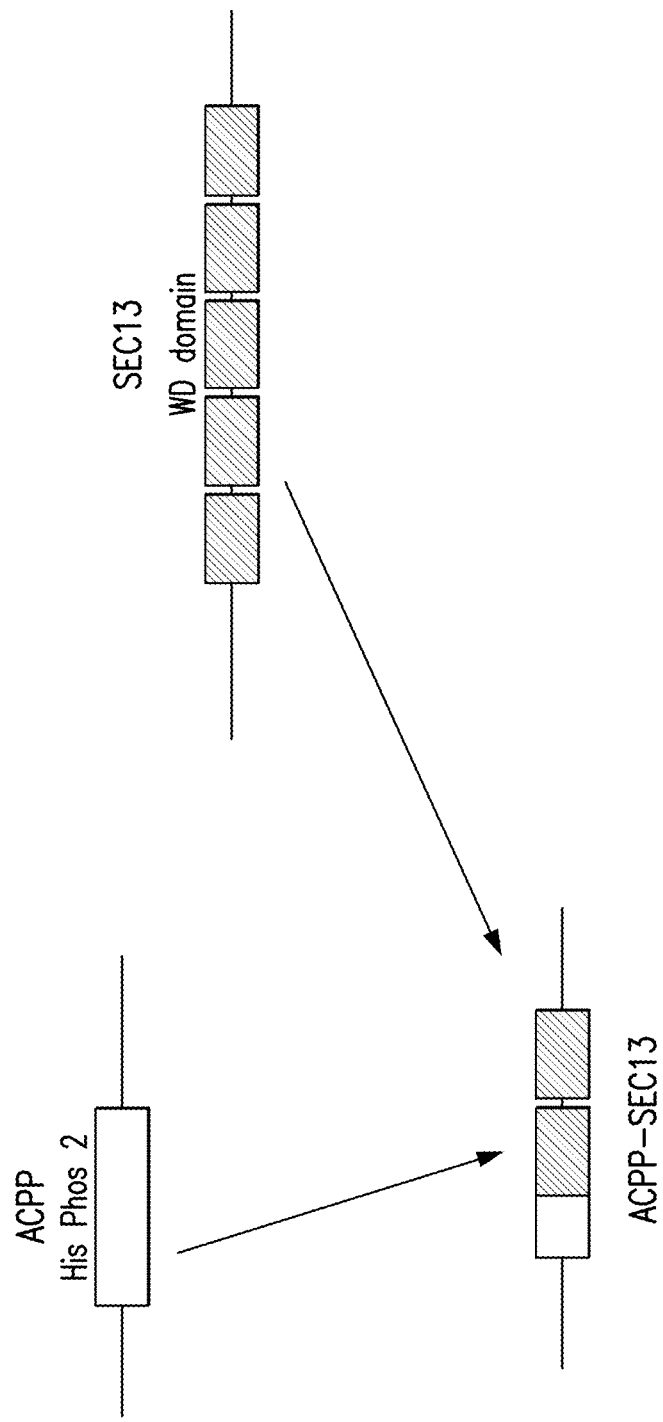

FIG. 19. Schematic diagram of ACPP-SEC13 fusion formation. Functional domains are indicated.

Figure 20:
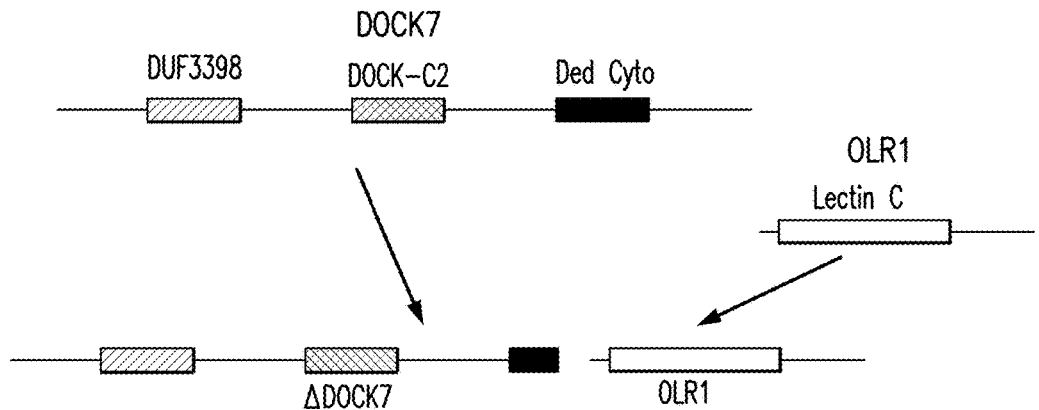

FIG. 20. Schematic diagram of DOCK7-OLR1 fusion formation. Functional domains are indicated.

Figure 21:
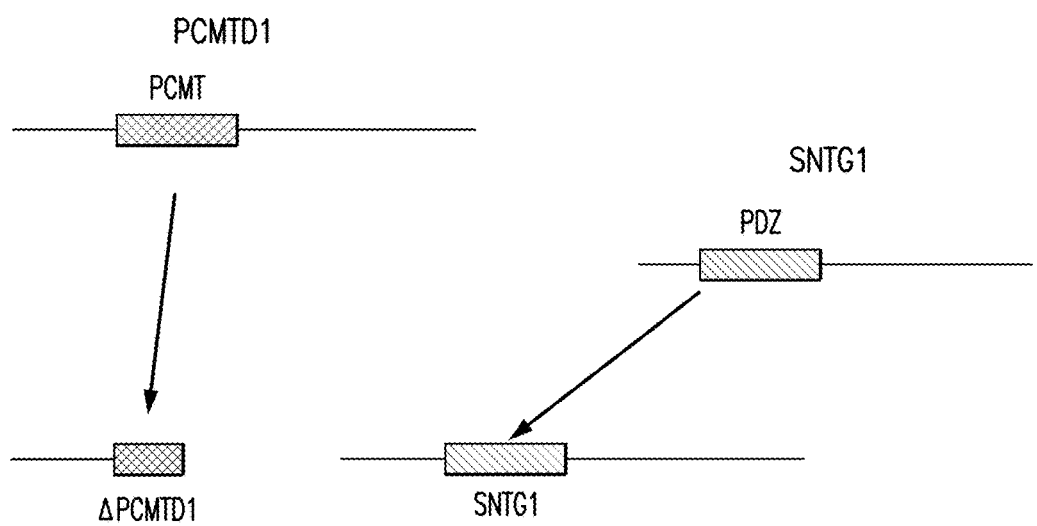
Figure 22A:
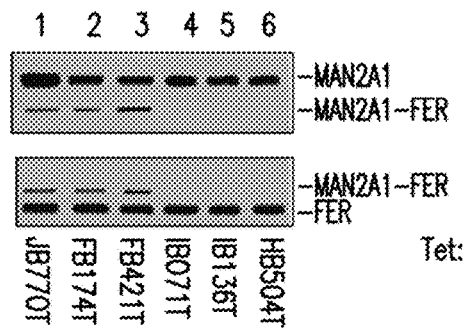
Figure 22B:
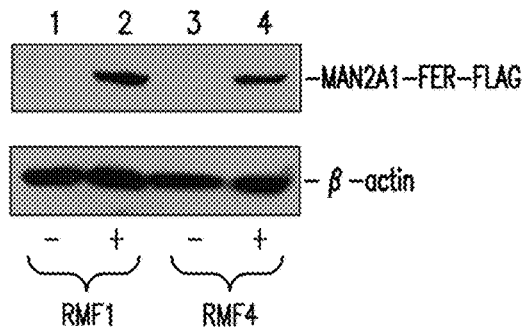
Figure 22C:
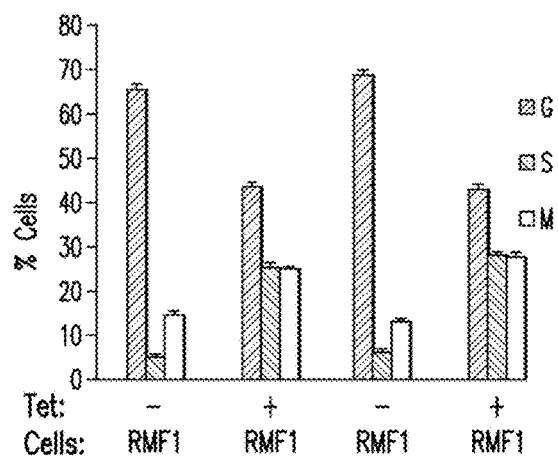
Figure 22D:
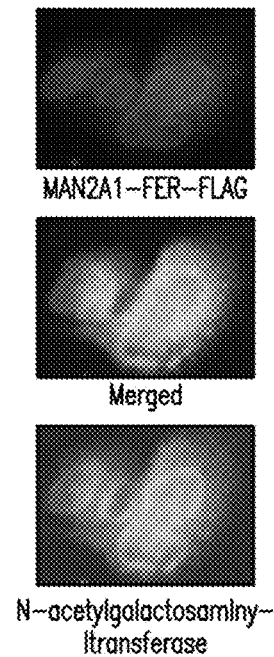
Figure 22E:
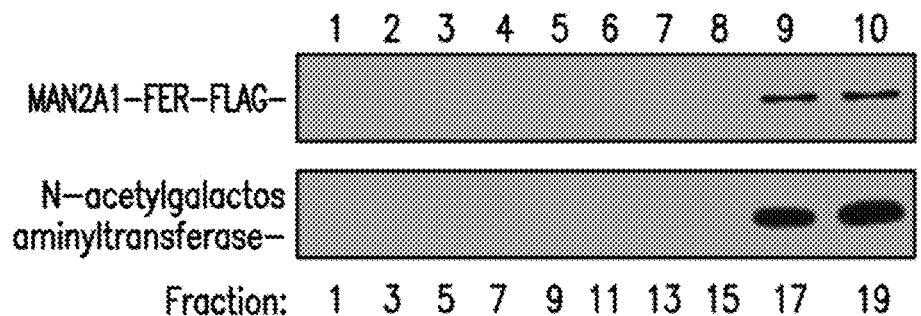
Figure 22F:
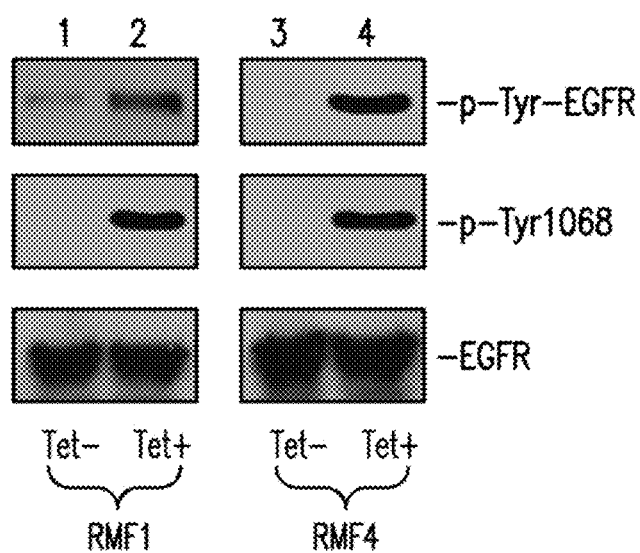

FIG. 21. Schematic diagram of PCMTD1-SNTG1 fusion formation. Functional domains are indicated.

FIG. 22A-F. Pro-growth activity of MAN2A1-FER. (A) Expression of MAN2A1-FER in primary Prostate cancer Samples Immunoblottings were performed using antibodies specific for MAN2A1 (upper panel) or FER (lower panel) on MAN2A1-FER RNA positive (JB770T, FB174T and FB421T) or MAN2A1-FER negative (IB071T, IB136T and HB504T) samples. (B) Expression of MAN2A1-FER-FLAG in RWPE-1 cells. RWPE-1 cells were transfected with pCDNA4-MAN2A1-FER-FLAG/pCDNA6 vectors. Two stable cell lines (RMF1 and RMF4) were selected to demonstrate tetracycline induced expression of MAN2A1-FER-FLAG using anti-FLAG antibodies. (C) Expression of MAN2A1-FER-FLAG accelerates entry to S phase of cell cycle. Cell cycle phases were quantified by flow cytometry analysis of BrdU incorporation and propidium iodine labeling. (D) Co-localization of MAN2A1-FER-FLAG and Golgi resident enzyme N-acetylgalactosaminyltransferase. MAN2A1-FER-FLAG was labeled with FITZ conjugated antibodies specific for FLAG, while N-acetylgalactosaminyltransferase was labeled with Rhodamine-conjugated antibodies specific for N-acetylgalactosaminyltransferase. (E) Co-segregation of MAN2A1-FER-FLAG and Nacetylgalactosaminyltranferase in sucrose gradient ultra-centrifugation. (F) Expression of MAN2A1-FER-FLAG induced tyrosine phosphorylation of EGFR in the absence of EGFR ligand. RMF1 and RMF4 cells were serum starved for 72 hrs, and were subsequently induced with tetracycline (5 µg/ml) for 12 hrs. EGFR was immunoprecipitated with anti-EGFR antibodies, and immunoblotted with anti-phosphotyrosine or anti-pTyr1068 of EGFR or anti-EGFR antibodies.

Figure 23:
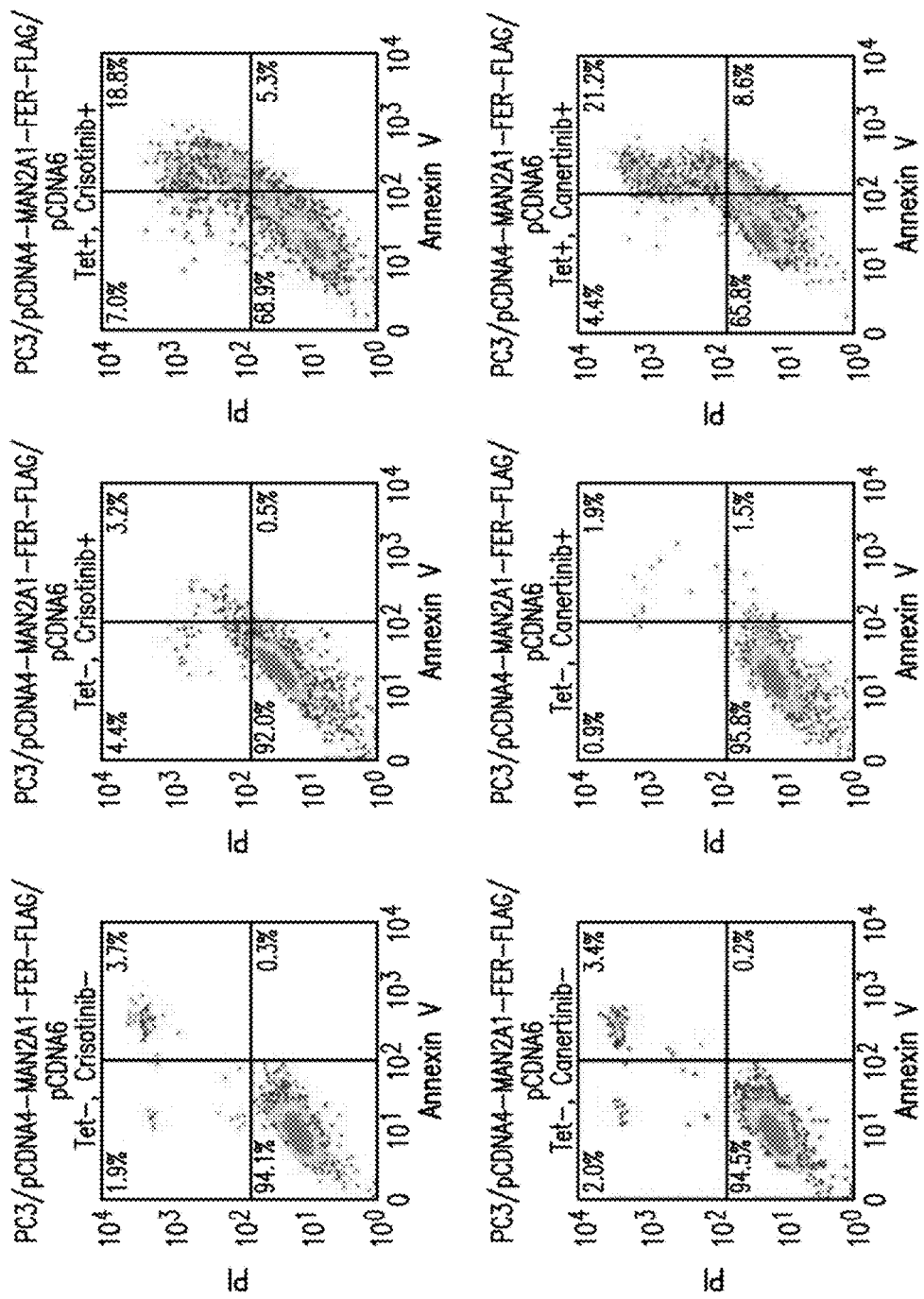

FIG. 23. Specific killing of MAN2A1-FER expressing cells by Crisotinib and Canertinib. Prostate cancer cell line PC3 was transformed with pCDNA4-MAN2A1-FER-FLAG/pCDNA6. Expression of MAN2A1-FER was induced with 5 µg/mL tetracycline. Cells not treated with tetracycline nor any drug were used as background controls. Upper panel: Crisotinib specifically kills cells expressing MAN2A1-FER. Lower panel: Canertinib specifically kills cells expressing MAN2A1-FER.

Figure 24:
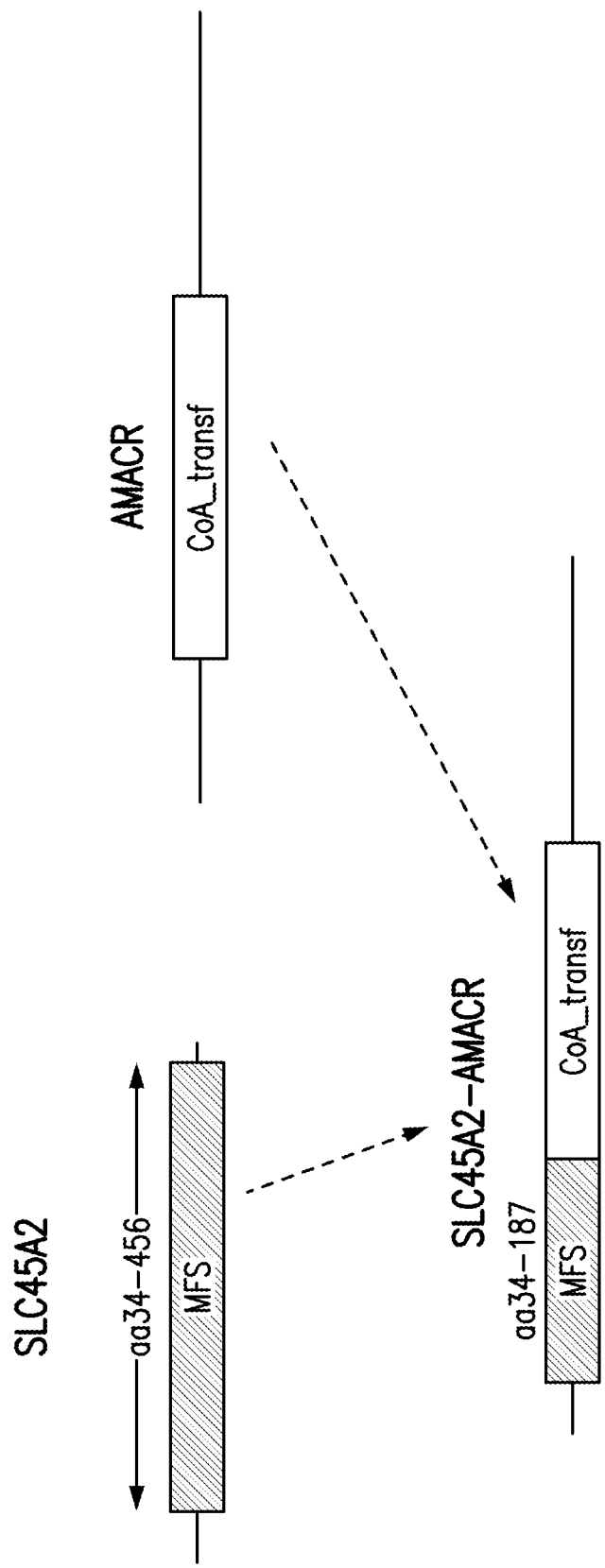

FIG. 24. Schematic diagram of SLC45A2-AMACR chimera protein. Fusion between SLC45A2 and AMACR results in truncation of two-third of (MFS) domain in SLC45A2, but largely retains CoA-transferase domain of AMACR.

FIG. 25A-I. Pro-growth activity of SLC45A2-AMACR. (A) Expression of SLC45A2-AMACR in primary Prostate cancer samples Immunoblottings were performed using antibodies specific for AMACR (upper panel) or SLC45A2 (lower panel) on SLC45A2-AMACR RNA positive (FB174T, HB207T, HB305T and FB238T) or SLC45A2-AMACR negative (6637T, 6647T and 1199T) samples. (B) Expression of SLC45A2-AMACR-FLAG in RWPE-1 cells. RWPE-1 cells were transfected with pCDNA4-SLC45A2-AMACR-FLAG/pCDNA6 vectors. Two stable cell lines (RSLAM#2 and RSLAM#3) were selected to demonstrate tetracycline induced expression of SLC45A2-AMACR-FLAG using anti-FLAG antibodies. (C) SLC45A2-AMACR is primarily located in plasma membrane Immunoblottings were performed on membranous fraction (M) and non-membranous fraction (NM) of RSLAM#2 cells treated without tetracycline (upper panel) or with tetracycline (lower panel), using antibodies specific for AMACR (upper panel) and for FLAG (lower panel). (D) Immunofluorescence staining of AMACR (upper panel) in RSLAM#2 cells treated without tetracycline using antibodies specific for AMACR or of SLC45A2-AMACR-FLAG in RSLAM#2 cells treated with tetracycline using antibodies specific for FLAG. (E) Expression of SLC45A2-AMACR increases cell growth in MTT assays. (F) Expression of SLC45A2-AMACR-FLAG accelerates entry to S phase of cell cycle. Cell cycle phases were quantified by flowcytometry analysis of BrdU incorporation and propidium iodine labeling. (G) Expression of SLC45A2-AMACR increases intracellular levels of PIP2(3, 4). (H) Yeast Two-Hybrid validation of LC45A2-AMACR/SHIP2 interaction. (I) Co-immunoprecipitation of SHIP2 and SLC45A2-AMACR-FLAG in RSLAM#2 cells.

Figure 26:
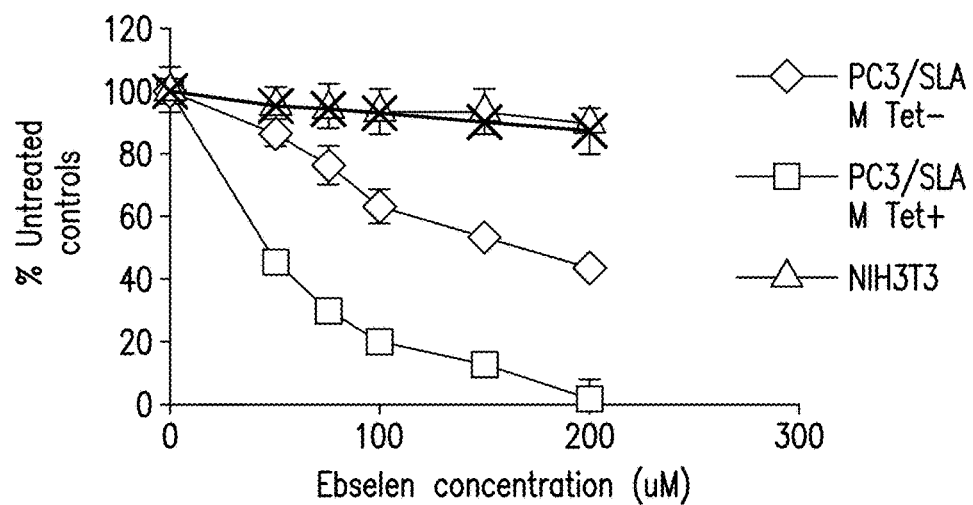

FIG. 26. Ebselen specifically inhibits SLC45A2-AMACR expressing PC3 cells. Untransformed RWPE1, NIH3T3 cells and SLC45A2-AMACR transformed PC3 cells treated with (PC3/SLAM tet+) or without tetracycline (PC3/SLAM tet-) were applied with indicated concentration of Ebselen. Cell growths relative to unapplied controls were examined. IC50 for PC3/SLAM tet+ is 37 µM, while for PC3/SLAM tet- is 173 µM. For NIH3T3 and RWPE1 cells, IC50s are >300 µM.

FIG. 27A-D. PTEN-NOLC1 is localized in the nucleus and promotes cell growth. (A) Immunofluorescence staining of PTEN and PTEN-NOLC1-FLAG. NIH3T3 and PC3 cells were transformed with pCDNA4-Pten-NOLC1-FLAG/pCDNA6 and induced with tetracycline Immunofluorescence staining were performed using antibodies specific for FLAG epitope. Uninduced NIH3T3 cells and PC3 cells transfected with pCMV-Pten immunostained with antibodies specific for Pten were controls. (B) Cell proliferation induced by Pten-NOLC1-FLAG. Cells (2000/well) from (A) were grown for 4 days with tetracycline. Cell numbers were then quantified. Cells not treated with tetracycline were negative controls. (C) Cell cycle analysis of NIH3T3 and PC3 cells transformed with pCDNA4-Pten-NOLC1-FLAG/pCDNA6. (D) Colony formation analysis of NIH3T3 and PC3 cells transformed with pCDNA4-Pten-NOLC1-FLAG/pCDNA6.

Figure 28A:
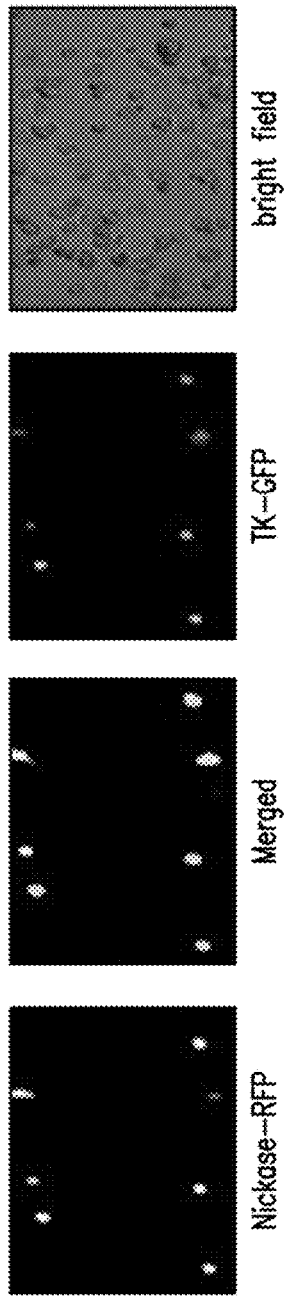
Figure 28B:
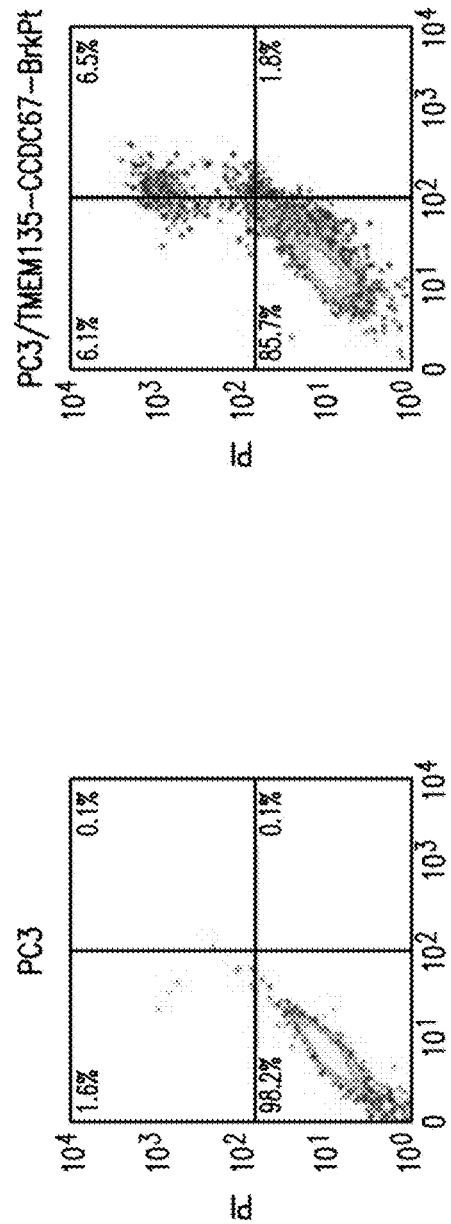

FIG. 28A-B. Genetic therapy targeting at TMEM135-CCDC67 genome breakpoint. (A) Transfection of PC3 cells containing TMEM135-CCDC67 breakpoint with pTMEM135-CCDC67-TK-GFP and pNicKase-RFP-gRNA-TMEM135-CCDC67-BrkPt resulted in integration and expression of TK-GFP. (B) Treatment of ganciclovir of PC3 cells and PC3/TMEM135-CCDC67-BrkPt transfected with pTMEM135-CCDC67-TK-GFP and pNicKase-RFP-gRNA-TMEM135-CCDC67-BrkPt resulted in specific killing of TMEM135-CCDC67 breakpoint containing PC3 cells.

5. DETAILED DESCRIPTION OF THE INVENTION

For clarity and not by way of limitation the detailed description of the invention is divided into the following subsections:
(i) fusion genes;
(ii) fusion gene detection;
(iii) diagnostic methods and methods of treatment; and
(vi) kits.

5.1 Fusion Genes

The term "fusion gene," as used herein, refers to a nucleic acid or protein sequence which combines elements of the recited genes or their RNA transcripts in a manner not found in the wild type/normal nucleic acid or protein sequences. For example, but not by way of limitation, in a fusion gene in the form of genomic DNA, the relative positions of portions of the genomic sequences of the recited genes is altered relative to the wild type/normal sequence (for example, as reflected in the NCBI chromosomal positions or sequences set forth herein). In a fusion gene in the form of mRNA, portions of RNA transcripts arising from both component genes are present (not necessarily in the same register as the wild-type transcript and possibly including portions normally not present in the normal mature transcript). In non-limiting embodiments, such a portion of genomic DNA or mRNA may comprise at least about 10 consecutive nucleotides, or at least about 20 consecutive nucleotides, or at least about 30 consecutive nucleotides, or at least 40 consecutive nucleotides. In a fusion gene in the form of a protein, portions of amino acid sequences arising from both component genes are present (not by way of limitation, at least about 5 consecutive amino acids or at least about 10 amino acids or at least about 20 amino acids or at least about 30 amino acids). In this paragraph, portions arising from both genes, transcripts or proteins do not refer to sequences which may happen to be identical in the wild type forms of both genes (that is to say, the portions are "unshared"). As such, a fusion gene represents, generally speaking, the splicing together or fusion of genomic elements not normally joined together.

The fusion gene TRMT11-GRIK2 is a fusion between the tRNA methyltransferase 11 homolog ("TRMT11") and glutamate receptor, ionotropic, kainate 2 ("GRIK2") genes. The human TRMT11 gene is typically located on chromosome 6q11.1 and the human GRIK2 gene is typically located on chromosome 6q16.3. In certain embodiments, the TRMT11 gene is the human gene having NCBI Gene ID No: 60487, sequence chromosome 6; NC_000006.11 (126307576..126360422) and/or the GRIK2 gene is the human gene having NCBI Gene ID No:2898, sequence chromosome 6; NC_000006.11 (101841584..102517958).

The fusion gene SLC45A2-AMACR is a fusion between the solute carrier family 45, member 2 ("SLC45A2") and alpha-methylacyl-CoA racemase ("AMACR") genes. The human SLC45A2 gene is typically located on human chromosome 5p13.2 and the human AMACR gene is typically located on 5p13. In certain embodiments the SLC45A2 gene is the human gene having NCBI Gene ID No: 51151, sequence chromosome 5; NC_000005.9 (33944721..33984780, complement) and/or the AMACR gene is the human gene having NCBI Gene ID No:23600, sequence chromosome 5; NC_000005.9 (33987091..34008220, complement).

The fusion gene MTOR-TP53BP1 is a fusion between the mechanistic target of rapamycin ("MTOR") and tumor protein p53 binding protein 1 ("TP53BP1") genes. The human MTOR gene is typically located on chromosome 1p36.2 and the human TP53BP1 gene is typically located on chromosome 15q15-q21. In certain embodiments, the MTOR gene is the human gene having NCBI Gene ID No:2475, sequence chromosome 1 NC_000001.10 (11166588..11322614, complement) and/or the TP53BP1 gene is the human gene having NCBI Gene ID No: 7158, sequence chromosome 15; NC_000015.9 (43695262..43802707, complement).

The fusion gene LRRC59-FLJ60017 is a fusion between the leucine rich repeat containing 59 ("LRRC59") gene and the "FLJ60017" nucleic acid. The human LRRC59 gene is typically located on chromosome 17q21.33 and nucleic acid encoding human FLJ60017 is typically located on chromosome 11q12.3. In certain embodiments, the LRRC59 gene is the human gene having NCBI Gene ID No:55379, sequence chromosome 17; NC_000017.10 (48458594..48474914, complement) and/or FLJ60017 has a nucleic acid sequence as set forth in GeneBank AK_296299.

The fusion gene TMEM135-CCDC67 is a fusion between the transmembrane protein 135 ("TMEM135") and coiled-coil domain containing 67 ("CCDC67") genes. The human TMEM135 gene is typically located on chromosome 11q14.2 and the human CCDC67 gene is typically located on chromosome 11q21. In certain embodiments the TMEM135 gene is the human gene having NCBI Gene ID No: 65084, sequence chromosome 11; NC_000011.9 (86748886..87039876) and/or the CCDC67 gene is the human gene having NCBI Gene ID No: 159989, sequence chromosome 11; NC_000011.9 (93063156..93171636).

The fusion gene CCNH-C5orf30 is a fusion between the cyclin H ("CCNH") and chromosome 5 open reading frame 30 ("C5orf30") genes. The human CCNH gene is typically located on chromosome 5q13.3-q14 and the human C5orf30gene is typically located on chromosome 5q21.1. In certain embodiments, the CCNH gene is the human gene having NCBI Gene ID No: 902, sequence chromosome 5; NC_000005.9 (86687310..86708850, complement) and/or the C5orf30gene is the human gene having NCBI Gene ID No: 90355, sequence chromosome 5; NC_000005.9 (102594442..102614361).

The fusion gene KDM4B-AC011523.2 is a fusion between lysine (K)-specific demethylase 4B ("KDM4B") and chromosomal region "AC011523.2". The human KDM4B gene is typically located on chromosome 19p13.3 and the human AC011523.2 region is typically located on chromosome 19q13.4. In certain embodiments the KDM4B gene is the human gene having NCBI Gene ID NO: 23030, sequence chromosome 19; NC_000019.9 (4969123..5153609); and/or the AC011523.2 region comprises a sequence as shown in FIG. 1.

The fusion gene MAN2A1-FER is a fusion between mannosidase, alpha, class 2A, member 1 ("MAN2A1") and (fps/fes related) tyrosine kinase ("FER"). The human MAN2A1 gene is typically located on chromosome 5q21.3 and the human FER gene is typically located on chromosome 5q21. In certain embodiments, the MAN2A1gene is the human gene having NCBI Gene ID NO: 4124, sequence chromosome 5; NC_000005.9 (109025156..109203429) or NC_000005.9 (109034137..109035578); and/or the FER gene is the human gene having NCBI Gene ID NO: 2241, sequence chromosome 5: NC_000005.9 (108083523..108523373).

The fusion gene PTEN-NOLC1 is a fusion between the phosphatase and tensin homolog ("PTEN") and nucleolar and coiled-body phosphoprotein 1 ("NOLC1"). The human PTEN gene is typically located on chromosome 10q23.3 and the human NOLC1 gene is typically located on chromosome 10q24.32. In certain embodiments, the PTEN gene is the human gene having NCBI Gene ID NO: 5728, sequence chromosome 10; NC_000010.11 (87863438..87970345) and/or the NOLC1 gene is the human gene having NCBI Gene ID NO: 9221, sequence chromosome 10; NC_000010.11 (102152176..102163871).

The fusion gene ZMPSTE24-ZMYM4 is a fusion between zinc metallopeptidase STE24 ("ZMPSTE24") and zinc finger, MYM-type 4 ("ZMYM4"). The human ZMPSTE24 is typically located on chromosome 1p34 and the human ZMYM4 gene is typically located on chromosome 1p32-p34. In certain embodiments, the ZMPSTE24 gene is the human gene having NCBI Gene ID NO: 10269, sequence chromosome 1; NC_000001.11 (40258050..40294184) and/or the ZMYM4 gene is the human gene having NCBI Gene ID NO: 9202, sequence chromosome 1; NC_000001.11 (35268850..35421944).

The fusion gene CLTC-ETV1 is a fusion between clathrin, heavy chain (Hc) ("CLTC") and ets variant 1 ("ETV1"). The human CLTC is typically located on chromosome 17q23.1 and the human ETV1 gene is typically located on chromosome 7p21.3. In certain embodiments, the CLTC gene is the human gene having NCBI Gene ID NO: 1213, sequence chromosome 17; NC_000017.11 (59619689..59696956) and/or the ETV1gene is the human gene having NCBI Gene ID NO: 2115, sequence chromosome 7; NC_000007.14 (13891229..13991425, complement).

The fusion gene ACPP-SEC13 is a fusion between acid phosphatase, prostate ("ACPP") and SEC13 homolog ("SEC13"). The human ACPP is typically located on chromosome 3q22.1 and the human SEC13 gene is typically located on chromosome 3p25-p24. In certain embodiments, the ACPP gene is the human gene having NCBI Gene ID NO: 55, sequence chromosome 3; NC_000003.12 (132317367..132368302) and/or the SEC13 gene is the human gene having NCBI Gene ID NO: 6396, sequence chromosome 3; NC_000003.12 (10300929..10321188, complement).

The fusion gene DOCK7-OLR1 is a fusion between dedicator of cytokinesis 7 ("DOCK7") and oxidized low density lipoprotein (lectin-like) receptor 1 ("OLR1"). The human DOCK7 is typically located on chromosome 1p31.3 and the human OLR1 gene is typically located on chromosome 12p13.2-p12.3. In certain embodiments, the DOCK7 gene is the human gene having NCBI Gene ID NO: 85440, sequence chromosome 1; NC_000001.11 (62454726..62688368, complement) and/or the OLR1 gene is the human gene having NCBI Gene ID NO: 4973, sequence chromosome 12; NC_000012.12 (10158300..10172191, complement).

The fusion gene PCMTD1-SNTG1 is a fusion between protein-L-isoaspartate (D-aspartate) O-methyltransferase domain containing 1 ("PCMTD1") and syntrophin, gamma 1 ("SNTG1"). The human PCMTD1 is typically located on chromosome 8q11.23 and the human SNTG1 gene is typically located on chromosome 8q11.21. In certain embodiments, the PCMTD1 gene is the human gene having NCBI Gene ID NO: 115294, sequence chromosome 8; NC_000008.11 (51817575..51899186, complement) and/or the SNTG1gene is the human gene having NCBI Gene ID NO: 54212, sequence chromosome 8; NC_000008.11 (49909789..50794118).

5.2 Fusion Gene Detection

Any of the foregoing fusion genes described above in section 5.1 may be identified by methods known in the art. The fusion genes may be detected by detecting the gene fusion manifested in DNA, RNA or protein. For example, and not by way of limitation, the presence of a fusion gene may be detected by determining the presence of the protein encoded by the fusion gene.

The fusion gene may be detected in a sample of a subject. A "patient" or "subject," as used interchangeably herein, refers to a human or a non-human subject. Non-limiting examples of non-human subjects include non-human primates, dogs, cats, mice, etc.

The subject may or may not be previously diagnosed as having prostate cancer.

In certain non-limiting embodiments, a sample includes, but is not limited to, cells in culture, cell supernatants, cell lysates, serum, blood plasma, biological fluid (e.g., blood, plasma, serum, stool, urine, lymphatic fluid, ascites, ductal lavage, saliva and cerebrospinal fluid) and tissue samples. The source of the sample may be solid tissue (e.g., from a fresh, frozen, and/or preserved organ, tissue sample, biopsy, or aspirate), blood or any blood constituents, bodily fluids (such as, e.g., urine, lymph, cerebral spinal fluid, amniotic fluid, peritoneal fluid or interstitial fluid), or cells from the individual, including circulating cancer cells. In certain non-limiting embodiments, the sample is obtained from a cancer. In certain embodiments, the sample may be a "biopsy sample" or "clinical sample," which are samples derived from a subject. In certain embodiments, the sample includes one or more prostate cancer cells from a subject. In certain embodiments, the one or more fusion genes can be detected in one or more samples obtained from a subject.

In certain non-limiting embodiments, the fusion gene is detected by nucleic acid hybridization analysis.

In certain non-limiting embodiments, the fusion gene is detected by fluorescent in situ hybridization (FISH) analysis.

In certain non-limiting embodiments, the fusion gene is detected by DNA hybridization, such as, but not limited to, Southern blot analysis.

In certain non-limiting embodiments, the fusion gene is detected by RNA hybridization, such as, but not limited to, Northern blot analysis.

In certain non-limiting embodiments, the fusion gene is detected by nucleic acid sequencing analysis.

In certain non-limiting embodiments, the fusion gene is detected by probes present on a DNA array, chip or a microarray.

In certain non-limiting embodiments, the fusion gene is detected by a method comprising Reverse Transcription Polymerase Chain Reaction ("RT-PCR"). In certain embodiments, the fusion gene is detected by a method comprising RT-PCR using the one or more pairs of primers disclosed herein (see Table 3).

In certain non-limiting embodiments, the fusion gene is detected by antibody binding analysis such as, but not limited to, Western Blot analysis and immunohistochemistry.

In certain non-limiting embodiments, where a fusion gene combines genes not typically present on the same chromosome, FISH analysis may demonstrate probes binding to the same chromosome. For example, analysis may focus on the chromosome where one gene normally resides and then hybridization analysis may be performed to determine whether the other gene is present on that chromosome as well.

5.3 Diagnostic Methods and Methods of Treatment

The present invention provides methods for assessing whether a subject having prostate cancer is at increased risk of developing progressive disease, at an increased risk of relapse and/or at an increased risk of rapid relapse. The present invention further provides methods of treating subjects at an increased risk of developing progressive disease, at an increased risk of relapse and/or at an increased risk of rapid relapse.

"Increased risk," as used herein, means at higher risk than subjects lacking one or more of the disclosed fusion genes; in certain non-limiting embodiments, the risk is increased such that progressive prostate cancer occurs in more than 50%, more than 60% or more than 70% of individuals bearing said fusion gene in one or more cells of their prostate cancer.

5.3.1 Diagnostic Methods for Assessing the Risk of Progressive Cancer

The present invention provides for methods of determining whether a subject is at increased risk of manifesting progressive prostate cancer.

In certain non-limiting embodiments, the method of determining whether a subject is at increased risk of manifesting progressive prostate cancer comprises determining whether a sample of the subject contains one or more fusion genes selected from the group consisting of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1, PCMTD1-SNTG1 or a combination thereof, where the presence of one or more fusion genes in the sample is indicative that the subject is at increased risk of manifesting progressive prostate cancer.

In certain embodiments, the method of determining whether a subject is at increased risk of manifesting progressive prostate cancer comprises determining the presence and/or absence of one or more, two or more, three or more, four or more, five or more, six or more, seven or more, eight or more, nine or more, ten or more, eleven or more, twelve or more, thirteen or more, fourteen or more of the fusion genes disclosed herein in a sample of a subject. In certain embodiments, the sample can include one or more prostate cancer cells of a subject.

In certain non-limiting embodiments, the method of determining whether a subject is at increased risk of manifesting progressive prostate cancer comprises determining whether a sample of the subject contains one or more fusion genes selected from the group consisting of TRMT11-GRIK2, SLC45A2-AMACR, PTEN-NOLC1 or MTOR-TP53BP1, where the presence of one or more fusion genes in the sample is indicative that the subject is at increased risk of manifesting progressive prostate cancer.

5.3.2 Diagnostic Methods for Assessing the Risk of Relapse of Prostate Cancer The present invention provides for methods for determining whether a subject is at risk for relapse or rapid relapse of prostate cancer.

In certain non-limiting embodiments, a method of determining whether a subject is at risk for rapid relapse of prostate cancer (as reflected, for example, in a doubling of serum prostate specific antigen (PSA) in less than 4 months), comprises determining the sum of:

{[the vector of whether the fusion gene TMEM135-CCDC67 is present in a tumor cell of the subject] times 0.4127877};

plus

{[the vector of whether the fusion gene KDM4B-AC011523.2 is present in a tumor cell of the subject] times 0.4091903};

plus

{[the vector of whether the fusion gene MAN2A1-FER is present in a tumor cell of the subject] times 0.3879886};

plus

{[the vector of whether the fusion gene CCNH-C5orf30 is present in a tumor cell of the subject] times (−2.0193237)};

plus

{[the vector of whether the fusion gene TRMT11-GRIK2 is present in a tumor cell of the subject] times (−2.3301892)};

plus

{[the vector of whether the fusion gene SLC45A2-AMACR is present in a tumor cell of the subject] times (−2.1499750)};

plus

{[the vector of whether the fusion gene MTOR-TP53BP1 is present in a tumor cell of the subject] times (−2.1140216)};

plus

{[the vector of whether the fusion gene LRRC59-FLJ60017 is present in a tumor cell of the subject] times (−0.8611482)};

where if the sum of the above is less than 0.0716, then the subject is at increased risk for exhibiting rapid relapse of prostate cancer. In the above, where the particular fusion gene is present, the value of the vector is [+1] and where the particular fusion gene is absent, the value of the vector is [0].

In certain non-limiting embodiments, a method of determining whether a subject is at risk for relapse of prostate cancer comprises determining the sum of:

{[the vector of whether the fusion gene TMEM135-CCDC67 is present in a tumor cell of the subject] times (−0.01752496)};

plus

{[the vector of whether the fusion gene KDM4B-AC011523.2 is present in a tumor cell of the subject] times (−0.16638222)};

plus

{[the vector of whether the fusion gene MAN2A1-FER is present in a tumor cell of the subject] times 0.67180725};

plus

{[the vector of whether the fusion gene CCNH-C5orf30 is present in a tumor cell of the subject] times (−0.62367777)};

plus

{[the vector of whether the fusion gene TRMT11-GRIK2 is present in a tumor cell of the subject] times (−2.44068688)};

plus

{[the vector of whether the fusion gene SLC45A2-AMACR is present in a tumor cell of the subject] times (−2.18012958)};

plus

{[the vector of whether the fusion gene MTOR-TP53BP1 is present in a tumor cell of the subject] times (−1.79668048)};

plus

{[the vector of whether the fusion gene LRRC59-FLJ60017 is present in a tumor cell of the subject] times (−1.75487809)};

where if the sum of the above is less than 0.056, then the subject is at increased risk for exhibiting relapse of prostate cancer. In the above, where the particular fusion gene is present, the value of the vector is [+1] and where the particular fusion gene is absent, the value of the vector is [0].

In certain non-limiting embodiments, the method of determining whether a subject is at increased risk of relapse of prostate cancer comprises determining whether a sample of the subject contains one or more fusion genes selected from the group consisting of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1, PCMTD1-SNTG1 or a combination thereof, where the presence of one or more fusion genes in the sample is indicative that the subject is at increased risk of relapse, using the following formula:

$$Z=-0.0325*X+1.6219*Y \quad \quad \text{[Formula 1]}$$

where X % is the Nomogram score of the five-year progression free probability after surgery (X can be between 0 and 100) and Y is the presence of any of the fusion genes (where Y=0 if no fusion genes are present, and Y=+1 if one or more fusion genes are present). In the above, when $Z>=-1.9$, then the patient is at risk for exhibiting relapse of prostate cancer and when $Z<-1.9$, then the patient is not at risk for exhibiting relapse of prostate cancer.

5.3.3 Methods of Treatment

The invention further provides methods for treating a subject having an increased risk for progressive prostate cancer, prostate cancer relapse or prostate cancer rapid relapse.

In certain embodiments, the method of treating a subject comprises determining if the subject is at an increased risk for progressive prostate cancer by determining the presence of one or more fusion genes selected from the group consisting of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1, PCMTD1-SNTG1 or a combination thereof in a sample of the subject, where if one or more fusion genes are present in the sample so that the subject is at risk then treating the subject to produce an anti-cancer effect. In certain embodiments, the method can include determining the presence or absence of one or more, two or more, three or more, four or more, five or more, six or more, seven or more, eight or more or all nine of the fusion genes disclosed herein.

An "anti-cancer effect" refers to one or more of a reduction in aggregate cancer cell mass, a reduction in cancer cell growth rate, a reduction in cancer progression, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse), a response with a later relapse or progression-free survival in a patient diagnosed with cancer.

In certain embodiments, the method of treating a subject comprises determining if the subject is at an increased risk for progressive prostate cancer by determining the presence of one or more fusion genes selected from the group consisting TRMT11-GRIK2, SLC45A2-AMACR, PTEN-NOLC1 or MTOR-TP53BP1 or a combination thereof in a sample of the subject, where if one or more fusion genes are detected in the sample so that the subject is at risk then treating the subject to produce an anti-cancer effect.

In certain embodiments, the method of treating a subject comprises determining if a patient is at an increased risk for prostate cancer relapse or rapid relapse as described above in section 5.3, where if the subject is at increased risk for prostate cancer rapid relapse then treating the subject to produce an anti-cancer effect in the subject.

In certain embodiments, the method of treating a subject comprises determining if the subject is at an increased risk for progressive prostate cancer, prostate cancer relapse or rapid relapse as described above, where if the subject is at increased risk for progressive prostate cancer, prostate cancer relapse or rapid relapse, then administering to the subject a therapeutically effective amount of an inhibitor. In certain embodiments, the inhibitor can be administered to produce an anti-cancer effect in a subject.

A "therapeutically effective amount" refers to an amount that is able to achieve one or more of the following: an anti-cancer effect, prolongation of survival and/or prolongation of period until relapse.

In certain embodiments, the method of treating a subject is directed to inhibiting the fusion gene and/or inhibiting the fusion gene product, e.g., the protein and/or RNA encoded by the fusion gene.

Examples of inhibitors include, but are not limited to, compounds, molecules, chemicals, polypeptides and proteins that inhibit and/or reduce the expression and/or activity of the protein encoded by a fusion gene. Alternatively or additionally, the inhibitor can include compounds, molecules, chemicals, polypeptides and proteins that inhibit and/or reduce the expression and/or activity of one or more downstream targets of the fusion gene.

Additional non-limiting examples of inhibitors include ribozymes, antisense oligonucleotides, shRNA molecules and siRNA molecules that specifically inhibit or reduce the expression and/or activity of the fusion gene and/or inhibit or reduce the expression and/or activity of one or more downstream targets of the fusion gene. One non-limiting example of an inhibitor comprises an antisense, shRNA or siRNA nucleic acid sequence homologous to at least a portion of the fusion gene sequence, wherein the homology of the portion relative to the fusion gene sequence is at least about 75 or at least about 80 or at least about 85 or at least about 90 or at least about 95 or at least about 98 percent, where percent homology can be determined by, for example, BLAST or FASTA software. In certain embodiments, the antisense, the shRNA or siRNA nucleic acid sequence can be homologous to the sequence at the "junction fragment" that encompasses the boundary between the spliced genes of the fusion gene. Non-limiting examples of siRNAs homologous to the junction fragment sequences of the disclosed fusion genes are shown in Table 1.

In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. Antisense, shRNA or siRNA molecules may comprise DNA or atypical or non-naturally occurring residues, for example, but not limited to, phosphorothioate residues and locked nucleic acids.

In certain embodiments, an inhibitor can include an antibody, or a derivative thereof, that specifically binds to and inhibits and/or reduces the expression and/or activity of the protein that is encoded by the fusion gene, e.g., an antagonistic antibody. Alternatively or additionally, an inhibitor can include an antibody, or derivative thereof, that specifically binds to and inhibits and/or reduces the expression and/or activity of one or more downstream targets of the fusion gene. The phrase "specifically binds" refers to binding of, for example, an antibody to an epitope or antigen or antigenic determinant in such a manner that binding can be displaced or competed with a second preparation of identical or similar epitope, antigen or antigenic determinant. Non-limiting examples of antibodies, and derivatives thereof, that can be used in the disclosed methods include polyclonal or monoclonal antibodies, chimeric, human, humanized, primatized (CDR-grafted), veneered or single-chain antibodies, phase produced antibodies (e.g., from phage display libraries), as well as functional binding fragments of antibodies. Antibody binding fragments, or portions thereof, include, but are not limited to, Fv, Fab, Fab' and F(ab')$_2$. Such fragments can be produced by enzymatic cleavage or by recombinant techniques.

In certain embodiments, where the protein encoded by the fusion gene detected in the sample of the subject exhibits kinase activity, the method of treating a subject can include administering a therapeutically effective amount of an inhibitor to the subject that inhibits and/or reduces the kinase activity of the protein encoded by the fusion gene, i.e., a kinase inhibitor. Non-limiting examples of kinase inhibitors include afatinib, alectinib, axitinib, bevacizumab, bosutinib, cetuximab, crizotinib, dasatinib, erlotinib, fostamatinib, gefitinib, GSK1838705A, ibrutinib, imatinib, lapatinib, lenvatinib, mubritinib, nilotinib, panitumumab, pazopanib, pegaptanib, ranibizumab, ruxolitinib, sorafenib, sunitinib, su6656, trastuzumab, tofacitinib, vandetanib and vemurafenib. For example, and not by way of limitation, if the protein encoded by the fusion gene detected in a sample of the subject exhibits tyrosine kinase activity, a therapeutically effective amount of a tyrosine kinase inhibitor can be administered to the subject.

In certain embodiments, a method of treating a subject can comprise determining if the subject is at an increased risk for progressive prostate cancer by determining the presence of MAN2A1-FER in a sample of the subject, where if the MAN2A1-FER fusion gene is present in the sample, then treating the subject with a therapeutically effective amount of a FER inhibitor. Non-limiting examples of FER inhibitors include crisotinib, TAE684, WZ-4-49-8 and WZ-4-49-10. In particular non-limiting embodiments, the FER inhibitor can be derived from diaminopyrimidine or pyrazologyrididine compounds.

Further non-limiting examples of FER inhibitors are disclosed in PCT Application No. WO 2009/019708, the content of which is hereby incorporated by reference in its entirety. In certain embodiments, the FER inhibitor can include tyrosine kinase inhibitors and ALK inhibitors as FER exhibits high sequence similarity to ALK. In certain embodiments, the FER inhibitor is an antibody that reduces and/or inhibits the expression and/or activity of the MAN2A1-FER protein. In certain embodiments, the FER inhibitor comprises an siRNA targeting the MAN2A1-FER fusion gene or the juncture sequence of the MAN2A1-FER fusion gene. A non-limiting example of an siRNA sequence targeting the MAN2A1-FER fusion gene is shown in Table 1.

Alternatively or additionally, the method of treating a subject expressing the MAN2A1-FER fusion gene can comprise administering to the subject a compound that reduces and/or inhibits the activity and/or expression of one or more downstream targets of the MAN2A1-FER fusion gene. For example, and not by way of limitation, the method can include the inhibition of the EGFR-RAS-BRAF-MEK signaling pathway. Non-limiting examples of compounds that inhibit EGFR activity include erlotinib, cetuximab, gefitinib, bevacizumab, panitumumab and bortezomib. A non-limiting example of a compound that inhibits BRAP activity includes RAF265. Non-limiting examples of compounds that inhibits MEK activity includes binimetinib, vemurafenib, PD-325901, selumetinib and trametinib. Additional non-limiting examples of compounds that inhibit the EGFR-RAS-BRAF-MEK signaling pathway include TAK-733, Honokiol, AZD8330, PD318088, BIX 02188, pimasertib, SL-327, BIX 02189, PD98059, MEK162, PD184352 and U0126-EtOH.

In certain embodiments, a method of treating a subject can comprise determining if the subject is at an increased risk for progressive prostate cancer by determining the presence of SLC45A2-AMACR in a sample of the subject, where if the SLC45A2-AMACR fusion gene is present in the sample, then treating the subject with a therapeutically effective amount of a racemase inhibitor and/or an AMACR inhibitor. A non-limiting example of a racemase and/or AMACR inhibitors includes ebselen, 2-(2,5-dihydroxy-4-methylphenyl)-5-methyl benzene-1,4-diol (DMPMB), 2-methylsulfanyl-7,9-dihydro-3H-purine-6,8-dithione (MSDTP), 2,5-di (pyrazol-1-yl)benzene-1,4-diol (DPZBD), Rose Bengal, Congo Red, 3,5-di(pyridin-4-yl)-1,2,4-thiadiazole (DPTD), ebselen oxide and 3,7,12-trihydroxycholestanoyl Coenzyme A (THCA-CoA). In particular non-limiting embodiments, the racemase inhibitor can be a N-methylthiocarbamate. Further non-limiting examples of AMACR inhibitors are disclosed in Wilson et al., Mol. Cancer Ther. (2011), 10(5): 825-838, the content of which is hereby incorporated by reference in its entirety.

In certain embodiments, the method of treating a subject comprises determining if the subject is at an increased risk for progressive prostate cancer, prostate cancer relapse or rapid relapse as described above, where if the subject is at increased risk for progressive prostate cancer, prostate cancer relapse or rapid relapse, then administering a therapeutically effective amount of an anti-cancer agent. An anti-cancer agent can be any molecule, compound chemical or composition that has an anti-cancer effect. Anti-cancer agents include, but are not limited to, chemotherapeutic agents, radiotherapeutic agents, cytokines, anti-angiogenic agents, apoptosis-inducing agents or anti-cancer immunotoxins. In certain non-limiting embodiments, an inhibitor can be administered in combination with one or more anti-cancer agents. "In combination with," as used herein, means that the inhibitor and the one or more anti-cancer agents are administered to a subject as part of a treatment regimen or plan. This term does not require that the inhibitor and/or kinase inhibitor and one or more anti-cancer agents are physically combined prior to administration nor that they be administered over the same time frame. Non-limiting examples of anti-cancer agents include Abiraterone Acetate, Bicalutamide, Cabazitaxel, Casodex (Bicalutamide), Degarelix, Docetaxel, Enzalutamide, Goserelin Acetate, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Mitoxantrone Hydrochloride, Prednisone, Provenge (Sipuleucel-T), Radium 223 Dichloride, Sipuleucel-T, Taxotere (Docetaxel), Viadur (Leuprolide Acetate), Xofigo (Radium 223 Dichloride), Xtandi (Enzalutamide), Zoladex (Goserelin Acetate) and Zytiga (Abiraterone Acetate).

In certain embodiments, the method of treating a subject comprises determining if the subject is at an increased risk for progressive prostate cancer, prostate cancer relapse or rapid relapse as described above, where if the subject is at increased risk for progressive prostate cancer, prostate cancer relapse or rapid relapse, then performing one or more of cryotherapy, radiation therapy, chemotherapy, hormone therapy, biologic therapy, bisphosphonate therapy, high-intensity focused ultrasound, frequent monitoring, frequent prostate-specific antigen (PSA) checks and radical prostatectomy. A non-limiting example of a biologic therapeutic is Sipuleucel-T. Bisphosphonate therapy includes, but is not limited to, clodronate or zoledronate. In certain embodiments, these methods can be used to produce an anti-cancer effect in a subject.

Hormone therapy can include one or more of orchiectomy and the administration of luteinizing hormone-releasing hormone (LHRH) analogs and/or agonists, LHRH antagonists, anti-androgens or androgen-suppressing drugs. Non-limiting examples of LHRH analogs and/or agonists include leuprolide, goserelin and buserelin. Non-limiting examples of LHRH antagonists include abarelix, cetrorelix, ganirelix and degarelix. Anti-androgen drugs include, but are not limited to, flutamide, bicalutamide, enzalutamide and nilutamide. Non-limiting examples of androgen-suppressing drugs include estrogens, ketoconazole and aminoglutethimide. Frequent monitoring can include PSA blood tests, digital rectal exams, ultrasounds and/or transrectal ultrasound-guided prostate biopsies at regular intervals, e.g., at about 3 to about 6 month intervals, to monitor the status of the prostate cancer. Radical prostatectomy is a surgical procedure that involves the removal of the entire prostate gland and some surrounding tissue. Prostatectomies can be performed by open surgery or it may be performed by laparoscopic surgery.

In certain embodiments, the method of treating a subject comprises determining if a subject is at an increased risk for progressive prostate cancer by determining the presence of one or more fusion genes selected from the group consisting of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30 ZMPSTE24-ZMYM4, CLTC-ETV1, ACPP-SEC13, DOCK7-OLR1, PCMTD1-SNTG1 or a combination thereof in a sample of the subject, where if one or more fusion genes are detected in the sample then performing a targeted genome editing technique on one or more prostate cancer cells within the subject.

In certain embodiments, the method of treating a subject comprises determining if a patient is at an increased risk for prostate cancer relapse or rapid relapse as described above in section 5.3, where if the subject is at increased risk for prostate cancer relapse or rapid relapse then performing a targeted genome editing technique on one or more prostate cancer cells within the subject.

Genome editing is a method in which endogenous chromosomal sequences present in one or more cells within a subject, can be edited, e.g., modified, using targeted endonucleases and single-stranded nucleic acids. The genome editing method can result in the insertion of a nucleic acid sequence at a specific region within the genome, the excision of a specific sequence from the genome and/or the replacement of a specific genomic sequence with a new nucleic acid sequence. For example, and not by way of limitation, the genome editing method can include the use of a guide RNA (gRNA), including protospacer adjacent motifs (PAMs), complementary to a specific sequence within a genome, e.g., a chromosomal breakpoint associated with a fusion gene, to guide a nuclease, e.g., an endonuclease, to the specific genomic sequence. A non-limiting example of an endonuclease includes CRISPR associated protein 9 (Cas9). The endonuclease can result in the cleavage of the targeted genome sequence and allow modification of the genome at the cleavage site through nonhomologous end joining (NHEJ) or homologous recombination. A non-limiting example of genome editing method is disclosed in PCT Application No. WO 2014/093701, the contents of which is hereby incorporated by reference in its entirety.

In certain embodiments, the genome editing method can be used to target specific chromosomal breakpoints of a fusion gene present in prostate cancer cells. As normal, non-cancerous, prostate cells do not contain the fusion gene, and therefore do not contain the chromosomal breakpoint associated with the fusion gene, prostate cancer cells can be specifically targeted using this genome editing method. For example, and not by way of limitation, genome editing can be used to promote homologous recombination at a chromosomal breakpoint of a fusion gene in one or more cells of a subject to insert a nucleic acid sequence encoding the Herpes Simplex Virus 1 (HSV-1) thymidine kinase at the chromosomal breakpoint. In certain non-limiting embodiments, the HSV-1 thymidine kinase nucleic acid sequence lacks a promoter and requires integration into the genome for expression. In certain embodiments, a therapeutically effective amount of the guanine derivative, ganciclovir, or its oral homolog, valganciclovir, can be administered to a subject expressing HSV-1 thymidine kinase. HSV-1 thymidine kinase can phosphorylate and convert ganciclovir and/or valganciclovir into the triphosphate forms of ganciclovir and/or valganciclovir in the one or more cells of a subject. The triphosphate form of ganciclovir and/or valganciclovir is as competitive inhibitor of deoxyguanosine triphosphate (dGTP) and is a poor substrate of DNA elongation, and can result in the inhibition of DNA synthesis. The inhibition of DNA synthesis, in turn, can result in the reduction and/or inhibition of growth and/or survival of prostate cancer cells that contain the targeted chromosomal breakpoint and the integrated Herpes Simplex Virus 1 (HSV-1) thymidine kinase nucleic acid sequence. This genome editing method can be used to produce an anti-cancer effect in a subject that has been determined to have an increased risk for progressive prostate cancer, prostate cancer relapse or rapid relapse.

TABLE 1 siRNA sequences.

MAN2A1-FER

```
                 MAN2A1                         FER
GCAAATACTATTTCAGAAACAGCCTATGAGGGAAATTTTGGTGAAGTATATAAGGGCA
CA (SEQ ID NO: 1)
siRNA sequence for MAN2A1-FER:
Sense Strand:      5' RCrArGrCrCrUrArUrGrArGrGrGrArArArUrUrUrGrGrUGA (SEQ ID
                      NO: 2)
Antisense Strand:  5' RUrCrArCrCrArArArUrUrUrCrCrCrUrCrArUrArGrGrCrUrGrUrU
                      (SEQ ID NO: 3)
```

TABLE 1-continued siRNA sequences.

SLC45A2-AMACR

```
              SLC45A2             AMACR
TCCACTACCATGCCCTCTTCACAGGTGTCATGGAGAAACTCCAGCTGGGCCCAGAGA
(SEQ ID NO: 4)
```
siRNA sequence for SLC45A2-AMACR:
Sense Strand: 5' RUrGrCrCrUrCrUrUrCrArCrArGrGrUrGrUrCrArUrGrGAG (SEQ ID NO: 5)
Antisense Strand: 5' RCrUrCrCrArUrGrArCrArCrCrUrGrUrGrArArGrArGrGrGrCrArUG (SEQ ID NO: 6)

MTOR-TP53BP1

```
              MTOR              TP53BP1
TGTCAGAATCCAAGTCAAGTCAGGATTCCTTGTTCTGGGAATGTCAGTGGAATCTGCT
CCTGC (SEQ ID NO: 7)
```
siRNA sequence for MTOR-TP53BP1:
Sense Strand: 5' RGrUrCrArGrArUrUrCrCrUrUrGrUrUrCrUrGrGrGrArATG (SEQ ID NO: 8)
Antisense Strand: 5' RCrArUrUrCrCrCrArGrArArCrArArGrGrArArUrCrCrUrGrArCrUrU (SEQ ID NO: 9)

TMEM135-CCDC67

```
         TMEM135              CCDC67
TTTTAAGACTCACCAAGGGCAAATAAGAAGCCAACTCCAACAGGTGGAAGAGTACCA
(SEQ ID NO: 10)
```
siRNA sequence for TMEM135-CCDC67:
Sense Strand: 5' RGrArCrUrCrArCrCrArArGrGrGrCrArArArUrArArGrArAGC (SEQ ID NO: 11)
Antisense Strand: 5' RGrCrUrUrCrUrUrArUrUrUrGrCrCrCrUrUrGrGrUrGrArGrUrCrUrU (SEQ ID NO: 12)

CCNH-C5orf30

```
           CCNH              C5ORF30
TGTCACAGTTACTAGATATAATGAAAATACCTGGAGTAGAACAGAAAAATTATTATGT
CT (SEQ ID NO: 13)
```
siRNA sequence for CCNH-C5orf30:
Sense Strand: 5' RArUrGrArArArArUrArCrCrUrGrGrArGrUrArGrArArCrAGA (SEQ ID NO: 14)
Antisense Strand: 5' RUrCrUrGrUrUrCrUrArCrUrCrCrArGrGrUrArUrUrUrUrCrArUrUrA (SEQ ID NO: 15)

KDM4B-AC011523.2

```
           KDM4B                   AC011523.2
AACTACCTGCACTTTGGGGAGCCTAAGTCCTGGACAGTAAGCAAGCCTGGATCTGAGA
GA (SEQ ID NO: 16)
```
siRNA sequence for KDM4-AC011523.2:
Sense Strand: 5' RGrArGrCrCrUrArArGrUrCrCrUrGrGrArCrArGrUrArArGCA (SEQ ID NO: 17)
Antisense Strand: 5' RUrGrCrUrUrArCrUrGrUrCrCrArGrGrArCrUrUrArGrGrCrUrCrCrC (SEQ ID NO: 18)

TRMT11-GRIK2

```
            TRMT11                    GRIK2
AGCATCTGGAGTTCCGCCTGCCGGTGGTATTTTTGAATATGTGGAATCTGGCCCAATG
GGAGCTG (SEQ ID NO: 19)
```
siRNA sequence for TRMT11-GRIK2:
Sense Strand: 5' RCrCrGrCrCrUrGrCrCrGrGrUrGrGrUrArUrUrUrUrUrGrAAT (SEQ ID NO: 20)
Antisense Strand: 5' RArUrUrCrArArArArUrArCrCrArCrCrGrGrCrArGrGrCrGrGrArA (SEQ ID NO: 21)

LRRC59-FLJ60017

```
            LRRC69                    FLJ60017
CTGCTTGGATGAGAAGCAGTGTAAGCAGTGTGCAAACAAGGTGACTGGAAGCACCTG
CTCAATGGCTG (SEQ ID NO: 22)
```
siRNA sequence for LRRC59-FLJ60017:
Sense Strand: 5' RArCrArArGrGrUrGrArCrUrGrGrArArGrCrArCrCrUrGrCTC (SEQ ID NO: 23)
Antisense Strand: 5' RGrArGrCrArGrGrUrGrCrUrUrCrCrArGrUrCrArCrCrUrUrGrUrUrU (SEQ ID NO: 24)

TABLE 1-continued siRNA sequences.

PTEN-NOLC1

```
           PTEN                          NOLC1
AAGCCAACCGATACTTTTCTCCAAATTTTAAGACACAGCAGGATGCCAATGCCTCTTCCCTCTTA
GAC (SEQ ID NO: 25)
siRNA sequence for PTEN-NOLC1:
Sense Strand:         5' RCrUrCrCrArArArUrUrUrArArGrArCrArCrAGrCrArGGA
                         (SEQ ID NO: 26)
Antisense             5' RUrCrCrUrGrCrUrGrUrGrUrCrUrUrArArArUrUrUrGrGrAr
Strand:                  GrArA (SEQ ID NO: 27)
```

Head gene is in highlighted in green and tail gene in yellow. Targeted sequences are underlined and bolded.

5.4 Kits

The present invention further provides kits for detecting one or more fusion genes disclosed herein and/or for carrying any one of the above-listed detection and therapeutic methods.

Types of kits include, but are not limited to, packaged fusion gene-specific probe and primer sets (e.g., TaqMan probe/primer sets), arrays/microarrays, antibodies, which further contain one or more probes, primers, or other reagents for detecting one or more fusion genes of the present invention.

In certain non-limiting embodiments, a kit is provided comprising one or more nucleic acid primers or probes and/or antibody probes for use in carrying out any of the above-listed methods. Said probes may be detectably labeled, for example with a biotin, colorimetric, fluorescent or radioactive marker. A nucleic acid primer may be provided as part of a pair, for example for use in polymerase chain reaction. In certain non-limiting embodiments, a nucleic acid primer may be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length. An nucleic acid probe may be an oligonucleotide probe and/or a probe suitable for FISH analysis. In specific non-limiting embodiments, the kit comprises primers and/or probes for analysis of at least two, at least three, at least four, at least five, six, seven, eight, nine, ten, eleven, twelve, thirteen, fourteen of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1.

In certain non-limiting embodiments, the nucleic acid primers and/or probes may be immobilized on a solid surface, substrate or support, for example, on a nucleic acid microarray, wherein the position of each primer and/or probe bound to the solid surface or support is known and identifiable. The nucleic acid primers and/or probes can be affixed to a substrate, such as glass, plastic, paper, nylon or other type of membrane, filter, chip, bead, or any other suitable solid support. The nucleic acid primers and/or probes can be synthesized directly on the substrate, or synthesized separate from the substrate and then affixed to the substrate. The arrays can be prepared using known methods.

In non-limiting embodiments, a kit provides nucleic acid probes for FISH analysis of one or more fusion gene selected from the group consisting of: TRMT11-GRIK2, SLC45A2-AMACR, MTOR-TP53BP1, LRRC59-FLJ60017, TMEM135-CCDC67, CCNH-C5orf30, TRMT11-GRIK2, SLC45A2-AMACR, KDM4B-AC011523.2, MAN2A1-FER, PTEN-NOLC1, MTOR-TP53BP1, ZMPSTE24-ZMYM4, CLTC-ETV1, ACPP-SEC13, DOCK7-OLR1 or PCMTD1-SNTG1. In non-limiting embodiments, a kit provides nucleic acid probes for FISH analysis of one or more fusion gene selected from the group consisting of: TRMT11-GRIK2, SLC45A2-AMACR, MTOR-TP53BP1, LRRC59-FLJ60017, TMEM135-CCDC67, PTEN-NOLC1 and CCNH-C5orf30, and TRMT11-GRIK2, SLC45A2-AMACR, KDM4B-AC011523.2, MAN2A1-FER, MTOR-TP53BP1, ZMPSTE24-ZMYM4, CLTC-ETV1, ACPP-SEC13, DOCK7-OLR1 or PCMTD1-SNTG1. In specific non-limiting embodiments, probes to detect a fusion gene may be provided such that separate probes each bind to the two components of the fusion gene or a probe may bind to a "junction fragment" that encompasses the boundary between the spliced genes. In specific non-limiting embodiments, the kit comprises said probes for analysis of at least two, at least three, at least four, at least five, six, seven, eight or all nine of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 or PCMTD1-SNTG1. An example of FISH analysis used to identify a fusion gene is provided in Example 1 below.

In non-limiting embodiments, a kit provides nucleic acid primers for PCR analysis of one or more fusion gene selected from the group consisting of: TRMT11-GRIK2, SLC45A2-AMACR, MTOR-TP53BP1, LRRC59-FLJ60017, TMEM135-CCDC67, PTEN-NOLC1, CCNH-C5orf30, TRMT11-GRIK2, SLC45A2-AMACR, KDM4B-AC011523.2, MAN2A1-FER, MTOR-TP53BP1, ZMPSTE24-ZMYM4, CLTC-ETV1, ACPP-SEC13, DOCK7-OLR1 or PCMTD1-SNTG1. In non-limiting embodiments, a kit provides nucleic acid primers for PCR analysis of one or more fusion gene selected from the group consisting of: TRMT11-GRIK2, SLC45A2-AMACR, MTOR-TP53BP1, LRRC59-FLJ60017, TMEM135-CCDC67, PTEN-NOLC1 and CCNH-C5orf30, and TRMT11-GRIK2, SLC45A2-AMACR, KDM4B-AC011523.2, MAN2A1-FER, MTOR-TP53BP1, ZMPSTE24-ZMYM4, CLTC-ETV1, ACPP-SEC13, DOCK7-OLR1 or PCMTD1-SNTG1. In specific non-limiting embodiments, the kit comprises said primers for analysis of at least two, at least three, at least four, at least five, six, seven, eight, nine, ten, eleven, twelve, thirteen, fourteen of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH- C5orf30, ZMPSTE24-ZMYM4, CLTC-ETV1, ACPP-SEC13, DOCK7-OLR1 and PCMTD1-SNTG1.

The following Examples are offered to more fully illustrate the disclosure, but are not to be construed as limiting the scope thereof.

6. EXAMPLE 1: TRANSLOCATION AND FUSION GENE EVENTS IN PROGRESSIVE PROSTATE CANCER

6.1 Abstract

Importance:

Prediction of prostate cancer clinical outcome remains a major challenge after the diagnosis. An accurate and reproducible test predicting the behavior of prostate cancer is urgently needed.

Objective:

To identify biomarkers that are predictive of prostate cancer recurrence or prostate cancer related death.

Design:

Genome DNA and/or total RNA from Nineteen specimens of prostate cancer (T), matched adjacent benign prostate tissues (AT), matched bloods (B) and organ donor prostates (OD) were sequenced. Eight novel fusion genes were discovered and validated. These 8 novel fusion genes were then analyzed on 174 prostate samples, including 164 prostate cancer and 10 healthy prostate organ donor samples. Up to 15 years of clinical follow-ups on prostate cancer patients were conducted.

Setting:

University of Pittsburgh Medical Center, Presbyterian and Shadyside Campus.

Participants:

One hundred sixty-four prostate cancer patients underwent radical prostatectomy from 1998-2012 were selected for fusion gene expression analysis. 80.5% (132/164) patients had been followed-up for at least 5 years.

Main Measure:

To identify the presence of any of the following fusion genes in prostate cancer samples: TMEM135-CCDC67, KDM4B-AC011523.2, MAN2A1-FER, TRMT11-GRIK2, CCNH-C5orf30, SLC45A2-AMACR, MTOR-TP53BP1 and LRRC59-FLJ60017.

Results:

Approximately 90% of men carrying at least one of six of these fusion genes (TRMT11-GRIK2, SLC45A2-AMACR, MTOR-TP53BP1, LRRC59-FLJ60017, TMEM135-CCDC67 and CCNH-C5orf30) experienced prostate cancer recurrence, metastases and/or prostate cancer-specific death after radical prostatectomy, while these outcomes occurred in only 36% of men not carrying those fusion genes. Four fusion genes occurred exclusively in prostate cancer samples from patients who experienced recurrence or prostate cancer related death. The formation of these fusion genes is the result of genome recombination events.

Conclusion and Relevance:

These findings suggest that the formation of these fusion genes are associated with prostate cancer recurrence and may drive the progression.

6.2. Introduction

Despite a high incidence[1,2], only a fraction of men diagnosed with prostate cancer develop metastases and even fewer die from the disease. The majority of prostate cancers remain asymptomatic and clinically indolent. The precise mechanisms for the development of progressive, clinically concerning prostate cancer remain elusive. Furthermore, the inability to predict prostate cancer's potential aggressiveness has resulted in significant overtreatment of the disease. The dichotomous nature of prostate cancer—a subset of life-threatening malignancies in the larger background of histological alterations lacking the clinical features implicit with that label—is a fundamental challenge in disease management.

To identify genome markers for prostate cancer, whole genome sequencing was performed on 14 prostate tissue samples from 5 prostate cancer patients: five prostate cancers (T) from patients who experienced poor clinical outcomes (reoccurrence with fast rise of prostate cancer antigen doubling time (PSADT <4 months)), five matched blood (B) samples and four matched benign prostate tissues from the prostate cancer patients (AT) (Table 2). In one patient, normal adjacent prostate tissue was not available. An average of 200 GB was sequenced per sample to achieve 33 fold coverage of the entire genome. Total RNA from all T and AT samples was sequenced to achieve >1333 (average 400 million reads/sample) fold coverage per gene. Total RNA from four age-matched, entirely histologically benign prostate tissues harvested from healthy organ donors was similarly sequenced as a tissue control. The sequencing data were aligned to human reference genome HG19[3]. Fusion genes were then identified and validated. We hypothesize that these fusion genes from cancer samples that prove metastatic are associated poor clinical outcome for prostate cancer patients. A prediction model for prostate cancer recurrence and short post-operative prostate specific antigen doubling time (PSADT) was built. This model was then applied to 89 additional prostate cancer samples from University of Pittsburgh Medical Center, 30 samples from Stanford University Medical Center, and 36 samples from University of Wisconsin Madison Medical Center with follow-up ranging from 1 to 15 years. One hundred twenty-seven of these samples are from patients who experienced prostate cancer recurrence after radical prostatectomy, and 106 are from patients with no evidence of recurrence for at least 5 years after the surgery. The remaining 46 samples are from patients who had less than 5 years of follow-up and had not yet experienced biochemical recurrence.

The newly validated fusion genes were then analyzed on 164 prostate cancer samples with clinical follow-up ranging from 2 to 15 years. Seventy-eight of these samples are from patients who experienced prostate cancer recurrence after radical prostatectomy, while 54 are from patients had no recurrence for at least 5 years after the surgery. The remainder samples are from patients who had radical prostatectomy less than 5 years ago. Association of fusion gene expression with prostate cancer recurrence was analyzed.

6.3 Methods

Tissue samples. Nineteen specimens of prostate cancer (T), matched adjacent benign prostate tissues (AT), matched bloods (B) and organ donor prostates (OD) were obtained from University of Pittsburgh Tissue Bank in compliance with institutional regulatory guidelines (Table 2). To ensure high purity (L80%) of tumor cells, needle-microdissection was performed by pathologists to isolate the tumor cells from adjacent normal tissues (≥3 mm distance from the tumor). For AT and OD samples, similar needle-microdissections were performed to achieve 80% epithelial purity. Genomic DNA of these tissues was extracted using a commercially available tissue and blood DNA extraction kit (Qiagen, Hilden, Germany). The protocols of tissue procurement and procedure were approved by Institution Board of Review of University of Pittsburgh.

Whole Genome and Transcriptome Sequencing Library Preparation.

To prepare the genomic DNA libraries, 50 ng DNA was subjected to the tagmentation reactions using the NEXTERA DNA sample prep kit (Madison, Wis.) for 5 min at 55° C. The DNA was then amplified with adaptor and sequencing primers for 9 cycles of the following procedure: 95° C. for 10s, 62° C. for 30s and 72° C. for 3 min. The PCR products were purified with Ampure beads. The quality of genomic DNA libraries was then analyzed with qPCR using Illumina sequencing primers and quantified with Agilent 2000 bioanalyzer. For transcriptome sequencing, total RNA was extracted from prostate samples using Trizol, and treated with DNAse1. Ribosomal RNA was then removed from the samples using RIBOZERO™ Magnetic kit (Epicentre, Madison, Wis.). The RNA was reverse-transcribed to cDNA and amplified using TRUSEQ™ RNA Sample Prep Kit v2 from Illumina, Inc (San Diego, Calif.). The library preparation process such as adenylation, ligation and amplification was performed following the manual provided by the manufacturer. The quantity and quality of the libraries were assessed as those described in genome DNA library preparation.

Whole Genome and Transcriptome Sequencing.

The Illumina whole genome sequencing system was applied to the analysis. The operation procedures strictly followed the manufacturer's instructions. Briefly, DNA libraries were hybridized to flowcells and subjected to primer extension and bridge amplification in an automatic cBot process for 4 h to generate clusters of DNA sequencing templates. These clustered flowcells were then subjected to the sequencing analysis in the Illumina HiSeq2000 system. All samples were sequenced with paired-end runs for 200 cycles.

Read Alignment.

Whole genome DNA-seq reads from 5 Ts, 4 ATs and 5 Bs were aligned by BWA[3] version 1.4.1 against the UCSC hg19 human reference genome allowing maximal 2 base mismatches per (100 nucleotide) read. After alignment, the average coverage of whole genome is above 30× for all 14 samples. Picard tool (http://picard.sourceforge.net) was applied to remove duplicate reads after the alignment. RNA-seq reads (from 5 T, 4 matched AT and 4 OD samples) were at an average of 1333× coverage. Whole transcriptome RNA-seq reads were aligned with the UCSC hg19 reference genome using Tophat[4-6] version 1.4.1. Maximal 2 mismatches per read were allowed.

Fusion Gene Detection.

To identify fusion gene events, we applied a Fusion-catcher (v0.97) algorithm[7] on RNA sequencing samples. The analysis results by the software had been validated with high precision rate in breast cancer cell lines. Both BOWTIE and BLAT alignment were applied in the analysis and were plotted with CIRCOS software[8]. The preliminary list of candidate fusion transcripts are filtered in Fusioncatcher based on the existing biological knowledge of the literature including: (1) If the genes are known to be the other's paralog in Ensembl; (2) If one of the fusion transcripts are the partner's pseudogene; (3) If one of the fusion transcripts are micro/transfer/small-nuclear RNA; (4) If the fusion transcript is known to be a false positive event (e.g., Conjoin gene database[21]); (5) If it has been found in healthy samples (Illumina Body Map 2.0[http://www.ebi.ac.uk/arrayexpress/experiments/E-MTAB-513/]); (6) If the head and tail genes are overlapping with each other on the same strand. Fusion genes were visualized with CIRCOS software[8] as shown in FIG. 6.

TABLE 2

| Case | TNM | Margin | Relapse | Relapse fast | Relapse simple | Gleason | Age | Gender | Race |
|---|---|---|---|---|---|---|---|---|---|
| Case 1 | T3bN1MX | Negative | fast | f | y | 7 | 50s | M | W |
| Case 2 | T3aN0MX | Negative | slow | nf | y | 7 | 60s | M | W |
| Case 3 | T2cN0MX | Negative | fast | f | y | 8 | 60s | M | W |
| Case 4 | T3bN1MX | Negative | fast | f | y | 10 | 50s | M | W |
| Case 5 | T3bN1MX | Negative | fast | f | y | 10 | 50s | M | W |

| Case | PSA pre-operative | Time to progression (Months) | PSADT | Radiology follow-up | Time interval of follow-up (Months) | Length of follow-up (Months) | Additional treatment |
|---|---|---|---|---|---|---|---|
| Case 1 | 14.6 | 1.41 | 3.7 | NEGATIVE | 2.76 | 29.09 | ADT |
| Case 2 | 4.1 | 43.75 | 39.96 | NO | 2.56 | 133.3 | RT |
| Case 3 | 2.38 | 33.76 | 2.99 | NEGATIVE | 3.42 | 33.93 | RT |
| Case 4 | 29.3 | 1.35 | 0.93 | POSITIVE FOR BONE METASTASIS | 1.02 | 15.48 | ADT, CHEMO |
| Case 5 | 9.17 | 1.35 | 1.83 | POSITIVE FOR BONE METASTASIS | 2.4 | 149.6 | ADT |

Machine Learning Classifier to Predict Relapse Status.

8 fusion genes from 5 tumor samples validated by RT-PCR, Sanger sequencing and Fluorescence In-situ Hybridization (FISH) analyses were used as features to predict the relapse status (fast vs non-fast and relapse vs non-relapse) in a large validation cohort (PSADT<4 months vs PSADT>15 months or non-recurrent). The presence for each fusion pair was coded either as 1 or 0 to represent whether the fusion gene exist in the sample. Linear discriminant analysis (LDA) was used to build a classifier. In light of relatively rare occurrence of the fusion transcripts (4.4%-9.0%) in our 90-sample Pittsburgh training cohort, we also applied a simple prediction rule based on the presence in any subset of the eight fusion genes (i.e., a patient is predicted as recurrence if any fusion transcript in a designated subset exists). Leave-one-out cross validation (LOOCV) was applied to construct the model and evaluate the prediction performance. ROC curves were constructed by varying the parameters in the LDA classifier construction and the optimal prediction model was selected with the best Youden index (=sensitivity+specificity-1)[22], and was then evaluated in a 89-sample Pittsburgh test cohort, a 21-sample Stanford test cohort and a 30-sample Wisconsin test cohort. To compare the statistical significance of AUC difference between two models, a bootstrap test is used to generate p-values[23]. To compare accuracy of two models, a test for equal proportions using "prop.test" in R is applied.

To demonstrate the potential translational predictive value of these fusion transcripts, information of Nomogram estimated five-year PSA free survival probability and Gleason scores of the patients was incorporated into our prediction models. The following models were generated: (I) 8 fusion transcripts alone, (II) Gleason scores alone, (III) Nomogram values alone, (IV) Gleason scores+8 fusion transcripts, (V) Nomogram values+8 fusion transcripts. Complete information of prediction accuracy, sensitivity, specificity and Youden index for these eight models is available in Tables 7-16.

RT-PCR.

To verify fusion genes detected by transcriptome and whole genome sequencing, total RNA was reverse-transcribed with random hexamer. Double strand cDNA was synthesized as described previously[9,10]. PCRs were performed using primers indicated in Table 3 using the following condition: 94° C. for 5 min, followed by 30 cycles of 94° C. for 30 seconds, 61° C. for 1 min and 72° C. for 2 min.

Fluorescence In-Situ Hybridization.

Formalin-fixed and paraffin-embedded tissue slides (5 microns) were placed in 2×SSC at 37° C. for 30 min. Slides were then removed and dehydrated in 70% and 85% ethanol for 2 min each at room temperature, and air dried. The DNA from the selected clones (Table 4) was extracted using Nucleobond Ax kit (Macherey-Nagel, Easton, Pa.). The biotin-labeled probes were prepared using standard nick-translation procedure and hybridized to sample slides as described previously[11, 12].

TABLE 4

Bacterial artificial chromosome clone for FISH.

| Fusion genes | Probe 1 | Probe 2 |
| --- | --- | --- |
| TMEM135-CCDC67 | RP11-80F20 | RP11-1034E22 |
| Mtor-TP53BP1 | RP4-647M16 | RP11-114F23 |
| TRMT11-GRIK2 | RP11-92N18 | RP11-70I17 |
| CCNH-C5orf30 | RP11-111M24 | RP11-244M13 |
| SLC45A2-AMACR | RP11-179D3 | RP11-1072I21 |
| KDM4B- AC011523.2 | RP11-241K5 | RP11-655K24 |
| MAN2A1-FER | RP11-452L20 | RP11-328A14 |
| LRRC59-SLC35B3 | RP11-269I10 | RP11-360D22 |
| LRRC59-FLJ60017 | RP11-269I10 | CTD-2116N11 |

6.4. Results

Fusion Genes Discovered by RNA and Whole Genome Sequencing.

A total of 76 RNA fusion events were identified in prostate cancer samples by the Fusioncatcher[7] program. Thirteen of these fusion events were suggested by genome sequencing. To control for tissue-based fusion gene events, fusion genes present in any of the four age-matched organ donor prostate tissues were eliminated (Table 5). Further, fusion genes with less than 20 kb between each element and read in the cis direction were also eliminated. As a result of this filtering, 28 of 76 fusion gene events were identified as prostate cancer specific (Table 6 and FIG. 6). Among these fusion events, TMPRSS2-ERG, the most common prostate cancer fusion gene[13-15], was found in two prostate cancer samples. Majority of the fusion events identified are novel and not reported in the literature. None of the 29 fusion

TABLE 3

Primer sequences for RT-PCR.

| Fusion genes | Sequences |
| --- | --- |
| TMEM135-CCDC67 | 5'-TTGGCATGATAGACCAGTCCC-3/5'-CAGCACCAAGGGAATGTGTAG-3' (SEQ ID NO: 58/SEQ ID NO: 59) |
| Mtor-TP53BP1 | 5'-TTGGCATGATAGACCAGTCCC-3/5'-CAGCACCAAGGGAATGTGTAG-3' (SEQ ID NO: 60/SEQ ID NO: 61) |
| TRMT11-GRIK2 | 5'-GCGCTGTCGTGTACCCTTAAC-3/5'-GGTAAGGGTAGTATTGGGTAGC-3' (SEQ ID NO: 62/SEQ ID NO: 63) |
| CCNH-C5orf30 | 5'-CCAGGGCTGGAATTACTATGG-3/5'-AAGCACCAGTCTGCACAATCC-3' (SEQ ID NO: 64/SEQ ID NO: 65) |
| SLC45A2-AMACR | 5'-TTGATGTCTGCTCCCATCAGG-3/5'-TGATATCGTGGCCAGCTAACC-3' (SEQ ID NO: 66/SEQ ID NO: 67) |
| KDM4B-AC011523.2 | 5'-AACACGCCCTACCTGTACTTC-3/5'-CTGAGCAAAGACAGCAACACC-3' (SEQ ID NO: 68/SEQ ID NO: 69) |
| MAN2A1-FER | 5'-TGGAAGTTCAAGTCAGCGCAG-3/5'-GCTGTCTTTGTGTGCAAACTCC-3' (SEQ ID NO: 70/SEQ ID NO: 71) |
| LRRC59-FLI60017 | 5'-GTGACTGCTTGGATGAGAAGC-3/5'-CCAGCATGCAGCTTTTCTGAG-3' (SEQ ID NO: 72/SEQ ID NO: 73) |
| TMPRSS2-ERG | 5'-AGTAGGCGCGAGCTAAGCAGG-3/5'-GGGACAGTCTGAATCATGTCC-3' (SEQ ID NO: 74/SEQ ID NO: 75) |
| β-actin | 5'-TCAAGATCATTGCTCCTCCTGAGC-3/5'-TGCTGTCACCTTCACCGTTCCAGT-3' (SEQ ID NO: 76/SEQ ID NO: 77) | genes were identified in the matched AT transcriptome analysis. To validate these fusion genes, RT-PCR was performed using primers specific for fusion gene regions encompassing the fusion breakpoints and the PCR products were sequenced. Eight of these fusion gene events were validated through sequencing (FIG. 1).

Five of the eight fusion events resulted in truncation of a driver gene and frameshift in translation of a passenger gene. One of the fusion genes produced a truncated cyclin H and an independent open reading frame of a novel protein whose function is not known. Two fusion events, however, produced chimera proteins that possibly retain at least partial function of both genes. One of these fusion products is N-terminus 703 amino acids of a-Mannosidase 2A (MAN2A1) fusing to the C-terminus 250 amino acids of FER, a Feline tyrosine kinase. The fusion protein retains the glycoside hydrolase domain but has its manosidase domain replaced with a tyrosine kinase domain from FER. Another fusion protein product produces a chimera of membrane-associated transporter protein (SLC45A20) and alpha-methylacyl-CoA racemase (AMACR). The chimera protein has 5 of its 10 transmembrane domains deleted from SLC45A2 and replaced with methyl-acyl CoA transferase domain from AMACR. Interestingly, both MAN2A1-FER and SLC45A2-AMACR fusions are in the trans-direction, eliminating the possibility of a fusion event from simple chromosome deletion or collapse of extremely large RNA transcript.

Fluorescence In Situ Hybridization Suggests Genome Recombination Underlying Fusion Gene Formation.

Figure 2A:
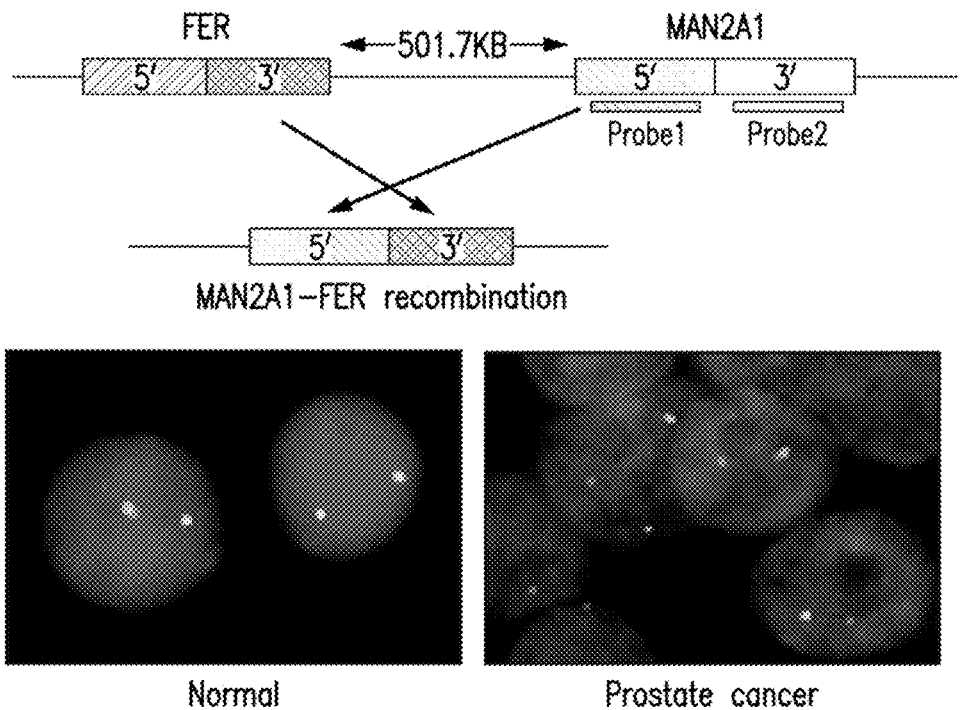
Figure 2B:
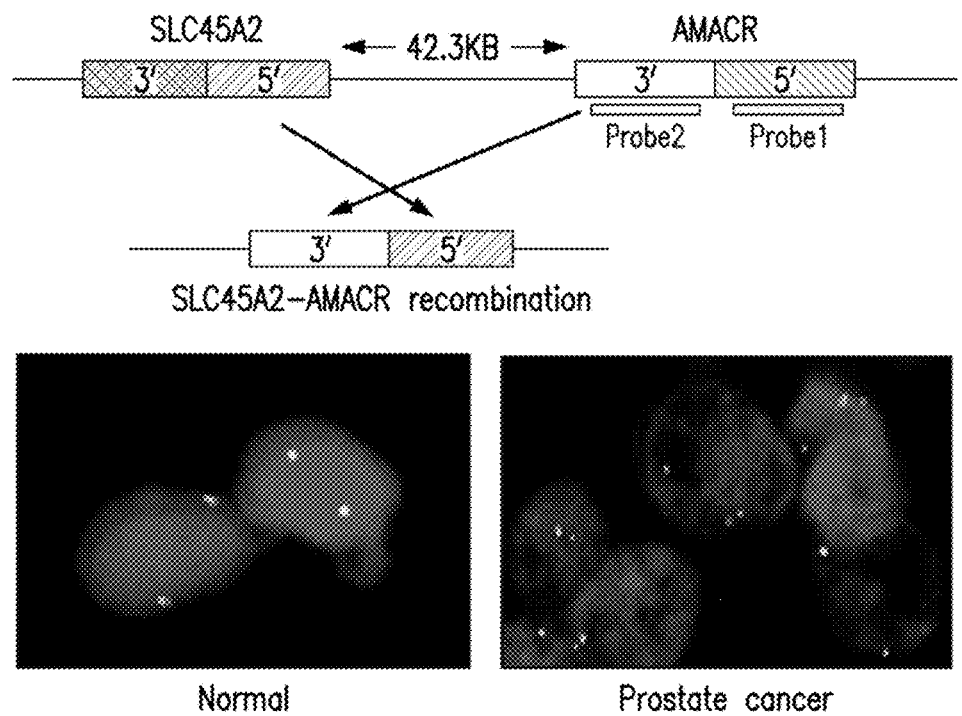
Figure 2C:
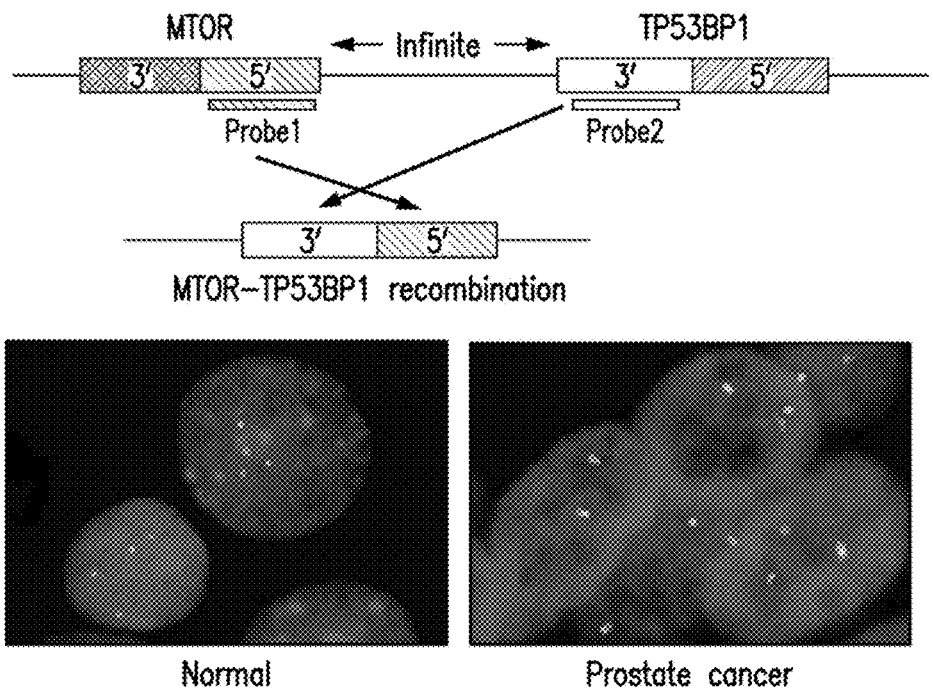
Figure 2D:
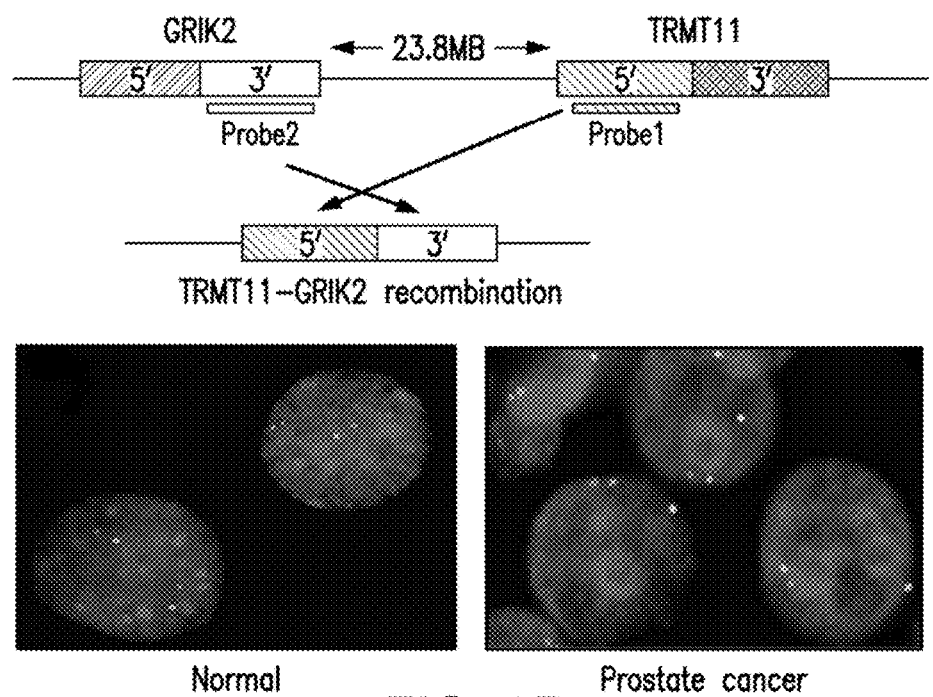
Figure 2E:
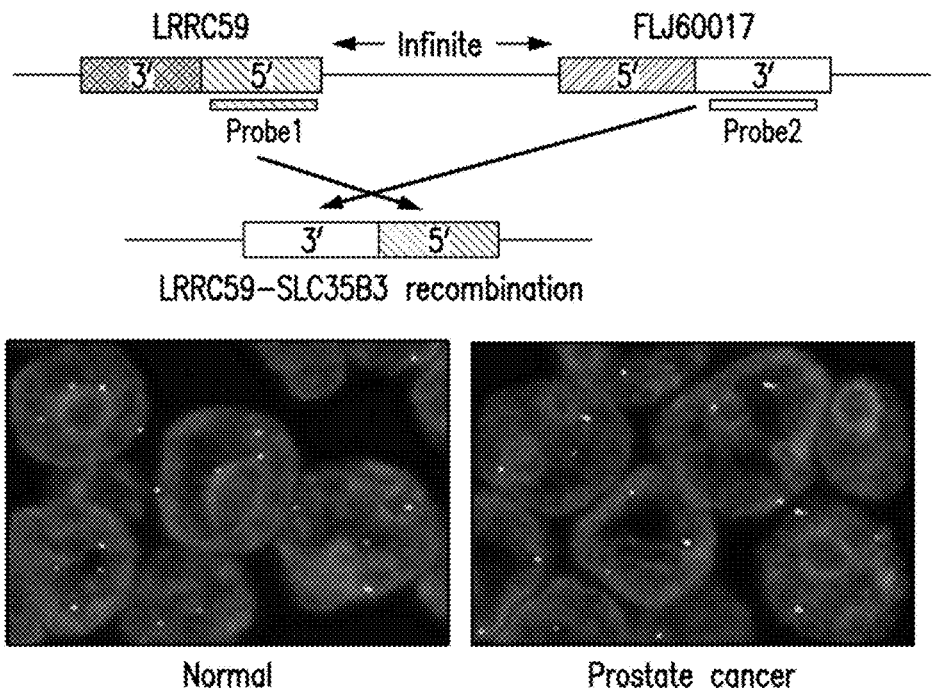
Figure 2F:
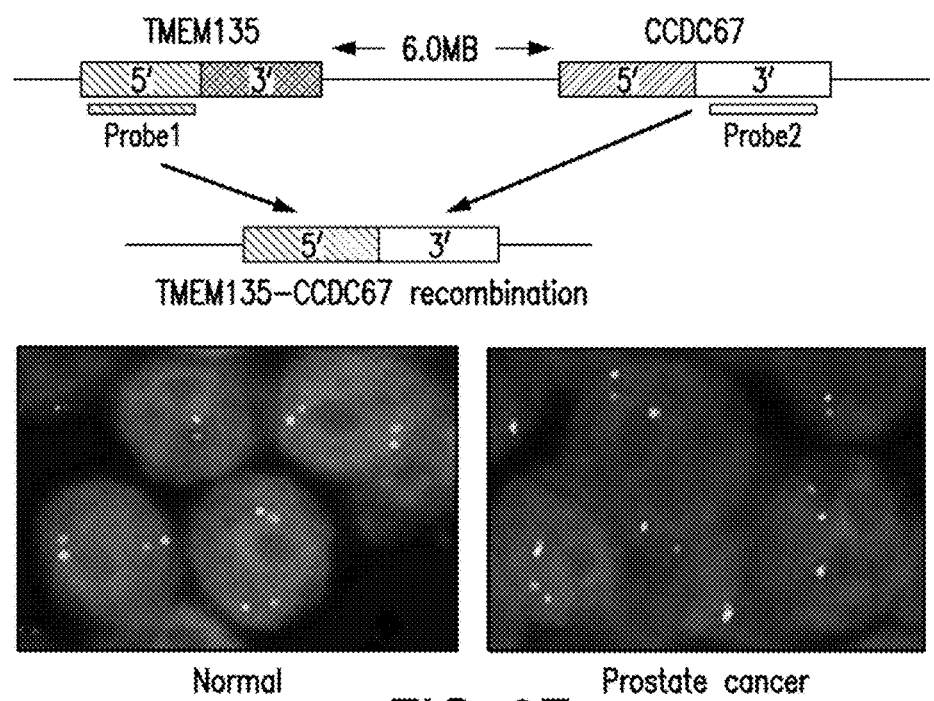
Figure 2G:
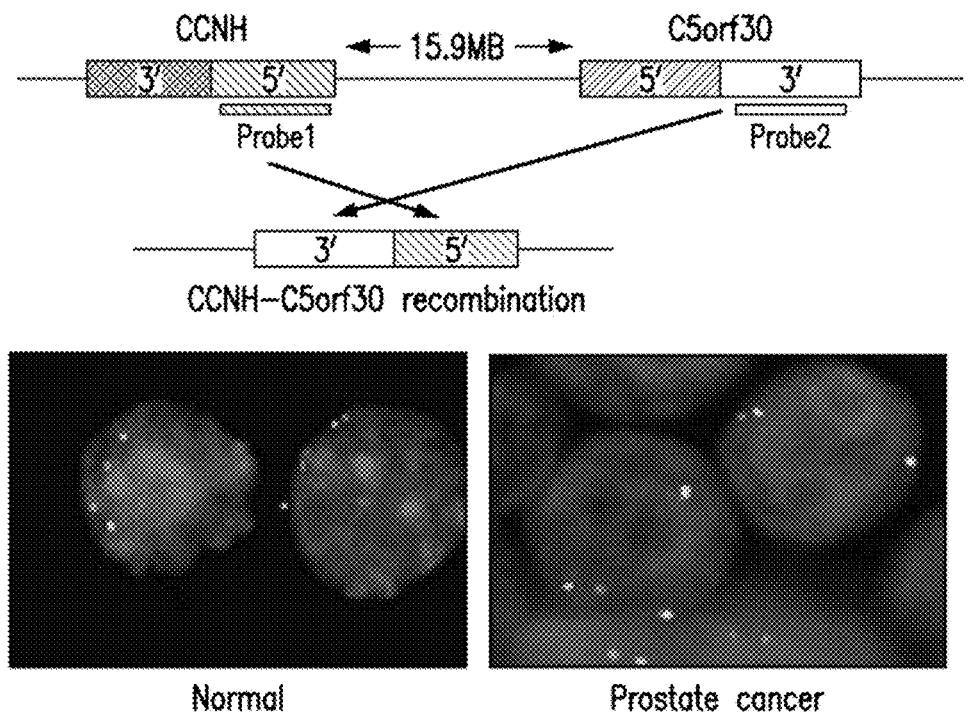
Figure 2H:
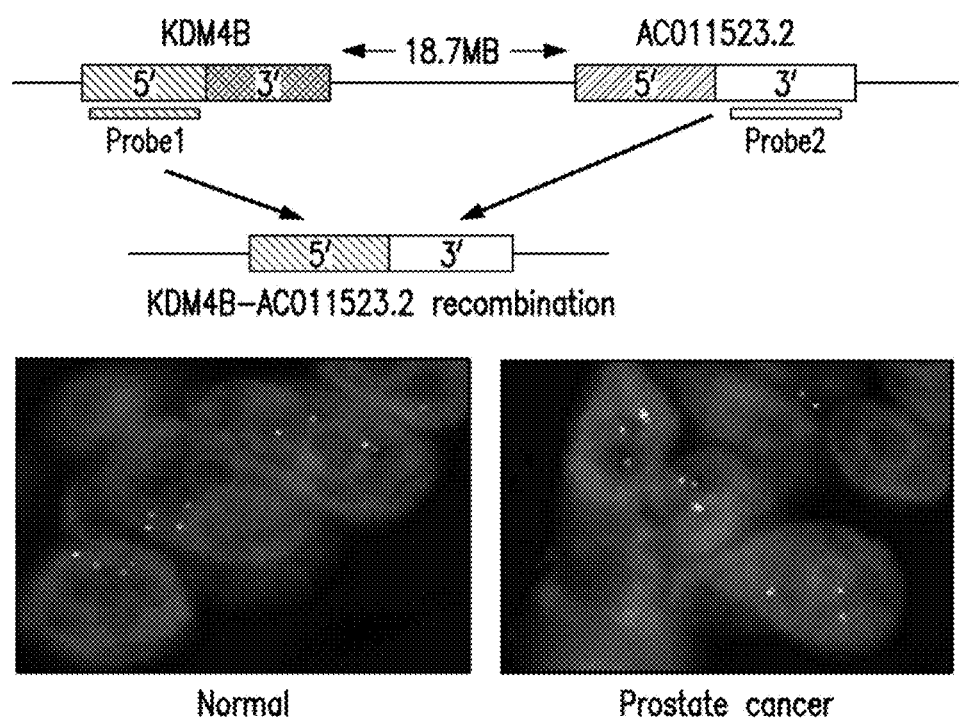

To investigate the mechanism of these fusion events, fluorescence in situ hybridization (FISH) was performed on prostate cancer tissues where the fusion gene was present. Using the probes surrounding MAN2A1 breakpoint, a physical separation of signals between 5' and 3' MAN2A1 in cancer cells containing the fusion gene was observed, in contrast to the overlapping nature of these signals in the wild type alleles in normal prostate epithelial cells (FIG. 2). Similar "break-apart" hybridization occurred in SLC45A2-AMACR positive prostate cancer samples (FIG. 2B). These findings indicate that MAN2A1-FER and SLC45A2-AMACR fusions are the result of chromosome recombination. Interestingly, in prostate cancer cells containing "break-apart" signals of MAN2A1, only 31% of the cells retained the 3' end signal, suggesting that the recombination of genome DNA in most prostate cancer cells results in truncation of the C-terminus of MAN2A1. A similar "collateral loss" of the N-terminus of AMACR was found in prostate cancer cells expressing SLC45A2-AMACR fusion (29% retaining the N-terminus signal of AMACR). Other FISH analyses confirm that genome translocations occur in cancer cells expressing TRMT11-GRIK2, MTOR-TP53BP1, LRRC59-FLJ60017, TMEM137-CCDC67, CCNH-C5orf30 and KDM4B-AC011523.2 fusion genes (FIGS. 2C-G). These fusion genes are either separated by a large segment of genome DNA (TRMT11-GRIK2, TMEM135-CCDC67, CCNH-C5orf30 and KDM4B-AC011523.2) or located in separate chromosomes (MTOR-TP53BP1 and LRRC59-FLJ60017). The joining signals of hybridizations in prostate cancer cells suggest that these fusion genes were relocated to juxtapose to their fusion partners. Finally, genomic breakpoints were identified in 3 fusion pair through Sanger sequencing of the cancer genomic DNA (CCNH-C5orf30, TMEM135-CCDC67 and LRRC59-FLJ60017) (FIG. 11).

Fusion Genes Association with Prostate Cancer Recurrence.

Figure 3A:
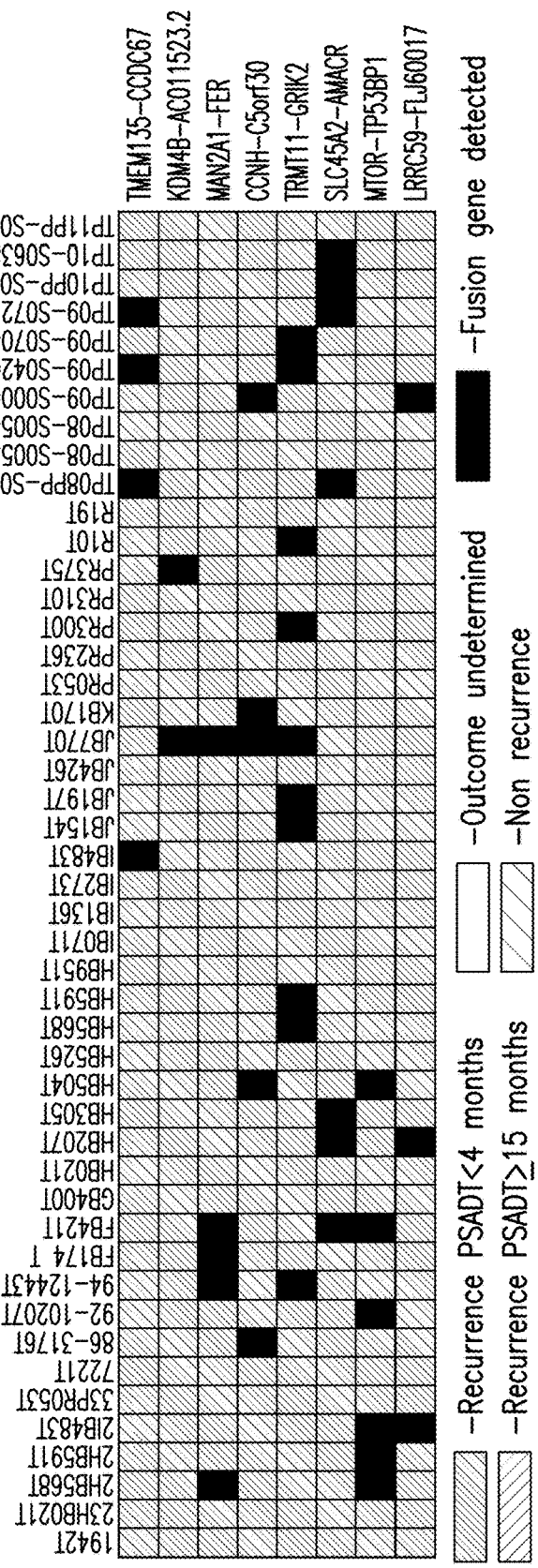
Figure 3A:
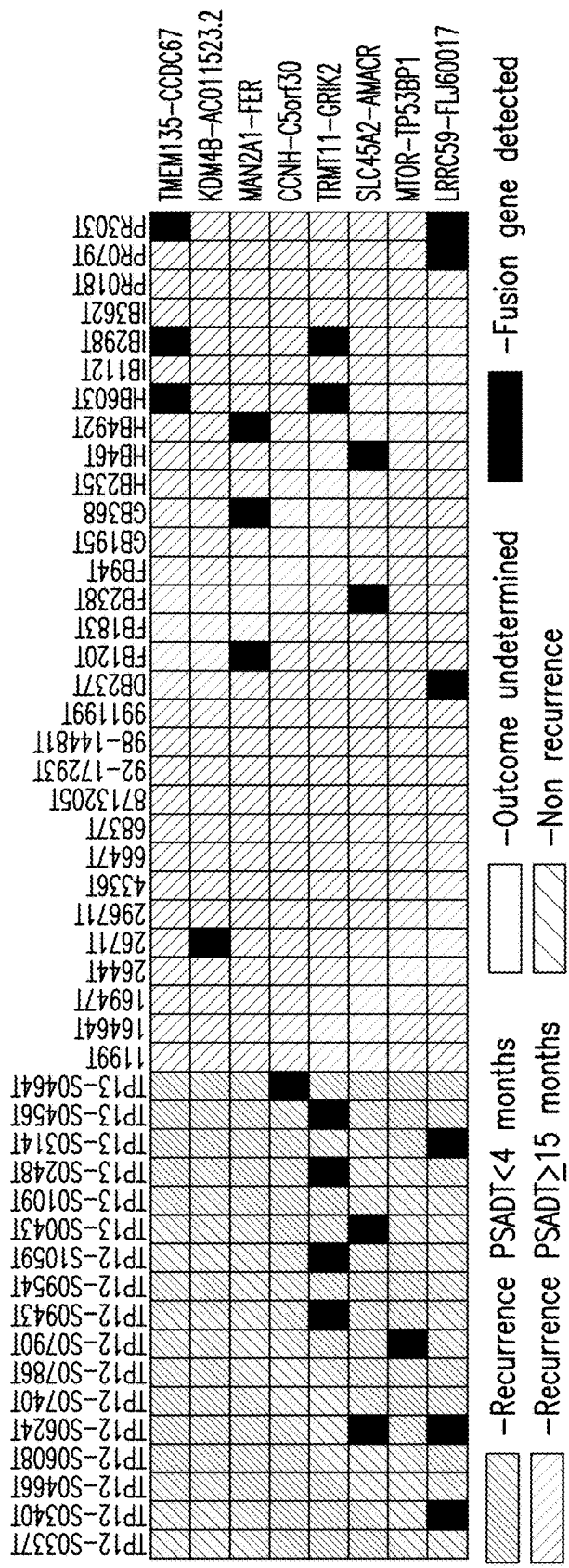
Figure 3A:
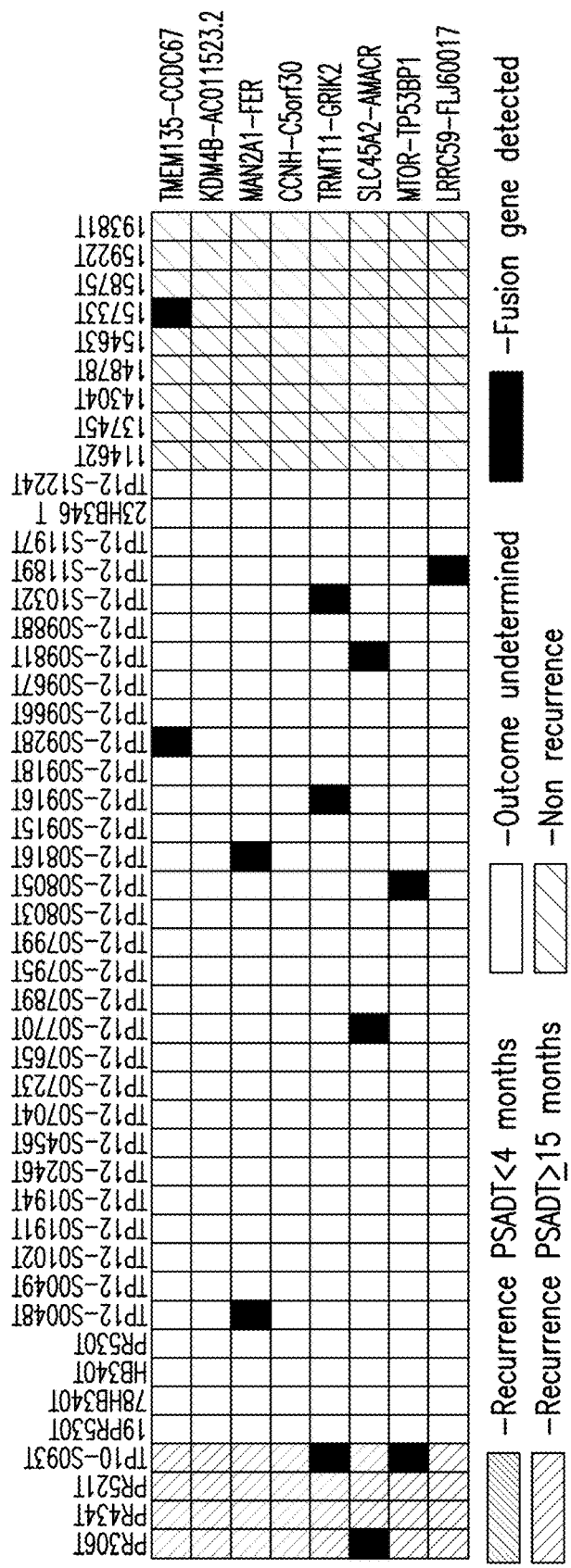
Figure 3A:
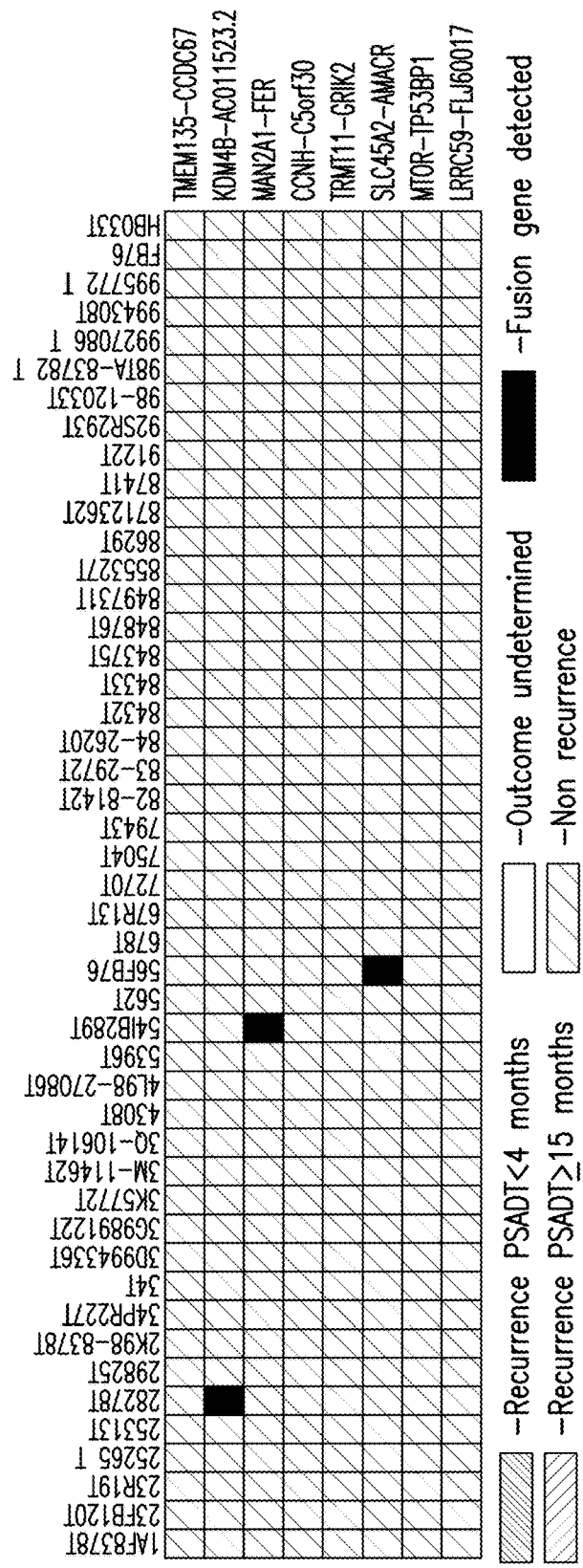
Figure 3A:
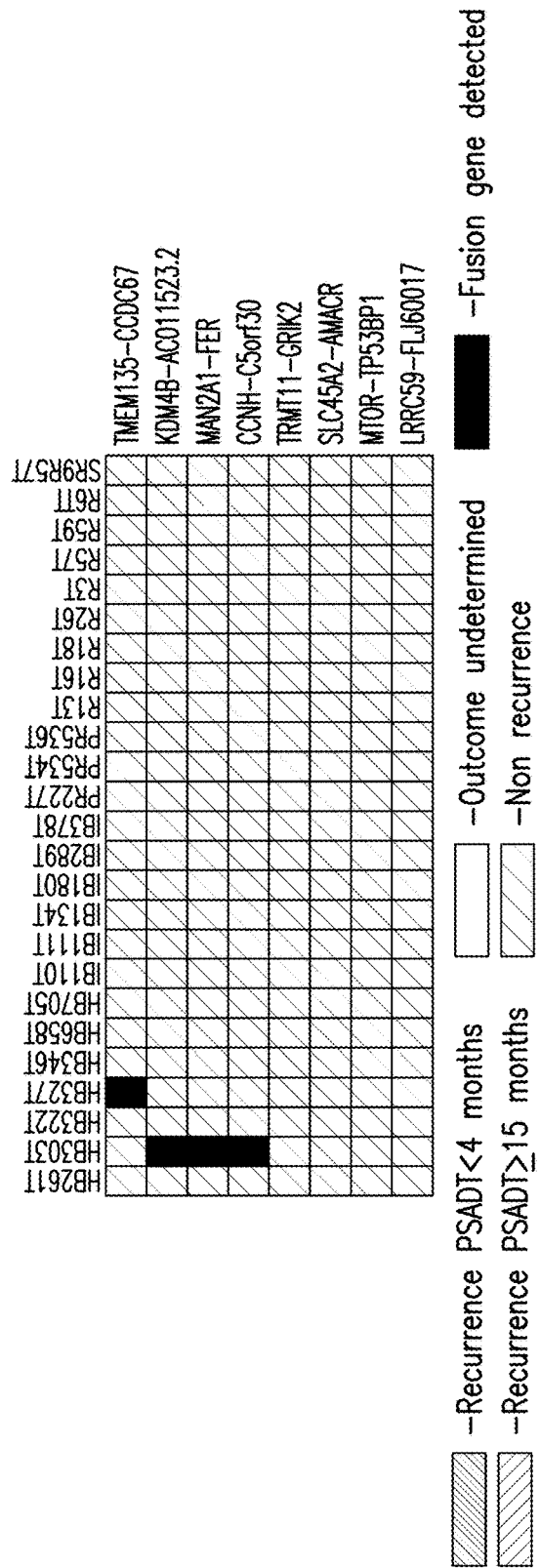
Figure 3A:
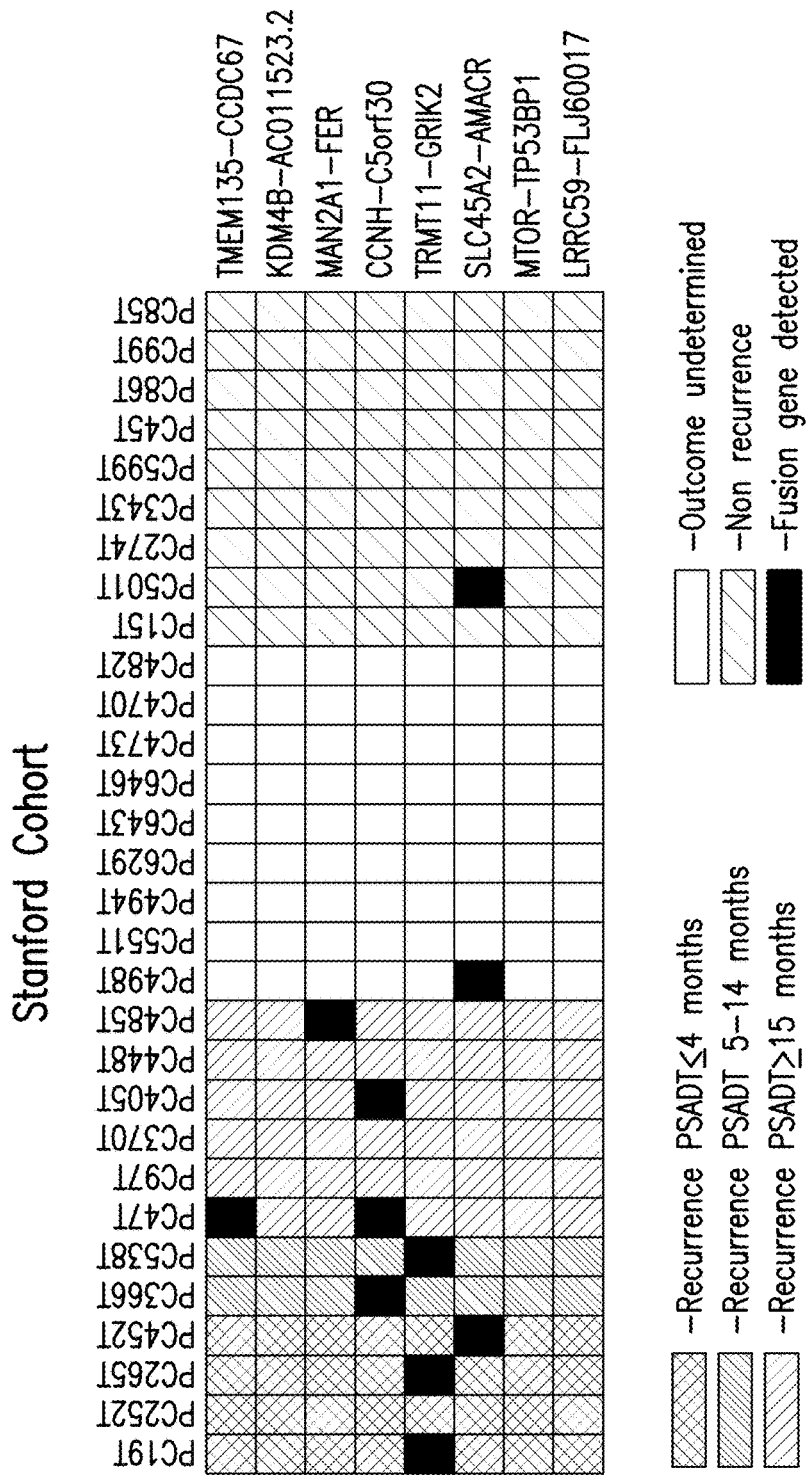
Figure 3A:
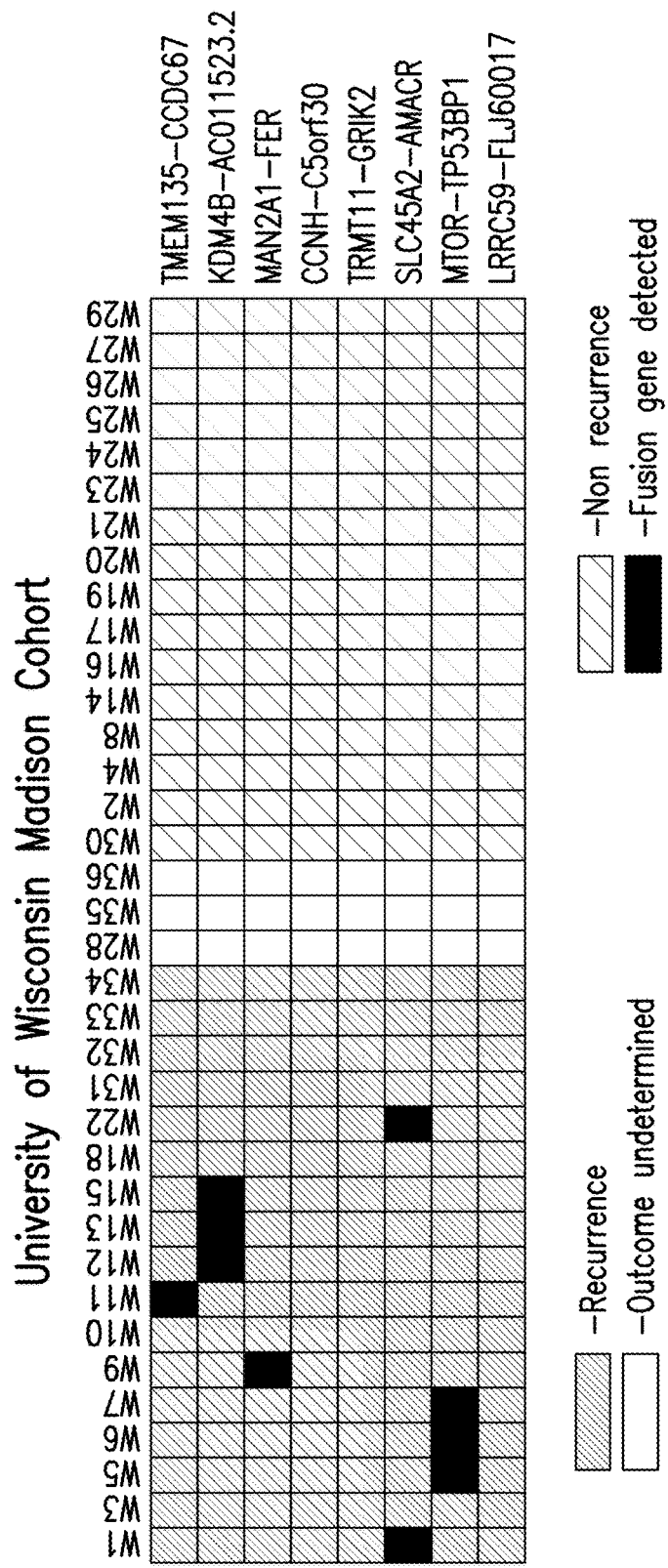
Figure 3B:
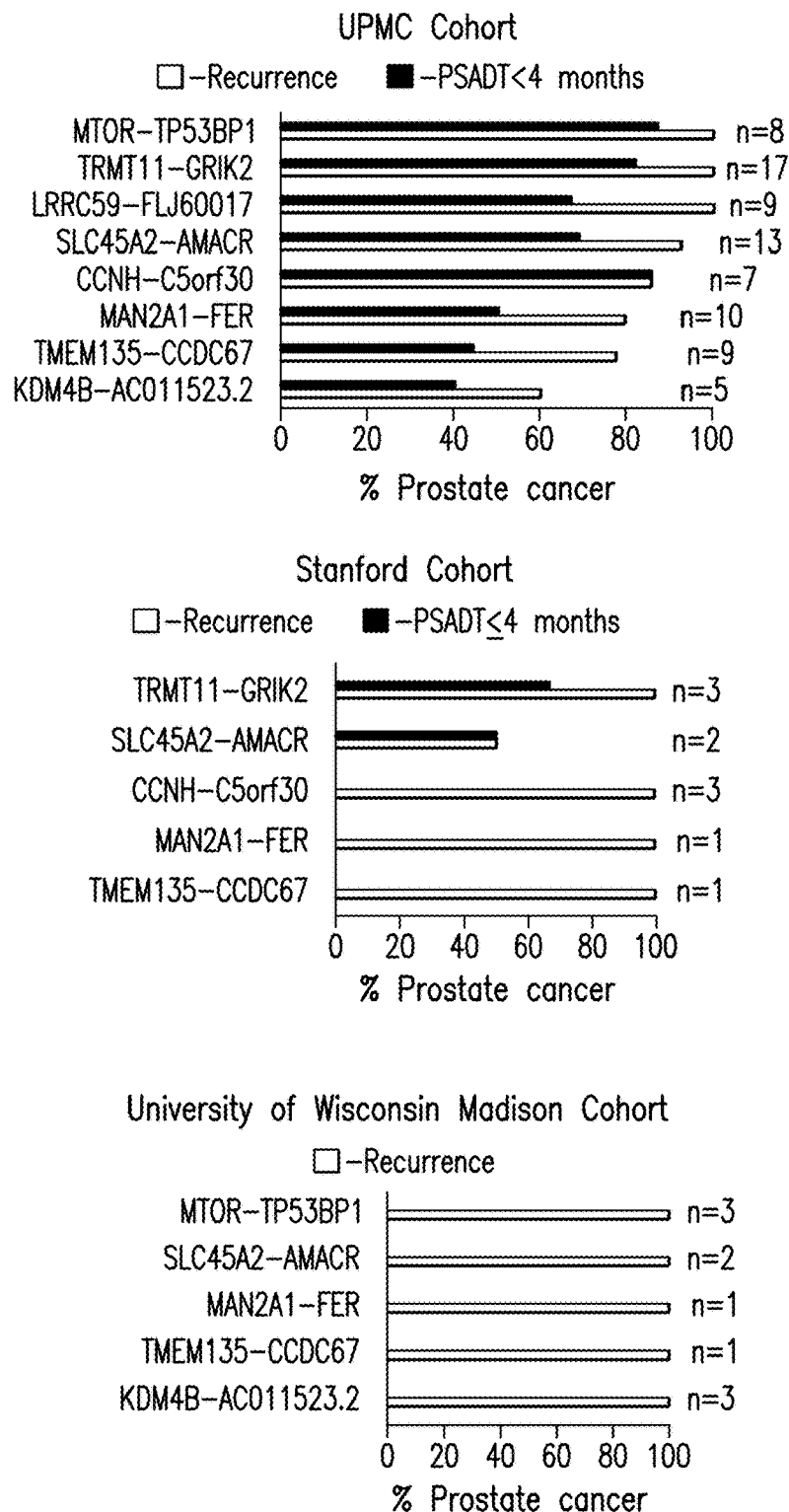

A genomic alteration in prostate cancer without clinical consequence is of limited significance. Therefore, the association of these fusion genes with prostate cancer progression was investigated in prostate cancer specimens obtained from 213 men and from entirely benign prostate tissues obtained from 10 organ donors free of urological disease aged 20 to 70. The prostate cancer samples were linked to the clinical outcomes after radical prostatectomy: those with no detectable prostate specific antigen (PSA) recurrence after a minimum of five years of observation, those whose clinical outcomes remain unknown and those who had an observed PSA recurrence within five years. For 179 of the 223 prostate cancer samples, clinical outcome data after radical prostatectomy were available, and 81 had no detectable prostate specific antigen (PSA) recurrence after a minimum of five years of follow-up, while 98 developed biochemical recurrence (defined as a measurable PSA >0.2 ng/ml). Only 7.4% (6/81) primary prostate cancers expressed one of the fusion genes in non-recurrent patients. In contrast, 52% (51/98) primary prostate cancers expressed at least one fusion in patients who developed recurrence (FIG. 3 and FIG. 7A). No fusion genes were detected in benign prostate tissues obtained from healthy organ donors (FIG. 7B). Three fusion events were observed exclusively in recurrent prostate cancer after radical prostatectomy (TRMT11-GRIK2, MTOR-TP53BP1 and LRRC59-FLJ60017; FIGS. 3A and B).

Fisher's exact test showed a significant difference in recurrent status between patients with at least one of the 8 fusion transcripts and those without ($p=6.8\times10^{-16}$). In the combined UPMC, Stanford and Wisconsin data sets, 91% (69/76) of patients positive for one of the fusion transcripts experienced prostate cancer recurrence in 5 years after prostate resection. Based on the hypothesis that the presence of at least one of the 8 fusion transcripts would indicate a recurrence for a prostate cancer patient, a prostate cancer prediction model was built and tested, using 90 randomly selected prostate cancer samples from University of Pittsburgh Medical Center (training set). This training cohort yielded an accuracy of prostate cancer recurrence prediction of 71% with 89% specificity and 58% sensitivity ($p<0.005$) (FIG. 12A, Table 10). When this model was applied to a separate cohort of 89 samples (test set), the model correctly predicted recurrence in 70% of patients. To further validate this model, we tested its performance in a 30-patient (21 with qualified clinical follow-up) cohort from Stanford University Medical Center and a 36-patient (30 with qualified clinical follow-up) cohort from University of Wisconsin Madison Medical Center (FIG. 3, FIG. 8 and FIG. 9). Once again, the model correctly predicted recurrence with 76.2% accuracy and with 89% specificity and 67% sensitivity on the prostate cancer cohort from Stanford, and 80% accuracy and with 100% specificity and 63% sensitivity on the cohort from Wisconsin (Table 11).

Figure 3D:
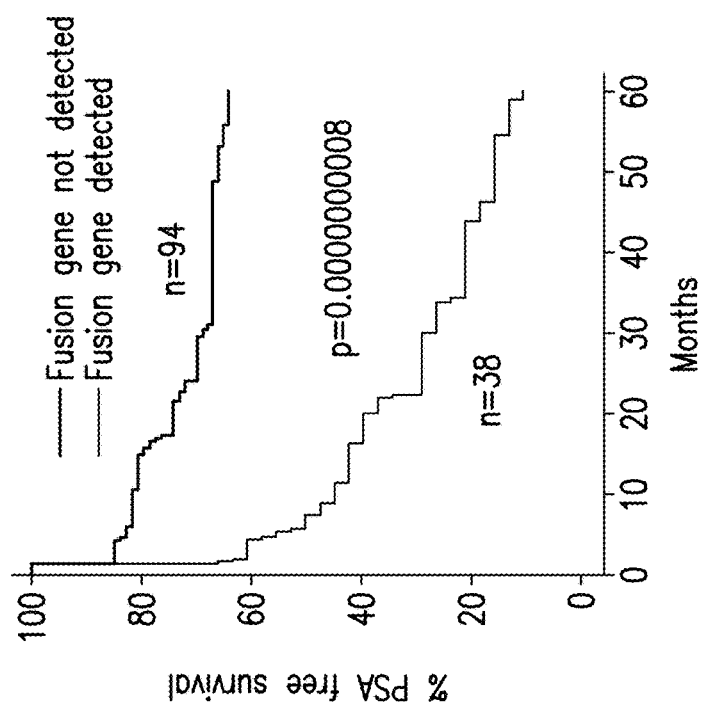
Figure 3C:
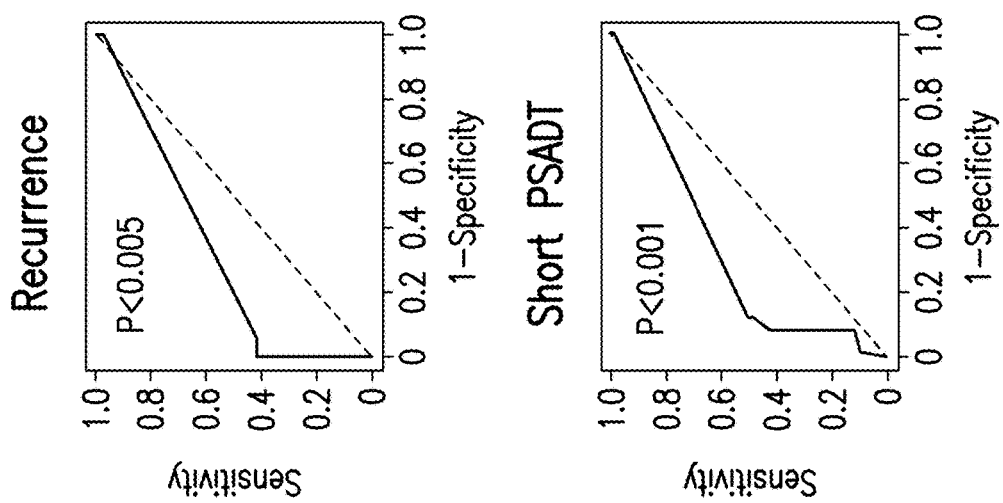

Similar to the dichotomous nature of prostate cancer in general, recurrent prostate cancer can progress in an indolent or aggressive manner. A PSA doubling time (PSADT) less than four months after radical prostatectomy is strongly associated with the early development of metastatic disease and prostate cancer-specific death, whereas these events are rare and remote in men with a PSADT of greater than 15 months[16, 17]. Strong association was found between the fusion genes (e.g., TRMT11-GRIK2, SLC45A2-AMACR, MTOR-TP53BP1, LRRC59-FLJ60017, TMEM135-CCDC67 and CCNH-C5orf30) with prostate cancer recurrence ($p=4.2\times10^{-9}$) and a PSADT less than four months ($p=6\times10^{-9}$). To examine whether these fusion gene events have prognostic value for prostate cancer clinical outcome, receiver operator curve (ROC) analyses with varying weights of fusion genes were performed. As shown in FIG. 3C, the panel of eight fusion genes correctly predicted 74.4% for PSA doubling time less than four months in the 90-sample training cohort, and 67% for prostate cancer recurrence. To optimize the prediction model, six fusion genes were selected for an improved association with disease-free survival after radical prostatectomy. When the same algorithm was applied to a separate 89-sample test set from University of Pittsburgh Medical Center and 21-sample cohort from Stanford University Medical Center, the prediction rate for PSADT<4 months was found to be 78% and 71%, respectively (FIG. 4B). As shown in FIG. 3D, 89.5% of patients had an observed disease recurrence within five years of radical prostatectomy if they carried any of the six fusion genes. In addition, and as shown in FIG. 4C, 84.2% of patients had an observed disease recurrence within five years of radical prostatectomy if they carried any of the eight fusion genes. No patient survived five years without recurrence if their primary prostate cancer contained a TRMT11-GRIK2 or MTOR-TP53BP1 gene fusion. In contrast, 68% patients were free of disease recurrence if any of the novel fusion genes were not detected in their primary prostate cancer. Similar findings were also identified in the Stanford cohort: 88.9% patients experienced recurrence of prostate cancer if they carried any fusion transcript, while 66.7% patients were free of the disease recurrence if they are negative.

TABLE 5

| Fusion gene 1 | Fusion_gene2 | read pairs | Validation Status |
|---|---|---|---|
| SORBS1 | RP11-476E15.3 | 25 | |
| AHCY | RP11-292F22.3 | 25 | |
| DCUN1D3 | ERI2 | 12 | |
| MACF1 | KIAA0754 | 11 | |
| C10orf68 | CCDC7 | 11 | RT-PCR and sequencing |
| RP11-166D19.1 | BLID | 7 | |
| ASS1 | ASS1P9 | 6 | |
| BACH1 | BACH1-IT1 | 6 | RT-PCR |
| MPDZ | RP11-272P10.2 | 5 | |
| LIG3 | RP5-837J1.2 | 4 | |
| ACAD8 | GLB1L3 | 4 | RT-PCR |
| IGSF9B | RP11-259P6.1 | 3 | |
| EYA1 | RP11-1102P16.1 | 3 | |
| TTC33 | PRKAA1 | 3 | RT-PCR |
| DNAH1 | GLYCTK | 3 | |
| PSPC1 | ZMYM5 | 3 | |
| HSP90AB3P | RP11-759L5.2 | 3 | |
| LSAMP | RP11-384F7.2 | 3 | |
| RNF4 | FAM193A | 81 | RT-PCR |
| AHCY | RP11-292F22.3 | 9 | |
| LSAMP | RP11-384F7.2 | 8 | |
| CBLL1 | AC002467.7 | 4 | |
| FNBP4 | Y_RNA | 4 | |
| TBCE | RP11-293G6_A.2 | 4 | |
| TRIM58 | RP11-634B7.4 | 4 | |
| DCUN1D3 | ERI2 | 4 | |
| PHPT1 | MAMDC4 | 3 | |
| TRIP6 | SLC12A9 | 3 | |
| NAT14 | ZNF628 | 3 | |
| TLL2 | RP11-35J23.5 | 3 | |
| UFSP2 | Y_RNA | 3 | |
| TSPAN33 | Y_RNA | 3 | |
| CADM3 | DARC | 3 | |
| KIF27 | RP11-213G2.3 | 3 | |
| RABL6 | KIAA1984 | 3 | |
| ZNF615 | ZNF350 | 3 | |
| ZYG11A | RP4-631H13.2 | 3 | |
| RP11-522L3.6 | MTND4P32 | 3 | |
| MTND3P10 | AC012363.10 | 3 | |
| RP11-464F9.1 | BMS1P4 | 3 | |
| RNF4 | FAM193A | 14 | RT-PCR |
| GBP3 | Y_RNA | 3 | |
| NACA | PRIM1 | 1 | |
| AHCY | RP11-292F22.3 | 3 | |
| GBP3 | Y_RNA | 3 | |
| HARS2 | ZMAT2 | 2 | RT-PCR and sequencing |
| EED | C11orf73 | 1 | RT-PCR |
| CNPY3 | RP3-475N16.1 | 1 | RT-PCR |
| RN7SL2 | Metazoa_SRP | 1 | |
| SLC16A8 | BAIAP2L2 | 2 | RT-PCR |
| KLK4 | KLKP1 | 2 | RT-PCR and sequencing |
| ZNF137P | ZNF701 | 1 | RT-PCR |
| AZGP1 | GJC3 | 1 | RT-PCR |
| USP7 | RP11-252I13.1 | 1 | |
| TRRAP | AC004893.11 | 1 | |
| C6orf47 | BAG6 | 1 | RT-PCR |
| TTTY15 | USP9Y | 9 | |
| AC005077.12 | LINC00174 | 2 | |
| ADCK4 | NUMBL | 2 | |
| ZNF606 | C19orf18 | 2 | |
| SLC45A3 | ELK4 | 3 | RT-PCR and sequencing |

The most frequent fusion events in prostate cancer are TRMT11-GRIK2 (7.9%, or 22/279) and SLC45A2-AMACR (7.2%, or 20/279) (FIGS. 3A, 7-9). TRMT11-GRIK2 fusion represents a giant truncation of TRMT11, a tRNA methyltransferase, and elimination of GRIK2, a glutamate receptor but reported to possess tumor suppressor activity[18]. Indeed, GRIK2 was not expressed in prostate cancer samples that contain TRMT11-GRIK2 fusions, while it was detected in organ donor prostate samples (FIG. 10). Only 4 of 14 samples with TRMT11-GRIK2 expressed full length non-fusion TRMT11. Thus, the fusion event of TRMT11-GRIK2 represents a loss of function instead of a gain.

Combining Detection of Fusion Transcripts and Clinical/Pathological Parameters Improved the Prediction Rate of Prostate Cancer Recurrence.

Prostate cancer samples with at least one fusion transcript correlate with more advanced stage of prostate cancer (p=0.004), Lymph node involvement status (P=0.005) and lower nomogram scores (p=0.0003) (Table 12). Gleason grading alone produced a prostate cancer recurrence prediction rate of 61.1%, with 85.7% specificity and 39.6% sensitivity in the 90-sample UPMC training cohort, when Gleason≥8 was used as cutoff to predict prostate cancer recurrence. The Gleason model yielded prediction accuracy ranging from 57-60% in 3 separate testing cohorts (Tables 13 and 14). However, when fusion transcript status was combined with Gleason Grade>8, improvement of prediction was found for all 4 cohorts: 72% for the UPMC training cohort, 74% for the UPMC test cohort, 76% for the Stanford cohort and 90% for the Wisconsin cohort. ROC showed a significant larger AUC (area under the curve) (0.84 versus 0.67, P=6.6×10-7) and higher testing accuracy (77.7% versus 59.7%, P=0.0019) (FIG. 5A) when Gleason score was combined with detection of any of 8 fusion transcripts. Similarly, Nomogram prediction of prostate cancer recurrence has the best accuracy of 76% with 68.8% sensitivity and 83.3% specificity in the analysis of 90-sample UPMC training cohort (Table 15). When this model was applied to UPMC testing, Stanford and Wisconsin cohorts independently, the results showed that the prediction accuracy ranged from 60% to 75% among the 3 cohorts (Table 16). When Nomogram was combined with the status of 8 fusion transcripts using LDA technique to build a classifier, the accuracy of prediction improves to 81-83% among the testing cohorts (Table 16). ROC showed an increase of AUC from 0.76 to 0.87 (P=0.0001) and an improvement of accuracy from 69% to 81% (P=0.026, FIG. 5B). As a result, we concluded that classifier combining Nomogram and the 8 fusion gene panel generated the best prediction accuracy that outperforms each diagnostic tool alone.

6.5. Discussion

Transcriptome and whole genome sequencings revealed numerous fusion RNA transcripts occurring not just in prostate cancer but also in healthy organ donor prostate samples (Table 17). Some of these fusion events are verifiable by sequencing on the cDNA products. The functions of these new transcripts are not known. Since most of these chimeric RNA transcripts in healthy individuals are the splicing products of two adjacent genes, they are likely the new isoforms of the existing genes. These previously defined independent "genes" in the transcript could be one of the preferred spliced isoforms of the existing larger genes.

TABLE 6

Putative fusion transcripts from 5 prostate cancer samples

1T

| Fusion gene 1 | Fusion gene2 | Gene 1 breakpoint | Gene2 breakpoint | Reads | in DNAseq | Distance |
|---|---|---|---|---|---|---|
| TMPRSS2 | ERG | 21: 42870046: − | 21: 39817544: − | 8 | 2 | 3052502 |
| FZD4 | RP11-736K20.5 | 11: 86665843: − | 11: 86633140: − | 7 | 0 | 32703 |
| ZNF720 | RP11-488L18.4 | 16: 31734674: + | 1: 247363495: − | 3 | 0 | Inf |
| RP11-356O9.1 | TTC6 | 14: 38033571: + | 14: 38075868: + | 12 | 0 | 42297 |
| IGLV2-8 | IGLL5 | 22: 23165779: + | 22: 23235961: + | 5 | 0 | 70182 |
| RP11-381K20.2 | KLHL3 | 5: 137150022: − | 5: 137056273: − | 3 | 0 | 93749 |
| ADAP2 | RNF135 | 17: 29286022: + | 17: 29311635: + | 3 | 0 | 25613 |
| LRRC59 | FLJ60017 | 17: 48469759: − | 11: 63129852: + | 3 | 7 | Inf |
| RIPK1 | SERPINB9 | 6: 3064293: + | 6: 2900855: − | 5 | 24 | 163438 |

2T

| Fusion gene 1 | Fusion gene2 | Gene 1 breakpoint | Gene2 breakpoint | Read pairs | in DNAseq | Distance |
|---|---|---|---|---|---|---|
| MTOR | TP53BP1 | 1: 11290982: − | 15: 43773220: − | 12 | 2 | Inf |

3T

| Fusion gene 1 | Fusion gene2 | Gene 1 breakpoint | Gene2 breakpoint | Read pairs | in DNAseq | Distance |
|---|---|---|---|---|---|---|
| MAN2A1 | FER | 5: 109153139: + | 5: 108380381: + | 7 | 4 | 772758 |
| KDM4B | AC011523.2 | 19: 5047680: + | 19: 51354167: + | 7 | 0 | 46306487 |
| TRMT11 | GRIK2 | 6: 126307768: + | 6: 102069824: + | 11 | 0 | 24237944 |
| NAP1L1 | CCDC88C | 12: 76444311: − | 14: 91850880: − | 3 | 2 | Inf |
| RP11-386M24.4 | H2AFV | 15: 93277091: − | 7: 44874151: − | 6 | 0 | Inf |
| CCNH | C5orf30 | 5: 86697519: − | 5: 102601609: + | 3 | 8 | 15904090 |
| UBA52 | CTA-242H14.1 | 19: 18685741: + | 7: 252729331: − | 3 | 3 | Inf |
| C1orf196 | KAZN | 1: 14507087: + | 1: 14925479: + | 3 | 0 | 418392 |
| MTIF2 | AL592494.3 | 2: 55473480: − | 1: 121244615: + | 6 | 0 | Inf |
| RP11-168J18.6 | PPP2R5C | 3: 52408762: + | 14: 102368056: + | 3 | 2 | Inf |
| RPL38 | AC007283.4 | 17: 72205448: + | 2: 202027232: − | 3 | 0 | Inf |
| ACSS1 | APMAP | 20: 24988402: − | 20: 24964655: − | 3 | 0 | 23747 |

4T

| Fusion gene 1 | Fusion gene2 | Gene 1 breakpoint | Gene2 breakpoint | Read pairs | in DNAseq | Distance |
|---|---|---|---|---|---|---|
| RP11-443D10.3 | ACACB | 12: 109551220: + | 12: 109577202: + | 4 | 0 | 25982 |
| SLC45A2 | AMACR | 5: 33982341: − | 5: 34006004: − | 3 | 0 | 23663 |
| RP11-550F7.1 | CAP1 | 3: 76483671: + | 1: 40529899: + | 7 | 9 | Inf |
| TMC5 | CCP110 | 16: 19508485: + | 16: 19539189: + | 6 | 0 | 30704 |
| TLK2 | RP11-274B21.1 | 17: 60631098: + | 7: 128248237: + | 6 | 126 | Inf |
| TMEM135 | CCDC67 | 11: 87030419: + | 11: 93127625: + | 7 | 26 | 6097206 |

5T

| Fusion gene 1 | Fusion gene2 | Gene 1 breakpoint | Gene2 breakpoint | Spanning_pairs | in DNAseq | Distance |
|---|---|---|---|---|---|---|
| TMPRSS2 | ERG | 21: 42870046: − | 21: 39947671: − | 12 | 2 | 2922375 |

This analysis reveals significant number of cancer specific fusion gene events. These fusions are not detectable in either organ donor prostate or benign prostate tissues from prostate cancer patients. Most of these fusion transcripts appear to express in low abundance, with only an average 6.6 reads of these fusion transcripts detected in >1333× sequencing. Indeed, when the coverage was reduced to 600× in simulation studies, only MTOR-TP53BP1 was detected consistently. The characteristics of these fusion genes are that they either have a large distance between the joining genes or have trans-direction of fusion that could only occur when chromosome recombination happens. In either scenario, DNA alteration in genome level must be the underlying mechanism.

Although the association between the eight novel fusion transcripts and prostate cancer recurrence is striking, the biological roles of these fusion transcripts are not yet elucidated. Given the known function of the genes contributing to the fusion transcripts, their formation may have impact on several cell pathways such as RNA stability[24] (TRMT11-GRIK2), protein glycosylation[25] (MAN2A1-FER), cell cycle progression[26,27,28] (CCNH-C5orf50 and MTORTP53BP1), fibroblast growth factor nuclear import[29] (LRRC59-FLJ60017), histone demethylation[30] (KDM4B-AC011523.2), and fatty acid metabolism[31] (SLC45A2-AMACR). Many of these pathways appear to be fundamental to cell growth and survival.

Two of the fusion genes are of particular interest: MAN2A1-FER and SLC45A2-AMACR. First, MAN2A1 is a mannosidase critical in glycosylation of proteins[19]. It is usually located in Golgi apparatus. The truncation in MAN2A1-FER replaces the mannosidase domain with a tyrosine kinase domain from FER[20], while leaves the glycosyl transferase domain intact. The chimera protein likely loses the mannosidase function. The new kinase domain in MAN2A1-FER may confer the chimera protein a tyrosine kinase activity. Thus, the impact of this fusion gene could be profound: abnormal glycosylation and phosphorylation in hundreds of secreted or plasma membrane proteins. It may impact on cell-cell interactions and signal transduction, and generate a new immune response to the cancer cells. Second, AMACR is a racemase that catalyzes 2R stereoisomers of phytanic and pristanic acid to their S counterparts. AMACR is essential for β-oxidation of branch fatty acid in mitochondria. SLC45A2 is a transmembrane solute carrier known for its protective role in melanoma. SLC45A2-AMACR chimeric protein has 5 transmembrane domains of SLC45A2 truncated and replaced with a largely intact racemase. SLC45A2-AMACR also loses the mitochondria target site in AMACR. Presumably, the fusion protein would be located in the plasma membrane. It is of interest that all prostate cancer samples with SLC45A2-AMACR fusion proved highly aggressive. Identification of the signaling pathways of this chimeric protein may gain critical insight into the behavior of prostate cancer.

Even though the prevalence of each fusion transcript in prostate cancer samples is low (ranging from 2.9% to 7.9%), up to 60% of prostate cancers that later recurred and had short PSADT were positive for at least one of these fusion transcripts. The specificity of these fusion transcripts in predicting prostate cancer recurrence appears remarkably high, ranging from 89-100% among 4 separate prediction cohorts. There were no long term recurrence-free survivors if the primary tumor contained either TRMT11-GRIK2, MTOR-TP53BP1 or LRRC59-FLJ60017 fusion transcripts.

To our knowledge, this is the first report showing that a set of fusion genes is strongly associated with poor prognosis of prostate cancer. This discovery may have salient impact on clinical practice in light of the limit of serum PSA and Gleason's grading from biopsy samples in predicting prostate cancer clinical outcome. Detection of one of these prostate cancer recurrence association fusion genes in prostate cancer sample may warrant a more aggressive treatment regimen. The fusion RNA and chimera proteins validated in this study may lay down the foundation for future molecular targeting therapy for prostate cancer patients carrying these genes.

TABLE 7

Clinical and pathological characteristics of 213 cases of prostate cancer from UPMC cohort

| Sample | Type | TNM | Margin | Recurrence | Recurrence fast | Recurrence simple | Gleason | Age | Sex | Race | PSA pre-operative | Time to progession (Months) | PSADT (months) | Radiology follow-up | Length of follow-up (Months) | Additional Treatment |
|---|---|---|---|---|---|---|---|---|---|---|---|---|---|---|---|---|
| 11462T | T | T3aN0MX | Negative | none | nf | n | 7.0 | 50s | M | W | 25.0 | N/A | N/A | NEGATIVE | 158.0 | None |
| 1199T | T | T3bN0MX | Negative | slow | nf | y | 8.0 | 50s | M | W | 40.0 | 15.0 | 33.7 | NEGATIVE | 150.0 | NK |
| 13745T | T | T1cN0MX | Negative | none | nf | n | 7.0 | 60s | M | W | 6.8 | N/A | N/A | NO | 151.0 | None |
| 14304T | T | T2BN0MX | Negative | none | nf | n | 6.0 | 50s | M | W | 7.8 | N/A | N/A | NO | 156.0 | None |
| 14878T | T | T2bN0MX | Negative | none | nf | n | 8.0 | 60s | M | W | 6.2 | N/A | N/A | NO | 151.0 | None |
| 15463T | T | T2bN0MX | Negative | none | nf | n | 7.0 | 50s | M | W | 7.8 | N/A | N/A | NO | 149.0 | None |
| 15733T | T | T3bN0MX | Negative | none | nf | n | 7.0 | 50s | M | W | 6.4 | N/A | N/A | NO | 152.0 | None |
| 15875T | T | T3aN0MX | Negative | none | nf | n | 7.0 | 40s | M | W | 5.6 | N/A | N/A | NO | 154.0 | None |
| 15922T | T | T3bN0MX | Negative | slow | nf | y | 7.0 | 60s | M | W | 16.0 | N/A | N/A | NO | 154.0 | NK |
| 16464T | T | T3aN1MX | Negative | slow | nf | y | 7.0 | 60s | M | W | 8.5 | 88.5 | 24.6 | NEGATIVE | 149.0 | NK |
| 16947T | T | T2bN0MX | Negative | slow | nf | y | 8.0 | 70s | M | W | 6.1 | 31.0 | 15.6 | NEGATIVE | 148.0 | NK |
| 19381T | T | T2bN0MX | Negative | none | nf | n | 6.0 | 50s | M | AA | 2.5 | N/A | N/A | NO | 154.0 | None |
| 1942T | T | T3bN0MX | Positive | fast | f | y | 9.0 | 60s | M | W | 7.5 | 80.1 | 14.8 | NEGATIVE | 157.0 | NK |
| 19PR530T | T | T2cN0MX | Negative | ND | ND | ND | 7.0 | 60s | M | W | 4.4 | N/A | N/A | not done | 21.0 | None |
| 1AF8378T | T | T3aN0MX | Negative | none | nf | n | 6.0 | 60s | M | W | 12.9 | N/A | N/A | NO | 153.0 | None |
| 23FB120T | T | T3bN0MX | Negative | none | nf | n | 7.0 | 60s | M | W | 11.4 | N/A | N/A | NEGATIVE | 104.0 | None |
| 23HB021T | T | T2bN0MX | Negative | Fast | f | y | 7.0 | 50s | M | W | 6.4 | 23.0 | 3.0 | NEGATIVE | 78.0 | ADT, RT |
| 23R19T | T | T2bN0MX | Negative | none | nf | n | 7.0 | 50s | M | W | 7.2 | N/A | NA | NEGATIVE | 151.0 | None |
| 23HB8346T | T | T2cN0MX | Negative | ND | ND | ND | 6.0 | 60s | M | W | 7.3 | N/A | N/A | NO | 34.0 | None |
| 25265T | T | T3bN0MX | Negative | none | nf | n | 7.0 | 60s | M | W | 3.4 | N/A | N/A | NO | 156.0 | None |
| 25313T | T | T3bN0MX | Negative | none | nf | n | 8.0 | 50s | M | W | 9.5 | N/A | N/A | NO | 156.0 | None |
| 2644T | T | T3aN0MX | Negative | slow | nf | y | 9.0 | 60s | M | W | 11.2 | 5.9 | 31.2 | NEGATIVE | 164.0 | NK |
| 2671T | T | T2cN0MX | Positive | slow | nf | y | 7.0 | 60s | M | W | 8.9 | 17.0 | 17.0 | NEGATIVE | 164.0 | NK |
| 28278T | T | T3aN0MX | Negative | none | nf | n | 7.0 | 50s | M | W | 4.0 | N/A | N/A | NO | 157.0 | None |
| 29671T | T | T3AN0MX | Negative | slow | nf | y | 7.0 | 60s | M | W | 8.9 | 15.4 | 15.4 | NEGATIVE | 155.0 | NK |
| 29825T | T | T3aN0MX | Negative | none | nf | n | 7.0 | 50s | M | W | 12.0 | N/A | N/A | NEGATIVE | 159.0 | None |
| 2HB568T | T | T3bN0MX | Negative | fast | f | y | 7.0 | 60s | M | W | 5.7 | 24.1 | 3.9 | NEGATIVE | 70.3 | ADT, RT |
| 2HB591T | T | T3bN1MX | Negative | fast | f | y | 7.0 | 60s | M | W | 18.3 | 1.5 | 3.8 | POSITIVE FOR BONE AND HEPATIC METASTASIS | 47.0 | ADT, CHEMO |
| 21B483T | T | T2bN0MX | Negative | fast | f | y | 7.0 | 50s | M | W | 6.2 | 1.7 | 1.9 | NO | 58.0 | ADT, CHEMO |
| 2K98-8378T | T | T3AN0MX | Positive | none | nf | n | 7.0 | 60s | M | W | 8.6 | N/A | N/A | NO | 158.0 | None |
| 33PR053T | T | T3bN1MX | Negative | fast | f | y | 8.0 | 60s | M | W | 21.0 | 1.0 | 0.4 | bone metastasis | 16.0 | CHEMO |
| 34PR227T | T | T3bN0MX | Negative | none | nf | n | 7.0 | 60s | M | W | 11.6 | N/A | N/A | NO | 123.0 | None |
| 34T | T | T2CN0MX | Positive | none | nf | n | 7.0 | 50s | M | U | 3.6 | N/A | N/A | NEGATIVE | 159.0 | None |
| 3D94336T | T | T2bN0MX | Negative | none | nf | n | 6.0 | 60s | M | W | 6.6 | N/A | N/A | NO | 164.0 | None |
| 3G989122T | T | T3bN0MX | Negative | none | nf | n | 7.0 | 50s | M | U | 9.0 | N/A | N/A | NO | 164.0 | None |
| 3K5772T | T | T3aN0MX | Negative | none | nf | n | 7.0 | 60s | M | W | 6.7 | N/A | N/A | NO | 160.0 | None |
| 3M-11462T | T | T3bN0MX | Negative | none | nf | n | 7.0 | 50s | M | W | 22.0 | N/A | N/A | NEGATIVE | 158.0 | None |
| 3Q-10614T | T | T3bN0MX | Negative | none | nf | n | 7.0 | 70s | M | W | 12.5 | N/A | N/A | NO | 77.0 | None |

TABLE 7-continued

Clinical and pathological characteristics of 213 cases of prostate cancer from UPMC cohort

| Sample | Type | TNM | Margin | Recurrence | Recurrence fast | Recurrence simple | Gleason | Age | Sex | Race | PSA pre-operative | Time to progession (Months) | PSADT (months) | Radiology follow-up | Length of follow-up (Months) | Additional Treatment |
|---|---|---|---|---|---|---|---|---|---|---|---|---|---|---|---|---|
| 4308T | T | T1CN0MX | Negative | none | nf | n | 6.0 | 60s | M | W | 12.4 | N/A | N/A | NO | 153.0 | None |
| 4336T | T | T1cN0MX | Positive | slow | nf | y | 6.0 | 60s | M | W | 2.5 | 21.7 | 22.0 | NEGATIVE | 165.0 | NK |
| 4L98-27086T | T | T3aN0MX | Negative | none | nf | n | 7.0 | 60s | M | W | 12.2 | N/A | N/A | NO | 78.0 | None |
| 5396T | T | T2bN1MX | Negative | none | nf | n | 9.0 | 60s | M | W | 8.9 | N/A | N/A | NO | 156.0 | None |
| 54IB289T | T | T2bN0MX | Negative | none | nf | n | 6.0 | 50s | M | W | 9.6 | N/A | N/A | not done | 89.0 | None |
| 562T | T | T2bN0MX | Negative | none | nf | n | 6.0 | 60s | M | W | 11.3 | N/A | N/A | NO | 157.0 | None |
| 56FB76T | T | T3bN0MX | Negative | none | nf | n | 6.0 | 60s | M | W | 6.6 | N/A | N/A | not done | 137.0 | None |
| 6647T | T | T3AN0MX | Negative | none | nf | y | 7.0 | 40s | M | AA | 6.1 | 95.6 | 45.5 | NEGATIVE | 150.0 | NK |
| 678T | T | T2bN0MX | Positive | none | nf | n | 7.0 | 60s | M | W | 5.3 | N/A | N/A | NO | 152.0 | None |
| 67R13T | T | T2bN0MX | Negative | none | nf | n | 6.0 | 60s | M | W | 10.8 | N/A | N/A | NO | 145.0 | None |
| 6837T | T | T3aN0MX | Negative | slow | nf | y | 6.0 | 70s | M | W | 10.4 | 87.4 | 15.4 | NEGATIVE | 155.0 | NK |
| 7221T | T | T3bN0MX | Negative | fast | f | y | 7.0 | 50s | M | W | 13.5 | 16.6 | 2.4 | POSITIVE FOR BONE METASTASIS | 124.0 | ADT, CHEMO, RT |
| 7270T | T | T3BN1MX | Negative | none | nf | n | 9.0 | 70s | M | W | 15.9 | N/A | N/A | NO | 98.0 | None |
| 7504T | T | T3bN0MX | Positive | none | nf | n | 9.0 | 70s | M | U | 10.5 | N/A | N/A | NO | 143.0 | None |
| 78HB340T | T | T3b1N0MX | Negative | ND | ND | ND | 7.0 | 60s | M | W | 9.6 | N/A | N/A | not done | 14.0 | None |
| 7943T | T | T3AN0MX | Positive | none | nf | n | 7.0 | 60s | M | W | 9.6 | N/A | N/A | NO | 137.0 | None |
| 828142T | T | T2bN0MX | Negative | none | nf | n | 8.0 | 60s | M | W | 7.4 | N/A | N/A | NO | 160.0 | None |
| 832972T | T | T2bN0MX | Negative | none | nf | n | 10.0 | 50s | M | W | 7.5 | N/A | N/A | NO | 160.0 | None |
| 842620T | T | T2bN0MX | Negative | none | nf | n | 7.0 | 50s | M | W | 7.7 | N/A | N/A | NO | 159.0 | None |
| 8432T | T | T2aN0MX | Positive | none | nf | n | 7.0 | 60s | M | W | 6.6 | N/A | N/A | NO | 166.0 | None |
| 84375T | T | T2bN0MX | Negative | none | nf | n | 6.0 | 60s | M | W | 6.8 | N/A | N/A | NO | 161.0 | None |
| 84876T | T | T2bN0MX | Negative | none | nf | n | 7.0 | 60s | M | W | 8.9 | N/A | N/A | NO | 160.0 | None |
| 84973T | T | T2bN0MX | Negative | none | nf | n | 7.0 | 50s | M | W | 6.1 | N/A | N/A | NO | 153.0 | None |
| 855327T | T | T2bN0MX | Negative | none | nf | n | 6.0 | 60s | M | W | 9.1 | N/A | N/A | NO | 137.0 | None |
| 8629T | T | T1CN0MX | Negative | none | nf | n | 6.0 | 50s | M | W | 6.5 | N/A | N/A | NO | 163.0 | None |
| 863176T | T | T3bN0MX | Negative | none | nf | n | 8.0 | 60s | M | W | 11.7 | 1.4 | 1.0 | NO | 151.0 | ADT, CHEMO |
| 8712362T | T | T2bN0MX | Negative | none | nf | n | 8.0 | 50s | M | W | 10.4 | N/A | N/A | NO | 155.0 | None |
| 8713205T | T | T2bN0MX | Negative | slow | nf | y | 10.0 | 60s | M | W | 8.3 | 12.0 | 18.3 | NO | 161.0 | NK |
| 8741T | T | T2bN0MX | Negative | none | nf | n | 6.0 | 60s | M | W | 9.1 | N/A | N/A | NO | 151.0 | None |
| 8433T | T | T3bN0MX | Negative | none | nf | n | 8.0 | 60s | M | W | 9.6 | N/A | N/A | NO | 160.0 | None |
| 9122T | T | T1CN0MX | Negative | none | nf | n | 7.0 | 50s | M | W | 13.0 | N/A | N/A | NO | 164.0 | None |
| 9210207T | T | T3bN0MX | Negative | slow | nf | y | 8.0 | 60s | M | W | 14.6 | 20.0 | 3.2 | NO | 105.0 | NK |
| 9217293T | T | T2bN0MX | Negative | slow | nf | y | 8.0 | 60s | M | W | 7.8 | 20.0 | 16.9 | NO | 132.0 | NK |
| 92SR293T | T | T3bN0MX | Negative | none | nf | y | 6.0 | 50s | M | W | 6.5 | N/A | N/A | NO | 155.0 | NK |
| 9412443T | T | T3bN0MX | Negative | fast | f | y | 8.0 | 50s | M | W | 11.1 | 4.3 | 2.1 | NO | 78.0 | ADT, CHEMO |
| 9812033T | T | T2bN0MX | Negative | none | nf | n | 6.0 | 50s | M | W | 7.9 | N/A | N/A | NO | 165.0 | None |
| 9814481T | T | T3bN0MX | Negative | slow | nf | y | 9.0 | 60s | M | W | 11.3 | 38.0 | 21.0 | NO | 160.0 | NK |
| 98TA-83782T | T | T3bN0MX | Negative | none | nf | n | 7.0 | 60s | M | W | 13.2 | N/A | N/A | NO | 151.0 | None |

TABLE 7-continued

Clinical and pathological characteristics of 213 cases of prostate cancer from UPMC cohort

| Sample | Type | TNM | Margin | Recurrence | Recurrence fast | Recurrence simple | Gleason | Age | Sex | Race | PSA pre-operative | Time to progression (Months) | PSADT (months) | Radiology follow-up | Length of follow-up (Months) | Additional Treatment |
|---|---|---|---|---|---|---|---|---|---|---|---|---|---|---|---|---|
| 991199T | T | T3bN0MX | Negative | slow | nf | y | 8.0 | 50s | M | W | 15.5 | 15.0 | 24.0 | NO | 151.0 | ADT, CHEMO |
| 9927086T | T | T2BN0MX | Negative | none | nf | n | 6.0 | 50s | M | W | 9.5 | N/A | N/A | NO | 158.0 | None |
| 994308T | T | T1cN0MX | Negative | none | nf | n | 6.0 | 60s | M | W | 8.3 | N/A | N/A | NO | 160.0 | None |
| 995772T | T | T3bN0MX | Negative | none | nf | n | 7.0 | 60s | M | W | 8.7 | N/A | N/A | NO | 163.0 | None |
| DB8237T | T | TbN0MX | Negative | slow | nf | y | 6.0 | 70s | M | W | 6.3 | 46.0 | 26.0 | NO | 123.4 | NK |
| FB120T | T | T3aN0MX | Negative | slow | nf | y | 7.0 | 60s | M | W | 61.1 | 1.3 | 20.8 | NEGATIVE | 94.9 | NK |
| FB174T | T | T3aN0MX | Negative | fast | f | y | 7.0 | 60s | M | W | 6.9 | 30.5 | 3.2 | NEGATIVE | 94.7 | ADT, CHEMO, RT |
| FB183T | T | T2cN0MX | Negative | slow | nf | y | 7.0 | 60s | M | W | 9.7 | 78.8 | 25.6 | NO | 99.1 | NK |
| FB238T | T | T3bN0MX | Negative | slow | nf | y | 7.0 | 60s | M | W | 15.9 | 41.0 | 30.0 | NO | 101.7 | NK |
| FB421T | T | T3aN0MX | Negative | fast | f | y | 7.0 | 60s | M | W | 4.5 | 1.3 | 4.4 | POSITIVE FOR BONE METASTASIS | 92.1 | ADT |
| FB76T | T | T2cN0MX | Negative | none | nf | n | 7.0 | 50s | M | W | 6.5 | N/A | N/A | not done | 130.0 | None |
| FB94T | T | T2cN0MX | Negative | slow | nf | y | 7.0 | 60s | M | W | 5.1 | 48.6 | 15.2 | NEGATIVE | 96.6 | NK |
| GB195T | T | T2cN0MX | Negative | slow | nf | y | 7.0 | 60s | M | W | 10.1 | 53.2 | 23.8 | NEGATIVE | 65.2 | RT |
| GB368T | T | T3aN0MX | Negative | slow | nf | y | 7.0 | 50s | M | W | 5.5 | 70.0 | 15.0 | not done | 112.0 | None |
| GB400T | T | T3bN0MX | Negative | fast | f | y | 7.0 | 60s | M | W | 3.5 | 29.6 | 4.2 | NEGATIVE | 78.9 | ADT, RT |
| HB021T | T | T2bN0MX | Negative | fast | f | y | 6.0 | 50s | M | W | 5.9 | 24.2 | 4.0 | NEGATIVE | 80.1 | ADT, RT |
| HB033T | T | T2cN0MX | Negative | none | nf | n | 7.0 | 50s | M | W | 8.4 | N/A | N/A | NO | 87.0 | None |
| HB207T | T | T3bN0MX | Negative | fast | f | y | 9.0 | 60s | M | W | 6.3 | 5.5 | 0.6 | POSITIVE FOR BONE METASTASIS | 74.7 | ADT, CHEMO |
| HB235T | T | T3bN1MX | Negative | slow | nf | y | 9.0 | 60s | M | W | 4.6 | 1.3 | 20.8 | POSITIVE FOR BONE METASTASIS | 10.7 | ADT, CHEMO |
| HB261T | T | T3aN0MX | Negative | none | nf | n | 7.0 | 50s | M | W | 5.4 | N/A | N/A | NO | 74.0 | None |
| HB303T | T | T2cN0MX | Negative | none | nf | n | 7.0 | 60s | M | W | 31.3 | N/A | N/A | not done | 102.0 | None |
| HB305T | T | T3bN0MX | Negative | fast | f | y | 6.0 | 60s | M | W | 10.1 | 1.4 | 3.9 | NO | 68.8 | ADT, CHEMO |
| HB322T | T | T2cN0MX | Negative | none | nf | n | 7.0 | 60s | M | W | 4.9 | N/A | N/A | not done | 102.0 | None |
| HB327T | T | T2cN0MX | Negative | none | nf | n | 8.0 | 50s | M | W | 9.5 | N/A | N/A | not done | 102.0 | None |
| HB340T | T | T2cN0MX | Negative | ND | ND | ND | 7.0 | 60s | M | W | 9.6 | N/A | N/A | not done | 32.0 | None |
| HB346T | T | T3aN0MX | Negative | none | nf | n | 7.0 | 60s | M | W | 17.2 | N/A | N/A | not done | 102.0 | None |
| HB46T | T | T3bN0MX | Negative | slow | nf | y | 8.0 | 60s | M | W | 4.7 | 20.1 | 15.3 | NO | 69.1 | NK |
| HB492T | T | T2cN0MX | Negative | slow | nf | y | 7.0 | 50s | M | W | 7.4 | 82.0 | 25.0 | negative | 99.0 | None |
| HB504T | T | T3bN0MX | Positive | fast | f | y | 8.0 | 50s | M | U | 70.0 | 4.3 | 0.7 | NEGATIVE | 58.7 | ADT, CHEMO |
| HB526T | T | T3bN0MX | Positive | fast | f | y | 6.0 | 60s | M | W | 8.7 | 1.4 | 2.7 | POSITIVE FOR BONE METASTASIS | 23.9 | ADT, CHEMO |

TABLE 7-continued

Clinical and pathological characteristics of 213 cases of prostate cancer from UPMC cohort

| Sample | Type | TNM | Margin | Recurrence | Recurrence fast | Recurrence simple | Gleason | Age | Sex | Race | PSA pre-operative | Time to progession (Months) | PSADT (months) | Radiology follow-up | Length of follow-up (Months) | Additional Treatment |
|---|---|---|---|---|---|---|---|---|---|---|---|---|---|---|---|---|
| HB568T | T | T3bN0MX | Negative | fast | f | y | 7.0 | 60s | M | W | 4.4 | 22.4 | 4.2 | NEGATIVE | 68.2 | ADT, RT |
| HB591T | T | T3bN1MX | Negative | fast | f | y | 7.0 | 60s | M | W | 17.6 | 1.3 | 3.6 | POSITIVE FOR BONE AND HEPATIC METASTASIS | 47.0 | ADT, CHEMO |
| HB603T | T | T3aN1MX | Negative | slow | nf |  | 7.0 | 60s | M | W | 8.4 | 22.1 | 15.9 | NO | 70.7 | None |
| HB658T | T | T3bN0MX | Negative | none | nf | n | 7.0 | 70s | M | W | 20.6 | N/A | N/A | not done | 97.0 | None |
| HB705T | T | T2cN0MX | Negative | none | nf |  | 7.0 | 60s | M | W | 9.8 | N/A | N/A | not done | 97.0 | None |
| HB951T | T | T3bN1MX | Negative | fast | f | y | 7.0 | 60s | M | W | 23.1 | 15.9 | 4.0 | POSITIVE FOR BONE AND HEPATIC METASTASIS | 47.0 | ADT, CHEMO |
| IB071T | T | T3aN0MX | Negative | fast | f | y | 7.0 | 60s | M | W | 2.6 | 4.3 | 1.6 | POSITIVE FOR BONE METASTASIS | 45.6 | ADT, RT |
| IB110T | T | T2cN0MX | Negative | none | nf | n | 8.0 | 60s | M | W | 2.7 | N/A | N/A | not done | 94.0 | None |
| IB111T | T | T2cN0MX | Negative | none | nf | n | 7.0 | 60s | M | W | 9.5 | N/A | N/A | not done | 94.0 | None |
| IB112T | T | T3aN0MX | Negative | slow | nf | y | 7.0 | 60s | M | W | 4.7 | 55.8 | 30.6 | not done | 67.2 | NK |
| IB134T | T | T3bN0MX | Negative | none | nf | n | 9.0 | 70s | M | W | 15.7 | N/A | N/A | NO | 77.0 | None |
| IB136T | T | T3bN1MX | Negative | fast | f | y | 8.0 | 50s | M | W | 19.6 | 1.8 | 2.2 | POSITIVE FOR BONE METASTASIS | 69.2 | ADT, CHEMO |
| IB180T | T | T2cN0MX | Negative | none | nf | n | 7.0 | 60s | M | W | 3.0 | N/A | N/A | not done | 93.0 | None |
| IB273T | T | T2bN0MX | Negative | fast | f | y | 7.0 | 50s | M | W | 4.3 | 10.6 | 4.0 | NEGATIVE | 60.8 | RT |
| IB289T | T | T2aN0MX | Negative | none | nf | n | 7.0 | 60s | M | W | 10.0 | N/A | N/A | not done | 91.0 | None |
| IB298T | T | T3bN0MX | Negative | slow | nf | y | 7.0 | 60s | M | W | 5.3 | 34.3 | 20.4 | NO | 67.0 | NK |
| IB362T | T | T3bN0MX | Negative | slow | nf | y | 9.0 | 50s | M | W | 18.9 | 4.6 | 16.0 | NEGATIVE | 65.2 | RT |
| IB378T | T | T3bN0MX | Negative | none | nf | n | 7.0 | 60s | M | W | 2.8 | N/A | N/A | not done | 90.0 | None |
| IB483T | T | T2bN0MX | Negative | fast | f | y | 7.0 | 50s | M | W | 5.2 | 1.4 | 1.7 | NO | 54.8 | ADT, CHEMO |
| JB154T | T | T3bN0MX | Negative | fast | f | y | 8.0 | 50s | M | U | 70.0 | 3.5 | 0.9 | NEGATIVE | 58.7 | ADT, CHEMO |
| JB197T | T | T3bN0MX | Positive | fast | f | y | 7.0 | 50s | M | W | 11.2 | 1.4 | 8.85 (death) | SINGLE FOCUS OF INCREASED ACTIVITY | 48.4 | ADT, CHEMO |
| JB426T | T | T2cN0MX | Negative | fast | f | y | 7.0 | 60s | M | W | 5.7 | 17.4 | 2.3 | NEGATIVE | 50.9 | ADT, RT |
| JB770T | T | T2cN0MX | Negative | fast | f | y | 8.0 | 60s | M | W | 2.4 | 33.8 | 3.0 | NEGATIVE | 33.9 | RT |
| KB170T | T | T3bN1MX | Negative | fast | f | y | 7.0 | 70s | M | W | 14.1 | 1.8 | 4.2 | POSITIVE FOR NODAL METASTASIS | 37.2 | ADT |
| PR018ST | T | T3aN0MX | Positive | slow | nf | y | 7.0 | 60s | M | W | 9.0 | 78.0 | 55.0 | NO | 140.2 | ADT, CHEMO |
| PR053T | T | TURP | Negative | fast | f | y | TURP | 60s | M | W | 182.5 | 1.0 | 0.2 | bone metastasis | 15.0 | |

TABLE 7-continued

Clinical and pathological characteristics of 213 cases of prostate cancer from UPMC cohort

| Sample | Type | TNM | Margin | Recurrence | Recurrence fast | Recurrence simple | Gleason | Age | Sex | Race | PSA pre-operative | Time to progression (Months) | PSADT (months) | Radiology follow-up | Length of follow-up (Months) | Additional Treatment |
|---|---|---|---|---|---|---|---|---|---|---|---|---|---|---|---|---|
| PR079T | T | T3aN0MX | Positive | slow | nf | y | 7.0 | 60s | M | W | 5.1 | 95.3 | 17.3 | NO | 129.8 | None |
| PR227T | T | T2cN0MX | Negative | none | nf | n | 7.0 | 60s | M | W | 4.5 | N/A | N/A | not done | 135.0 | ADT, CHEMO |
| PR236T | T | T3bN0MX | Negative | fast | f | y | 10.0 | 60s | M | W | 9.9 | 1.3 | 3.9 | POSITIVE FOR BLASTIC METASTASIS | 64.7 | NK |
| PR300T | T | T3bN1MX | Negative | fast | f | y | 7.0 | 50s | M | W | 20.3 | 71.5 | 3.9 | NEGATIVE | 98.5 | NK |
| PR303T | T | T3bN0MX | Negative | slow | nf | y | 6.0 | 70s | M | W | 10.5 | 54.6 | 43.3 | NO | 79.7 | RT |
| PR306T | T | T3bN0MX | Positive | slow | nf | y | 7.0 | 60s | M | W | 11.5 | 16.4 | 52.9 | NEGATIVE | 109.1 | ADT, CHEMO, RT |
| PR310T | T | T3bN0MX | Negative | fast | f | y | 7.0 | 60s | M | W | 5.1 | 22.8 | 1.6 | POSITIVE FOR BONE AND ILIAC METASTASIS | 47.7 | |
| PR375T | T | T3bN1MX | Negative | fast | f | y | 7.0 | 50s | M | W | 11.3 | 1.2 | 1.1 | POSITIE FOR BONE AND PELVIC METASTASIS | 114.9 | ADT, CHEMO, RT |
| PR434T | T | T3aN0MX | Negative | slow | nf | y | 7.0 | 60s | M | W | 6.4 | 72.8 | 30.8 | NO | 137.6 | RT |
| PR521T | T | T2bN0MX | Negative | slow | nf | y | 7.0 | 50s | M | W | 6.4 | 79.2 | 15.5 | NO | 126.2 | RT |
| PR530T | T | T2cN0MX | Negative | ND | ND | ND | 7.0 | 60s | M | W | 4.4 | N/A | N/A | Not Done | 25.0 | None |
| PR534T | T | T2bN0MX | Negative | none | nf | n | 6.0 | 60s | M | W | 8.4 | N/A | N/A | not done | 13.0 | None |
| PR536T | T | T2bN0MX | Negative | none | nf | n | 7.0 | 50s | M | W | 5.4 | N/A | N/A | not done | 136.0 | None |
| R10T | T | T3bN0MX | Negative | fast | f | y | 8.0 | 60s | M | W | 13.1 | 11.0 | 2.3 | NO | 74.0 | ADT, CHEMO |
| R13T | T | T3bN0MX | Negative | none | nf | n | 7.0 | 60s | M | W | 10.4 | N/A | N/A | NO | 157.0 | None |
| R16T | T | T2bN0MX | Negative | none | nf | n | 5.8 | 50s | M | W | 5.8 | N/A | N/A | NO | 159.0 | None |
| R18T | T | T2bN0MX | Negative | none | nf | n | 7.0 | 50s | M | W | 9.1 | N/A | N/A | NO | 163.0 | None |
| R19T | T | T3bN0MX | Negative | slow | nf | y | 9.0 | 60s | M | W | 13.8 | 2.0 | 1.1 | NO | 60.0 | ADT, CHEMO |
| R26T | T | T3aN0MX | Negative | none | nf | n | 7.0 | 60s | M | W | 7.7 | N/A | N/A | NO | 146.0 | None |
| R3T | T | T2bN0MX | Negative | none | nf | n | 7.0 | 60s | M | W | 7.1 | N/A | N/A | NO | 137.0 | None |
| R57T | T | T2bN0MX | Negative | none | nf | n | 7.0 | 50s | M | W | 8.8 | N/A | N/A | NO | 107.0 | None |
| R59T | T | T3bN0MX | Negative | none | nf | n | 7.0 | 60s | M | W | 9.8 | N/A | N/A | NO | 127.0 | None |
| R61T | T | T2bN0MX | Negative | none | nf | n | 7.0 | 50s | M | W | 12.5 | N/A | N/A | NO | 160.0 | None |
| SR9R57T | T | T2bN0MX | Negative | none | nf | n | 7.0 | 60s | M | W | 7.2 | N/A | N/A | NO | 161.0 | None |
| TP08PP-S0721T | T | T3bN1MX | Negative | fast | f | y | 9.0 | 50s | M | W | 20.2 | 1.3 | 1.1 | POSITIVE FOR BONE METASTASIS | 17.0 | ADT, CHEMO |
| TP08-S00530T | T | T3bN0MX | Negative | fast | f | y | 7.0 | 60s | M | W | 11.1 | 1.3 | 3.3 | NEW LEFT EXTERNAL ILIAC LYMPH NODE; NO METASTASIS | 37.2 | ADT |

TABLE 7-continued

Clinical and pathological characteristics of 213 cases of prostate cancer from UPMC cohort

| Sample | Type | TNM | Margin | Recurrence | Recurrence fast | Recurrence simple | Gleason | Age | Sex | Race | PSA pre-operative | Time to progession (Months) | PSADT (months) | Radiology follow-up | Length of follow-up (Months) | Additional Treatment |
|---|---|---|---|---|---|---|---|---|---|---|---|---|---|---|---|---|
| TP08-S00542T | T | T2cN0MX | Negative | fast | f | y | 7.0 | 50s | M | W | 4.3 | 1.9 | 3.6 | POSITIVE FOR BLASTIC AND HEPATIC METASTASIS | 30.6 | RT |
| TP09-S0006T | T | T3bN1MX | Negative | fast | f | y | 8.0 | 50s | M | W | 4.9 | 4.6 | 1.2 | NEW SCLEROTIC FOCUS @T12 | 27.1 | ADT |
| TP09-S0420T | T | T3bN1MX | Negative | fast | f | y | 7.0 | 50s | M | W | 14.6 | 1.4 | 3.7 | NEGATIVE | 29.1 | ADT |
| TP09-S0704T | T | T4N1MX | Negative | fast | f | y | 9.0 | 60s | M | W | 55.0 | 29.3 | 1.9 | not done | 67.0 | ADT, CHEMO |
| TP09-S0721T | T | T3bN1MX | Negative | fast | f | y | 10.0 | 50s | M | W | 29.3 | 1.4 | 0.9 | POSITIVE FOR BONE METASTASIS | 15.5 | ADT, CHEMO |
| TP10PP-S0420T | T | T3bN1MX | Negative | fast | f | y | 7.0 | 50s | M | W | 15.8 | 1.7 | 3.3 | NEGATIVE | 30.6 | ADT |
| TP10-S0638T | T | T3bN1MX | Negative | fast | f | y | 10.0 | 50s | M | W | 9.2 | 1.4 | 1.8 | POSITIVE FOR BONE METASTASIS | 149.6 | ADT |
| TP10-S093T | T | T3aN0MX | Negative | slow | nf | y | 7.0 | 60s | M | W | 4.1 | 43.8 | 40.0 | NO | 133.3 | RT |
| TP11PP-S0638T | T | T3bN1MX | Negative | fast | f | y | 9.0 | 50s | M | W | 11.3 | 1.6 | 1.9 | POSITIVE FOR BONE METASTASIS | 137.0 | ADT |
| TP12-S0048T | T | T3aN0MX | Negative | ND | ND | ND | 8.0 | 70s | M | W | 7.9 | ND | ND | Not Done | 23.0 | None |
| TP12-S0049T | T | T2cN0MX | Negative | ND | ND | ND | 7.0 | 60s | M | W | 13.6 | ND | ND | Not Done | 23.0 | None |
| TP12-S0102T | T | T3aN1MX | Negative | ND | ND | ND | 7.0 | 60s | M | W | 10.7 | ND | ND | Not Done | 23.0 | None |
| TP12-S0191T | T | T3aN0MX | Negative | ND | ND | ND | 7.0 | 50s | M | W | 4.2 | ND | ND | Not Done | 22.0 | None |
| TP12-S0194T | T | T2cN0MX | Negative | ND | ND | ND | 7.0 | 50s | M | AA | 7.3 | ND | ND | Not Done | 22.0 | None |
| TP12-S0246T | T | T2cN1MX | Negative | ND | ND | ND | 7.0 | 60s | M | W | 3.9 | ND | ND | Not Done | 22.0 | None |
| TP12-S0337T | T | T2aN1MX | Negative | fast | f | y | 7.0 | 60s | M | W | 13.8 | 1.4 | 0.3 | Bone/CT Scan(s) - negative | 33.0 | ADT |
| TP12-S0340T | T | T3bN1MX | Negative | fast | f | y | 9.0 | 60s | M | W | 5.5 | 7.4 | 2.6 | Not Done | 33.0 | ADT |
| TP12-S0456T | T | T3aN1MX | Negative | ND | ND | ND | 8.0 | 60s | M | W | 6.0 | ND | ND | Not Done | 20.0 | None |

TABLE 7-continued

Clinical and pathological characteristics of 213 cases of prostate cancer from UPMC cohort

| Sample | Type | TNM | Margin | Recurrence | Recurrence fast | Recurrence simple | Gleason | Age | Sex | Race | PSA pre-operative | Time to progession (Months) | PSADT (months) | Radiology follow-up | Length of follow-up (Months) | Additional Treatment |
|---|---|---|---|---|---|---|---|---|---|---|---|---|---|---|---|---|
| TP12-S0466T | T | T3bN1MX | Negative | fast | f | y | 8.0 | 50s | M | W | 6.1 | 1.4 | 0.2 | negative | 22.0 | ADT |
| TP12-S0608T | T | T3aN1MX | Negative | fast | f | y | 8.0 | 60s | M | W | 20.3 | 1.5 | 0.8 | not done | 19.0 | ADT |
| TP12-S0624T | T | T3bN1MX | Negative | fast | f | y | 7.0 | 70s | M | W | 3.3 | 1.4 | 2.0 | not done | 19.0 | none |
| TP12-S0704T | T | T3aN0MX | Negative | ND | ND | ND | 7.0 | 50s | M | W | 5.0 | N/A | N/A | not done | 17.0 | none |
| TP12-S0723T | T | T2cN0MX | Negative | ND | ND | ND | 7.0 | 60s | M | W | 5.4 | ND | ND | Not Done | 16.0 | None |
| TP12-S0740T | T | T3bN0MX | Negative | fast | f | y | 9.0 | 50s | M | W | 25.0 | 1.6 | 0.5 | Bone/CT Scan(s) - negative | 30.0 | None |
| TP12-S0765T | T | T3aN0MX | Negative | ND | ND | ND | 7.0 | 50s | M | W | 5.0 | ND | ND | Not Done | 17.0 | None |
| TP12-S0770T | T | T3aN0MX | Negative | ND | ND | ND | 7.0 | 40s | M | W | 9.0 | ND | ND | Not Done | 19.0 | None |
| TP12-S0786T | T | T3bN1MX | Negative | fast | f | y | 7.0 | 60s | M | W | 4.5 | 1.3 | 0.6 | not done | 30.0 | ADT |
| TP12-S0789T | T | T3bN1MX | Negative | ND | ND | ND | 7.0 | 50s | M | W | 10.6 | ND | ND | Not Done | 17.0 | None |
| TP12-S0790T | T | T3aN0MX | Negative | Fast | f | y | 7.0 | 60s | M | W | 24.2 | 11.7 | 3.7 | Not Done | 29.0 | None |
| TP12-S0795T | T | T2cN0MX | Negative | ND | ND | ND | 7.0 | 50s | M | W | 2.4 | ND | ND | Not Done | 17.0 | None |
| TP12-S0799T | T | T3aN0MX | Negative | ND | ND | ND | 7.0 | 50s | M | W | 6.4 | ND | ND | CT Scan(s) - negative | 17.0 | None |
| TP12-S0803T | T | T2cNXMX | Negative | ND | ND | ND | 7.0 | 60s | M | W | unknown | ND | ND | Not Done | 17.0 | None |
| TP12-S0805T | T | T2cN0MX | Negative | ND | ND | ND | 7.0 | 50s | M | W | 4.0 | ND | ND | Not Done | 22.0 | None |
| TP12-S0816T | T | T3aN0MX | Negative | ND | ND | ND | 7.0 | 50s | M | W | 6.5 | ND | ND | Not Done | 17.0 | None |
| TP12-S0915T | T | T3aNXMX | Negative | ND | ND | ND | 7.0 | 60s | M | W | 5.0 | ND | ND | Not Done | 16.0 | None |
| TP12-S0916T | T | T3aN0MX | Negative | ND | ND | ND | 7.0 | 60s | M | W | 5.0 | N/A | N/A | not done | 16.0 | none |
| TP12-S0918T | T | T3bN1MX | Negative | fast | f | y | 9.0 | 70s | M | W | 6.8 | 0.9 | 2.2 | CT Scan(s) - negative | 28.0 | ADT |
| TP12-S0928T | T | T3aN0MX | Negative | ND | ND | ND | 7.0 | 60s | M | W | 5.3 | ND | ND | Not Done | 16.0 | None |
| TP12-S0943T | T | T3aN1MX | Negative | fast | f | y | 9.0 | 50s | M | W | 10.3 | 9.1 | 3.1 | Not Done | 28.0 | None |

TABLE 7-continued

Clinical and pathological characteristics of 213 cases of prostate cancer from UPMC cohort

| Sample | Type | TNM | Margin | Recurrence | Recurrence fast | Recurrence simple | Gleason | Age | Sex | Race | PSA pre-operative | Time to progression (Months) | PSADT (months) | Radiology follow-up | Length of follow-up (Months) | Additional Treatment |
|---|---|---|---|---|---|---|---|---|---|---|---|---|---|---|---|---|
| TP12-S0954T | T | T3bN0MX | Negative | fast | f | y | 7.0 | 60s | M | W | 15.7 | 1.5 | 0.4 | not done | 16.0 | None |
| TP12-S0966T | T | T3aN0MX | Negative | ND | ND | ND | 7.0 | 50s | M | W | 12.2 | ND | ND | Not Done | 16.0 | None |
| TP12-S0967T | T | T3aN0MX | Negative | ND | ND | ND | 7.0 | 60s | M | W | 6.0 | N/A | N/A | Not Done | 14.0 | None |
| TP12-S0981T | T | T3bN0MX | Negative | ND | ND | ND | 7.0 | 60s | M | W | 56.4 | ND | ND | Not Done | 16.0 | None |
| TP12-S0988T | T | T3aN0MX | Negative | ND | ND | ND | 7.0 | 60s | M | W | 16.6 | ND | ND | Not Done | 13.0 | None |
| TP12-S1032T | T | T3aN0MX | Negative | ND | ND | ND | 7.0 | 60s | M | W | 9.2 | ND | ND | Not Done | 141.0 | None |
| TP12-S1059T | T | T3aN0MX | Negative | fast | f | y | 8.0 | 60s | M | W | 10.6 | 1.3 | 0.4 | not done | 15.0 | none |
| TP12-S1189T | T | T2cN0MX | Negative | ND | ND | ND | 7.0 | 60s | M | W | 18.5 | ND | ND | Not Done | 15.0 | None |
| TP12-S1197T | T | T2cN0MX | Negative | ND | ND | ND | 7.0 | 70s | M | W | 5.0 | ND | ND | Not Done | 14.0 | None |
| TP12-S1224T | T | T2cN0MX | Negative | ND | ND | ND | 7.0 | 60s | M | W | 4.9 | ND | ND | Not Done | 16.0 | None |
| TP13-S0043T | T | T3aN0MX | Negative | fast | f | y | 8.0 | 60s | M | W | 22.0 | 1.5 | 0.2 | NO | 12.0 | None |
| TP13-S0109T | T | T3bN1MX | Negative | fast | f | y | 8.0 | 70s | M | W | 21.5 | 1.6 | 1.1 | NO | 12.0 | None |
| TP13-S0248T | T | T3bN1MX | Negative | fast | f | y | 8.0 | 60s | M | W | 6.8 | 2.1 | 0.5 | NO | 11.0 | ADT |
| TP13-S0314T | T | T3aN0MX | Negative | fast | f | y | 7.0 | 60s | M | W | 3.6 | 7.8 | 2.0 | NO | 9.0 | None |
| TP13-S0456T | T | T3aN0MX | Negative | fast | f | y | 9.0 | 50s | M | W | 29.9 | 1.9 | 1.9 | NO | 7.0 | None |
| TP13-S0464T | T | T3bN1MX | Negative | fast | f | y | 9.0 | 50s | M | W | 10.0 | 1.1 | 0.3 | NO | 7.0 | None | f-PSADT ≤4 months;
nf-PSADT ≥15 months;
y—yes;
n—no;
ADT—androgen deprivation therapy;
RT—radiation therapy;
Chemo—chemotherapy;
ND—not determined.

TABLE 8

Clinical and pathological characteristics of 30 cases of prostate cancer from Stanford cohort.

| Sample | Age | Ethnicity | Preop RX | Pre-PSA | T | N | M | Path Grade | Angio | Margins | Months followup |
|---|---|---|---|---|---|---|---|---|---|---|---|
| PC 19T | 50s | Caucasian | None | 4.42 | T3a | N1 | M0 | 4 + 5 | Yes | Negative | 116.2 |
| PC 252T | 60s | Caucasian | None | 42 | T4 | N0 | M0 | 3 + 4 | Unknown | Positive | 22.86666667 |
| PC 265T | 50s | African American | None | 4.53 | T2b | N0 | M0 | 4 + 4 | Unknown | Negative | 20.76666667 |
| PC 452T | 60s | Caucasian | None | 5.12 | T2b | N0 | M0 | 4 + 3 | Unknown | Negative | 89.3 |
| PC 366T | 50s | African American | Horm | 4.01 | T3b | N0 | M0 | 4 + 3 | Unknown | Negative | 82.7 |
| PC 538T | 60s | Caucasian | None | 10.7 | T2b | N0 | M0 | 3 + 4 | No | Negative | 73 |
| PC 47T | 50s | Caucasian | None | 9.92 | T2b | N0 | M0 | 3 + 4 | Unknown | Negative | 64.66666667 |
| PC 97T | 50s | Caucasian | None | 4.1 | T2b | N0 | M0 | 4 + 3 | Unknown | Negative | 117 |
| PC 370T | 50s | Caucasian | None | 10.76 | T3b | N1 | M0 | 4 + 4 | Yes | Negative | 68.8 |
| PC 405T | 60s | Caucasian | None | 15.44 | T2b | N1 | M0 | 3 + 4 | Unknown | Negative | 40.06666667 |
| PC 448T | 60s | Caucasian | None | 7.1 | T3b | N0 | M0 | 3 + 4 | Unknown | Negative | 72 |
| PC 485T | 60s | Caucasian | None | 5.91 | T2b | N0 | M0 | 3 + 4 | Yes | Negative | 71.6 |
| PC 498T | 50s | Caucasian | None | 4.68 | T2b | N0 | M0 | 3 + 3 | Unknown | Negative | 50.66666667 |
| PC 551T | 40s | Caucasian | None | 4.8 | T2b | N0 | M0 | 3 + 3 | Unknown | Negative | 47.6 |
| PC 494T | 60s | Caucasian | None | 2.38 | T2b | N0 | M0 | 3 + 4 | Unknown | Negative | 41.43333333 |
| PC 629T | 70s | African American | None | 3.2 | T2b | N0 | M0 | 3 + 3 | Unknown | Negative | 48.3 |
| PC 643T | 60s | Caucasian | None | 7.16 | T2b | N0 | M0 | 3 + 4 | No | Negative | 43.8 |
| PC 646T | 60s | Caucasian | None | 4.9 | T2b | N0 | M0 | 3 + 4 | Unknown | Negative | 49 |
| PC 473T | 60s | Asian | None | 4.64 | T2b | N0 | M0 | 3 + 4 | Unknown | Negative | 52.83333333 |
| PC 470T | 70s | Caucasian | None | 6.8 | T2b | N0 | M0 | 3 + 4 | Unknown | Negative | 47.86666667 |
| PC 482T | 70s | Caucasian | None | 2.84 | T2b | N0 | M0 | 3 + 3 | Unknown | Negative | 45.9 |
| PC 15T | 40s | Caucasian | None | 5.12 | T2b | N0 | M0 | 3 + 3 | Unknown | Negative | 118 |
| PC 501T | 60s | Caucasian | None | 3.93 | T2b | N0 | M0 | 4 + 3 | Unknown | Negative | 74.6 |
| PC 274T | 60s | Caucasian | None | 3.9 | T2b | N0 | M0 | 3 + 4 | Unknown | Positive | 105.5 |
| PC 343T | 60s | Caucasian | None | 10.77 | T2b | N0 | M0 | 3 + 3 | Unknown | Negative | 61.96666667 |
| PC 599T | 40s | Caucasian | None | 8.9 | T2b | N0 | M0 | 3 + 4 | Unknown | Negative | 61.3 |
| PC 45T | 50s | Caucasian | None | 6.58 | T2b | N0 | M0 | 3 + 4 | No | Negative | 118.1 |
| PC 86T | 60s | Caucasian | None | 2.1 | T2b | N0 | M0 | 3 + 4 | Unknown | Negative | 105.6 |
| PC 99T | 70s | Hispanic | None | 6.26 | T2b | N0 | M0 | 3 + 4 | Unknown | Negative | 120.6 |
| PC 85T | 40s | Caucasian | None | 4.8 | T2a | N0 | M0 | 3 + 4 | Unknown | Positive | 98 |

| Sample | Recurrence | Months to recurrent | PSADT | Relapse | Relapse fast | Relapse simple |
|---|---|---|---|---|---|---|
| PC 19T | Biochemical | 19.13333333 | 4.11 | fast | f | y |
| PC 252T | Biochemical | 10.2 | 3.85 | fast | f | y |
| PC 265T | Biochemical | 2.77 | 3.89 | fast | f | y |
| PC 452T | Biochemical | 19.17 | 4.32 | fast | f | y |
| PC 366T | Biochemical | 12.33 | 9.04 | Intermediate | nf | y |
| PC 538T | Biochemical | 24.86666667 | 8.55 | Intermediate | nf | y |
| PC 47T | Biochemical | 37.6 | 98.58 | slow | nf | y |
| PC 97T | Biochemical | 61.13333333 | >20 | slow | nf | y |
| PC 370T | Biochemical | 15.83 | 21.89 | slow | nf | y |
| PC 405T | Biochemical | 2.5 | >20 | slow | nf | y |
| PC 448T | Biochemical | 35.63 | >20 | slow | nf | y |

TABLE 8-continued

Clinical and pathological characteristics of 30 cases of prostate cancer from Stanford cohort.

| | | | | | | | |
|---|---|---|---|---|---|---|---|
| | PC 485T | Biochemical | 49.7 | 20.69 | slow | nf | y |
| | PC 498T | None | ND | n/a | ND | ND | ND |
| | PC 551T | None | ND | n/a | ND | ND | ND |
| | PC 494T | None | ND | n/a | ND | ND | ND |
| | PC 629T | None | ND | n/a | ND | ND | ND |
| | PC 643T | None | ND | n/a | ND | ND | ND |
| | PC 646T | None | ND | n/a | ND | ND | ND |
| | PC 473T | None | ND | n/a | ND | ND | ND |
| | PC 470T | None | ND | n/a | ND | ND | ND |
| | PC 482T | None | ND | n/a | ND | ND | ND |
| | PC 15T | None | >60 | n/a | none | nf | n |
| | PC 501T | None | >60 | n/a | none | nf | n |
| | PC 274T | None | >60 | n/a | none | nf | n |
| | PC 343T | None | >60 | n/a | none | nf | n |
| | PC 599T | None | >60 | n/a | none | nf | n |
| | PC 45T | None | >60 | n/a | none | nf | n |
| | PC 86T | None | >60 | n/a | none | nf | n |
| | PC 99T | None | >60 | n/a | none | nf | n |
| | PC 85T | None | >60 | n/a | none | nf | n | f-PSADT ≤4 months;
nf-PSADT ≥5 months;
y—yes;
n—no;
ADT—androgen deprivation therapy;
RT—radiation therapy Chemo-chemotherapy;
ND—not determined.

TABLE 9

Clinical and pathological characteristics of 36 cases of prostate cancer from Wisconsin cohort.

| Sample ID | Age | Stage | Margin | Pre-operational PSA | Grade | PSA recurrence |
|---|---|---|---|---|---|---|
| W1 | 60s | T1C | +, and lymph node | 12 | 3 + 3 | yes |
| W2 | 50s | T1C | − | 4.5 | 3 + 4 | no |
| W3 | 50s | T3a | + | 2.9 | 3 + 4 | yes |
| W4 | 70s | T3a | + | 5 | 3 + 4 | no |
| W5 | 50s | T2A | + | 5.1 | 3 + 4 | yes |
| W6 | 60s | T2A | +, and lymph node | 4.13 | 4 + 5 | yes |
| W7 | 60s | T1C | − | 5.2 | 3 + 3 | yes |
| W8 | 40s | T1C | − | 7 | 4 + 4 | no |
| W9 | 60s | T1C | − | 4.95 | 3 + 4 | yes |
| W10 | 40s | T1C | +, and lymph node | 42 | 3 + 4 | yes |
| W11 | 40s | unknown | + | 5 | 4 + 3 | yes |
| W12 | 60s | D0 | − | 6.3 | 4 + 5 | yes |
| W13 | 60s | unknown | − | 4.3 | 3 + 4 | yes |
| W14 | 50s | T2B | − | 2.5 | 3 + 3 | no |
| W15 | 70s | T2B | − | 7.9 | 4 + 3 | yes |
| W16 | 60s | T3A | + | 4.2 | 3 + 4 | no |
| W17 | 60s | T2C | + | 5 | 3 + 4 | no |
| W18 | 60s | T2C | + | 5.6 | 3 + 4 | yes |
| W19 | 60s | T2C | − | unknown | 4 + 3 | no |
| W20 | 60s | T2C | + | 4.47 | 3 + 4 | no |
| W21 | 60s | T2A | − | 4 | 3 + 3 | no |
| W22 | 60s | T3B | + | 6.7 | 3 + 4 | yes |
| W23 | 50s | T2C | − | 5.7 | 3 + 4 | no |
| W24 | 50s | T3A | − | 5 | 3 + 4 | no |

TABLE 9-continued

Clinical and pathological characteristics of 36 cases of prostate cancer from Wisconsin cohort.

| Sample ID | Age | Stage | Margin | Pre-operational PSA | Grade | PSA recurrence |
|---|---|---|---|---|---|---|
| W25 | 50s | T2C | − | 5.4 | 3 + 4 | no |
| W26 | 60s | T2C | − | 4.6 | 3 + 4 | no |
| W27 | 50s | T2C | − | 4.1 | 3 + 3 | no |
| W28 | unknown | unknown | unknown | unknown | 4 + 4 | ND |
| W29 | 60s | T2C | + | 4.6 | 3 + 4 | no |
| W30 | 60s | unknown | unknown | unknown | 5 + 5 | no |
| W31 | 60s | T2c | − | 4 | 4 + 5 | Yes |
| W32 | 40s | T3b | + | 27 | 4 + 5 | Yes |
| W33 | 50s | unknown | unknown | unknown | 4 + 4 | Yes |
| W34 | 50s | T3b | + | 3.7 | 4 + 5 | Yes |
| W35 | unknown | unknown | unknown | unknown | 4 + 5 | ND |
| W36 | 50s | unknown | unknown | unknown | 4 + 4 | ND |

TABLE 10

The status of 8 fusion genes predicting prostate cancer recurrence on 90 training cohort from UPMC*.

| Number of fusion | accuracy | sensitivity | specificity | Youden Inex |
|---|---|---|---|---|
| Panel of 8 fusion transcripts | | | | |
| 1 | 0.567 | 0.19 | 1 | 0.19 |
| 2 | 0.644 | 0.33 | 1 | 0.33 |
| 3 | 0.622 | 0.33 | 0.95 | 0.29 |
| 4 | 0.622 | 0.33 | 0.95 | 0.29 |
| 5 | 0.644 | 0.38 | 0.95 | 0.33 |
| 6 | 0.711 | 0.5 | 0.95 | 0.45 |
| 7 | 0.689 | 0.5 | 0.91 | 0.40 |
| 8 | 0.711 | 0.58 | 0.89 | 0.47 |
| Panel of 8 fusion transcripts plus TMPRSS2-ERG | | | | |
| 1 | 0.589 | 0.42 | 0.79 | 0.20 |
| 2 | 0.622 | 0.48 | 0.79 | 0.27 |
| 3 | 0.6 | 0.48 | 0.74 | 0.22 |
| 4 | 0.6 | 0.48 | 0.74 | 0.22 |
| 5 | 0.611 | 0.5 | 0.74 | 0.24 |
| 6 | 0.656 | 0.58 | 0.74 | 0.32 |
| 7 | 0.633 | 0.58 | 0.69 | 0.27 |
| 8 | 0.656 | 0.63 | 0.69 | 0.32 |

*Using any fusion transcript as cutoff.

TABLE 11

The status of 8 fusion genes with or without TMPRSS2-ERG predicting prostate cancer recurrence*.

| Cohort | accuracy | sensitivity | specificity |
|---|---|---|---|
| 8 fusion transcript | | | |
| UPMC training | 0.711 | 0.58 | 0.89 |
| UPMC testing | 0.705 | 0.51 | 0.95 |
| Wisconsin | 0.8 | 0.63 | 1 |
| Stanford | 0.762 | 0.67 | 0.89 |
| Combined testing" | 0.734 | 0.56 | 0.951 |
| 8 fusion transcript plus TMPRSS2-ERG | | | |
| UPMC training | 0.656 | 0.63 | 0.69 |
| UPMC testing | 0.681 | 0.67 | 0.69 |
| Wisconsin | 0.767 | 0.69 | 0.86 |
| Stanford | 0.762 | 0.83 | 0.67 |
| Combined testing" | 0.712 | 0.70 | 0.73 |

*Using any fusion transcript as cutoff;
**-Combining UPMC testing, Stanford and Wisconsin data set.

TABLE 12

Association of fusion transcript with clinical/pathological parameters.

| | P value | | | | |
|---|---|---|---|---|---|
| Fusion gene | Gleason | PSA (pre-operation) | Tumor stage | Lymph node | Nomogram |
| TMEM135-CCDC67 | 0.59 | 0.98 | 0.432 | 0.082 | 0.21 |
| KDM4B-AC011523.2 | 0.64 | 0.726 | 0.688 | 0.588 | 0.588 |
| MAN2A1-FER | 0.781 | 0.721 | 0.679 | 0.140 | 1.07E−03 |
| CCNH-C5orf30 | 0.14 | 0.313 | 0.254 | 0.059 | 0.156 |
| TRMT11-GRIK2 | 0.012 | 0.227 | 5.38E−04 | 0.013 | 8.56E−03 |
| SLC45A2-AMACR | 0.566 | 0.441 | 0.022 | 0.181 | 0.015 |
| MTOR-TP53BP1 | 0.993 | 0.57 | 0.731 | 1 | 0.775 |
| LRRC59-FLJ60017 | 0.877 | 0.034 | 0.226 | 0.206 | 0.188 |
| At least one | 0.064 | 0.138 | 3.852e−3 | 4.77e−3 | 2.86E−04 |
| TMPRSS2-ERG | 0.869 | 0.306 | 0.642 | 0.042 | 0.325 |

TABLE 13

Gleason score prediction of recurrent status of 90 samples of UPMC training Cohort.

| Score | accuracy | sensitivity | specificity | Youden Index |
|---|---|---|---|---|
| 6 | 0.5333333 | 1 | 0 | 0 |
| 7 | 0.6111111 | 0.95833333 | 0.2142857 | 0.17261905 |
| 8 | 0.6111111 | 0.39583333 | 0.8571429 | 0.25297619 |
| 9 | 0.5111111 | 0.16666667 | 0.9047619 | 0.07142857 |
| 10 | 0.4666667 | 0.02083333 | 0.9761905 | −0.00297619 |

TABLE 14

Gleason score prediction of recurrent status of 229[¦] samples of training and testing cohorts from UPMC, Stanford and Wisconsin*.

| Cohort | accuracy | sensitivity | specificity |
|---|---|---|---|
| Gleason alone | | | |
| UPMC training | 0.611 | 0.40 | 0.86 |
| UPMC testing | 0.602 | 0.41 | 0.85 |
| Wisconsin | 0.6 | 0.31 | 0.93 |
| Stanford | 0.571 | 0.25 | 1 |
| Combined testing" | 0.597 | 0.37 | 0.89 |
| Gleason plus 8 fusion transcripts[+] | | | |
| UPMC training | 0.722 | 0.65 | 0.81 |
| UPMC testing | 0.739 | 0.59 | 0.92 |
| Wisconsin | 0.9 | 0.81 | 1 |
| Stanford | 0.762 | 0.67 | 0.89 |
| Combined testing" | 0.777 | 0.65 | 0.94 |
| Gleason plus 8 fusion transcripts plus TMPRSS2-ERG' | | | |
| UPMC training | 0.644 | 0.73 | 0.55 |
| UPMC testing | 0.705 | 0.80 | 0.59 |
| Wisconsin | 0.833 | 0.88 | 0.79 |
| Stanford | 0.762 | 0.83 | 0.67 |
| Combined testing" | 0.741 | 0.82 | 0.65 |

*Using Gleason >= 8 as cutoff;
[+]Using Gleason >= 8 or presence of any fusion transcript as cutoff;
[¦]Using <88 or presence of any fusion transcript or TMPRSS2-ERG as cutoff;
**-Combining UPMC testing, Stanford and Wisconsin data set;
[|]Gleason score is not graded in one sample and not included in the analysis.

TABLE 15

Nomogram prediction of recurrent status of 90 samples of UPMC training Cohort.

| Probability* | accuracy | sensitivity | specificity | Youden index |
|---|---|---|---|---|
| 0 | 0.4666667 | 0 | 1 | 0 |
| 1 | 0.4666667 | 0 | 1 | 0 |
| 2 | 0.4666667 | 0 | 1 | 0 |
| 3 | 0.4666667 | 0 | 1 | 0 |
| 4 | 0.4666667 | 0 | 1 | 0 |
| 5 | 0.4666667 | 0 | 1 | 0 |
| 6 | 0.4666667 | 0 | 1 | 0 |
| 7 | 0.4666667 | 0 | 1 | 0 |
| 8 | 0.4666667 | 0 | 1 | 0 |
| 9 | 0.4666667 | 0 | 1 | 0 |
| 10 | 0.4666667 | 0 | 1 | 0 |
| 11 | 0.4666667 | 0 | 1 | 0 |
| 12 | 0.4666667 | 0 | 1 | 0 |
| 13 | 0.4777778 | 0.02083333 | 1 | 0.02083333 |
| 14 | 0.4777778 | 0.02083333 | 1 | 0.02083333 |
| 15 | 0.4777778 | 0.02083333 | 1 | 0.02083333 |
| 16 | 0.4777778 | 0.02083333 | 1 | 0.02033333 |
| 17 | 0.4777778 | 0.02083333 | 1 | 0.02083333 |
| 18 | 0.4777778 | 0.02083333 | 1 | 0.02083333 |
| 19 | 0.4888889 | 0.04166667 | 1 | 0.04166667 |
| 20 | 0.4888889 | 0.04166667 | 1 | 0.04166667 |
| 21 | 0.4888889 | 0.04166667 | 1 | 0.04166667 |
| 22 | 0.4888889 | 0.04166667 | 1 | 0.04166667 |
| 23 | 0.4888889 | 0.04166667 | 1 | 0.04166667 |
| 24 | 0.4888889 | 0.04166667 | 1 | 0.04166667 |
| 25 | 0.5 | 0.0625 | 1 | 0.0625 |
| 26 | 0.5 | 0.0625 | 1 | 0.0625 |
| 27 | 0.5111111 | 0.08333333 | 1 | 0.08333333 |
| 28 | 0.5111111 | 0.08333333 | 1 | 0.08333333 |
| 29 | 0.5333333 | 0.125 | 1 | 0.125 |
| 30 | 0.5222222 | 0.125 | 0.97619048 | 0.10119048 |
| 31 | 0.5222222 | 0.125 | 0.97619048 | 0.10119048 |
| 32 | 0.5222222 | 0.125 | 0.97619048 | 0.10119048 |
| 33 | 0.5333333 | 0.14583333 | 0.97619048 | 0.12202381 |
| 34 | 0.5444444 | 0.16666667 | 0.97619048 | 0.14285714 |
| 35 | 0.5444444 | 0.16666667 | 0.97619048 | 0.14285714 |
| 36 | 0.5444444 | 0.16666667 | 0.97619048 | 0.14285714 |
| 37 | 0.5444444 | 0.16666667 | 0.97619048 | 0.14285714 |
| 38 | 0.5555556 | 0.1875 | 0.97619048 | 0.16369048 |
| 39 | 0.5555556 | 0.1875 | 0.97619048 | 0.16369048 |
| 40 | 0.5555556 | 0.1875 | 0.97619048 | 0.16369048 |
| 41 | 0.5555556 | 0.1875 | 0.97619048 | 0.16369048 |
| 42 | 0.5555556 | 0.1875 | 0.97619048 | 0.16369048 |
| 43 | 0.5777778 | 0.22916667 | 0.97619048 | 0.20535714 |
| 44 | 0.5888889 | 0.25 | 0.97619048 | 0.22619048 |
| 45 | 0.5888889 | 0.25 | 0.97619048 | 0.22619048 |
| 46 | 0.5888889 | 0.25 | 0.97619048 | 0.22619048 |
| 47 | 0.6 | 0.27083333 | 0.97619048 | 0.24702381 |
| 48 | 0.6 | 0.27033333 | 0.97619048 | 0.24702381 |
| 49 | 0.6 | 0.27083333 | 0.97619048 | 0.24702381 |
| 50 | 0.6111111 | 0.29166667 | 0.97619048 | 0.26785714 |
| 51 | 0.6111111 | 0.29166667 | 0.97619048 | 0.26785714 |
| 52 | 0.6111111 | 0.29166667 | 0.97619048 | 0.26785714 |
| 53 | 0.6222222 | 0.3125 | 0.97619048 | 0.28869048 |
| 54 | 0.6222222 | 0.3125 | 0.97619048 | 0.28869048 |
| 55 | 0.6222222 | 0.3125 | 0.97619048 | 0.28869048 |
| 56 | 0.6222222 | 0.3125 | 0.97619048 | 0.28869048 |
| 57 | 0.6333333 | 0.33333333 | 0.97619048 | 0.30952381 |
| 58 | 0.6444444 | 0.35416667 | 0.97619048 | 0.33035714 |
| 59 | 0.6444444 | 0.35416667 | 0.97619048 | 0.33035714 |
| 60 | 0.6555556 | 0.375 | 0.97619048 | 0.35119048 |
| 61 | 0.6555556 | 0.375 | 0.97619048 | 0.35119048 |
| 62 | 0.6555556 | 0.375 | 0.97619048 | 0.35119048 |
| 63 | 0.6444444 | 0.375 | 0.95238095 | 0.32738095 |
| 64 | 0.6333333 | 0.375 | 0.92857143 | 0.30357143 |
| 65 | 0.6333333 | 0.375 | 0.92857143 | 0.30357143 |
| 66 | 0.6444444 | 0.39583333 | 0.92857143 | 0.32440476 |
| 67 | 0.6555556 | 0.41666667 | 0.92857143 | 0.3452381 |
| 68 | 0.6555556 | 0.41666667 | 0.92857143 | 0.3452381 |
| 69 | 0.6555556 | 0.41666667 | 0.92857143 | 0.3452381 |
| 70 | 0.6777778 | 0.45833333 | 0.92857143 | 0.38690476 |
| 71 | 0.6777778 | 0.47916667 | 0.9047619 | 0.38392857 |
| 72 | 0.6777778 | 0.5 | 0.88095238 | 0.38095238 |
| 73 | 0.6888889 | 0.52083333 | 0.88095238 | 0.40178571 |
| 74 | 0.6888889 | 0.52083333 | 0.88095238 | 0.40178571 |
| 75 | 0.6888889 | 0.52083333 | 0.88095238 | 0.40178571 |
| 76 | 0.6838889 | 0.52083333 | 0.88095238 | 0.40178571 |
| 77 | 0.7 | 0.54166667 | 0.88095238 | 0.42261905 |
| 78 | 0.7 | 0.54166667 | 0.88095238 | 0.42261905 |
| 79 | 0.7 | 0.54166667 | 0.88095238 | 0.42261905 |
| 80 | 0.7111111 | 0.5625 | 0.88095238 | 0.44345238 |
| 81 | 0.7111111 | 0.5625 | 0.88095238 | 0.44345238 |
| 82 | 0.7111111 | 0.58333333 | 0.85714286 | 0.44047619 |
| 83 | 0.7 | 0.58333333 | 0.83333333 | 0.41666667 |
| 84 | 0.7 | 0.58333333 | 0.83333333 | 0.41666667 |
| 85 | 0.7111111 | 0.60416667 | 0.83333333 | 0.4375 |
| 86 | 0.7333333 | 0.64583333 | 0.83333333 | 0.47916667 |
| 87 | 0.7444444 | 0.66666667 | 0.83333333 | 0.5 |
| 88 | 0.7555556 | 0.6875 | 0.83333333 | 0.52083333 |
| 89 | 0.7333333 | 0.70833333 | 0.76190476 | 0.4702381 |
| 90 | 0.7222222 | 0.70833333 | 0.73809524 | 0.44642857 |
| 91 | 0.7111111 | 0.72916667 | 0.69047619 | 0.41964286 |
| 92 | 0.7 | 0.75 | 0.64285714 | 0.39285714 |
| 93 | 0.7111111 | 0.83333333 | 0.57142857 | 0.4047619 |
| 94 | 0.6777778 | 0.85416667 | 0.47619048 | 0.33035714 |
| 95 | 0.6888889 | 0.875 | 0.47619048 | 0.35119048 |
| 96 | 0.6777778 | 0.875 | 0.45238095 | 0.32738095 |
| 97 | 0.6222222 | 0.95833333 | 0.23809524 | 0.19642857 |

TABLE 15-continued

Nomogram prediction of recurrent status of 90 samples of UPMC training Cohort.

| Probability* | accuracy | sensitivity | specificity | Youden index |
|---|---|---|---|---|
| 98 | 0.5444444 | 1 | 0.02380952 | 0.02380952 |
| 99 | 0.5333333 | 1 | 0 | 0 |
| 100 | 0.5333333 | 1 | 0 | 0 |

*Probability of PSA free survival for 5 years

TABLE 16

Nomogram prediction of recurrent status of 229[|] samples of training and testing cohorts from UPMC, Stanford and Wisconsin.

| Cohort | accuracy | sensitivity | specificity |
|---|---|---|---|
| *Nomogram alone** | | | |
| UPMC training | 0.756 | 0.69 | 0.83 |
| UPMC testing | 0.75 | 0.80 | 0.69 |
| Wisconsin | 0.6 | 0.31 | 0.93 |
| Stanford | 0.619 | 0.33 | 1 |
| Combined testing" | 0.691 | 0.57 | 0.84 |
| *Nomogram plus 8 fusion transcripts+* | | | |
| UPMC training | 0.778 | 0.69 | 0.88 |
| UPMC testing | 0.807 | 0.76 | 0.87 |
| Wisconsin | 0.833 | 0.69 | 1 |
| Stanford | 0.81 | 0.75 | 0.89 |
| Combined testing" | 0.813 | 0.74 | 0.90 |
| *Nomogram plus 8 fusion transcripts plus TMPRSS2-ERG'* | | | |
| UPMC training | 0.656 | 0.63 | 0.69 |
| UPMC testing | 0.681 | 0.67 | 0.69 |
| Wisconsin | 0.767 | 0.69 | 0.86 |
| Stanford | 0.762 | 0.83 | 0.67 |
| Combined testing" | 0.719 | 0.62 | 0.84 |

*Using <88 as cutoff;
+Using <88 or any fusion transcript as cutoff;
[|]Using <88 or any fusion transcript or TMPRSS2-ERG as cutoff;
**-Combining UPMC testing, Stanford and Wisconsin data set;
[|]Gleason score is not graded in one sample and not included in the analysis.

TABLE 17

Putative fusion transcripts from benign prostate of healthy organ donors.

| Fusion gene 1 | Fusion_gene2 | read pairs | Validation Status |
|---|---|---|---|
| SORBS1 | RP11-476E15.3 | 25 | |
| AHCY | RP11-292F22.3 | 25 | |
| DCUN1D3 | ERI2 | 12 | |
| MACF1 | KIAA0754 | 11 | |
| C10orf68 | CCDC7 | 11 | RT-PCR and sequencing |
| RP11-166D19.1 | BLID | 7 | |
| ASS1 | ASS1P9 | 6 | |
| BACH1 | BACH1-IT1 | 6 | RT-PCR |
| MPDZ | RP11-272P10.2 | 5 | |
| LIG3 | RP5-837J1.2 | 4 | |
| ACAD8 | GLB1L3 | 4 | RT-PCR |
| IGSF9B | RP11-259P6.1 | 3 | |
| EYA1 | RP11-1102P16.1 | 3 | |
| TTC33 | PRKAA1 | 3 | RT-PCR |
| DNAH1 | GLYCTK | 3 | |
| PSPC1 | ZMYM5 | 3 | |
| HSP90AB3P | RP11-759L5.2 | 3 | |
| LSAMP | RP11-384F7.2 | 3 | |
| RNF4 | FAM193A | 81 | RT-PCR |
| AHCY | RP11-292F22.3 | 9 | |
| LSAMP | RP11-384F7.2 | 8 | |
| CBLL1 | AC002467.7 | 4 | |
| FNBP4 | Y_RNA | 4 | |
| TBCE | RP11-293G6_—A.2 | 4 | |
| TRIM58 | RP11-63487.4 | 4 | |
| DCUN1D3 | ERI2 | 4 | |
| PHPT1 | MAMDC4 | 3 | |
| TRIP6 | SLC12A9 | 3 | |
| NAT14 | ZNF628 | 3 | |
| TLL2 | RP11-35J23.5 | 3 | |
| UFSP2 | Y_RNA | 3 | |
| TSPAN33 | Y_RNA | 3 | |
| CADM3 | DARC | 3 | |
| KIF27 | KP11-213G2.3 | 3 | |
| RABL6 | KIAA1984 | 3 | |
| ZNF615 | ZNF350 | 3 | |
| ZYG11A | RP4-631H13.2 | 3 | |
| RP11-522L3.6 | MTND4P32 | 3 | |
| MTND3P10 | AC012363.10 | 3 | |
| RP11-464F9.1 | BMS1P4 | 3 | |
| RNF4 | FAM193A | 14 | RT-PCR |
| GBP3 | Y_RNA | 3 | |
| NACA | PRIM1 | 1 | |
| AHCY | RP11-292F22.3 | 3 | |
| GBP3 | Y_RNA | 3 | |
| HARS2 | ZMAT2 | 2 | RT-PCR and sequencing |
| EED | C11orf73 | 1 | RT-PCR |
| CNPY3 | RP3-475N16.1 | 1 | RT-PCR |
| RN7SL2 | Metazoa_SRP | 1 | |
| SLC16A8 | BAIAP2L2 | 2 | RT-PCR |
| KLK4 | KLKP1 | 2 | RT-PCR and sequencing |
| ZNF137P | ZNF701 | 1 | RT-PCR |
| AZGP1 | GJC3 | 1 | RT-PCR |
| USP7 | RP11-252I13.1 | 1 | |
| TRRAP | AC004893.11 | 1 | |
| C6orf47 | BAG6 | 1 | RT-PCR |
| TTTY15 | USP9Y | 9 | |
| AC005077.12 | LINC00174 | 2 | |
| ADCK4 | NUMBL | 2 | |
| ZNF606 | C19orf18 | 2 | |
| SLC45A3 | ELK4 | 3 | RT-PCR and sequencing |

6.6. References

1. Jemal A, Bray F, Center M M, Ferlay J, Ward E, Forman D. Global cancer statistics. C A Cancer *J Clin*. Feb. 4 2012.
2. Siegel R, Naishadham D, Jemal A. Cancer statistics, 2012. *CA Cancer J Clin*. January-February 2012; 62(1):10-29.
3. Li H, Durbin R. Fast and accurate short read alignment with Burrows-Wheeler transform. *Bioinformatics*. Jul. 15, 2009; 25(14):1754-1760.
4. Trapnell C, Roberts A, Goff L, et al. Differential gene and transcript expression analysis of RNA-seq experiments with TopHat and Cufflinks. *Nat Protoc*. March 2012; 7(3):562-578.
5. Trapnell C, Williams B A, Pertea G, et al. Transcript assembly and quantification by RNA-Seq reveals unannotated transcripts and isoform switching during cell differentiation. *Nat Biotechnol*. May 2010; 28(5):511-515.
6. Trapnell C, Pachter L, Salzberg S L. TopHat: discovering splice junctions with RNA-Seq. *Bioinformatics*. May 1, 2009; 25(9):1105-1111.
7. Edgren H, Murumagi A, Kangaspeska S, et al. Identification of fusion genes in breast cancer by paired-end RNA-sequencing. *Genome Biol*. 12(1):R6.

8. Wei Zeng C-W F, Stefan Muller Arisona, Huamin Qu. Visualizing Interchange Patterns in Massive Movement Data. *Computer Graphics Forum.* 2013(32):271-280.
9. Luo J H, Yu Y P, Cieply K, et al. Gene expression analysis of prostate cancers. *Mol Carcinog.* January 2002; 33(1): 25-35.
10. Yu Y P, Landsittel D, Jing L, et al. Gene expression alterations in prostate cancer predicting tumor aggression and preceding development of malignancy. *J Clin Oncol.* Jul. 15, 2004; 22(14):2790-2799.
11. Ren B, Yu G, Tseng G C, et al. MCM7 amplification and overexpression are associated with prostate cancer progression. *Oncogene.* Feb. 16, 2006; 25(7):1090-1098.
12. Yu Y P, Yu G, Tseng G, et al. Glutathione peroxidase 3, deleted or methylated in prostate cancer, suppresses prostate cancer growth and metastasis. *Cancer Res.* Sep. 1, 2007; 67(17):8043-8050.
13. Tomlins S A, Rhodes D R, Perner S, et al. Recurrent fusion of TMPRSS2 and ETS transcription factor genes in prostate cancer. *Science.* Oct. 28, 2005; 310(5748):644-648.
14. Berger M F, Lawrence M S, Demichelis F, et al. The genomic complexity of primary human prostate cancer. *Nature.* February 10; 470(7333):214-220.
15. Baca S C, Prandi D, Lawrence M S, et al. Punctuated evolution of prostate cancer genomes. *Cell.* April 25; 153(3):666-677.
16. Freedland S J, Humphreys E B, Mangold L A, et al. Death in patients with recurrent prostate cancer after radical prostatectomy: prostate-specific antigen doubling time subgroups and their associated contributions to all-cause mortality. *J Clin Oncol.* May 1, 2007; 25(13):1765-1771.
17. Antonarakis E S, Zahurak M L, Lin J, Keizman D, Carducci M A, Eisenberger M A. Changes in PSA kinetics predict metastasis-free survival in men with PSA-recurrent prostate cancer treated with nonhormonal agents: combined analysis of 4 phase II trials. *Cancer. March* 15; 118(6):1533-1542.
18. Sinclair P B, Sorour A, Martineau M, et al. A fluorescence in situ hybridization map of 6q deletions in acute lymphocytic leukemia: identification and analysis of a candidate tumor suppressor gene. *Cancer Res.* Jun. 15, 2004; 64(12):4089-4098.
19. Misago M, Liao Y F, Kudo S, et al. Molecular cloning and expression of cDNAs encoding human alpha-mannosidase II and a previously unrecognized alpha-mannosidase IIx isozyme. *Proc Natl Acad Sci USA.* Dec. 5, 1995; 92(25):11766-11770.
20. Krolewski J J, Lee R, Eddy R, Shows T B, Dalla-Favera R. Identification and chromosomal mapping of new human tyrosine kinase genes. *Oncogene.* March 1990; 5(3):277-282.
21. Prakash T, Sharma V K, Adati N, Ozawa R, Kumar N, Nishida Y, Fujikake T, Takeda T, Taylor T D: Expression of conjoined genes: another mechanism for gene regulation in eukaryotes, PLoS One 2010, 5:e13284.
22. Youden W J: Index for rating diagnostic tests, Cancer 1950, 3:32-35.
23. Robin X, Turck N, Hainard A, Tiberti N, Lisacek F, Sanchez J C, Muller M: pROC: an open-source package for R and S+ to analyze and compare ROC curves, BMC Bioinformatics 12:77.
24. Towns W L, Begley T J: Transfer RNA methyltransferases and their corresponding modifications in budding yeast and humans: activities, predications, and potential roles in human health, DNA Cell Biol 2012, 31:434-454.
25. Misago M, Liao Y F, Kudo S, Eto S, Mattei M G, Moremen K W, Fukuda M N: Molecular cloning and expression of cDNAs encoding human alpha-mannosidase II and a previously unrecognized alphamannosidase IIx isozyme, Proc Natl Acad Sci USA 1995, 92:11766-11770.
26. Fisher R P, Morgan D O: A novel cyclin associates with MO15/CDK7 to form the CDK-activating kinase, Cell 1994, 78:713-724.
27. Yang H, Rudge D G, Koos J D, Vaidialingam B, Yang H J, Pavletich N P: mTOR kinase structure, mechanism and regulation, Nature 2013, 497:217-223.
28. Wang H, Luo K, Tan L Z, Ren B G, Gu L Q, Michalopoulos G, Luo J H, Yu Y P: p53-induced gene 3 mediates cell death induced by glutathione peroxidase 3, J Biol Chem 2012, 287:16890-16902.
29. Zhen Y, Sorensen V, Skjerpen C S, Haugsten E M, Jin Y, Walchli S, Olsnes S, Wiedlocha A: Nuclear import of exogenous FGF1 requires the E R-protein LRRC59 and the importins Kpnalpha1 and Kpnbeta1, Traffic 2012, 13:650-664.
30. Yang J, Jubb A M, Pike L, Buffa F M, Turley H, Baban D, Leek R, Gatter K C, Ragoussis J, Harris A L: The histone demethylase JMJD2B is regulated by estrogen receptor alpha and hypoxia, and is a key mediator of estrogen induced growth, Cancer Res 70:6456-6466.
31. Savolainen K, Kotti T J, Schmitz W, Savolainen T I, Sormunen R T, Ilves M, Vainio S J, Conzelmann E, Hiltunen J K: A mouse model for alpha-methylacyl-CoA racemase deficiency: adjustment of bile acid synthesis and intolerance to dietary methyl-branched lipids, Hum Mol Genet 2004, 13:955-965.

7. EXAMPLE 2: PTEN-NOLC1 FUSION GENES

Transcriptome sequencing was performed on 15 samples of prostate cancer from patients who experienced prostate cancer recurrence after radical prostatectomy. One of the candidate gene fusion transcripts is PTEN-NOLC1. To validate the fusion transcript, RT-PCRs using primers specific for PTEN-NOLC1 were performed on the prostate cancer sample that was positive for the fusion transcript, using the following primers: 5'-GCATTTGCAGTATAGAGCGTGC3' (SEQ ID NO: 28)/5'GTCTAAGAGGGAAGAGGCATTG3' (SEQ ID NO: 29), under the following conditions: 94° C. for 5', then 30 cycles of 94° C. for 10 seconds, 61° C. for 1 min and 72° C. for 3 min, followed by 10 min at 72° C. for extension. A 158 bp PCR product was generated. The PCR product was subsequently sequenced. PTEN-NOLC1 fusion transcript was confirmed (FIG. 13A). To investigate the mechanism of PTEN-NOLC1 fusion transcript, Fluorescence In Situ Hybridizations (FISH) were performed using probes corresponding to 5'-end of PTEN genome (RP11-124B18) and 3'-end of NOLC1 genome (CTD-3082D22), respectively. In normal prostate epithelial cells, these 2 probes were hybridized to distinct separate locations in the genome due to more than 14 megabase separation of these 2 genes (FIG. 13B). In contrast, these two signals appeared to merge to generate an overlapped signal in prostate cancer genome from a sample that is positive for PTEN-NOLC1 fusion transcript. Interestingly, non-fusion PTEN was virtually undetectable in this prostate cancer sample, suggesting that PTEN-NOLC1 fusion was accompanied with PTEN deletion in another allele. These results suggest that genome rearrangement is the underlying mechanism for PTEN-NOLC1 transcription. To investigate the clinical significance of PTEN-NOLC1 fusion, 215 prostate cancer samples were analyzed for PTEN-NOLC1 expression. Over 14% (31/215) prostate cancer samples were found to express PTEN-NOLC1 (FIG. 13C). Among the positive samples, 77% (24/31, p=0.03) patients experienced prostate cancer recurrence. This indicates that PTEN-NOLC1 fusion is associated with poor clinical outcome. Interestingly, our analysis of lung adenocarcinoma, Glioblastoma multiforme, and hepatocellular carcinoma indicates that significant number of these cancers are also positive for PTEN-NOLC1 fusion: 35/38 glioblastoma multiformis, 3/20 hepatocellular carcinoma and 29/40 lung adenocarcinoma. These results suggest that PTEN-NOLC1 fusion may have broad implication for cancer development.

Expression of Pten-NOLC1 in NIH3T3 and PC3 Cells Increased Cell Growth.

Figure 27A:
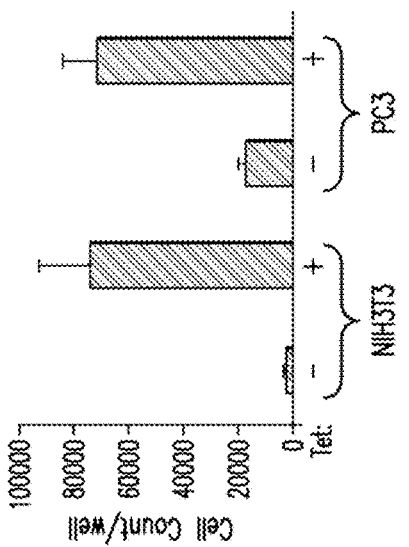
Figure 27B:
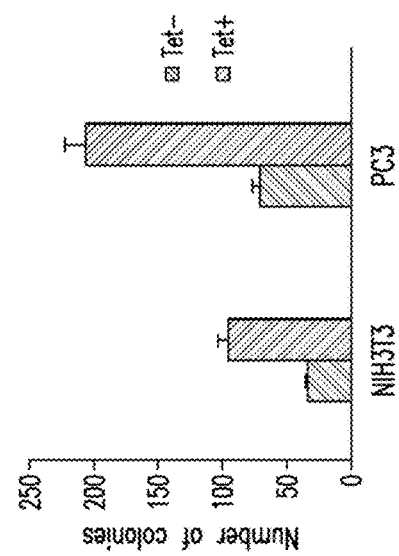
Figure 27C:
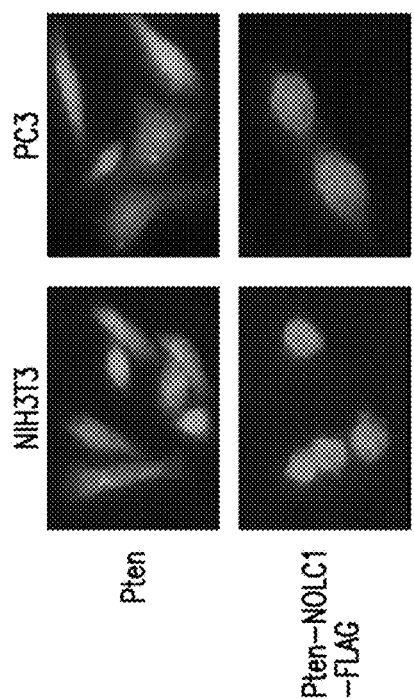
Figure 27D:
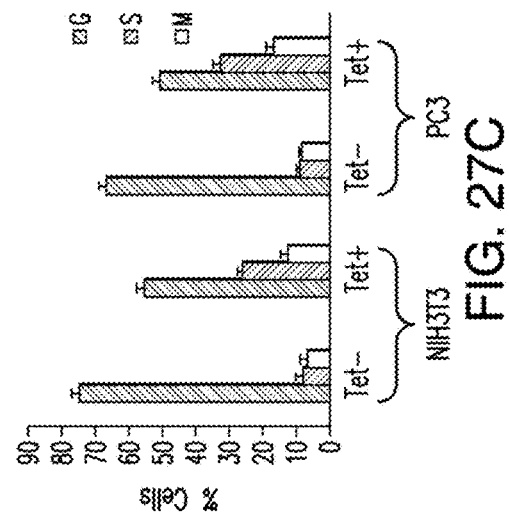

To investigate whether PTEN-NOLC1 has pro-growth activity, we ligated PTEN-NOLC1 cDNA into pCDNA-FLAG vector to create pCDNA4-PTEN-NOLC1-FLAG. Subsequently, we transfected NIH3T3 and PC3 cells (a human prostate cancer cell line) with pCDNA4-PTEN-NOLC1-FLAG/pCDNA6. As shown in FIG. 27B, induction of NIH3T3 and PC3 cells produces 10.3 (p<0.01) and 3.1 fold (p<0.01) increase of cell growth, respectively. These were accompanied with 2.3 fold (p<0.01) and 2.7 fold (p<0.001) increase of cell entry into S-phase in NIH3T3 and PC3 cells in cell cycle analysis (FIG. 27C). Colony formation analyses indicate that expression of PTEN-NOLC1 produced 2.2 fold (p<0.001) higher numbers of colonies from single cell suspension for NIH3T3 cells than the un-induced controls and 2.7 fold (p<0.01) more colonies for PC3 cells when they were induced to express PTEN-NOLC1-FLAG (FIG. 27D).

To investigate the subcellular localization of PTEN-NOLC1, NIH3T3 cells were transformed with pCDNA4-PTEN-NOLC1-FLAG/pCDNA6 were induced with tetracycline to express PTEN-NOLC1-FLAG. As shown in FIG. 27A, most PTEN-NOLC1-FLAG was localized in the nucleus of the cells. This is contrary to cytoplasmic localization of PTEN. PTEN-NOLC1-FLAG was also detected in purified nucleus fraction. Without being bound to a particular theory, these results indicate that fusion formation with NOLC1 alters the subcellular localization of PTEN-NOLC1 from cytoplasm to nucleus.

8. EXAMPLE 3: THERAPEUTIC TARGETING AT FUSION TRANSCRIPT CONTAINING CHIMERA PROTEIN MAN2A1-FER

8.1. Results

MAN2A1-FER likely produces activated FER kinase. MAN2A1-FER was present in prostate cancer, hepatocellular carcinoma and Glioblastoma multiforme. MAN2A1 is a Golgi enzyme required for conversion of high mannose to complex type structure of N-glycan for mature glycosylation of a membrane protein[1, 2]. Little is known about its relation with human malignancies. On the other hand, FER, a tyrosine kinase, is a well-documented oncogene[3, 4]. Several studies showed that FER activate androgen receptor (AR) by phosphorylating Tyr223 in AR[5], and is essential for NFκB activation of EGFR[6]. Some studies indicate that FER is an essential component of stem cell tyrosine kinase 1 (STK1)[6] and mast cell growth factor receptor (kit)[7, 8] signaling. Over-expression of FER is associated with poor clinical outcomes of breast cancer[9], renal cell carcinoma[10, 11], non-small cell lung cancer[12, 13] and hepatocellular carcinoma[14]. The N-termini of many tyrosine protein kinases serve to constrain the kinase activity and are regulated by other molecules. Domains of some N-termini bind and select specific targets for the kinases. Removal of the N-terminus from a protein kinase may produce constitutively activated kinase activity that may alter the signaling pathways and generates uninhibited cell growth. The best analogy to MAN2A1-FER is BCR-Abl. When c-Abl is intact, its kinase activity is constrained. Removal of SH3 domain in c-Abl in the BCR-Abl fusion protein converts the mutant Abl tyrosine kinase into an oncogene that plays key role in developing acute lymphoblastic leukemia and chronic myelogenous leukemia. Wild type FER with intact SH2 domain is inactive in kinase activity when assayed in cell free system. In the fusion gene MAN2A1-FER, the N-terminus of FER suffers a loss of SH2 and FHC domain (FIG. 14). These domains were replaced with glycoside hydrolase and α-mannosidase middle domain from MAN2A1. As a result, the kinase activity may be activated and substrate targets of FER tyrosine kinase may be altered.

MAN2A1-FER Expression Accelerates Cell Cycle Entry into S Phase and Increased Tyrosine Phosphorylation of EGFR in the Absence of EGFR Ligand.

To investigate whether MAN2A1-FER chimera protein is expressed in prostate cancer samples that contain MAN2A1-FER transcript, protein extracts from 5 prostate cancer samples positive for MAN2A1-FER RNA were analyzed using antibodies specific for MAN2A1 or FER. These results showed that the samples expressed a 115 Kd protein recognized by both MAN2A1 and FER antibodies (FIG. 22). This protein is not detected in prostate cancer samples that are negative for MAN2A1-FER transcript.

When MAN2A1-FER was forced to express in RWPE1 cells, a non-transformed prostate epithelial cell line, it increase the proportion of cells in S phase by 4.6-5 fold (p<0.001). MAN2A1-FER was determined to be co-localized with Golgi protein in both immunofluorescence and sucrose gradient analysis, supporting the notion that MAN2A1-FER is primarily located in Golgi apparatus. Interestingly, expression of MAN2A1-FER increased tyrosine phosphorylation of EGFR in RWPE1 cells in the absence of EGFR ligand, suggesting that MAN2A1-FER may ectopically phosphorylate the EGFR extracellular domain. Thus, MAN2A1-FER may function as a transforming oncogene and possess intrinsic tyrosine kinase activity derived from its FER kinase domain. Not to be limited to any particular theory, the kinase domain of MAN2A1-FER may be the driver of its oncogenic activity through ectopic phosphorylation of transmembrane proteins such as EGFR.

Therapeutic Targeting at MAN2A1-FER Results in Specific Cell Death Prostate Cancer Cells Expressing MAN2A1-FER.

Based on the analyses above, we reason that the altered subcellular location and substrate specificity of FER kinase will create oncogenic activity of MAN2A1-FER. A large part of this oncogenic activity results from ectopic phosphorylation and activation of EGFR and its down-stream signaling pathways. Thus, we can intervene and disrupt the oncogenic pathways of MAN2A1-FER using 2 different approaches. The first approach is inhibiting the kinase activity of MAN2A1-FER by targeting MAN2A1-FER proteins using small molecules that can inhibit tyrosine kinase. Several small molecules specific for FER such as diaminopyrimidine TAE684, and pyrazologyrididines WZ-4-49-8 and WZ-4-49-10, generic ALK/FER inhibitor crisotinib are available. Among these compound inhibitors, Crisotinib has been approved by FDA to treat advanced and metastatic non-small cell lung cancer positive for EML4-ALK, another tyrosine kinase fusion protein. The drug has been shown to be able to shrink tumor mass by at least 30% in most patients.

To investigate whether Crisotinib is also effective against MAN2A1-FER positive cancer cells, we transformed human prostate cancer cell line PC3 with pCDNA4-MAN2A1-FER-FLAG/pCDNA6 to express MAN2A1-FER fusion protein. These cells were treated with low dosage of Crisotinib for 24 hours. As shown in FIG. 22, the treatment resulted in 31% cell death in MAN2A1-FER expressing cells, while it hardly killed the same type of cancer cells that do not express this fusion protein. A dosage effect analysis showed that expression of MAN2A1-FER lowers the cancer killing $EC_{50}$ by at least 2 magnitudes (~100 fold). Thus, it is reasonable to treat MAN2A1-FER positive prostate cancer with Crisotinib at a dosage that is not harmful to normal human cells.

The second approach is to target EGFR activation by EGFR inhibitors. These include erlotinib, cetuximab, bevacizumab, canertinib and bortezomib. Many of these drugs were FDA approved and is widely used in a variety of human solid tumors. To interrogate the effectiveness of EGFR activation interruption in treating prostate cancer, we treated MAN2A1-FER transformed PC3 cells with canertinib. As shown in FIG. 23, the treatment also produced 34% cell death of cells expressing MAN2A1-FER. In contrast, the effect on cells not expressing MAN2A1-FER (Tet−) was minimal: The cell death level is similar to those untreated controls. These results suggest EGFR activation is one of the critical pathways for MAN2A1-FER oncogenic activity. Interesting, when we tried to intercept the down-streaming signaling molecule of EGFR, MEK, using an experimental drug AZD6244, the differential killing effect was largely moderated and vanished (data not shown). It suggests that other signaling pathways for EGFR may bypass MEK signaling.

8.2. References

1. Moremen K W, Robbins P W: Isolation, characterization, and expression of cDNAs encoding murine alpha-mannosidase II, a Golgi enzyme that controls conversion of high mannose to complex N-glycans, J Cell Biol 1991, 115:1521-1534
2. Misago M, Liao Y F, Kudo S, Eto S, Mattei M G, Moremen K W, Fukuda M N: Molecular cloning and expression of cDNAs encoding human alpha-mannosidase II and a previously unrecognized alpha-mannosidase IIx isozyme, Proc Natl Acad Sci USA 1995, 92:11766-11770
3. Hao Q L, Heisterkamp N, Groffen J: Isolation and sequence analysis of a novel human tyrosine kinase gene, Mol Cell Biol 1989, 9:1587-1593
4. Krolewski J J, Lee R, Eddy R, Shows T B, Dalla-Favera R: Identification and chromosomal mapping of new human tyrosine kinase genes, Oncogene 1990, 5:277-282
5. Rocha J, Zouanat F Z, Zoubeidi A, Hamel L, Benidir T, Scarlata E, Brimo F, Aprikian A, Chevalier S: The Fer tyrosine kinase acts as a downstream interleukin-6 effector of androgen receptor activation in prostate cancer, Mol Cell Endocrinol 381:140-149
6. Guo C, Stark G R: FER tyrosine kinase (FER) overexpression mediates resistance to quinacrine through EGF-dependent activation of NF-kappaB, Proc Natl Acad Sci USA 108:7968-7973
7. Kwok E, Everingham S, Zhang S, Greer P A, Allingham J S, Craig A W: FES kinase promotes mast cell recruitment to mammary tumors via the stem cell factor/KIT receptor signaling axis, Mol Cancer Res 10:881-891
8. Voisset E, Lopez S, Dubreuil P, De Sepulveda P: The tyrosine kinase FES is an essential effector of KITD816V proliferation signal, Blood 2007, 110:2593-2599
9. Ivanova I A, Vermeulen J F, Ercan C, Houthuijzen J M, Saig F A, Vlug E J, van der Wall E, van Diest P J, Vooijs M, Derksen P W: FER kinase promotes breast cancer metastasis by regulating alpha6- and beta1-integrin-dependent cell adhesion and anoikis resistance, Oncogene 32:5582-5592
10. Miyata Y, Kanda S, Sakai H, Greer P A: Feline sarcoma-related protein expression correlates with malignant aggressiveness and poor prognosis in renal cell carcinoma, Cancer Sci 104:681-686
11. Wei C, Wu S, Li X, Wang Y, Ren R, Lai Y, Ye J: High expression of FER tyrosine kinase predicts poor prognosis in clear cell renal cell carcinoma, Oncol Lett 5:473-478
12. Ahn J, Truesdell P, Meens J, Kadish C, Yang X, Boag A H, Craig A W: Fer protein-tyrosine kinase promotes lung adenocarcinoma cell invasion and tumor metastasis, Mol Cancer Res 11:952-963
13. Kawakami M, Morita S, Sunohara M, Amano Y, Ishikawa R, Watanabe K, Hamano E, Ohishi N, Nakajima J, Yatomi Y, Nagase T, Fukayama M, Takai D: FER overexpression is associated with poor postoperative prognosis and cancer-cell survival in non-small cell lung cancer, Int J Clin Exp Pathol 6:598-612
14. Li H, Ren Z, Kang X, Zhang L, Li X, Wang Y, Xue T, Shen Y, Liu Y: Identification of tyrosine-phosphorylated proteins associated with metastasis and functional analysis of FER in human hepatocellular carcinoma cells, BMC Cancer 2009, 9:366
15. Zha S, Ferdinandusse S, Denis S, Wanders R J, Ewing C M, Luo J, De Marzo A M, Isaacs W B: Alpha-methylacyl-CoA racemase as an androgen-independent growth modifier in prostate cancer, Cancer Res 2003, 63:7365-7376
16. Krastev D B, Slabicki M, Paszkowski-Rogacz M, Hubner N C, Junqueira M, Shevchenko A, Mann M, Neugebauer K M, Buchholz F: A systematic RNAi synthetic interaction screen reveals a link between p53 and snoRNP assembly, Nature cell biology 2011, 13:809-818

9. EXAMPLE 4. ELIMINATION OF CANCER CELLS POSITIVE FOR FUSION TRANSCRIPTS THROUGH GENOME EDITING

Recent advances in genome editing using ZFN and CAS9 has made it possible to target a specific cancer genome sequence that is not present in normal cells. The mechanism of formation of fusion transcript is chromosome rearrangement. As a result, breakpoints in the chromosome are readily identified in a cancer genome. Normal cells do not have similar chromosome rearrangements, and are thus negative for the breakpoint. Targeting a specific breakpoint in the prostate cancer genome will likely generate an effective treatment for prostate cancer. Since the genomic breakpoint of CCNH-C5ORF30 and TMEM135-CCDC67 has been identified, genome editing technology targeting at the breakpoint of CCNH-C5orf30 or TMEM135-CCDC67 can be used to kill cancer cells.

As shown in FIG. 15, genome recombination in prostate cancer case 3T produced a breakpoint in chromosome 5 that connect intron 6 of CCNH with intron 1 of C5orf30. The resulting breaking point is unique in prostate cancer case 3T. The breakpoint is positive in most prostate cancer tissues but negative for normal tissues from this patient. A guide RNA (gRNA) of 23 bp including protospacer adjacent motif (PAM) sequence is designed specific for the breakpoint region. The DNA sequence corresponding to this target sequence is artificially ligated into vector containing the remainder of gRNA and CAS9. This sequence is recombined and packaged into recombinant virus (Adenovirus or lentivirus). A promoterless Herpes Simplex Virus Type 1 (HSV-1) thymidine kinase is constructed into a shuttle vector for adenovirus along with splice tag sequence from intron/exon juncture of CCNH exon 7. A 500 bp sequence surrounding the CCNH-C5orf30 breakpoint from each side is also ligated into the shuttle vector in order to produce efficient homologous recombination to complete the donor DNA construction. The vector is recombined and packaged into AdEasy to generate recombinant viruses. These viruses are administered to patients or animals that have cancer positive for CCNH-C5orf30 fusion transcript. This leads to insertion of donor DNA into the target site (fusion breakpoint). Since HSV-1 TK in recombinant virus is promoterless, no transcription will occur if HSV-1 TK cDNA does not integrate into a transcription active genome. However, transcription of HSV-1 TK is active if HSV-1 TK is integrated into the target site of CCNH-C5orf30, since this transcript is readily detectable in the prostate cancer sample of this patient. When patient 3T takes ganciclovir or its oral homologue valganciclovir, the homologue is readily converted to triphosphate guanine analogue by HSV-1 TK and incorporated into the genomes of cancer cells. This leads to stoppage of DNA elongation in cells that are positive for CCNH-C5orf30. Since mammalian TK does not phosphorylate ganciclovir, ganciclovir is not converted to active (triphosphate) form in cells that are negative for HSV-1 TK protein. Thus, the impact of ganciclovir on normal cells is minimized.

The technique described above was applied to cells having the TMEM135-CCDC67 breakpoint. Since none of the fusion genes we identified so far was present in prostate cancer cell lines, we created a TMEM135-CCDC67 genome breakpoint that is identical to the prostate cancer sample we analyzed. The expression of the TMEM135-CCDC67 breakpoint was driven by a CMV promoter. Subsequently, we constructed a donor DNA that encompassed HSV-1 TK and the splicing sites of TMEM135 exon 14. When we co-transfected this donor DNA with a vector that expresses gRNA targeting at the TMEM135-CCDC67 breakpoint into PC3 cells containing this genome breakpoint, integration of TK into the genome was identified (FIG. 28A). In contrast, when we transfected the same pairs of DNA into cells that do not contain the breakpoint, no integration of TK was found (data not shown). Treatment of PC3 cells without TMEM135-CCDC67 breakpoint has minimal cell death, while the same treatment of PC3 cells containing the breakpoint with ganciclovir resulted in 8 fold increase of cell death (FIG. 28B). This is remarkable in considering only 5-10% transfection efficiency using conventional liposome method. Without being limited to a particular theory, these data suggest that almost all the cells receiving the DNA died when treated with ganciclovir, if they contain the breakpoint. In light of this promising result, both TMEM135-CCDC67-TK cassette and NicKase-gRNATMEM135-CCDC67-BrkPt DNA are now in the process of packaging into Adenovirus. We will infect the recombinant virus into these cells in the future experiments. This will dramatically improve the delivery efficiency in the subsequent animal study and probably human.

10. EXAMPLE 5: NOVEL FUSION TRANSCRIPTS ASSOCIATE WITH PROGRESSIVE PROSTATE CANCER

The analysis of an additional 68 prostate cancer samples by transcriptome sequencing leads to the discovery of 5 additional novel fusion transcripts present in prostate cancer. It is noted that significant number of prostate cancers contained no fusion transcripts in RNA sequencing. Even though extensive transcriptome sequencings were performed on 30 prostate cancer samples that prove non-recurrent for extended period of time, no viable fusion transcripts were identified in these samples using fusion catcher software. These 5 fusion transcripts were validated through Sanger sequencing of the RT-PCR products (FIG. 16). The following primers were used: ACPP-SEC13: 5'-TCCCATTGACACCTTTCCCAC (SEQ ID NO: 30)/5'-TGAGGCTTCCAGGTACAACAG (SEQ ID NO: 31); CLTC-ETV1: 5'-GCCCAGTTGCAGAAAGGAATG (SEQ ID NO: 32)/5'-CTTGATTTTCAGTGGCAGGCC (SEQ ID NO: 33); DOCK7-OLR1: 5'-GACTACGTCTCATGC-CTTTCC (SEQ ID NO: 34)/5'-TTCTCATCAGGCTGGTC-CTTC (SEQ ID NO: 35); PCMTD1-SNTG: 5'-GATGTG-GTGGAATATGCCAAGG (SEQ ID NO: 36)/5'-AAATCCATGTGCTGTGGCACC (SEQ ID NO: 37); and ZMPSTE24-ZMYM4: 5'-CGCAATGAG-GAAGAAGGGAAC (SEQ ID NO: 38)/5'-CATAAATCTG-GAATAGGGCTCAG (SEQ ID NO: 39).

10.1. Results

ZMPSTE24-ZMYM4 Fusion Genes.

This fusion transcript was discovered in a prostate cancer sample from a patient who experienced prostate cancer recurrence 1.8 month after radical prostatectomy. The patient's pelvic lymph nodes were positive for metastatic prostate cancer, while his primary cancer sample was graded with Gleason 7. In addition to ZMPSTE24-ZMYM4, his prostate cancer sample was also positive for CCNH-c5orf30. ZMPSTE24 is a zinc-metalloproteinase involved in post-translational proteolytic cleavage that coverts farnesylated prelamin A to form mature lamin A. Mutation of this protein is associated with mandibuloacral dysplasia[1]. It was suggested that ZMPSTE24 may be a mediator promoting invasive prostate cancer[2]. ZMYM4 is an anti-apoptotic gene whose function domain is located in the 3' untranslated region. Expression of ZMYM4 3' UTR has been shown to resist cell death induced by interferon γ through inhibition of AUF1 activity[3]. The fusion formation between ZMPSTE24 and ZMYM4 produces a truncation of 159 amino acids from the C-terminus of ZMPSTE24 and 1315 amino acids from the N-terminus of ZMYM4. Motif analysis suggests that ZMPSTE24-ZMYM4 fusion will delete about 50% of the peptidase domain from ZMPSTE24 and remove all zinc fingers from ZMYM4, but leave ZUF3504 (domain of unknown function) and apoptosis inhibitor domain intact (FIG. 17). Thus, ZMPSTE24-ZMYM4 fusion may provide cancer cells an important tool to resist program cell death.

CLTC-ETV1 Fusion Genes.

CLTC-ETV1 was discovered in a prostate cancer sample that has Gleason's grade of 7. The patient experienced prostate cancer recurrence 22 months after radical prostatectomy, and had been rapidly progressing. In addition to CLTC-ETV1, the prostate cancer sample was also positive for TRMT11-GRIK2 fusion. CLTC is a major protein component of coated vesicles and coated pits, and is universally expressed. Its presence is essential for cell shape formation and cell motility. ETV1 is a transcription factor that was shown to over-express in prostate cancer. ETV1 had been shown to partner at least 12 different head genes in prostate cancer and Ewing's sarcoma[4,5]. However, most of these fusions do not produce a functional transcription factor from ETV1 due to frameshift in the fusion or few amino acids left after the fusion. In contrary, CLTC-ETV1 fusion preserves a largely intact transcription domain in ETV1, and probably represents the first example of potential functional ETV1 fusion in prostate cancer. CLTC-ETV1 fusion deletes 3 clathrin domains from CLTC (FIG. 18). This may impair the function of CLTC for coated pit formation. ETV1 has been shown to be oncogenic in several organ systems[6-8]. The regulatory domain is located in the N-terminus. The regulatory domain contains MAPK phosphorylation site as well as ubiquitination site by COP1[9,10]. Truncation in the N-terminus of ETV1 eliminates all these regulatory elements from ETV1. Thus, the protein level CLTC-ETV1 may be increased due to less degradation and activity of ETV1 may become constitutive due to the lack of regulatory constraint in the fusion protein. Since ETV1 has been shown to overexpress in many prostate cancers, CLTC-ETV1 fusion might be the underlying mechanism.

ACPP-SEC13 Fusion Genes.

The ACPP-SEC13 fusion transcript was discovered in a prostate cancer sample from patients who experienced recurrence but also had a slow rise of PSA with doubling time more than 20 months. The Gleason's grade is 7. The pathological examination reveals invasion into seminal vesicle by prostate cancer cells. ACPP is prostate specific acid phosphatase and is abundantly expressed in prostate acinar cells, while SEC13 belongs to the family of WD-repeat proteins, and is required for vesicle biogenesis from endoplasmic reticulum[11]. Recent studies suggest that SEC13 is a subunit of GATOR2, an octomeric GTPase activating protein. Inhibition of SEC13 suppresses mTOR activation[12]. In ACPP-SEC13 fusion, only the N-terminus 72 amino acids of ACPP is preserved, and over 2/3 of the phosphatase domain is truncated, while SEC13 loses 196 amino acids from its N-terminus and has 3 WD-repeat domains deleted (FIG. 19). Due to the large truncation of critical domains in both proteins, it is expected that ACPP-SEC13 contains neither phosphatase nor GTPase-activation activity. Such loss of function may lead to hyperactivity of mTOR and may make it insensitive to amino acid deprivation. A potential targeted treatment for patients positive for ACPP-SEC13 might be using mTOR inhibitor since cancer cells may become hypersensitive to mTOR inhibitors when SEC13 is not functional.

DOCK7-OLR1 Fusion Genes.

DOCK7-OLR1 fusion transcript was discovered in a prostate cancer sample from a patient who experienced recurrent prostate cancer 30.5 months after the radical prostatectomy. However, the rise of PSA appeared rapid with PSADT less than 3 months. The prostate cancer Gleason's grade was 7, and there was no invasion into seminal vesicle or other adjacent organs at the time of surgery. The surgical margin was negative. It clearly suggests that some prostate cancer cells had escaped the primary location before the surgery. DOCK7 is a guanine nucleotide exchange factor involving in migration and cell polarization[13,14], while OLR1 is a low density lipoprotein receptor that belongs to the C-type lectin superfamily. OLR1 binds, internalizes and degrades oxidized low-density lipoprotein[15]. Unlike the above 3 fusion transcripts, DOCK7-OLR1 does not produce a chimera protein. Instead, separate translation of DOCK7 and OLR1 occurs from the fusion transcript. The fusion deleted a significant portion of cytokinesis domain of DOCK7 such that motility regulation by DOCK7 might be compromised. However, the fusion transcript will produce an intact OLR1 protein (FIG. 20). OLR1 was implicated in Fas-mediated apoptosis. The functional significance of its expression under the control of DOCK7 promoter is to be investigated.

PCMTD1-SNTG1 Fusion Genes.

PCMTD1-SNTG1 fusion transcript was discovered in a prostate cancer sample from a patient who experienced recurrent prostate cancer 5.5 months after the radical prostatectomy. The rise of PSA was rapid with PSADT less than 3 months. The Gleason's grade is 9. Seminal vesicle invasion was identified in the prostatectomy sample. The prostate cancer sample is also positive for SLC45A2-AMACR and LRRC59-FLJ60017. PCMTD1 is Daspartate methyltransferase domain containing protein. The function of PCMTD1 has not been studied. SNTG1 is a member of the syntrophin family. SNTG1 belongs to peripheral membrane protein. Recent study suggests that SNTG1 may regulate diacylglycerol kinase zeta subcellular localization and regulates the termination of diacylglycerol signaling. Similar to DOCK7-OLR1 fusion, PCMTD1-SNTG1 fusion does not produce a chimera protein. PCMTD1-SNTG1 fusion produces a truncated PCMTD1. The truncation removes half of the methyl-transferase domain of PCMTD1. However, SNTG1 is intact (FIG. 21). Since diacylglycerol kinase weakens protein kinase C activity by depleting the availability of diacylglycerol, higher level of SNTG1 might enhance PKC signaling If PCMDT1-SNTG1 fusion drives up the expression of SNTG1. Alternatively, impairing the function of PCMTD1 may have impact on cell metabolism and cell growth that are yet to be delineated.

10.2. References

1. Agarwal, A. K., Fryns, J. P., Auchus, R. J., and Garg, A. (2003) Zinc metalloproteinase, ZMPSTE24, is mutated in mandibuloacral dysplasia. *Human molecular genetics* 12(16), 1995-2001.
2. Parr-Sturgess, C. A., Tinker, C. L., Hart, C. A., Brown, M. D., Clarke, N. W., and Parkin, E. T. Copper modulates zinc metalloproteinase-dependent ectodomain shedding of key signaling and adhesion proteins and promotes the invasion of prostate cancer epithelial cells. *Mol Cancer Res* 10(10), 1282-1293.
3. Shchors, K., Yehiely, F., Kular, R. K., Kotlo, K. U., Brewer, G., and Deiss, L. P. (2002) Cell death inhibiting RNA (CDIR) derived from a 3'-untranslated region binds AUF1 and heat shock protein. 27. *The Journal of biological chemistry* 277(49), 47061-47072.
4. Clark, J. P., and Cooper, C. S. (2009) ETS gene fusions in prostate cancer. *Nat Rev Urol* 6(8), 429-439.
5. Jeon, I. S., Davis, J. N., Braun, B. S., Sublett, J. E., Roussel, M. F., Denny, C. T., and Shapiro, D. N. (1995) A variant Ewing's sarcoma translocation (7; 22) fuses the EWS gene to the ETS gene ETV1. *Oncogene* 10(6), 1229-1234.
6. Carver, B. S., Tran, J., Chen, Z., Carracedo-Perez, A., Alimonti, A., Nardella, C., Gopalan, A., Scardino, P. T., Cordon-Cardo, C., Gerald, W., and Pandolfi, P. P. (2009) ETS rearrangements and prostate cancer initiation. *Nature* 457(7231), E1; discussion E2-3.
7. Chi, P., Chen, Y., Zhang, L., Guo, X., Wongvipat, J., Shamu, T, Fletcher, J. A., Dewell, S., Maki, R. G., Zheng, D., Antonescu, C. R., Allis, C. D., and Sawyers, C. L.

ETV1 is a lineage survival factor that cooperates with KIT in gastrointestinal stromal tumours. *Nature* 467 (7317), 849-853.
8. Jane-Valbuena, J., Widlund, H. R., Perner, S., Johnson, L. A., Dibner, A. C., Lin, W. M., Baker, A. C., Nazarian, R. M., Vijayendran, K. G., Sellers, W. R., Hahn, W. C., Duncan, L. M., Rubin, M. A., Fisher, D. E., and Garraway, L. A. An oncogenic role for ETV1 in melanoma. *Cancer research* 70(5), 2075-2084.
9. Vitari, A. C., Leong, K. G., Newton, K., Yee, C., O'Rourke, K., Liu, J., Phu, L., Vij, R., Ferrando, R., Couto, S. S., Mohan, S., Pandita, A., Hongo, J. A., Arnott, D., Wertz, I. E., Gao, W. Q., French, D.
10. M., and Dixit, V. M. COP1 is a tumour suppressor that causes degradation of ETS transcriptionfactors. *Nature* 474(7351), 403-406
11. Willardsen, M., Hutcheson, D. A., Moore, K. B., and Vetter, M. L. The ETS transcription factor Etv1 mediates FGF signaling to initiate proneural gene expression during *Xenopus laevis* retinal development. *Mechanisms of development* 131, 57-67
12. Enninga, J., Levay, A., and Fontoura, B. M. (2003) Sec13 shuttles between the nucleus and the cytoplasm and stably interacts with Nup96 at the nuclear pore complex. *Molecular and cellular biology* 23(20), 7271-7284.
13. Bar-Peled, L., Chantranupong, L., Cherniack, A. D., Chen, W. W., Ottina, K. A., Grabiner, B. C., Spear, E. D., Carter, S. L., Meyerson, M., and Sabatini, D. M. A Tumor suppressor complex with GAP activity for the Rag GTPases that signal amino acid sufficiency to mTORC1. *Science* (New York, N. Y340(6136), 1100-1106.
14. Watabe-Uchida, M., John, K. A., Janas, J. A., Newey, S. E., and Van Aelst, L. (2006) The Rac activator DOCK7 regulates neuronal polarity through local phosphorylation of stathmin/Op18. *Neuron* 51(6), 727-739.
15. Nellist, M., Burgers, P. C., van den Ouweland, A. M., Halley, D. J., and Luider, T. M. (2005) Phosphorylation and binding partner analysis of the TSC1-TSC2 complex. *Biochemical and Biophysical Research Communications* 333(3), 818-826.

11. EXAMPLE 6: SLC45A2-AMACR FUSION GENES

11.1 Results

The fusion transcript of Solute carrier family 45, member 2-alpha-methylacyl-CoA racemase (SLC45A2-AMACR) produces a chimera protein with Nterminus 187 amino acids of SLC45A2 and the C-terminus 311 amino acids of AMACR. SLC45A2 is a transporter protein known to be overexpressed in melanoma[1], while AMACR is an enzyme involved in metabolism of branch fatty acid, and is known for its overexpression in several human malignancies. SLC45A2-AMACR replaces 5 transmembrane and cytosolic domains of SLC45A2 with an intact racemase domain from AMACR[2], while leaves the extracellular and the N-terminal transmembrane domains intact (FIG. 24). Most of prostate cancer patients who were positive for SLC45A2-AMACR experienced prostate cancer recurrence within 5 years of surgical treatment. Previous studies suggest that AMACR is essential for optimal growth of prostate cancer cells in vivo. Knocking down of AMACR or treatment of prostate cancer with AMACR inhibitors resulted in death of cancer cells both in vitro and in vivo[3]. Formation of SLC45A2-AMACR generates ectopic racemase for fatty acid metabolism to support the growth of prostate cancer cells.

Transformation of Prostate Epithelial Cells with SLC45A2 AMACR Results in Dramatic Cell Growth and Transformation, Possibly Through Activation of SHIP2-Akt Pathway.

Figure 25G:
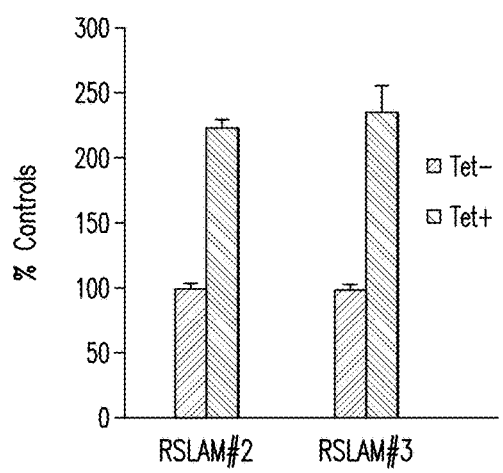
Figure 25H:
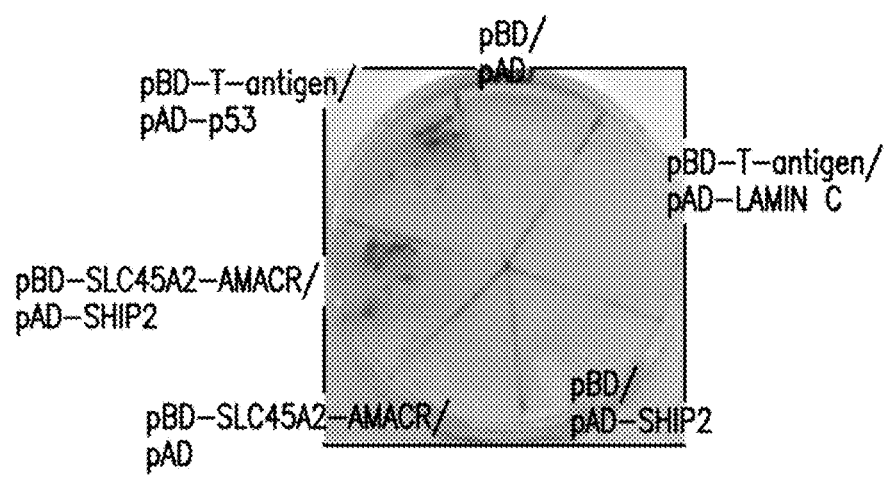
Figure 25I:
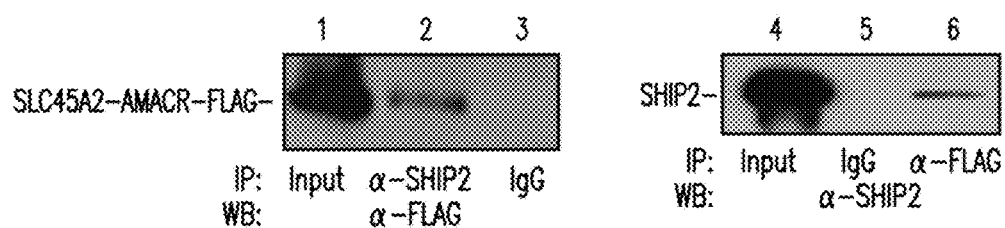

To investigate whether SLC45A2-AMACR chimera protein is expressed in prostate cancer samples that contain SLC45A2-AMACR transcript, protein extracts from 4 prostate cancer samples positive for SLC45A2-AMACR RNA were analyzed using antibodies specific for MAN2A1 or FER. The results showed that these samples expressed a 50 Kd protein recognized by both MAN2A1 and FER antibodies (FIG. 25A). This protein was not detected in prostate cancer samples that were negative for SLC45A2-AMACR transcript. When SLC45A2-AMACR was forced to express in RWPE1 cells, a non-transformed prostate epithelial cell line, it increased the proportion of cells in S phase by an average of 8.7 fold ($p<0.001$). MTT assays showed a 7.5 fold increase of cell proliferation ($p<0.001$)(FIG. 25 E-F). SLC45A2-AMACR was determined to be localized in the plasma membrane by immunofluorescence staining and membranous fractionation analyses. This is in contrast to native AMACR, which is located primarily in the mitochondria/cytoplasm. To investigate what are the potential signaling molecules mediating SLC45A2-AMACR induced cell growth and DNA synthesis. Yeast-two hybrid screening of prostate Yeast two-Hybrid library using pBD-SLC45A2-AMACR was performed. After 3 rounds of metabolic screening, 15 unique clones that contain SLC45A2-AMACR binding proteins were identified. One of these clones encodes inositol polyphosphate phosphatase-like 1 (INPPL1, also called SHIP2). SHIP2 is a SH2 domain containing inositol phosphatase that converts $PIP_3(3,4,5)$ to $PIP_2(3,4)$. In contrast to Pten, which converts $PIP_3(3,4,5)$ to an inactive $PIP_2(4,5)$, $PIP_2(3,4)$ generated by SHIP2 has higher affinity binding with AKT than $PIP_3(3,4,5)$, and thus hyper-activate AKT pathway. The interaction between SLC45A2 and SHIP2 was validated by both yeast Two-hybrid co-transfection analysis and co-immunoprecipitation assays in SLC45A2-AMACR expressing cells (FIG. 25G-H). Induction of SLC45A2-AMACR expression in 2 different clones of RWPE1 cells generated 2.1- and 2.3-fold higher level of PIP2(3,4), respectively. These results indicate that binding of SLC45A2-AMACR and SHIP2 leads to activation of SHIP2 phosphatase activity and probably AKT signaling pathway.

Therapeutic Targeting at SLC45A2-AMACR Using Racemase Inhibitor.

To investigate whether targeting SLC45A2-AMACR is a viable approach to treat prostate cancer, we chose 2 approaches: 1) To intercept SLC45A2-AMACR/SHIP2-Akt pathway with small molecules; and 2) to block the ectopic racemase activity of SLC45A2-AMACR with ebselen or trifluoro-ibuprofen. Surprisingly, both SHIP2 and MTOR inhibitors killed PC3 cells effectively, regardless whether they were transformed with SLC45A2-AMACR. Expression of SLC45A2-AMACR only moderately sensitized PC3 cells to Rapamycin. This is probably due to Pten negative status of PC3 cells such that Akt pathway is fully activated regardless the presence of SLC45A2-AMACR. On the other hand, when we applied ebselen, the potent inhibitor of racemase of AMACR, to SLC45A2-AMACR expressing PC3 cells, 5 fold higher sensitivity of cell growth inhibition was found for PC3 cells transformed with pCDNA4-

SLC45A2-AMACR-FLAG/pCDNA6 over the controls. In contrast, non-transformed RWPE1 cells and NIH3T3 cells that expressed little AMACR was largely insensitive to ebselen killing (FIG. 26). The differential sensitivity of normal cells versus cancer cells to AMACR inhibitors may prove very useful in treating prostate cancer positive for this fusion gene.

11.2. References

1. Misago, M., Liao, Y. F., Kudo, S., Eto, S., Mattei, M. G., Moremen, K. W., and Fukuda, M. N. (1995) Molecular cloning and expression of cDNAs encoding human alpha-mannosidase II and a previously unrecognized alpha-mannosidase IIx isozyme. Proceedings of the National Academy of Sciences of the United States of America 92(25), 11766-11770.
2. Krolewski, J. J., Lee, R., Eddy, R., Shows, T. B., and Dalla-Favera, R. (1990) Identification and chromosomal mapping of new human tyrosine kinase genes. Oncogene 5(3), 277-282.
3. Zha, S., Ferdinandusse, S., Denis, S., Wanders, R. J., Ewing, C. M., Luo, J., De Marzo, A. M., and Isaacs, W. B. (2003) Alpha-methylacyl-CoA racemase as an androgen-independent growth modifier in prostate cancer. Cancer research 63(21), 7365-7376.

Various references are cited in this document, which are hereby incorporated by reference in their entireties herein.

---

What is claimed is:

1. A method of treating a subject, comprising (i) determining whether a subject is at increased risk of manifesting progressive prostate cancer comprising determining whether a prostate cancer cell of the subject contains a SLC45A2-AMACR fusion gene; and (ii) where the cell contains the SLC45A2-AMACR fusion gene so that the subject is at increased risk, performing one or more of cryotherapy, radiation therapy, chemotherapy, hormone therapy, and radical prostatectomy.

2. The method of claim 1, wherein the fusion gene is detected by fluorescence in situ hybridization (FISH) analysis.

3. The method of claim 1, wherein the fusion gene is detected by polymerase chain reaction (PCR).

4. The method of claim 1, wherein the fusion gene is detected by Western blot analysis.

5. The method of claim 1, wherein the subject is determined to be at increased risk of rapid relapse.

6. The method of claim 1, wherein the subject is determined to be at increased risk of relapse.

7. The method of claim 1, further comprising determining a nomogram score of the subject.

8. A method of treating a subject, comprising:
   (i) determining whether a subject is at increased risk of manifesting progressive prostate cancer comprising determining whether a prostate cancer cell of the subject contains a SLC45A2-AMACR fusion gene; and
   (ii) where the cell contains the SLC45A2-AMACR fusion gene so that the subject is at increased risk;
   (a) administering a therapeutically effective amount of an inhibitor of the SLC45A2-AMACR fusion protein;
   (b) administering a therapeutically effective amount of an agent that inhibits the SLC45A2-AMACR fusion protein;
   (c) administering a therapeutically effective amount of an siRNA targeting the SLC45A2-AMACR fusion gene contained within the prostate cancer cell;
   (d) administering a therapeutically effective amount of an anti-cancer agent selected from the group consisting of chemotherapeutic agents, radiotherapeutic agents, cytokines, anti-angiogenic agents, apoptosis-inducing agents, and anti-cancer immunotoxins; and/or
   (e) performing a targeted genome editing procedure on one or more prostate cancer cells within the subject.

9. The method of claim 8, wherein the fusion gene is detected by fluorescence in situ hybridization (FISH) analysis.

10. The method of claim 8, wherein the fusion gene is detected by polymerase chain reaction (PCR).

11. The method of claim 8, wherein the fusion gene is detected by Western blot analysis.

12. The method of claim 8, wherein the subject is determined to be at increased risk of rapid relapse.

13. The method of claim 8, wherein the subject is determined to be at increased risk of relapse.

14. The method of claim 8, wherein a therapeutically effective amount of an inhibitor of the SLC45A2-AMACR fusion protein is administered.

15. The method of claim 14, wherein the inhibitor of the SLC45A2-AMACR fusion protein is selected from the group consisting of ebselen, 2-(2,5-dihydroxy-4-methylphenyl)-5-methyl benzene-1,4-diol (DMPMB), 2-methylsulfanyl-7,9-dihydro-3H-purine-6,8-dithione (MSDTP), 2,5-di(pyrazol-1-yl)benzene-1,4-diol (DPZBD), Rose Bengal, Congo Red, 3,5-di(pyridin-4-yl)-1,2,4-thiadiazole (DPTD), ebselen oxide, 3,7,12-trihydroxycholestanoyl Coenzyme A (THCA-CoA), N-methylthiocarbamate, trifluoro-ibuprofen and combinations thereof.

16. The method of claim 14, wherein the inhibitor of the SLC45A2-AMACR fusion protein is a racemase inhibitor.

17. The method of claim 14, wherein the inhibitor of the SLC45A2-AMACR fusion protein is an AMACR inhibitor.

18. The method of claim 16, wherein the racemase inhibitor is ebselen.

19. The method of claim 16, wherein the method further comprises administering a therapeutically effective amount of an AMACR inhibitor.

* * * * *

SEQUENCE LISTING

<160> NUMBER OF SEQ ID NOS: 77

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcaaatacta tttcagaaac agcctatgag ggaaattttg gtgaagtata taagggcaca     60

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
cagccuauga gggaaauuuu gguga                                            25

<210> SEQ ID NO 3
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucaccaaaau uucccucaua ggcuguu                                          27

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tccactacca tgccctcttc acaggtgtca tggagaaact ccagctgggc ccagaga        57

<210> SEQ ID NO 5
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ugcccucuuc acagguguca uggag                                          25

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cuccaugaca ccugugaaga gggcaug                                        27

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgtcagaatc caagtcaagt caggattcct tgttctggga atgtcagtgg aatctgctcc    60
tgc                                                                  63

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gucaggauuc cuuguucugg gaatg                                          25

<210> SEQ ID NO 9
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cauucccaga acaaggaauc cugacuu                                        27

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
```

```
ttttaagact caccaagggc aaataagaag ccaactccaa caggtggaag agtacca        57
```

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11

```
gacucaccaa gggcaaauaa gaagc                                           25
```

<210> SEQ ID NO 12
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12

```
gcuucuuauu ugcccuuggu gagucuu                                         27
```

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
tgtcacagtt actagatata atgaaaatac ctggagtaga acagaaaaat tattatgtct     60
```

<210> SEQ ID NO 14
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14

```
augaaaauac cuggaguaga acaga                                           25
```

<210> SEQ ID NO 15
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15

```
ucuguucuac uccagguauu uucauua                                         27
```

<210> SEQ ID NO 16
<211> LENGTH: 60
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 16
aactacctgc actttgggga gcctaagtcc tggacagtaa gcaagcctgg atctgagaga    60

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
gagccuaagu ccuggacagu aagca                                          25

<210> SEQ ID NO 18
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ugcuuacugu ccaggacuua ggcuccc                                        27

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agcatctgga gttccgcctg ccggtggtat ttttgaatat gtggaatctg gcccaatggg    60
agctg                                                                65

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
ccgccugccg gugguauuuu ugaat                                          25

<210> SEQ ID NO 21
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
```

```
auucaaaaau accaccggca ggcggaa                                        27

<210> SEQ ID NO 22
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctgcttggat gagaagcagt gtaagcagtg tgcaaacaag gtgactggaa gcacctgctc    60
aatggctg                                                             68

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
acaaggugac uggaagcacc ugctc                                          25

<210> SEQ ID NO 24
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gagcaggugc uuccagucac cuuguuu                                        27

<210> SEQ ID NO 25
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagccaaccg atactttct ccaaatttta agacacagca ggatgccaat gcctcttccc     60
tcttagac                                                             68

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
cuccaaauuu uaagacacag cagga                                          25

<210> SEQ ID NO 27
```

<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uccugcugug ucuuaaaauu uggagaa                                        27

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcatttgcag tatagagcgt gc                                             22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtctaagagg gaagaggcat tg                                             22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcccattgac acctttccca c                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaggcttcc aggtacaaca g                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcccagttgc agaaaggaat g                                              21

<210> SEQ ID NO 33
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cttgattttc agtggcaggc c                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gactacgtct catgcctttc c                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttctcatcag gctggtcctt c                                              21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gatgtggtgg aatatgccaa gg                                             22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aaatccatgt gctgtggcac c                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgcaatgagg aagaagggaa c                                              21

<210> SEQ ID NO 39
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 39
cataaatctg gaatagggct cag                                             23

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
taaaagctaa agttaaatac ctgtttgaaa atggta                               36

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcactcataa agaagagctt gaatttggaa atgac                                35

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atagctttga taaactgctc tccagaatgt tg                                   32

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
accaactcac ccagattggc tgcaatgccg tcag                                 34

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgccaatact agtgtggctt ttcatggcct gccac                                35

<210> SEQ ID NO 45
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 45
tcagaaacag cctatgaggg aaatttggt ga                                      32

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gactcaccaa gggcaaataa gaagccaact ccaacag                                37

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
taagcagtgt gcaaacaagg tgactggaag cacctgctca at                          42

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gcatctggag ttccgcctgc cggtggtatt tttgaatatg                             40

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccagtcagtc aggattcctt gttctgggaa tgtcagtgg                              39

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gttactagat ataatgaaaa tacctggagt agaacagaaa                             40

<210> SEQ ID NO 51
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 51
ccactaccat gccctcttca caggtgtcat ggagaaactc ca                              42

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aactacctgc actttgggga gcctaagtcc tggacagtaa gcaagcc                         47

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aatgtttaaa tttggaacgt ggactttggg gcaggt                                     36

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
taataatgaa cctagctacc ctaaactcct                                            30

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tctcattatg ttgccgaagg ggatatcacc acca                                       34

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttttctccaa attttaagac acagcaggat gccaa                                      35

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 57
aatttggaac gtggactttg gg					22

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttggcatgat agaccagtcc c					21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cagcaccaag ggaatgtgta g					21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttggcatgat agaccagtcc c					21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagcaccaag ggaatgtgta g					21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcgctgtcgt gtacccttaa c					21

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 63
ggtaagggta gtattgggta gc                                              22

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccagggctgg aattactatg g                                               21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aagcaccagt ctgcacaatc c                                               21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ttgatgtctg ctcccatcag g                                               21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgatatcgtg gccagctaac c                                               21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aacacgccct acctgtactt c                                               21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 69
ctgagcaaag acagcaacac c                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tggaagttca agtcagcgca g                                              21

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gctgtctttg tgtgcaaact cc                                             22

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtgactgctt ggatgagaag c                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccagcatgca gcttttctga g                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agtaggcgcg agctaagcag g                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
```

-continued

```
gggacagtct gaatcatgtc c                                              21

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tcaagatcat tgctcctcct gagc                                           24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgctgtcacc ttcaccgttc cagt                                           24
```